US007910716B2

(12) United States Patent
Johnston et al.

(10) Patent No.: US 7,910,716 B2
(45) Date of Patent: Mar. 22, 2011

(54) NUCLEIC ACIDS ENCODING MODIFIED SOUTH AFRICAN HIV-1 SUBTYPE C GAG PROTEINS

(75) Inventors: Robert Edward Johnston, Chapel Hill, NC (US); Salim Abdol Karim, Durban (ZA); Lynn Morris, Randburg (ZA); Ronald Swanstrom, Chapel Hill, NC (US); Carolyn Williamson, Cape Town (ZA)

(73) Assignees: Medical Research Council, Cape Town (ZA); University of Cape Town Observatory, Cape Town (ZA); University of North Carolina at Chapel Hill, Chapel Hill, NC (US); Alphavax, Incorporated, Research Triangle Park, NC (US)

( * ) Notice: Subject to any disclaimer, the term of this patent is extended or adjusted under 35 U.S.C. 154(b) by 0 days.

(21) Appl. No.: 12/357,099

(22) Filed: Jan. 21, 2009

(65) Prior Publication Data
US 2009/0270488 A1 Oct. 29, 2009

Related U.S. Application Data

(63) Continuation-in-part of application No. 11/724,551, filed on Mar. 15, 2007, now abandoned, which is a continuation of application No. 10/332,413, filed as application No. PCT/IB01/01208 on Jul. 9, 2001, now abandoned.

(60) Provisional application No. 60/216,995, filed on Jul. 7, 2000.

(30) Foreign Application Priority Data

Jul. 10, 2000 (ZA) ..................................... 00/3437
Sep. 15, 2000 (ZA) ..................................... 00/4924

(51) Int. Cl.
*C07H 21/04* (2006.01)
*A61K 39/21* (2006.01)
(52) U.S. Cl. ................... 536/23.72; 424/188.1
(58) Field of Classification Search ........................ None
See application file for complete search history.

(56) References Cited

U.S. PATENT DOCUMENTS
5,817,637 A * 10/1998 Weiner et al. ............... 514/44 R
2005/0137387 A1* 6/2005 Mullins et al. ............. 536/23.72

FOREIGN PATENT DOCUMENTS
WO WO 02/04494 1/2002

OTHER PUBLICATIONS

Brown, T., 1993, Hybridization analysis of DNA blots, in Current Protocols in Molecular Biology, John Wiley and Sons, Inc., 2.10.1-2.10.16.*
Betts et al., "Cross-Clade Human Immunodeficiency Virus (HIV)-Specific Cytotoxic T-Lymphocyte Responses in HIV-Infected Zambians," J. Virol., 71:8908-8911, 1997.
Binley et al., "A Recombinant Human Immunodeficiency Virus Type 1 Envelope Glycoprotein Complex Stabilized by an Intermolecular Disulfide Bond between the gp120 and gp41 Subunits Is an Antigenic Mimic of the Trimeric Virion-Associated Structure," J. Virol., 74:627-643, 2000.
Connor et al., "Change in Coreceptor Use Correlates with Disease Progression in HIV-1-Infected Individuals," J. Exp. Med., 185:621-628, 1997.
Durali et al., "Cross-Reactions between the Cytotoxic T-Lymphocyte Responses of Human Immunodeficiency Virus-Infected African and European Patients," J. Virology, 1998, 72:3547-3553.
Ferrari et al., "Clade B-based HIV-1 vaccines elicit cross-clade cytotoxic T lymphocyte reactivities in uninfected volunteers," Proc. Natl. Acad. Sci. USA, 94:1396-1401, 1997.
Gao et al., "Molecular cloning and analysis of functional envelope genes from human immunodeficiency virus type 1 sequence subtypes A through G," J. Virology, 70:1651-1667, 1996.
Kostrikis et al., "Quantitative Analysis of Serum Neutralization of Human Immunodeficiency Virus Type 1 from Subtypes A, B, C, D, E, F, and I: Lack of Direct Correlation between Neutralization Serotypes and Genetic Subtypes and Evidence for Prevalent Serum-Dependent Infectivity Enhancement," J. Virology, 70:445-458, 1996.
Koup et al., "Temporal Association of Cellular Immune Responses with the Initial Control of Viremia in Primary Human Immunodeficiency Virus Type 1 Syndrome," J. Virology, 68:4650-4655, 1994.
Leigh Brown et al., "Reduced susceptibility of human immunodeficiency virus type 1 (HIV-1) from patients with primary HIV infection to nonnucleoside reverse transcriptase inhibitors is associated with variation at novel amino acid sites," J. Virology, 74:10269-10273, 2000.
Lole et al., "Full-length Human Immunodeficiency Virus Type 1 Genomes from Subtype C-infected Seroconverters in India, with Evidence of Intersubtype Recombination," J. Virology, 73:152-160, 1999.
Moore et al., "Inter- and Intraclade Neutralization of Human Immunodeficiency Virus Type 1: Genetic Clades Do Not Correspond to Neutralization Serotypes but Partially Correspond to gp120 Antigenic Serotypes," J. Virology, 70:427-444, 1996.
Novitsky et al., "Molecular cloning and phylogenetic analysis of human immunofeficiency virus type 1 subtype C: a set of 23 full-length clones from Botswana," J. Virology, 73:4427-4432, 1999.

(Continued)

*Primary Examiner* — Jeffrey S. Parkin
(74) *Attorney, Agent, or Firm* — Kilpatrick Townsend & Stockton LLP

(57) ABSTRACT

Embodiments of the invention provide processes for the selection of HIV-1 subtype (clade) C isolates, selected HIV-1 subtype C isolates, their genes and modifications and derivatives thereof for use in prophylactic and therapeutic vaccines to produce proteins and polypeptides for the purpose of eliciting protection against HIV infection or disease. A process for the selection of HIV subtype isolates comprises the steps of isolating viruses from recently infected subjects; generating a consensus sequence for at least part of at least one HIV gene by identifying the most common codon or amino acid among the isolated viruses; and selecting the isolated virus or viruses with a high sequence identity to the consensus sequence. HIV-1 subtype C isolates, designated Du422, Du 151 and Du 179 (assigned Accession Numbers 01032114, 00072724 and 00072725, respectively, by the European Collection of Cell Cultures) are also provided.

6 Claims, 51 Drawing Sheets

OTHER PUBLICATIONS

Ogg et al., "Longitudinal Phenotypic Analysis of Human Immunodeficiency Virus Type 1-Specific Cytotoxic T Lymphocytes: Correlation with Disease Progression," J. Virology, 73:9153-9160, 1999.

Rowland-Jones et al., "Cytotoxic T Cell Responses to Multiple Conserved HIV Epitopes in HIV-Resistant Prostitutes in Nairobi," J. Clin. Invest., 102:1758-1765, 1998.

De Baar et al., "Subtype-specific sequence variation of the HIV type 1 long terminal repeat and primer-binding site," Aids Res. and Human Retrovir., 16:499-504, 2000.

"HIV-1 Isolate BU/97/07, envelope," EMBL Online, Jan. 2, 1996, Database accession No. H11U39249.

Tscherning et al., "Differences in chemokine coreceptor usage between genetic subtypes of HIV-1," Virology, 241:181-188, 1998.

Van Harmelen et al., "A predominantly HIV Type 1 subtype C-restricted epidemic in South African urban populations," Aids Res. and Human Retrovir., 15:395-398, 1999.

Bjorndal et al., "Phenotypic characteristics of human immunodeficiency virus type 1 subtype C isolates of Ethiopian AIDS Patients," Aids Res. and Human Retrovir., 15:647-653, 1999.

Peeters et al., "Evidence for Differences in MT2 Cell Tropism According to Genetic Subtypes of HIV-1 : Syncytium-Inducing Variants Seem Rare Among Subtype C HIV-1 Viruses," J. Acquir. Imm. Def. Synd., 20:115-121, 1999.

Ping et al., "Characterization of V3 Sequence Heterogeneity in Subtype C Human Immunodeficiency Virus Type 1 Isolates from Malawi: Underrepresentation of X4 Variants," J. Virology, 73:6271-6281, 1999.

Richman et al., "The Impact of the Syncytium-Inducing Phenotype of Human Immunodeficiency Virus on Disease Progression," J. Infect. Dis, 169:968-974, 1994.

Scarlatti et al., "In vivo evolution of HIV-1 co-receptor usage and sensitivity to chemokine-mediated suppression," Nat. Med., 3:1259-1265, 1997.

Schmitz et al., "Control of Viremia in Simian Immunodeficiency Virus Infection by CD8+ Lymphocytes," Science, 283:857-860, 1999.

Wyatt et al., "The HIV-1 Envelope Glycoproteins: Fusogens, Antigens, and Immunogens," Science, 280:1884-1888, 1998.

Summary Report: National HIV and Syphilis Sero-Prevalence Survey of Women Attending Public Antenatal Clinics in South Africa, Department of Health, Apr. 2001.

Office Action mailed Nov. 15, 2006 for U.S. Appl. No. 10/332,413.

Office Action mailed Jun. 22, 2006 for U.S. Appl. No. 10/332,413.

International Search Report mailed Dec. 2, 2002 for Application No. PCT/IB01/01208.

Summary Report: National HIV and Syphilis Sero-Prevalence Survey of women attending Public Antenatal Clinics in South Africa, Department of Health, 2000.

Korber et al., "Numbering Positions in HIV Relative to HXB2CG," HIV Molecular Immunology Database, IV-27-35, 1998.

Robertson et al., "HIV-1 Nomenclature Proposal," Science, 288:55-56, 2000.

Wyatt et al., "The Antigenic Structure of the HIV gp120 Envelope Glycoprotein," Nature, 393:705-11, 1998.

\* cited by examiner

FIG. 5A

```
SEQ ID                1                                                        50
NO:
18   SAgagcon     GEKLDKWEKI RLRPGGKKHY MLKHLVWASR ELERFALNPG LLETSEGCKQ
19   DU115_gag    -g---a--r- --------q- -i-------- ---------- ----g-----
20   DU258_gag    -g-------- k--------- ---------- ---------- ----ad----
21   DU179_gag    -g-------- ---------- -i-------- ---------- --------r-
22   RB15gag      -g---a---- ---------- -i-------- ---------- -----a----
23   GG10gag      ---------- ---------- ---------- ---------- ----------
24   RB22gag      ---------- -------q- ---------- ---------- ----------
25   DU467_gag    -----t---- ---------r- ----i----- ---------- ----------
26   GG3gag       -----a---- ---------- ----i----- ---------- ----------
27   DU281_gag    ---------r- --------c- ----i----- ---------- ----------
28   DU368_gag    -----r--r- ---------- ----i----- ---------- --------r-
29   GG1gag       -----r---- ---------- ----i----- ---------- ----------
30   RB14gag      -g---a---- --------c- -i---i---- ---------- ----------
31   RB18gag      -----a---- k-------c- -i-------- ---------- ----------
32   GG4gag       -g---a---- ---------- -i-------- ---------- ----------
33   RB27gag      -gq------- ---------- ---------- ---------- ----------
34   DU422_gag    -----t---- ---------- ----i----- ---------- ----------
35   RB28gag      -----t--r- ---------- ----i----- ---------- ----------
36   DU457_gag    --n--r---- ---------r- ----i----- ---------- ----------
37   RB13gag      -k---s--r- ---------- -i-------- ---------- ----------
38   GG5gag       -g---t---- --------q- -i-------- ---------- --------r-
39   GG6gag       ---------- --------k- -----i---- ---------- ----a-----
40   CTSC2_gag    -g-------- --------c- ----ii---- ---------- ----k-----
41   RB12gag      -----r--r- --------t- ----i----- ---------- ----------
42   DU156        ---------- ---------- ---------- --------d- ----------
43   DU123_gag    --------r- k--------- r---i----- ---------- ----------
44   RB21gag      -g---t---- --------r- km--i----- ---------- ----a-----
45   DU172_gag    -g------r- ---------- ----i----- ---------- ----------
46   DU204_gag    -g-------- --------r- -i-------- ---------- ----a-----
47   DU174_gag    -gn--t---- --------q- k--------- ---------- ---sa-----
48   CTSC1_gag    -g---a--r- ---------- ----i---k ---------- ---n------
49   Cgagcon      -g---t---- ---------- -i-------- ---------- ----------

51                                                       100
Sagagcon         IMKQLQPALQ TGTEELRSLY NTVATLYCVH EKIEVRDTKE ALDKIEEEQN
DU115_gag        ---------- ---k------ ---------- ---------- ---------k
DU258_gag        -i-------- ---------f ---------- ke-------- ----------
DU179_gag        -ir------- ---------f ---------- -e-------- ---r-----k
RB15gag          -ir------- ---------- ---------- -r-------- ---------k
GG10gag          --s---s--- ---------- ----v-w--- nn-------- ---------k
RB22gag          ---------- ---------- ---------- sn-------- ----------
DU467_gag        --e------- ------k--f ---------- kr-d------ ----v----k
GG3gag           --n------- ---------- ---------- kr-d------ ----------
DU281_gag        --q------- ------k--- --i------- kg-------- ----------
DU368_gag        --n------- ------k--- ---------- ---d------ ----------
GG1gag           -it------- ------k--f ---------- k--d------ ----------
RB14gag          ---------- ---------- ---------- ---------- ----------
RB18gag          ---------- ---------- ---------- -----q---- ----------
GG4gag           -i-------- ---------- ---------- ---d------ ----------
RB27gag          -i-------- ---------- ---------- ---------- ----------
DU422_gag        ---------- ------k--- ---------- ---------- ----------
RB28gag          -ir------- ------k--f ---------- ---k------ ----------
DU457_gag        ---------- ------k--- ---------- k--d-q---- ----v-----
RB13gag          ---------- ---------f ---------- ---------- ----------
GG5gag           ---------- ---------f ---------- ---------- ----------
GG6gag           --q-i----- ---------f ---------- a--------- ----------
CTSC2_gag        -in--h---- ---------f ---------- ae-------- ----------
RB12gag          --n-----v- ------k--f ---------- ---d------ ----------
```

FIG. 5B

```
DU156        ---------- --------f- ---------- ----i----- ----------
DU123_gag    --n------- --------f- ---------- a--d------ ----------
RB21gag      -iq------k ------k--f ---------- kr-------- ----v-----
DU172_gag    -i---h---- ---------- --i-v----- kd-a-q---- ----------
DU204_gag    -iq------k ------k--- ---------- ae-------- ----------
DU174_gag    -i-------- ---------- ---------- -r---q---- ----------
CTSC1_gag    -----h---- ------k--- ---------- ---------- ----------
Cgagcon      -i-------- ---------- ---------- ---------- ----------

101                                              150
Sagagcon     KSQQ-CQQKT QQAKAADGG- KVSQNYPIVQ NLQGQMVHQA ISPRTLNAWV
DU115_gag    -....---ei ---e---k-. ---------- ---------- ----------
DU258_gag    -....----a ---e-s-k-. ---------- --------p  l---------
DU179_gag    --....---- ----e--k.. ---------- --------x- l---------
RB15gag      -c....---- ---..--e.. ---------- -a-------- ----------
GG10gag      --....---- ---------.. n--------- ----a----- l---------
RB22gag      --....---- ---g----.. ---------- --------p  l---------
DU467_gag    r-....---- -------e.. ---------- ---------- ----------
GG3gag       --....---- -------ekv ---------- --------p  ----------
DU281_gag    --....---- --t-----.-. ---------- ---------- ----------
DU368_gag    --....---- --e---g-.-. ---------- ---------- ----------
GG1gag       ----.v---- ----t--.-. ---------- ---------- ----------
RB14gag      --....---- ---q---.-. ---------- -v-------- l---------
RB18gag      --....---- ---q---.-. ---------- -v-------- l---------
GG4gag       -i....---- ---e---k-. ---------- ---------- ----------
RB27gag      --....---- ---e---k-. ---------- ---------- l---------
DU422_gag    -c....---- --------.-. ---------- ---------- ----------
RB28gag      --....---- --------.e. -i-------- ---------- ----------
DU457_gag    --....---- ---e---.-. ---------- ---------- ----------
RB13gag      --....---- ----e--.-. -t-------- ---------- l---------
GG5gag       --....---- ----g--.-. -i-------- ---------- ----------
GG6gag       --....---- --------.-. q--------- ---------- ----------
CTSC2_gag    ...n.i---- ---------. ---------- ---------- ----------
RB12gag      --....---- p-------.. ---------- ---------- ----------
DU156        -....----- ----e---.. ---------- ---------- ----------
DU123_gag    --....---- -.......... .--------- --------p  -t--------
RB21gag      --....---- ---d---k-. -----f---- -v-------- ----------
DU172_gag    -c--ks---- --ta----aa ..-------- ---------- s l--------
DU204_gag    -....----- k-t-ed--.. -a-------- -a--a---p  ----------
DU174_gag    -....i---- -----keadg -t-------- -i-------- l---------
CTSC1_gag    -.....--h-a ---etd-k-. ---------- ---------- l---------
Cgagcon      --....---- --------.-. ---------- ---------- ----------

151                                              200
Sagagcon     KVIEEKAFSP EVIPMFTALS EGATPQDLNT MLNTVGGHQA AMQMLKDTIN
DU115_gag    ---------- ---------- ---------- ---------- ----------
DU258_gag    ---------- ---------- ---------- ---------- ----------
DU179_gag    ---------- ---------- ---------- ---------- ----------
RB15gag      ---------- ---------- ---------- ---------- ----------
GG10gag      --------n- -i-------- ---------- ---------- ----------
RB22gag      --------n- ---------- ---------- ---------- ----------
DU467_gag    ---------- -i-------- ---------- ---------- ----------
GG3gag       ---------- ---------- ---------- ---------- ----------
DU281_gag    ---------- ---------- ---------- ---------- ----------
DU368_gag    ---------- ---------- ---------- ---------- ----------
GG1gag       ---k------ ---------- ---------- ---------- ----------
RB14gag      ---------- ---------- ---------- ---------- ----------
RB18gag      ---------- ---------- ---------- ---------- ----------
GG4gag       ---------- ---------- ---------- ---------- ----------
RB27gag      ---------- ---------- ---------- ---------- ----------
```

FIG. 5C

```
Sagagcon    ---------- ---------- ---------- ---------- ----------
DU422_gag   ---------- ---------- ---------- ---------- ----------
RB28gag     ---------- ---------- ---------- ---------- ----------
DU457_gag   ---------- ---------- ---------- ---------- ----------
RB13gag     --v------- ---------- --------s- ---------- ---i------
GG5gag      ---------- ---------- ---------- ---------- ---i------
GG6gag      ---------- ---------- ---------- ---------- ----------
CTSC2_gag   ---------- ---------- ---------- ---------- ----------
RB12gag     ---------- ---------- ---------- ---------- ----------
DU156       ---------- ---------- ---------- ---------- ----------
DU123_gag   ------g-n- ---------- ---------- ---------- ----------
RB21gag     ---------- ---------- ---------- ---------- ----------
DU172_gag   ---------- ---------- ---------- ---------- ----------
DU204_gag   ------g-n- ---------- ---------- ---------- ----------
DU174_gag   --v------q ---------- ---------- ---------- ---i------
CTSC1_gag   ------n--- ---------- ---------- ---------- ------e---
Cgagcon     ---------- ---------- ---------- ---------- ----------
```

```
            201                                                 250
Sagagcon    EEAAEWDRLH PVHAGPIAPG QMREPRGSDI AGTTSTLQEQ IAWMTSNPPI
DU115_gag   ---------- ---------- ---------- ---------- ----------
DU258_gag   ---------- ------n--- ---------- ---------- -t---n----
DU179_gag   ---------- ------np-- -i-------- ---------- -----g---v
RB15gag     ---------- ------v--- ---------- ---------- -----n----
GG10gag     ---------- ------v--- ---------- ---------- ---------v
RB22gag     ---------- ---------- ---------- -----n---- ---------v
DU467_gag   ---------- ---------- ---------- ---------- -t---n---v
GG3gag      ---------- ---s--v--- -v-------- ---------- -t--------
DU281_gag   d--------- -------q-- ---------- ---------- ----------
DU368_gag   ---------- ---------- ---------- ---------- -----n---v
GG1gag      d--------- ---------- ---------- ---------- ----------
RB14gag     ---------- ------v--- -l-------- ---------- -----n---v
RB18gag     ---------- ------v--- -l-------- ---------- -----n---v
GG4gag      ---------- ------v--- ---------- ---------- ----------
RB27gag     ---------- ---------- ---------- ---------- ----------
DU422_gag   ---------- ---------- ---------- ---------- ----------
RB28gag     d--------- ---------- ---------- ---------- ---------v
DU457_gag   --------m- ---------- ---------- ---------- -----n---v
RB13gag     ---------- ---------- ---------- ---------- -----n----
GG5gag      ---------- ---i------ -v-------- ---------- -t---a---v
GG6gag      ---------- ------a--- ---------- ---------- ---------v
CTSC2_gag   ---------- ------v--- ---------- ---------- -----a----
RB12gag     ---------- --q------- -i-------- --s--n---- -t--------
DU156       ---------- -aq---hpa- ---d------ ---------- ----------
DU123_gag   ---------- ---------- ---------- ---------- ---i-g----
RB21gag     ---------- --q---v--- -i-------- ---------- -----r---v
DU172_gag   ---------- ---------- ---------- ---------- -t-------v
DU204_gag   --------v- ---------- ---------- -----n---- -----n----
DU174_gag   --------v- --q------- -i-------- ---------- -t---n----
CTSC1_gag   -r-------- ---------- ---------- ---------- ----------
Cgagcon     ---------- ------v--- ---------- ---------- ----------
```

```
            251                                                 300
Sagagcon    PVGDIYKRWI ILGLNKIVRM YSPVSILDIK QGPKEPFRDY VDRFFKTLRA
DU115_gag   ---------- ---------- ---------- ---------- ----------
DU258_gag   ---------- ---------- ---------- ---------- ----------
DU179_gag   ---e------ ---------- ---------r ---------- ----------
RB15gag     ---------- -m-------- ---------- ---------- ----------
GG10gag     ---------- ---------- ---------- ---------- ----------
```

FIG. 5D

```
RB22gag       ---e------ ---------- ---------- ---------- ----------
DU467_gag     ---------- ---------- --------r- ---------- ----------
GG3gag        ---------- ---------- --------r- ---------- ----------
DU281_gag     ---------- ---------- --------r- ---------- ----------
DU368_gag     ---------- ---------- --------r- ---------- ------v---
GG1gag        ---------- ---------- --------r- ---------- ----------
RB14gag       ---e------ ---------- ---------- ---------- ----------
RB18gag       ---e------ ---------- ---------- ---------- ----------
GG4gag        ---------- ---------- ---------- ---------- ----------
RB27gag       ---------- ---------- ---------- ---------- ----------
DU422_gag     ---------- ---------- --------r- ---------- ----------
RB28gag       ---------- ---------- --------r- ---------- ----------
DU457_gag     ---------- ---------- --------r- ---------- ----------
RB13gag       ---e------ ---------- ---------- ---------- ----------
GG5gag        ---------- ---------- --------r- ---------- ----------
GG6gag        ---------- ---------- --------r- ---------- ----------
CTSC2_gag     ---------- ---------- --------r- ---------- ----------
RB12gag       ---------- ---------- ---------- ---------- ------a---
DU156         ---e------ ---------- ---------- ---------- ----------
DU123_gag     ---e------ ---------- ---------- ---------- ----------
RB21gag       ---------- -m-------- ---------- ---------- ----------
DU172_gag     ---e------ ---------- ---------- ---------- ----------
DU204_gag     ---e------ v--------- ---------- ---------- ----------
DU174_gag     ---e------ ---------- --------r- ---------- ----------
CTSC1_gag     ---e------ ---------- --------r- ----ra---- ----------
Cgagcon       ---------- ---------- ---------- ---------- ----------

301        313
Sagagcon      EQATQDVKNW MTD
DU115_gag     --s--e---- ---
DU258_gag     ---------- ---
DU179_gag     ---------- ---
RB15gag       ---------- ---
GG10gag       ---------- ---
RB22gag       ---------- ---
DU467_gag     -----e---- ---
GG3gag        ---------- --e
DU281_gag     -----e---- ---
DU368_gag     -----e---- --e
GG1gag        -----e---- ---
RB14gag       ---------- ---
RB18gag       ---------- ---
GG4gag        --s--e---- ---
RB27gag       -----e---- ---
DU422_gag     -----e---- ---
RB28gag       ---------- ---
DU457_gag     ---------- ---
RB13gag       -----e---- ---
GG5gag        ---------- ---
GG6gag        ---------- ---
CTSC2_gag     ---------- --e
RB12gag       ---------- ---
DU156         ---------- ---
DU123_gag     ---------- ---
RB21gag       -----e---- ---
DU172_gag     ---------- --e
DU204_gag     ---------- --e
DU174_gag     ---------- ---
CTSC1_gag     d-s--e---- ---
Cgagcon       ---------- ---
```

FIG. 6A

```
SEQ ID
NO:
                        1                                                     50
50 sapep.msf{SApolcon}  LTEEKIKALT AICEEMEKEG KITKIGPENP YNTPVFAIKK KDSTKWRKL
51 ctsc1               ---------- e--------- ---------- ---------- ---------
52 du422               ---------- ---------- ---------- ----i----- ---------
53 du457               ---------- e--------- ---------- ---------- ---------
54 GG5pol              ---------- ---d------ ---------- ---------- ---------
55 ctsc2               ---------- ---------- ---------- ---------- ---------
56 msfdu174            -s-------- ---------- ---------- ---------- ---------
57 du151}              ---------- ---------- ---------- ----i----- ---------
58 RB27pol             ---------- ---d------ ---------- ---------- ---------
59 du204               ---------- e--------- ---------- ---------- ---------
60 RB18pol             ---------- ---------- ---------- ---------- ---------
61 du156               ---------- ---------- ---------- ----i----- ---------
62 du179               ---------- ---------- ---------- ---------- ---------
63 GG3pol              -----x---- ---d------ ---------- ----i----- ---------
64 RB21pol             ---------- e--k------ ---------- ---------- ---------
65 GG10pol             --------k  e--------- ---------- ----i----- ---------
66 RB28pol             -r----x--- ---------- ---------- ----i----- ---------
67 GG6pol              ---------- ---------- ---------- ---------- ---------
68 RB13pol             ---------- ---------- ---------- ---------- ---------
69 RB15pol             -s-------- e--------- ---------- ---------- ---------
70 GG4pol              ---------- e--------- ---------- -x-------- ---------
71 RB22pol             ---------- ---------- ---------- ---------- ---------
72 du172               -s-------- e--------- ---------- ---------- ---------
73 du115               ---------- ---------- ---------- ---------- ---------
74 RB14po              pavfq-sv-- ---------- ---------- ---------- ---------
75 du368               ---------p -f-d------ ---------- ----i----- ---------v
76-77 du258            ---------- ---------- ---------- ---------- --------v
78 Cpolcon             ---------- ---d------ ---------- ----i----- ---------

51                                                    100
SApolcon              VDFRELNKRT QDFWEVQLGI PHPAGLKKKK SVTVLDVGDA YFSVPLDEGF
ctsc1                 ---------- ---------- ---------- ---------- ------h-d-
du422                 ---------- ---------- ---------- ---------- ----------
du457                 ---------- ---------- ---------- ---------- ----------
GG5pol                ---------- ---------- ---------- ---------- --------n-
ctsc2                 ---------- ---------- ---------- ---------- --------n-
du174                 ---------- ---------- ---------- ---------- --------n-
du151                 ---------- ---------- ---------- ---------- ----------
RB27pol               ---------- ---------- ---------- ---------- ----------
du204                 ---------- ---------- ---------- ---------- ----------
RB18pol               ---------- ---------- ---------- ---------- ----------
du156                 ---------- ---------- ---------- ---------- -------pd-
du179                 ---------- ---------- ---------- ---------- --------d-
GG3pol                ---------- ---------- ---------- ---------- --------n-
RB21pol               ---------- ---------- ---------- ---------- ----------
GG10pol               ---------- ---------- ---------- ---------- ----------
RB28pol               ---------- ---------- ---------- ---------- -------kd-
GG6pol                ---------- ---------- ---------r ---------- --------s-
RB13pol               ---------- ---------- ---------r ---------- --------s-
RB15pol               ---------- ---------- ---------- ---------- --------s-
GG4pol                ---------- ---------- ---------- ---------- --------s-
RB22pol               ---------- ---------- ---------- ---------- ---i--y-x-
du172                 ---------- ---------- ---------- ---------- -------kd-
```

FIG. 6B

```
du115         ---------- ---------- ---------- ---------- --------n-
RB14pol       ---------- ---------- ---------- ---------- ----------
du368         ---------- ---------- ---------- ---------- ----------
du258         ---------- ---------- ---------- ---------- --------s-
Cpolcon       ---------- ---------- ---------- ---------- ------y-d-

101                                                  150
SApolcon      RKYTAFTIPS INNETPGIRY QYNVLPQGWK GSPAIFQSSM TKILEPFRAK
ctsc1         ---------- ---------- ---------- ---------- --------tn
du422         ---------- ---------- ---------- --------rh a---------
du457         ---------- ---------- ---g------ --------rh a---------
GG5pol        ---------- ---------- ---------- ---------- ---------q
ctsc2         ---------- ---------- ---------- ---------- ---------q
du174         ---------- v------l-- ---------- ---------- ---------q
du151         ---------- ---------- ---------- -------a-- ----------
RB27pol       ---------- ---------- ---------- ---------- -r------tq
du204         ---------- ---------- ---------- ---------- --------t-
RB18pol       ---------- ---------- ---------- -------a-- --------tq
du156         ---------- v--------- ---------- ---------- ----------
du179         ---------- ---------- ---------- ---------- ---------q
GG3pol        ---------- --------x- ---------- -------a-- ----------
RB21pol       x--------- ---------- ---------- -------c-- ---------q
GG10pol       ---------- ---------- ---------- ---------- ----------
RB28pol       ---------- v-----v--- ---------- ---------- -r--------
GG6pol        ---------- t--------- ---------- -------a-- -r------t-
RB13pol       ---------- t--------- ---------- -------c-- -r------t-
RB15pol       ---------- t------t-- ---------- ---------- -r------tq
GG4pol        ---------- ---a------ ---------- ---------- --------tq
RB22pol       ---------- f--------f ---------- ---------- ---------q
du172         ---------- ---------- ---gs----- ---s------ ----------
du115         ---------- ---aa--t-- ---------- ---------- i-------kn
RB14pol       ---------- ---------- ---------- -------a-- -r------tq
du368         ---------- ----p----- ---------- --------rh vr--------
du258         ---------- v------n-- -*-------- --------rh a--------q
Cpolcon       ---------- ---------- ---------- ---------- --------dr 151                                                  200
sapep.msf{SApolcon}  NPEIVIYQYM DDLYVGSDLE IGQHRAKIEE LREHLLKWGF TTPDKKHQKE
ctsc1         ---l------ ---------- ---------- ------r--- ----------
du422         ---------- ---------- ---------- --k---r--- ----------
du457         ---------- ---------- ---------- ---------- ----------
GG5pol        --g------- ---------- ---------- ---------- ----------
ctsc2         --g------- ---------- ---------- ------r--- ----------
du174         --g------- ---------- ---------- ---d------ ----------
du151         ---------- ---------- ---------- --g------- ----------
RB27pol       --d------- ---------- --------k- ------r--- ----------
du204         --d------- ---------- ---------- ------r--- ----------
RB18pol       ---------- ---------- -------v-- ------r--- ----------
du156         ---------- ---------- ---------- ------r--- ----------
```

FIG. 6C

```
du179            ---------- ---------- ---------- ---------- ----------
GG3pol           ---------- ---------- ---------- ------r--- ----------
RB21pol          ---------- ---------- ---------- ---------- ----------
GG10pol          ---------- ---------- -r-------- ---------- ----------
RB28pol          ---------- ---------- ---------- --a------- ----------
GG6pol           --d------- ---------- ---------- --------1- ----------
RB13pol          ---------- ---------- ---------- ---------- ----------
RB15pol          ---------- ---------- -k-------- --a------- ----------
GG4pol           --d------- ---------- ---------- ------r--- ----------
RB22pol          ---1------ ---------- ----r--k-- ------r--- ----------
du172            --d--f---- ---------- -m-------d ---------- ----------
du115            --d------- ---------- ---------- --------1- ----------
RB14pol          ---------- ---------- -------v-- ------r--- ----------
du368            ---------- ---------- -------v-- --k-----1- ----------
du258            ---------- ---------- --------k- --d-----1- ----------
Cpolcon          ---1------ ---------- ---------- ---------- ----------

201                                                 250
sapep.msf{SApolcon}  PPFLWMGYEL HPDKWTVQPI QLPEKDSWTV NDIQKLVGKL NWASQIYPGI
ctsc1            ---------- ---------- -----ed--- ---------- ----------
du422            ---------- ---------- ---------- ---------- ----------
du457            ---------- ---------- ---------- ---------- ----------
GG5pol           ---------- ---------- ---d------ ---------- -------a--
ctsc2            ---------- ---------- e--------- ---------- -------s--
du174            ---------- ---------- ---------- ---------- ----------
du151            ---------- ---------- ---------- ---------- ----------
RB27pol          ---------- ---------- ---------- ---------- ----------
du204            ---------- ---------- ---------- ---------- ----------
RB18pol          ---------- ---------- k--------- ---------- ----------
du156            ---------- ---------- ------d--- ---------- ----------
du179            ---------- ---------- n--d------ ---------- ----------
GG3pol           ---------- ---------- ---------- ---------- ----------
RB21pol          ---------- ---------- ---------- ---------- ----------
GG10pol          ---------- ---------- ---------- ---------- ----------
RB28pol          ---------- ---------- ---------- ---------- ----------
GG6pol           ---------- ---------- ---n------ ---------- -------s--
RB13pol          ---------- ---------- ---------- ---------- ----------
RB15pol          ---------- ---------- ---------- ---------- ----------
GG4pol           ---q------ ---------- c--------- ---------- ----------
RB22pol          ---------- ---------- ------e--- ---------- ----------
du172            ---------- ---------- ---------- ---------- ----------
du115            ---------- ---------- ---d------ ---------- ----------
RB14pol          ---------- ---------- ---------- ---------- ----------
du368            ---------- ---------- ---------- ---------- ----------
du258            ---------- ---------- ---------x- ---------- ----------
Cpolcon          ---------- ---------- ---------- ---------- ----------
```

FIG. 6D

```
           251                             278
SApolcon)  KVRQLCKLLR GAKALTDIVP LTEEAELE
ctsc1      ---------- -t-------- --------
du422      --k------- ---------- --------
du457      ---------- ---------- --------
GG5pol     ---------- -------vi- --------
ctsc2      --------i- ---------- --------
du174      --k------- --------i- --------
du151      ---------- ---------- --------
RB27pol    ---------- --------i- --------
du204      ---------- ---------- --------
RB18pol    --k------- --------i- --------
du156      ---------- ---------- --------
du179      q--------- ---------- --------
GG3pol     -------r-- ---------- --------
RB21pol    ---------- -t-------- --------
GG10pol    --k-m----- -------vi- --------
RB28pol    ---------- ---------- --------
GG6pol     ---------- -t-------- --------
RB13pol    ---------- -t-----v-- --------
RB15pol    ---h------ -t-------- --------
GG4pol     ---h------ ---------- --------
RB22pol    --krm----- -------v-- --------
du172      ----m----- ---------- --------
du115      --kh--r--- ---------- --------
RB14pol    --k------- --------i- --------
du368      ---------- ---------a ------r-
du258      ---------- ---------- ----p---
Cpolcon    ---------- ---------- --------
```

FIGURE 7A

```
SEQ ID
NO:
                    1                                                      50
 79   SAenvcon    YCAPAGYAIL KCNNKTFNGT GPCNNVSTVQ CTHGIKPVVS TQLLLNGSLA
 80   GG5env     ------f--- --kd------ ---------- ---------- ----------
 81   du174env   ------f--- ---d------ ---------- ---------- ----------
 82   RB13env    ---------- ---------- ---------- ---------- --f-------
 83   du368env   ---------- ---------- ---h------ ---------- ----------
 84   du422env   ---------- ---------- ---------- w--------- ----------
 85   RB14env    ---------- ---------- ---h------ ---------- ----------
 86   RB18env    ---------- ---------- ---y------ ---------- ----------
 87   RB21env    ---------- ---------- ---------- ---------- ----------
 88   GG6env     ---------- ---------- ---------- ---------- ----------
 89   du123env   ---------- ---------- ---h------ ---------- ----------
 90   du172env   ---------- ---------- ---------- ---------- ----------
 91   du457env   ---------- ---------- ---h------ ---------- ----------
 92   du151env   ---------- ---------- ---------- ---------- ----------
 93   du467env   ---------- ---------- ---------- ---------- ----------
 94   du179env   ---------- ---------- ---q------ ---------- --------i-
 95   du204env   ---------- ---------- ---------- ---------- ----------
 96   RB22env    ---------- -------d-- ---------- ---------- ----------
 97   du258env   ---------- ----n----k ---t------ ---------- ----------
 98   du281env   ---------- ----e----- ---------- ---------- ----------
99-100 RB12env   ---------- ---d-k---- ---y------ ---------- ----------
101   GG10env    ---------- ----e----- ---------l ---------- ----------
102   du115env   ---------- ---------- s--------- ---------- ----------
103   du156env   ---------- --td-k---- -s-------- ---------- ----------
104   GG4env     ---------- --k-e----- ---------- ---------- ----------
105   RB28env    ---------- ---------- ---------- ---------- ----------
106,107,108 GG3env ------f--- ----q----- ---t------ ---------- ----------
109   RB27env    ---------- q--------- ---------- -----x---- ----------
110   Cenvcon    ---------- ---------- ---h------ ---------- ----------

51                                                    100
    Saenvcon    EEEIIIRSEN LTNNAKTIIV HLNESVEIVC TRPNNNTRKS IRIGPGQTFY
    GG5env      kg----s-q- --d------- -----i--t- i--------q- ----------
    du174env    -gg-----k- --d-s----- ----ti---- ---g-----q- -------a-f
    RB13env     --------k- --d--r---- ---------- ---------q- -------a-f
    du368env    -gkv----k- ----v----- ---k--n--- i---------g ----------
    du422env    -----v---- ---si----- ---k----k- ---------- v---------
    RB14en      -rd------- --d------- ---------- ---------p- -------a--
    RB18env     -rd------- --d------- ---------- ---------q- -------a--
    RB21env     ---------- ----v----- ---------- ---g------ v---------
    GG6env      ---------- ----v----- -f-------- ---g------ ----------
    du123env    ---------- ---------- -----i---- i--------- ----------
    du172env    ---vv--f-- -----i---- ---------n- ---s------ v--------f
    du457env    --d------- ---------- q--k------ ---------- ----------
    du151env    ---------- ----i----- ---k------ ---------- ----------
    du467env    -gk------- ---------- ---t--a--- ---------- ----------
    du179env    -g-------- ----v----- -----ig--- ---g------ -------a--
    du204env    --g------- ---------- q-----p--- i--------q- -------a-f
    RB22env     ---------- ----v-i--- ---q--p-e- ---g------ v---------
    du258env    -k--v----- ---------- q-enpi---- ---g------ v---------
    du281env    --g---k--- m-d-i----- ---kl-k-e- ---s------ -------a-f
    RB12env     ------k--d ----v----- -----ip--- i--g------ ----------
    GG10env     k.-t------ ------i--- -----q--- --------e- v---------
    du115env    --k------- --d-t----i --t-----l- i--g------ -------i--
    du156env    ------k--- --d-i----- q--q-ig-n- ---------- v---------
    GG4env      -k-------- m-d-g----- ------r-e- i--------- v---------
```

FIG. 7B

```
RB28env     -g-------- ----i----- ------t-n- --------r- ----------
GG3env      -g----x--- --d-t----- ----p-a-n- ---g------ v---------
RB27env     -k-------- i---v----- ------q-t- ---h------ m---------
Cenvcon     ---------- ----v----- ---------- ---------- ----------

101                                                 150
SAenvcon    ATGDIIGDIR QAHCNISEGK WNKTLQKVKK KLKEELYKYK VVEIKPLGIA
GG5env      --k------- ----t----- --------ig ---------- ----------
du174env    --ke------ ---------q --------ae ----k----- ----------
RB13env     --kg------ --y----k-- --e------i --g------- ----------
du368env    --na------ -------qa- --ta-kn--r --g-k----- ---------v-
du422env    ---a------ e------ret --s--kq--g --g------- ---------v-
RB14env     --h------- e--------n -t----r-g- t-e---f--- ----------
RB18env     --h----n-- e--------n -t----r-g- t-e------- ----------
RB21env     ---------- -------sd- --q---q-g- --a------- ---v----v-
GG6env      ---e------ -------gan -t--m-r-s- ---------- --------l-
du123env    --n------- -------kt- --t--e---e ---d------ ---------v-
du172env    ---------- -------re- --t---r--e ---------- ----------
du457env    --na------ --y----gad -----es--- --g------- ---------v-
du151env    --da---n-- e------ksn -ts--eq--- ---------- ----------
du467env    --n----n-- --------eq -st-vaq--e --ra------ ---------v-
du179env    .-nh------ --y----kqe -----ee-r- --q------- ----------
du204env    --k------- --y----..- --t--e---e r--------- --------v-
RB22env     ---------- --y--vt-er --i----ia- --lg------ ----------
du258env    ---------- ----t---e- --t-----ge --ik------ ----------
du281env    --na------ -------rdh -----e-i-g -f-------- ---------v-
RB12env     -nn------- -------kcn -kl--v---* --hy------ ---------v-
GG10env     --------l- --p-s--in- ------e-s- --qk------ -i--------
du115env    ---g------ --y---n-ys -----kr-se -fr------- ---vr-----
du156env    ---------- -------rnq --e--eq--- --g------- ---------v-
GG4env      ---qv----- --------rd --t---r-s- ---------- ----q---v-
RB28env     .-n------- -------rte --n--er-r- --e----l-t --------e--
GG3env      --dv-g-v-- a-r-dv-rxn --*-xeg--* --l------- ---v------
RB27env     ---v---i-q ppc-i-n-rx -wt-flh-gg e-l------- --------vv
Cenvcon     ---------- -------kd- --------s- --a------- ---------v-

151                                                 200
SAenvcon    PTEAKRRVVE REKRAVGIGA VFLGFLGAAG STMGAASITL TVQARQLLSG
GG5env      --g-n----- ---------- m--------- ---------- ----------
du174env    --gt-w---- ------tl-- -------m-- ---------- ----------
RB13env     --t------- ------.--- m------v-- -------l-- ------v---
du368env    --k------k ---------- -l-------- ---------- ----------
du422env    --ks--k--g -------l-- -l-------- ---------- ----------
RB14env     ---------- ---------- ---------- ---------- ----------
RB18env     ---------- ---------- ---------- ---------- ----------
RB21env     --a------- ---------- ---------- ---------- ----------
GG6env      ---------- ---------- ---------- ---------- ----------
du123env    --k------- ---------- -lf------- ---------- ----------
du172env    -dk------- ---------- ---------- -------m-- ----------
du457env    --k------- ---------- ---------- ---------- ----------
du151env    ---t------ ---------- --------e- -------l-- ----------
du467env    ---s------ ---------- -l-------- -------v-- ----------
du179env    ---------- ---------- -l-------- ---------- ----------
du204env    --k------- ---------- ---------- ---------- p---------
RB22env     ---------- ---------- ------a--- ---------- ----------
du258env    --t------- ---------- ---------- ---------- ----------
du281env    ---------- ---------- -l-------- ---------- ----------
RB12env     ---------- ------m--- ---------- ---------- ----------
GG10env     --t------- ---------- m--------- ---------- ----------
```

FIG. 7C

```
du115env      --r-------  -------a--  -if---a---  -------l--  ----------
du156env      --g---m--k  -------l--  -lf-------  ----------  -a--------
GG4env        --r-------  ----------  al--------  -------ma-  ----------
RB28env       -ik-------  --i-------  -l--------  ----------  ----------
GG3env        --ks------  -------m--  -if-------  -------va-  ----------
RB27env       ----------  ----------  ----------  ----------  ----------
Cenvcon       --k-------  ----------  ----------  ----------  ----------

201                              229
SAenvcon      IVQQQSNLLR  AIEAQQHMLQ  LTVWGIKQL
GG5env        ----------  ----------  ---------
du174env      ----------  ----------  ---------
RB13env       ---------k  ----------  ---------
du368env      ----------  -------l--  ---------
du422env      ----------  -------l--  ---------
RB14env       ----------  ----------  ---------
RB18env       ----------  ----------  ---------
RB21env       ----------  ---v------  ---------
GG6env        ----------  ----------  ---------
du123env      ----------  ----------  ---------
du172env      ----------  ----------  ---------
du457env      ----------  ----------  ---------
du151env      ----------  ----------  --g------
du467env      ----------  ----------  ---------
du179env      ----------  ----------  ---------
du204env      ----------  -------l--  ---------
RB22env       -----n----  ----------  ---------
du258env      ----------  ----------  ---------
du281env      ----------  ----------  ---------
RB12env       ----------  ----------  ---------
GG10env       -----n----  ----------  ---------
du115env      ----------  ----------  ---------
du156env      ----------  ----------  ---------
GG4env        ----------  ----p-----  -x-s-----
RB28env       v------e--  --q-----m-  -----v---
GG3env        -----n----  ----------  ---------
RB27env       ---------k  -------l--  ---------
Cenvcon       ----------  ----------  ---------
```

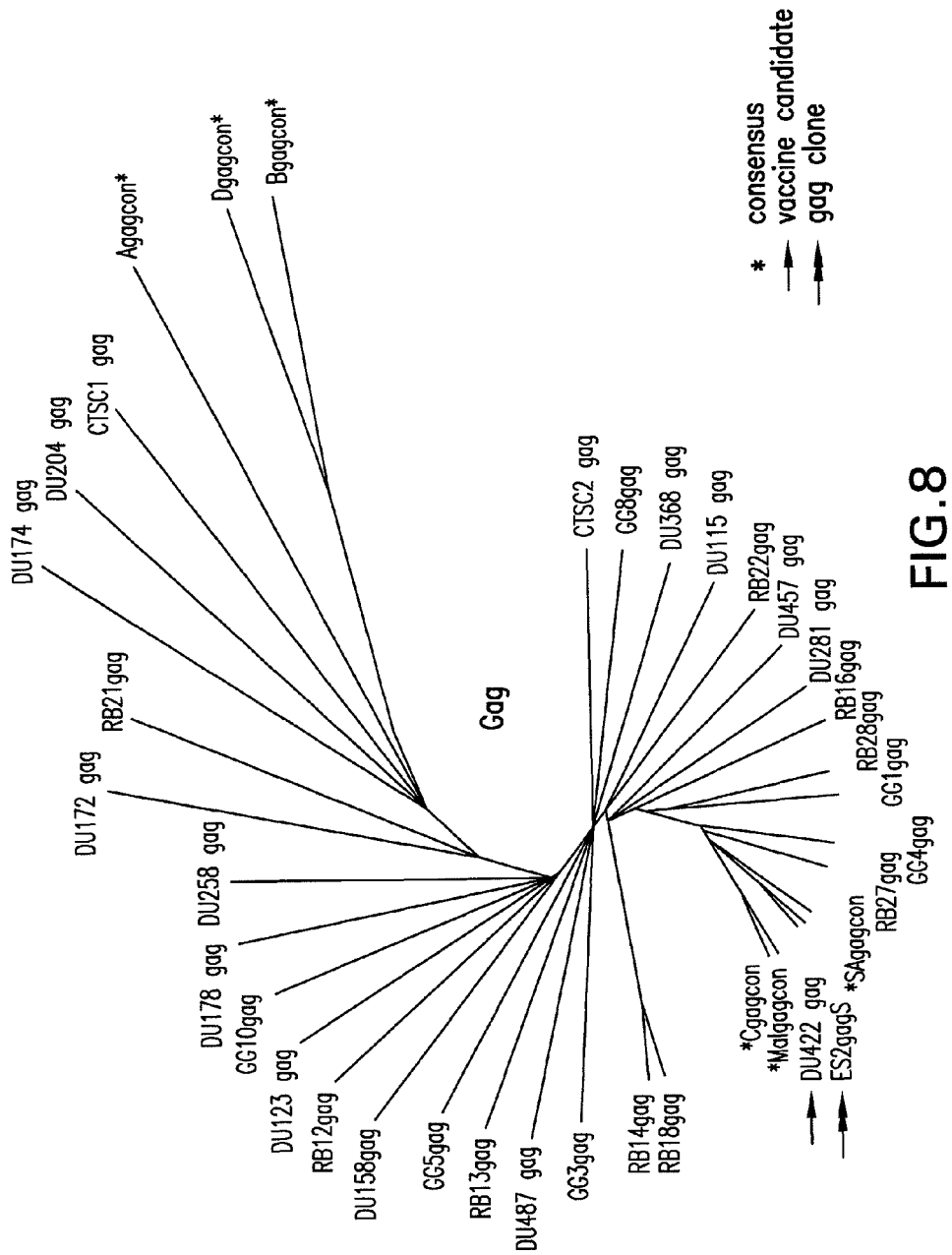

GAG Fasta analysis
5/10/00

|       | DU115 | DU123 | DU156 | DU172 | DU174 | DU179 | DU204 | DU258 |
|-------|-------|-------|-------|-------|-------|-------|-------|-------|
| DU115 |       | 88.9  | 92.2  | 89.1  | 88.6  | 90.9  | 88.9  | 92.5  |
| DU123 | 88.9  |       | 90.2  | 87.1  | 85.4  | 88.9  | 88.6  | 89.9  |
| DU156 | 92.2  | 90.2  |       | 89.1  | 89.6  | 92.5  | 89.3  | 91.9  |
| DU172 | 89.0  | 87.1  | 89.1  |       | 88.1  | 89.1  | 88.4  | 90.7  |
| DU174 | 88.6  | 85.4  | 89.6  | 88.1  |       | 90.0  | 88.7  | 90.3  |
| DU179 | 90.9  | 88.9  | 92.5  | 89.1  | 90.0  |       | 89.3  | 92.2  |
| DU204 | 88.9  | 88.6  | 89.3  | 88.4  | 88.7  | 89.3  |       | 90.6  |
| DU258 | 92.5  | 89.6  | 91.9  | 90.7  | 90.3  | 92.2  | 90.6  |       |
| DU281 | 92.8  | 90.6  | 92.2  | 90.7  | 88.7  | 90.9  | 89.9  | 90.9  |
| DU368 | 92.2  | 91.2  | 91.2  | 89.7  | 88.3  | 91.2  | 88.9  | 89.9  |
| DU422 | 95.1  | 91.2  | 84.8  | 90.4  | 91.3  | 92.2  | 90.6  | 92.9  |
| DU457 | 92.8  | 90.2  | 91.9  | 90.4  | 90.3  | 90.6  | 88.9  | 91.2  |
| DU467 | 91.2  | 89.6  | 90.6  | 88.4  | 89.0  | 91.2  | 87.9  | 90.9  |
| AVE   | 91.3  | 89.3  | 91.3  | 89.3  | 89.0  | 90.8  | 89.2  | 91.2  |

|       | DU281 | DU368 | DU422 | Gag clone | DU457 | DU467 | SAgag con |
|-------|-------|-------|-------|-----------|-------|-------|-----------|
| DU115 | 92.8  | 92.2  | 95.1  | 94.8      | 92.8  | 91.2  | 95.4      |
| DU123 | 90.6  | 91.2  | 91.2  | 91.2      | 90.2  | 89.6  | 92.5      |
| DU156 | 92.2  | 91.2  | 94.8  | 94.8      | 96.9  | 90.6  | 96.1      |
| DU172 | 90.7  | 89.7  | 90.4  | 90.4      | 90.4  | 88.4  | 92.0      |
| DU174 | 88.7  | 88.3  | 91.3  | 90.6      | 90.3  | 89.0  | 91.6      |
| DU179 | 90.9  | 92.1  | 92.2  | 92.2      | 90.6  | 91.2  | 93.5      |
| DU204 | 89.9  | 88.9  | 90.6  | 90.6      | 88.9  | 87.9  | 91.2      |
| DU258 | 90.9  | 89.9  | 92.9  | 92.9      | 91.2  | 90.9  | 94.2      |
| DU281 |       | 94.8  | 96.4  | 96.4      | 94.5  | 93.8  | 95.8      |
| DU368 | 94.8  |       | 96.1  | 95.8      | 94.8  | 94.1  | 95.1      |
| DU422 | 96.4  | 96.1  |       |           | 96.1  | 95.1  | 98.0      |
| DU457 | 94.5  | 94.8  | 96.1  | 95.8      |       | 95.1  | 95.8      |
| DU467 | 93.8  | 94.1  | 95.1  | 94.5      | 95.1  |       | 93.8      |
| AVE   | 92.2  | 91.9  | 93.5  | 93.3      | 92.7  | 91.4  | 94.2      |

FIGURE 11 lbp/POL fasta analysis
5/10/00

| | DU 115 | DU 151 | pol clone | DU 156 | DU 172 | DU 174 | DU 179 | DU 204 | DU 258 | DU 281 | DU 368 | DU 422 | DU 467 | Sa polcon |
|---|---|---|---|---|---|---|---|---|---|---|---|---|---|---|
| DU115 | | 94.2 | 93.1 | 93.5 | 92.1 | 94.6 | 94.5 | 94.9 | 92.4 | 95.3 | 91.7 | 93.9 | 93.9 | 93.5 |
| DU151 | 94.2 | | | 97.5 | 94.6 | 96.0 | 97.5 | 97.5 | 94.2 | 98.4 | 94.9 | 97.5 | 97.1 | 98.9 |
| DU156 | 93.5 | 97.5 | 96.4 | | 94.6 | 95.7 | 97.1 | 97.1 | 93.9 | 97.7 | 93.5 | 98.8 | 96.0 | 97.8 |
| DU172 | 92.1 | 94.6 | 93.5 | 94.6 | | 93.9 | 94.2 | 95.7 | 91.4 | 94.5 | 90.6 | 93.1 | 95.3 | 95.7 |
| DU174 | 94.6 | 96.0 | 94.6 | 95.7 | 93.9 | | 95.7 | 95.7 | 94.6 | 95.3 | 92.1 | 95.3 | 94.9 | 98.8 |
| DU179 | 94.6 | 97.5 | 96.4 | 97.1 | 94.2 | 95.7 | | 96.4 | 93.9 | 99.2 | 93.5 | 96.0 | 96.0 | 97.8 |
| DU204 | 94.9 | 97.5 | 96.4 | 97.1 | 95.7 | 95.7 | 96.4 | | 93.5 | 98.9 | 93.5 | 96.8 | 97.5 | 98.6 |
| DU258 | 92.4 | 94.2 | 92.8 | 93.9 | 91.4 | 94.8 | 93.9 | 93.6 | | 94.6 | 92.8 | 95.0 | 95.3 | 95.0 |
| DU281 | 95.3 | 98.4 | 96.9 | 97.7 | 94.5 | 95.3 | 99.2 | 96.8 | 94.6 | | 95.3 | 98.4 | 96.1 | 97.7 |
| DU368 | 91.7 | 94.9 | 93.5 | 93.5 | 90.6 | 92.1 | 93.5 | 93.5 | 92.8 | 95.3 | | 95.7 | 94.9 | 94.9 |
| DU422 | 93.9 | 97.5 | 96.0 | 96.8 | 93.1 | 95.3 | 96.0 | 96.8 | 95.0 | 98.4 | 95.7 | | 97.8 | 97.5 |
| DU457 | 93.9 | 97.1 | 96.0 | 96.0 | 95.3 | 94.9 | 96.0 | 97.5 | 95.3 | 96.1 | 94.9 | 97.8 | | 98.2 |
| AVE | 93.7 | 96.3 | 95.1 | 95.8 | 93.6 | 94.9 | 95.8 | 96.0 | 93.8 | 96.5 | 93.5 | 98.0 | 95.9 | 96.9 |

FIG. 12 lbp/Env fasta analysis
5/10/00

| | DU 115 | DU 123 | DU 151 | env clone | DU 156 | DU 172 | DU 174 | DU 179 | DU 204 | DU 258 | DU 281 | DU 368 | DU 422 | DU 457 | DU 467 | Sa envcon |
|---|---|---|---|---|---|---|---|---|---|---|---|---|---|---|---|---|
| DU115 | | 85.6 | 83.4 | 83.1 | 81.2 | 84.3 | 82.5 | 84.7 | 83.8 | 83.0 | 83.4 | 82.1 | 82.1 | 85.2 | 83.8 | 87.3 |
| DU123 | 85.8 | | 89.5 | 90.8 | 87.8 | 90.4 | 85.6 | 90.4 | 92.1 | 89.5 | 88.2 | 90.4 | 87.8 | 92.6 | 90.8 | 93.9 |
| DU151 | 83.4 | 89.5 | | | 85.2 | 87.8 | 84.3 | 88.2 | 87.3 | 85.2 | 87.3 | 88.0 | 89.1 | 90.8 | 89.5 | 92.8 |
| DU156 | 81.2 | 87.8 | 85.2 | 87.3 | | 85.2 | 82.5 | 85.2 | 84.3 | 83.8 | 85.6 | 83.8 | 87.8 | 87.3 | 85.2 | 87.8 |
| DU172 | 84.3 | 90.4 | 87.8 | 87.3 | 85.2 | | 84.7 | 86.0 | 89.1 | 89.5 | 85.2 | 88.0 | 87.3 | 88.6 | 87.8 | 93.0 |
| DU174 | 82.5 | 85.6 | 84.3 | 84.3 | 82.5 | 84.7 | | 86.0 | 86.5 | 84.7 | 87.3 | 83.0 | 81.7 | 84.7 | 84.3 | 89.1 |
| DU179 | 84.7 | 90.4 | 88.2 | 91.3 | 85.2 | 86.0 | 86.0 | | 87.8 | 88.5 | 87.8 | 86.9 | 84.7 | 90.4 | 87.8 | 91.3 |
| DU204 | 83.8 | 92.1 | 87.3 | 87.8 | 84.3 | 89.1 | 86.5 | 87.6 | | 86.5 | 87.3 | 87.8 | 85.8 | 91.3 | 86.9 | 91.7 |
| DU258 | 83.0 | 89.5 | 85.2 | 84.7 | 83.6 | 89.5 | 86.5 | 86.5 | 88.5 | | 83.4 | 83.8 | 84.3 | 87.8 | 86.5 | 91.3 |
| DU281 | 83.4 | 88.2 | 87.3 | 87.3 | 85.6 | 88.6 | 84.7 | 87.3 | 87.6 | 88.4 | | 85.6 | 86.5 | 89.1 | 88.2 | 89.5 |
| DU368 | 82.1 | 90.4 | 86.0 | 86.0 | 83.8 | 86.0 | 85.2 | 86.8 | 87.8 | 83.6 | 85.6 | | 87.8 | 90.8 | 87.3 | 88.6 |
| DU422 | 82.1 | 87.8 | 89.1 | 91.7 | 87.8 | 87.3 | 81.7 | 84.7 | 85.6 | 84.3 | 86.5 | 87.8 | | 89.1 | 89.5 | 89.1 |
| DU457 | 85.2 | 92.6 | 90.8 | 90.8 | 87.3 | 88.6 | 84.7 | 90.4 | 91.3 | 87.8 | 89.1 | 90.8 | 89.1 | | | 93.4 |
| DU467 | 83.8 | 90.8 | 89.5 | 90.0 | 85.2 | 87.8 | 84.3 | 87.8 | 87.8 | 86.9 | 86.5 | 88.2 | 87.3 | 89.5 | | 91.3 |
| AVE | 83.5 | 89.3 | 87.2 | 87.9 | 85.0 | 87.2 | 84.3 | 87.1 | 87.5 | 85.8 | 86.3 | 86.3 | 86.2 | 89.0 | 87.3 | 90.7 |

FIG. 13

```
ATGGGTGCGAGAGCGTCAATATTAAGAGGGGAAAAATTAGATAAATGGGAAAAAATTAG
GTTAAGGCCAGGGGGAAAGAAACATTATATGTTAAAACACATAGTATGGGCAAGCAGGG
AGCTGGAAAGATTTGCACTTAACCCTGGCCTTTTAGAAACATCAGAAGGATGTAAACAA
ATAATGAAACAGCTACAACCAGCTCTCCAGACAGGAACAGAGGAACTTAAATCATTATA
CAACACAGTAGCAACTCTCTATTGTGTACATGAAAAGATAGAAGTACGAGACACCAAGG
AAGCCTTAGATAAGATAGAGGAAGAACAAAACAAATGTCAGCAAAAAACGCAGCAGGCA
AAAGCGGCTGACGGGAAAGTCAGTCAAAATTATCCTATAGTGCAGAATCTCCAAGGGCA
AATGGTACATCAAGCCATATCACCTAGAACCTTGAATGCATGGGTAAAAGTAATAGAAG
AAAAGGCTTTTAGCCCAGAGGTAATACCCATGTTTACAGCATTATCAGAAGGAGCCACC
CCACAAGATTTAAACACCATGTTAAATACAGTGGGGGGACATCAAGCAGCCATGCAAAT
GTTAAAAGATACTATTAATGAAGAGGCTGCAGAATGGGATAGAGTACATCCAGTCCATG
CGGGGCCTATTGCACCAGGCCAGATGAGAGAACCAAGGGGAAGTGACATAGCAGGAACT
ACTAGTACCCTTCAGGAACAAATAGCATGGATGACAAGTAACCCACCTATTCCAGTGGG
AGACATCTATAAAAGATGGATAATTCTGGGGTTAAATAAAATAGTGAGAATGTATAGCC
CGGTCAGCATTTTGGACATAAGACAAGGGCCAAAGGAACCCTTTCGAGACTATGTAGAT
CGGTTCTTTAAAACTTTAAGAGCTGAACAAGCTACACAAGAAGTAAAAAATTGGATGAC
AGACACCTTGTTAGTCCAAAATGCGAACCCAGATTGTAAGACCATTTTGAGAGCATTAG
GACCAGGGGCTACATTAGAAGAAATGATGACAGCATGTCAAGGGGTGGGAGGACCTGGT
CACAAAGCAAGAGTATTGGCTGAGGCAATGAGTCAAGCAAACAGTGGAAACATAATGAT
GCAGAGAAGCAATTTTAAAGGCCCTAGAAGAATTGTTAAATGTTTTAACTGTGGCAAGG
AAGGGCACATAGCCAGAAATTGCAGAGCCCCTAGGAAAAAAGGCTGTTGGAAATGTGGA
AAGGAAGGACACCAAATGAAAGACTGTACTGAAAGGCAGGCTAATTTTTTAGGGAAAAT
TTGGCCTTCCCACAAGGGGAGGCCAGGGAATTTCCTTCAGAACAGACCAGAGCCAACAG
CCCCACCAGCAGAGAGCTTCAGGTTCGAAGAGACAACCCCCGCTCCGAAACAGGAGCCG
ATAGAAAGGGAACCCTTAACTTCCCTCAAATCACTCTTTGGCAGCGACCCCTTGTCTCA
ATAA
```

FIGURE 17

```
  1  MGARASILRG  EKLDKWEKIR  LRPGGKKHYM  LKHIVWASRE  LERFALNPGL  LETSEGCKQI
 61  MKQLQPALQT  GTEELKSLYN  TVATLYCVHE  KIEVRDTKEA  LDKIEEEQNK  CQQKTQQAKA
121  ADGKVSQNYP  IVQNLQGQMV  HQAISPRTLN  AWVKVIEEKA  FSPEVIPMFT  ALSEGATPQD
181  LNTMLNTVGG  HQAAMQMLKD  TINEEAAEWD  RVHPVHAGPI  APGQMREPRG  SDIAGTTSTL
241  QEQIAWMTSN  PPIPVGDIYK  RWIILGLNKI  VRMYSPVSIL  DIRQGPKEPF  RDYVDRFFKT
301  LRAEQATQEV  KNWMTDTLLV  QNANPDCKTI  LRALGPGATL  EEMMTACQGV  GGPGHKARVL
361  AEAMSQANSG  NIMMQRSNFK  GPRRIVKCFN  CGKEGHIARN  CRAPRKKGCW  KCGKEGHQMK
421  DCTERQANFL  GKIWPSHKGR  PGNFLQNRPE  PTAPPAESFR  FEETTPAPKQ  EPIEREPLTS
481  LKSLFGSDPL  SQ
```

FIGURE 18

```
TTTAGGGAAAATTTGGCCTTCCCACAAGGGGAGGCCAGGGAATTTCCTTCAGAACAGAC
CAGAGCCAACAGCCCCACCAGCAGAGAGCTTCAGGTTCGAAGAAACAACCCCCGCTCCG
AAACAGGAGCCGAGAGAAAGGGAACCCTTAACTTCCCTCAAATCACTCTTTGGCAGCGA
CCCCTTGTCTCAATAAAAATAGGGGGCCAGACAAGGGAGGCTCTCTTAGACACAGGAGC
AGATGATACAGTATTAGAAGACATAAATTTGCCAGGAAAATGGAAACCAAAAATGATAG
GAGGAATTGGAGGTTTTATCAAAGTAAGACAGTATGATCAAATACTTATAGAAATTTGT
GGAAAAAAGGCTATAGGTACAGTATTAGTAGGGCCTACACCTGTCAACATAATTGGCAG
AAACATGTTGACTCAGCTTGGATGCACACTAAACTTTCCAATCAGTCCCATTGAAACTG
TACCAGTAAAACTGAAGCCAGGAATGGATGGCCCAAAGGTTAAACAATGGCCGTTAACA
GAAGAGAAAATAAAAGCATTAACAGCAATTTGTGAAGAAATGGAAAAGGAAGGAAAAAT
TACAAAAATTGGGCCTGAAAATCCATATAACACTCCAATATTTGCCATAAAAAAGAAAG
ACAGCACTAAGTGGAGAAAATTAGTAGATTTCAGGGAACTCAATAAAAGAACTCAAGAC
TTTTGGGAGGTTCAATTAGGAATACCACACCCAGCAGGGTTAAAAAAGAAAAAATCAGT
GACAGTACTGGATGTGGGAGATGCATATTTTTCAGTTCCTTTAGATGAAGGCTTCAGGA
AATATACTGCATTCACCATACCTAGTATAAACAATGAAACACCAGGGATTAGATATCAA
TATAATGTGCTTCCACAAGGATGGAAAGGGTCACCAGCAATATTCCAGGGTAGCATGAC
AAAAATCTTAGAGCCCTTTAGAGCTCAAAATCCAGAAATAGTCATCTATCAATATATGG
ATGACTTGTATGTAGGATCTGACTTAGAAATAGGGCAACATAGAGCAAAAATAGAAGAG
TTAAGAGAACATCTATTAAAGTGGGGATTTACCACACCAGACAAAAAACATCAGAAAGA
ACCCCCATTTCTTTGGATGGGGTATGAACTCCATCCTGACAAATGGACAGTACAGCCTA
TACAGCTGCCAGAAAAGGATAGCTGGACTGTCAATGATATACAGAAGTTAGTGGGAAAA
TTAAACTGGGCAAGTCAGATTTACCCAGGGATTAAAGTAAGGCAACTTTGTAAGCTCCT
TAGGGGGACCAAAGCACTAACAGACATAGTACCACTAACTGAAGAAGCAGAATTAGAAT
TGGCAGAGAACAGGGAAATTCTAAAAGAACCAGTGCATGGAGTATATTATGACCCATCA
AAAGACTTGATAGCTGAAATACAGAAACAGGGGGATGACCAATGGACATATCAAATTTA
CCAAGAACCATTCAAAAACCTGAAGACAGGAAAGTATGCAAAAAGGAGGACTACCCACA
CTAATGATGTAAAACAGTTAACAGAGGCAGTGCAAAAAATATCCTTGGAAAGCATAGTA
ATATGGGGAAAGACTCCTAAATTTAGACTACCCATCCAAAAAGAAACATGGGAAATATG
GTGGACAGACTATTGGCAAGCCACATGGATTCCTGAGTGGGAGTTTGTTAATACCCCTC
CCCTAGTAAAACTATGGTACCAGCTAGAAAAAGAACCCATAGCAGGAGCAGAAACTTTC
TATGTAGATGGAGCAGCTAATAGGGAAACTAAAATAGGAAAAGCGGGGTATGTTACTGA
CAGAGGAAGGCAGAAAATTGTAACTCTAAGTGAAACAACAAATCAGAAGACTGAATTAC
AAGCAATTCAGCTAGCTTTGCAAGATTCAGAATCAGAAGTAAACATAATAACAGACTCA
CAGTACGCATTAGGAATCATTCAAGCACAACCAGATAGGAGTGAATCAGAGTTGGTCAA
TCAAATAATAGAACAATTAATAAAAAAGGAAAGGGTCTATCTGTCATGGGTACCAGCAC
ACAACGGACTTGCAGGAAATGAACATGTAGATAAATTAGTAAGTAGGGAATCAGGAAA
GTGCTGGTTCTAGATGGAATAGATAAGGCTCATGAAGAGCATGAAAAGTATCACAGCAA
TTGGAGAGCAATGGCTAGTGAGTTTAATCTGCCACCCGTAGTAGCAAGAGAAATAGTAG
CCAGCTGTGATAAATGTCAGCTAAAAGGGGAAGCCATACATGGACAAGTAGATTGTAGT
CCGGGGATATGGCAATTAGATTGTACACATTTAGAAGGAAAAATCATCCTGGTAGCAGT
CCATGTAGCCAGTGGCTACATAGAAGCAGAGGTTATCCCAGCAGAAACAGGACAAGAAA
```

FIGURE 19A

```
CAGCATACTATATACTAAAATTAGCAGGAAGATGGCCAGTCAAAGTAATACATACAGAC
AATGGCAGTAATTTCACCAGTGCTGCAGTTAAGGCAGCCTGTTGGTGGGCAGGTATCCA
ACAGGAATTTGGGATTCCCTACAATCCCCAAAGTCAGGGAGTAGTAGAATCCATGAATA
AAGAATTAAAGAAAATCATAGGGCAGGTAAGAGATCAAGCTGAGCACCTTAAGACAGCA
GTACAAATGGCAGTATTCATTCACAATTTTAAAAGAAAAGGGGGGATTGGGGGGTACAG
TGCAGGGGAAAGAATAATAGACATAATAGCAACAGACATACAAACTAAAGAATTACAAA
AACAAATTATAAAAATTCAAAATTTTCGGGTTTATTACAGAGACAGCAGAGATCCTATT
TGGAAAGGACCAGCCAAGCTACTCTGGAAAGGTGAAGGGGCAGTAGTAATACAAGACAA
CAGTGACATAAAGGTAGTACCAAGGAGGAAAGTAAAAATCATTAGGGACTATGGAAAAC
AGATGGCAGGTGCTGATTGTGTGGCAGGTAGACAGGATGAAGATTAG
```

FIGURE 19B

```
  1  FRENLAFPQG EAREFPSEQT RANSPTSREL QVRRNNPRSE TGAERKGTLN FPQITLWQRP
 61  LVSIKIGGQT REALLDTGAD DTVLEDINLP GKWKPKMIGG IGGFIKVRQY DQILIEICGK
121  KAIGTVLVGP TPVNIIGRNM LTQLGCTLNF PISPIETVPV KLKPGMDGPK VKQWPLTEEK
181  IKALTAICEE MEKEGKITKI GPENPYNTPI FAIKKKDSTK WRKLVDFREL NKRTQDFWEV
241  QLGIPHPAGL KKKKSVTVLD VGDAYFSVPL DEGFRKYTAF TIPSINNETP GIRYQYNVLP
301  QGWKGSPAIF QGSMTKILEP FRAQNPEIVI YQYMDDLYVG SDLEIGQHRA KIEELREHLL
361  KWGFTTPDKK HQKEPPFLWM GYELHPDKWT VQPIQLPEKD SWTVNDIQKL VGKLNWASQI
421  YPGIKVRQLC KLLRGTKALT DIVPLTEEAE LELAENREIL KEPVHGVYYD PSKDLIAEIQ
481  KQGDDQWTYQ IYQEPFKNLK TGKYAKRRTT HTNDVKQLTE AVQKISLESI VIWGKTPKFR
541  LPIQKETWEI WWTDYWQATW IPEWEFVNTP PLVKLWYQLE KEPIAGAETF YVDGAANRET
601  KIGKAGYVTD RGRQKIVTLS ETTNQKTELQ AIQLALQDSE SEVNIITDSQ YALGIIQAQP
661  DRSESELVNQ IIEQLIKKER VYLSWVPAHN GLAGNEHVDK LVSRGIRKVL VLDGIDKAHE
721  EHEKYHSNWR AMASEFNLPP VVAREIVASC DKCQLKGEAI HGQVDCSPGI WQLDCTHLEG
781  KIILVAVHVA SGYIEAEVIP AETGQETAYY ILKLAGRWPV KVIHTDNGSN FTSAAVKAAC
841  WWAGIQQEFG IPYNPQSGQV VESMNKELKK IIGQVRDQAE HLKTAVQMAV FIHNFKRKGG
901  IGGYSAGERI IDIIATDIQT KELQKQIIKI QNFRVYYRDS RDPIWKGPAK LLWKGEGAVV
961  IQDNSDIKVV PRRKVKIIRD YGKQMAGADC VAGRQDED
```

FIGURE 20

```
ATGAGAGTGATGGGGATACAGAGGAATTGGCCACAATGGTGGATATGGGGCACCTTAGG
CTTTTGGATGATAATAATTTGTAGGGTGGTGGGGAACTTGAACTTGTGGGTCACAGTCT
ATTATGGGGTACCTGTGTGGAAAGAAGCAAAAACTACTCTATTCTGTGCATCAGATGCT
AAAGCATATGATAAAGAAGTACATAATGTCTGGGCTACACATGCCTGTGTACCCACAGA
CCCCAACCCACGAGAAATAGTTTTGGAAAATGTAACAGAAAATTTTAACATGTGGAAAA
ATGACATGGTGGATCAGATGCATGAGGATATAATCAGTTTATGGATCAAAGCCTAAAA
CCATGTGTAAAGTTGACCCCACTCTGTGTCACTTTAAATTGTACAAATGCACCTGCCTA
CAATAATAGCATGCATGGAGAAATGAAAAATTGCTCTTTCAATACAACCACAGAGATAA
GAGATAGGAAACAGAAAGCGTATGCACTTTTTTATAAACCTGATGTAGTGCCACTTAAT
AGGAGAGAAGAGAATAATGGGACAGGAGAGTATATATTAATAAATTGCAATTCCTCAAC
CATAACACAAGCCTGTCCAAAGGTCACTTTTGACCCAATTCCTATACATTATTGTGCTC
CAGCTGGTTATGCGATTCTAAAGTGTAATAATAAGACATTCAATGGGACAGGACCATGC
AATAATGTCAGCACAGTACAATGTACACATGGAATTATGCCAGTGGTATCAACTCAATT
ACTGTTAAATGGTAGCCTAGCAGAAGAAGAGATAATAATTAGATCTGAAAATCTGACAA
ACAATATCAAAACAATAATAGTCCACCTTAATAAATCTGTAGAAATTGTGTGTACAAGA
CCCAACAATAATACAAGAAAAGTATAAGGATAGGACCAGGACAAACATTCTATGCAAC
AGGTGAAATAATAGGAAACATAAGAGAAGCACATTGTAACATTAGTAAAAGTAACTGGA
CCAGTACTTTAGAACAGGTAAAGAAAAAATTAAAAGAACACTACAATAAGACAATAGAA
TTTAACCCACCCTCAGGAGGGGATCTAGAAGTTACAACACATAGCTTTAATTGTAGAGG
AGAATTTTTCTATTGCAATACAACAAAACTGTTTTCAAACAACAGTGATTCAAACAACG
AAACCATCACACTCCCATGCAAGATAAAACAAATTATAAACATGTGGCAGAAGGTAGGA
CGAGCAATGTATGCCCCTCCCATTGAAGGAAACATAACATGTAAATCAAATATCACAGG
ACTACTATTGACACGTGATGGAGGAAAGAATACAACAAATGAGATATTCAGACCGGGAG
GAGGAAATATGAAGGACAATTGGAGAAGTGAATTATATAAATATAAAGTGGTAGAAATT
GAGCCATTGGGAGTAGCACCCACTAAATCAAAAGGAGAGTGGTGGAGAGAGAAAAAAG
AGCAGTGGGACTAGGAGCTGTACTCCTTGGGTTCTTGGGAGCAGCAGGAAGCACTATGG
GCGCGGCGTCAATAACGCTGACGGTACAGGCCAGACAACTGTTGTCTGGTATAGTGCAA
CAGCAAAGCAATTTGCTGAGAGCTATAGAGGCGCAACAGCATATGTTGCAACTCACGGT
CTGGGGCATTAAGCAGCTCCAGACAAGAGTCTTGGCTATAGAGAGATACCTAAAGGATC
AACAGCTCCTAGGGCTTTGGGGCTGCTCTGGAAAAATCATCTGCACCACTGCTGTGCCT
TGGAACTCCAGTTGGAGTAATAAATCTCAAGAAGATATTTGGGATAACATGACCTGGAT
GCAGTGGGATAGAGAAATTAGTAATTACACAGGCACAATATATAGGTTACTTGAAGACT
CGCAAAACCAGCAGGAGAAAAATGAAAAGATTTATTAGCATTGGACAGTTGGAAAAAC
TTGTGGAATTGGTTTAACATAACAAATTGGCTGTGGTATATAAAAATATTCATCATGAT
AGTAGGAGGCTTGATAGGTTTGAGAATAATTTTGGTGTACTCGCTATAGTGAAAAGAG
TTAGGCAGGGATACTCACCTTTGTCGTTTCAGACCCTTACCCCAAGCCCGAGGGGTCCC
GACAGGCTCGGAAGAATCGAAGAAGAAGGTGGAGAGCAAGACAAAGACAGATCCATTCG
ATTAGTGAGCGGATTCTTAGCACTTGCCTGGGACGATCTGCGGAGCCTGTGCCTCTTCA
GCTACCACCACTTGAGAGACTTCATATTGATTGCAGCGAGAGCAGCGGAACTTCTGGGA
CGCAGCAGTCTCAGGGGACTGCAGAGAGGGTGGGAAGCCCTTAAGTATCTGGGAAATCT
TGTGCAGTATGGGGGTCTGGAGCTAAAAAGAAGTGCTATTAAACTGTTTGATACCATAG
CAATAGCAGTAGCTGAAGGAACAGATAGGATTCTTGAAGTAATACAGAGAATTTGTAGA
GCTATCCGCCACATACCTATAAGAATAAGACAGGGCTTTGAAGCAGCTTTGCAATAA
```

FIGURE 21

```
MRVMGIQRNWPQWWIWGTLGFWMIIICRVVGNLNLWVTVYYGVPVWKEAKTT
LFCASDAKAYDKEVHNVWATHACVPTDPNPREIVLENVTENFNMWKNDMVDQ
MHEDIISLWDQSLKPCVKLTPLCVTLNCTNAPAYNNSMHGEMKNCSFNTTTE
IRDRKQKAYALFYKPDVVPLNRREENNGTGEYILINCNSSTITQACPKVTFD
PIPIHYCAPAGYAILKCNNKTFNGTGPCNNVSTVQCTHGIMPVVSTQLLLNG
SLAEEEIIIRSENLTNNIKTIIVHLNKSVEIVCTRPNNNTRKSIRIGPGQTF
YATGEIIGNIREAHCNISKSNWTSTLEQVKKKLKEHYNKTIEFNPPSGGDLE
VTTHSFNCRGEFFYCNTTKLFSNNSDSNNETITLPCKIKQIINMWQKVGRAM
YAPPIEGNITCKSNITGLLLTRDGGKNTTNEIFRPGGGNMKDNWRSELYKYK
VVEIEPLGVAPTKSKRRVVEREKRAVGLGAVLLGFLGAAGSTMGAASITLTV
QARQLLSGIVQQQSNLLRAIEAQQHMLQLTVWGIKQLQTRVLAIERYLKDQQ
LLGLWGCSGKIICTTAVPWNSSWSNKSQEDIWDNMTWMQWDREISNYTGTIY
RLLEDSQNQQEKNEKDLLALDSWKNLWNWFNITNWLWYIKIFIMIVGGLIGL
RIIFGVLAIVKRVRQGYSPLSFQTLTPSPRGPDRLGRIEEEGGEQDKDRSIR
LVSGFLALAWDDLRSLCLFSYHHLRDFILIAARAAELLGRSSLRGLQRGWEA
LKYLGNLVQYGGLELKRSAIKLFDTIAIAVAEGTDRILEVIQRICRAIRHIP
IRIRQGFEAALQ
```

FIGURE 22

```
   1 ATGGCTGCTC GCGCATCTAT CCTCAGAGGC GAAAAGTTGG ATAAGTGGGA AAAAATCAGA
  61 CTCAGGCCAG GAGGTAAAAA ACACTACATG CTGAAGCATA TCGTGTGGGC ATCTAGGGAG
 121 TTGGAGAGAT TTGCACTGAA CCCCGGACTG CTGGAAACCT CAGAGGGCTG TAAGCAAATC
 181 ATGAAACAGC TCCAACCAGC CTTGCAGACC GGAACAGAAG AGCTGAAGTC CCTTTACAAT
 241 ACCGTGGCAA CCCTCTATTG CGTCCACGAG AAGATCGAGG TGAGAGACAC AAAGGAGGCC
 301 CTGGACAAAA TCGAGGAGGA GCAGAATAAG TGCCAGCAGA AGACCCAGCA GGCAAAGGCT
 361 GCTGACGGAA AGGTCTCTCA GAACTATCCT ATCGTTCAGA ACCTTCAGGG GCAGATGGTG
 421 CACCAAGCAA TCAGCCCTAG AACCCTGAAC GCATGGGTGA AGGTGATCGA GGAGAAAGCC
 481 TTTTCTCCCG AGGTTATCCC CATGTTTACC GCCCTGAGCG AAGGCGCCAC TCCTCAAGAC
 541 CTGAACACTA TGCTGAACAC AGTGGGAGGA CACCAGGCCG CTATGCAGAT GTTGAAGGAT
 601 ACCATCAACG AGGAGGCAGC CGAATGGGAC CGCCTCCACC CGGTGCACGC CGGACCTATC
 661 GCCCCCGGAC AAATGAGAGA ACCTCGCGGA AGTGATATTG CCGGTACTAC CAGCACCCTT
 721 CAAGAGCAGA TTGCTTGGAT GACCAGCAAC CCACCCATCC CAGTGGGCGA TATTTACAAA
 781 AGGTGGATTA TTCTGGGGCT GAACAAAAAT GTGAGAATGT ACTCCCCCGT CTCCATCCTC
 841 GACATCCGCC AAGGACCCAA GGAGCCTTTT AGGGATTACG TGGACAGATT CTTCAAAACC
 901 CTTAGAGCTG AGCAAGCCAC TCAGGAGGTT AAGAACTGGA TGACAGATAC TCTGCTCGTG
 961 CAAAACGCTA ACCCCGATTG CAAAACCATC TTGAGAGCTC TCGGTCCAGG TGCCACCCTT
1021 GAGGAAATGA TGACAGCATG TCAAGGCGTG GGAGGACCTG GCACACAAGC CAGAGTTCTC
1081 GCTGAGGCCA TGAGCCAGAC AAACTCAGGC AATATCATGA TGCAGAGGAG TAACTTTAAG
1141 GGTCCCAGGA GAATCGTCAA GTGCTTCAAT TGTGGCAAGG AGGGTCACAT TGCCAGGAAC
1201 TGCCGCGCCC CCAGGAAGAA AGGCTGCTGG AAGTGTGGCA AAGAGGGCCA CCAGATGAAG
1261 GATTGCACCG AGCGCCAAGC AAACTTCCTG GGAAAGATTT GGCCCAGTCA TAAGGCCGC
1321 CCTGCAACT TCCTTCAAAA CAGACCCGAG CCTACCGCCC CCCCGCTGA GTCTTTCAGA
1381 TTTGAGGAGA CCACCCCCGC TCCAAAGCAG GAGCCAATTG AGAGAGAGCC TCTCACCAGT
1441 CTCAAAAGCC TCTTTGGTAG CGACCCCCTC AGCCAATAAG AATTCTAGCT TGGCGTAATC
1501 ATGGTCATAG TGTTTCCTG TTATCAGCTC TGTGAAATTG ACAATTCCAC ACAACATACG
1561 AGCCGGAAGC ATAA
```

| | | | | | |
|---|---|---|---|---|---|
| 1 | CCTTCCCACA | AGGGCCGGCC | AGGCAATTTC | CTTCAGAACA | GACCAGAGCC |
| 51 | AACAGCCCCA | CCAGCAGAGA | GCTTCAGGTT | CGAAGAGACA | ACCCCCGCTC |
| 101 | CGAAACAGGA | GCCGAGAGAA | AGGGAACCCT | TAACTTCCCT | CAAATCACTC |
| 151 | TTTGGCAGCG | ACCCCTTGTC | TCAATAAAAA | TCGGCGGCCA | GACCCGGGAG |
| 201 | GCCCTGCTGG | ACACCGGCGC | CGACGACACC | GTGCTGGAGG | ACATCAACCT |
| 251 | GCCCGGCAAG | TGGAAGCCCA | AGATGATCGG | CGGCATCGGC | GGCTTCATCA |
| 301 | AGGTGCGGCA | GTACGACCAG | ATCCTGATCG | AGATCTGCGG | CAAGAAGGCC |
| 351 | ATCGGCACCG | TGCTGGTGGG | CCCCACCCCC | GTGAACATCA | TCGGCCGGAA |
| 401 | CATGCTGACC | CAGCTGGGCT | GCACCCTGAA | CTTCCCCATC | AGCCCCATCG |
| 451 | AGACCGTGCC | CGTGAAGCTG | AAGCCCGGCA | TGGACGGCCC | CAAGGTGAAG |
| 501 | CAGTGGCCCC | TGACCGAGGT | GAAGATCAAG | GCCCTGACCG | CCATCTGCGA |
| 551 | GGAGATGGAG | AAGGAGGGCA | AGATCACCAA | GATCGGCCCC | GAGAACCCCT |
| 601 | ACAACACCCC | CATCTTCGCC | ATCAAGAAGG | AGGACAGCAC | CAAGTGGCGG |
| 651 | AAGCTGGTGG | ACTTCCGGGA | GCTGAACAAG | CGGACCCAGG | ACTTCTGGGA |
| 701 | GGTGCAGCTG | GGCATCCCCC | ACCCCGCCGG | CCTGAAGAAG | AAGAAGAGCG |
| 751 | TGACCGTGCT | GGACGTGGGC | GACGCCTACT | TCAGCGTGCC | CCTGGACGAG |
| 801 | GGCTTCCGGA | AGTACACCGC | CTTCACCATC | CCCAGCATCA | ACAACGAGAC |
| 851 | CCCCGGCATC | CGGTACCAGT | ACAACGTGCT | GCCCCAGGGC | TGGAAGGGCA |
| 901 | GCCCCGCCAT | CTTCCAGAGC | AGCATGACCA | AGATCCTGGA | GCCCTTCCGG |
| 951 | GCCAAGAACC | CCGAGATCGT | GATCTACCAG | TACATGGCCG | CCCTGTACGT |
| 1001 | GGGCAGCGAC | CTGGAAGTGG | GCCAGCACCG | CCCCCGACAA | GAGGAGCTGC |
| 1051 | GGGAGCACCT | GCTGAAGTGG | GGCTTCACCA | CCCCCGACAA | GAAGCACCAG |
| 1101 | AAGGAGCCCC | CCTTCCTGTG | GATGGGCTAC | GAGCTGCACC | CCGACAAGTG |
| 1151 | GACCGTGCAG | CCCATCCAGC | TGCCCGAGAA | GGACAGCTGG | ACCGTGAACG |
| 1201 | ACATCCAGAA | GCTGGTGGGC | AAGCTGAACT | GGACCAGCCA | GATCTACCCC |
| 1251 | GGCATCAAGG | TGCGCCAGCT | GTGCAAGCTG | CTGCGGGGCA | CCAAGGCCCT |
| 1301 | GACCGACATC | GTGCCCCTGA | CCGAGGAGGC | CGAGCTGGAG | CTGGCCGAGA |
| 1351 | ACCGGGAGAT | CCTGAAGGAG | CCCGTGCACG | CCCGTGCACG | CGAGCCCAGC | CGACCCCAGC |
| 1401 | AAGGACCTGA | TCGCCCGAGAT | CCAGAAGCAG | GGCGACGACC | AGTGGACCTA |

FIG. 25A

| | | | | |
|---|---|---|---|---|
| 1451 | CCAGATCTAC | CAGGAGCCCT | TCAAGAACCT | GAAAACCGGC | AAGTACGCCA |
| 1501 | AGCGGGCGGAC | CACCCACACC | AACGACGTGA | AGCAGCTGAC | CGAGGCCGTG |
| 1551 | CAGAAGATCA | GCCTGGAGAG | CATCGTGACC | TGGGGCAAGA | CCCCCAAGTT |
| 1601 | CCGGCTGCCC | ATCCAGAAGG | AGACCTGGGA | GATCTGGTGG | ACCGACTACT |
| 1651 | GGCAGGCCAC | CTGGATCCCC | GAGTGGGAGT | TCGTGAACAC | CCCCCCCCTG |
| 1701 | GTGAAGCTGT | GGTACCAGCT | GGAGAAGGAG | CCCATCGCCG | GCGCCGAGAC |
| 1751 | CTTCTACGTG | GACGGCGCCG | CCAACCGGGA | GACCAAGATC | GGCAAGGCCG |
| 1801 | GCTACGTGAC | CGACCGGGGC | CGGCAGAAGA | TCGTGACCCT | GAGCGAGACC |
| 1851 | ACCAACCAGA | AAACCGAGCT | GCAGGCCATC | CAGCTGGCCC | TGCAGGACAG |
| 1901 | CGAGAGCGAG | GTGAACATCG | TGACCGACAG | CCAGTACGCC | CTGGGCATCA |
| 1951 | TCCAGGCCCA | GCCCGACCGG | AGCGAGAGCG | AGCTGGTGAA | CCAGATCATC |
| 2000 | GAGCAGCTGA | TCAAGAAGGA | GCGGGCCTAC | CTGAGCTGGG | TGCCCGCCCA |
| 2051 | CAAGGGCATC | GGCGGCGACG | AGCAGGTGGA | CAAGCTGGTG | AGCAGCGGCA |
| 2101 | TCCGGAAGGT | GCTGTGA | | | |

FIG. 25B

```
1   FPSEQTRANS PTSRELQVRR DNPRSETGAE RKGTLNFPQI TLWQRPLVSI KIGGQTREAL
61  LDTGADDTVL EDINLPGKWK PKMIGGIGGF IKVRQYDQIL IEICGKKAIG TVLVGPTPVN
121 IIGRNMLTQL GCTLNFPISP IETVPVKLKP GMDGPKVKQW PLTEVKIKAL TAICEEMEKE
181 GKITKIGPEN PYNTPIFAIK KEDSTKWRKL VDFRELNKRT QDFWEVQLGI PHPAGLKKKK
241 SVTVLDVGDA YFSVPLDEGF RKYTAFTIPS INNETPGIRY QYNVLPQGWK GSPAIFQASM
301 TKILEPFRAK NPEIVIYQYM AALYVGSDLE IGQHRAKIEE LREHLLKWGF TTPDKKHQKE
361 PPFLWMGYEL HPDKWTVQPI QLPEKDSWTV NDIQKLVGKL NWTSQIYPGI KVRQLCKLLR
421 GTKALTDIVP LTEEAELELA ENREILKEPV HGVYYDPSKD LIAEIQKQGD DQWTYQIYQE
481 PFKNLKTGKY AKRRTTHTND VKQLTEAVQK ISLESIVTWG KTPKFRLPIQ KETWEIWWTD
541 YWQATWIPEW EFVNTPPLVK LWYQLEKEPI AGAETFYVDG AANRETKIGK AGYVTDRGRQ
601 KIVTLSETTN QKTELQAIQL ALQDSESEVN IVTDSQYALG IQAQPDRSE SELVNQIIEQ
661 LIKKERAYLS WVPAHKGIGG DEQVDKLVSS GIRKVL*
```

FIGURE 26

```
  1  AAGCTTATGA GGGTTATGGG GATTCAGAGA AACTGGCCTC AGTGGTGGAT TTGGGGGACA
 61  TTGGGATTTT GGATGATCAT CATCTGTCGC GTCGTGGGCA ACCTGAACCT GTGGGTCACT
121  GTCTACTATG GAGTGCCAGT TTGGAAGGAA GCCAAGACAA CTCTGTTTTG CGCCAGCGAC
181  GCCAAGGCTT ATGACAAGGA AGTCCACAAC GTGTGGGCCA CCCACGCATG TGTCCCAACC
241  GACCCCAACC CACGCGAAAT CGTGCTGGAA AACGTCACAG AAAATTTCAA CATGTGGAAA
301  AACGATATGG TGGATCAGAT GCATGAGGAT ATTATTAGCC TCTGGGACCA GTCTCTGAAG
361  CCATGTGTGA AGTTGACACC TCTCTGTGTG ACCCTTAACT GTACTAACGC CCCCGCCTAT
421  AACAACTCTA TGCACGGGGA GATGAAAAAC TGTTCCTTCA ACACCACCAC CGAAATCAGG
481  GACAGAAAAC AGAAAGCCTA TGCCCTGTTC TATAAGCCCG ATGTGGTGCC ACTTAACCGC
541  CGCGAAGAAA ATAATGGTAC TGGCGAATAT ATTCTGATTA ACTGTAACAG CTCTACAATT
601  ACTCAGGCTT GCCCTAAAGT CACCTTTGAC CCAATCCCAA TCCACTACTG CGCCCCTGCA
661  GGATACGCTA TCCTGAAATG CAATAATAAG ACCTTCAACG GAACTGGACC CTGCAATAAC
721  GTGTCTACAG TGCAATGTAC CCACGGCATT CTCTCCACCCA AAAACCTCAC ACTGCTGCTC
781  AATGGCAGCT TGGCAGAAGA GGAGATCATT ATGCCCGTCG ATGCCGTCAG GCCCAATAAC
841  AAGACAATCA TCGTGCACCT GAACAAGTCT GTGGAAATTG TGTGTACCAG CGGCGAAATC
901  AACACCAGGA AGAGCATCCG CATCGGACCT GGACAAACTT TCTACGCCAC ATCTACATTG
961  ATCGGGAACA TTAGAGAAGC CCACTGCAAC ATCTCTAAGA GCAATTGGAC CAACCCTCCT
1021 GAGCAAGTGA AAAAAAAGCT GAAAGAGCAC CCATCGAGTT GTTCTTTTAC
1081 TCCGGCGGCG ATCTGGAGGT CACAACACAC TACAATAAGA GTAGGGGGGA TATCACCCTG
1141 TGCAACACAA CAAAGCTGTT TAGCAACAAC CATCATTGGC TCCGACAGCA AATGTATGCA
1201 CCTTGCAAGA TCAAGCAAAT CATTAACATG TGGCAGAAAG TGGGAAGGGC AATGTATGCA
1261 CCTCCCATCG AGGGCAACAT CACATGCAAG TCTAATATCA CCGGCCTGTT GCTGACTAGA
1321 GACGGTGGCA AGAATACTAC TAACGAAATC TTCAGGCCAG GTGGAGGGAA CATGAAAGAT
1381 AATTGGCGCT CCGAACTGTA TAAGTACAAG GTGGTGGAGA TTGAGCCCCT CGGCGTCGCC
1441 CCCACAAAGT CTAAGCGCCG CGTGGTGGAA AGAGAGAAGA GGGCTGTGCG CCTCGGCGCA
```

FIG. 27A

| | | | | | |
|---|---|---|---|---|---|
| 1501 | GTGCTGCTGG | GGTTCTTGGG | TGCCGCTGGG | TCTACAATGG | GCGCTGCCTC | TATTACACTC |
| 1561 | ACCGTGCAAG | CTAGGCAGCT | GCTGTCCGGT | ATTGTGCAAC | AACAGAGCAA | TCTCTTGAGA |
| 1621 | GCTATCGAGG | CCCAGCAGCA | TATGCTGCAA | CTTACAGTGT | GGGGTATTAA | GCAGCTGCAA |
| 1681 | ACTCGCGTCC | TGGCAATCGA | ACGCTACCTG | AAAGACCAGC | AACTCCTGGG | TCTGTGGGGC |
| 1741 | TGCTCCGGTA | AGATCATCTG | TACCACAGCC | GTGCCCTGGA | ACAGCAGCTG | GTCCAATAAG |
| 1801 | AGCCAAGAGG | ATATTTGGGA | TAATATGACC | TGGATGCAAT | GGGATAGAGA | GATCAGCAAC |
| 1861 | TACACAGGAA | CCATTTATAG | GCTCCTGGAA | GATTCTCAGA | ACCAGCAGGA | GAAGAACGAG |
| 1921 | AAGGACTTGC | TCGCCCTGGA | TAGCTGGAAA | AACCTGTGGA | ATTGGTTTAA | CATCACCAAC |
| 1981 | TGGCTTTGGT | ACATTAAGAT | TTTCATCATG | GCTTGATCGG | GATACTCCCC | CCTGAGGATT |
| 2041 | ATCTTCGGGG | TGCTTGCCAT | TGTGAAAAGG | GTCAGACAAG | GATACTCCCC | ATTGTCCTTT |
| 2101 | CAGACCTTGA | CTCCAAGCCC | ACGCGGACCC | GACAGGTTGG | GCAGGATCGA | GGAGGAAGGA |
| 2161 | GGCGAACAGG | ATAAGGACCG | CTCCATCAGA | CTTGTTAGCG | GGTTTCTGGC | CCTGCCTGG |
| 2221 | GATGATCTGA | GGAGCCTGTG | CCTCTTCTCC | TATCACCACC | TCCGCGATTT | CATCCTCATT |
| 2281 | GCAGTAGGG | CTGCTGAGTT | GCTGGGACGC | TCCTCCCTGA | GAGGTCTCCA | GAGAGGCTGG |
| 2341 | GAGGCACTGA | AGTACCTCGG | GAACCTTGTG | CAATACGGCG | GGCTGGAGCT | GAAAAGATCC |
| 2401 | GCCATCAAGC | TGTTCGACAC | CATCGCAAAC | GCCGTTGCAG | AGGGCACCGA | CAGGATCTTG |
| 2461 | GAGGTCATTC | AGAGGATCTG | TCGCGCCATC | GCCACATCC | CCATCAGGAT | CAGACAAGGA |
| 2521 | TTCGAGGCAG | CACTGCAATG | ATAGTTAATT | AAACGCGTGG | ATCC | |

FIG. 27B

KLMRVMGIQRNWPQWWIWGTLGFWMIIICRVVGNLNLWVTVYYGVPVWKEAKTTLFCAS
DAKAYDKEVHNVWATHACVPTDPNPREIVLENVTENFNMWKNDMVDQMHEDIISLWDQS
LKPCVKLTPLCVTLNCTNAPAYNNSMHGEMKNCSFNTTTEIRDRKQKAYALFYKPDVVP
LNRREENNGTGEYILINCNSSTITQACPKVTFDPIPIHYCAPAGYAILKCNNKTFNGTG
PCNNVSTVQCTHGIMPVVSTQLLLNGSLAEEEIIIRSENLTNNIKTIIVHLNKSVEIVC
TRPNNNTRKSIRIGPGQTFYATGEIIGNIREAHCNISKSNWTSTLEQVKKKLKEHYNKT
IEFNPPSGGDLEVTTHSFNCRGEFFYCNTTKLFSNNSDSNNETITLPCKIKQIINMWQK
VGRAMYAPPIEGNITCKSNITGLLLTRDGGKNTTNEIFRPGGGNMKDNWRSELYKYKVV
EIEPLGVAPTKSKRRVVEREKRAVGLGAVLLGFLGAAGSTMGAASITLTVQARQLLSGI
VQQQSNLLRAIEAQQHMLQLTVWGIKQLQTRVLAIERYLKDQQLLGLWGCSGKIICTTA
VPWNSSWSNKSQEDIWDNMTWMQWDREISNYTGTIYRLLEDSQNQQEKNEKDLLALDSW
KNLWNWFNITNWLWYIKIFIMIVGGLIGLRIIFGVLAIVKRVRQGYSPLSFQTLTPSPR
GPDRLGRIEEEGGEQDKDRSIRLVSGFLALAWDDLRSLCLFSYHHLRDFILIAARAAEL
LGRSSLRGLQRGWEALKYLGNLVQYGGLELKRSAIKLFDTIAIAVAEGTDRILEVIQRI
CRAIRHIPIRIRQGFEAALQOOLIKRVD*

FIGURE 28

AGGCTAATTTTTTAGGGAAAATTTGGCCTTCCCACAAGGGGAGGCCAGGGAATTTCCTT
CAGAGCAGGCCAATGAGAGTGAGGGGGATACAGAGGAATTGGCCACAATGGTGGATATG
GGGCATCTTAGGCTTTTGGATGTTAATGATTTGTAGTGGGGTGGGAAACTTGTGGGTCA
CAATCTATTATGGGGTACCTGTGTGGAGAGAAGCAAAAACTACTCTATTCTGTGCATCA
GATGCTAAAGCATATGATAGAAGTGCATAATGTCTGGGCTACACATGCCTGTGTACC
CACAGACCCCAACCCACAAGAAATAGTTATGGGAAATGTAACAGAAAATTTTAACATGT
GGAAAAATGACATGGTGGATCAGATGCATGAGGATATAATCAATTTATGGGATCAAAGC
CTAAAGCCATGTGTAAAGTTAACCCCACTCTGTGTCACTTTAAAATGTAGTACCTATAA
TGGTAGTGATACCAACGATATGAGAAATTGCTCTTTCAATACAACTACAGAAATAAGGG
ACAAGAAACAGACAGTGTATGCACTTTTTTATAAACCTGATATAGTACCAATTAATGAG
AGTGAGTATATATTAATACATTGCAATACCTCAACCATAACACAAGCCTGTCCAAAGGT
CTCTTTTGACCCAATTCCTATACATTATTGTGCTCCAGCTGGTTATGCGATTCTAAAGT
GTAATAATAAGACATTCAATGGGACGGGACCATGCCAAAATGTCAGCACAGTACAATGC
ACACATGGAATTAAGCCAGTAGTATCAACTCAACTACTGTTAAATGGTAGCATAGCAGA
AGGAGAGATAATAATTAGATCTGAAAATCTGACAAACAATGTTAAAACAATAATAGTAC
ACCTTAATGAATCTATAGGAATTGTGTGTACAAGACCCGGCAATAATACAAGAAAAGT
ATAAGGATAGGACCAGGACAAGCATTCTATACAAATCACATAATAGGAGATATAAGACA
AGCATATTGTAACATTAGTAAACAAGAATGGAACAAAACTTTAGAAGAGGTGAGAAAAA
AATTGCAAGAACACTTCCCAAATAAAACAATAAAATTTAACTCATCCTCAGGAGGGGAC
CTAGAAATTACAACACATAGCTTTAATTGCAGAGGAGAATTTTTCTATTGCAATACATC
AAAACTATTTAATGATAGTCTAGTAAATGATACAGAAAGTAATTCAACCATCACTATTC
CATGCAGAATAAAACAAATTATAAACATGTGGCAGGAGGTAGGACGAGCAATGTATGCC
CCTCCCATTGCAGGAAACATAACATGTAAATCAAATATCACAGGACTACTATTGACACG
TGATGGAGGAACAGATAACACAACAGAGATATTCAGACCTGGAGGAGGAAATATGAAGG
ACAATTGGAGAAGTGAATTATATAAATATAAAGTAGTAGAAATTAAGCCATTGGGAATA
GCACCCACTGAAGCAAAAAGGAGAGTGGTGGAGAGAGAAAAAAGAGCAGTGGGAATAGG
AGCTGTGCTCCTTGGGTTCTTGGGAGCAGCAGGAAGCACTATGGGCGCGGCGTCAATAA
CGCTGACGGTACAGGCCAGACAACTGTTGTCTGGTATAGTGCAACAGCAAAGCAATTTG
CTGAGAGCTATAGAGGCGCAACAGCATATGTTGCAACTCACAGTCTGGGGCATTAAGCA
GCTCCAGACAAGAGTCCTGGCTATAGAAAGATACCTAAAGGATCAACAGCTCCTAGGAC
TTTGGGGCTGCTCTGGAAAACTCATCTGCACCACTAATGTGCCTTGGAACTCCAGTTGG
AGCAATAAATCTCAACAAGCTATTTGGGATAACATGACATGGATGCAGTGGGATAGAGA
AATTAATAATTACACAAACATAATATACCAGTTGCTTGAGGACTCGCAAATCCAGCAGG
AACAGAATGAAAAGATTTATTAGCATTGGACAAGTGGCAAAATCTGTGGAGTTGGTTT
AGCATAACAAATTGGCTATGGTATATAAAATATTCATAATGATAGTAGGAGGCTTAAT
AGGTTTAAGAATAATTTTTGCTGTGCTATCTATAGTAAATAGAGTTAGGCAGGGATACT
CACCTTTGTCGTTTCAGACCCTTACCCCAAACCCGAGGGGACCCGACAGGCTCGGAGAA
ATCGAAGAAGAAGGTGGAGAGCAAGACAGAGACAGATCCGTTCGATTAGTGAGCGGATT
CTTACCACTTGCCTGGGACGATCTGCGGAGCCTGTGCCTCTTCAGCTACCACCGATTGA
GAGACTTCATATTCGATTGCAGCGAGGACAGTGGAACTTCTGGGACGCAGCAGTCTCAG
GGGACTCCAGAGGGGTGGGAAGTCCTTAAATATCTGGGAAGCCTTGTGCAGTATTGGGG
TCTGGAGCTAAAAGAGTGCTATTAGTCTGCTTGATACCCATAGCAATAGCAGTAGCTG
AAGGAACAGATAGGATTATTGAATTAGTACTAAGATTTTGTAGAGCTATCCGCAACATA
CCTACAAGAGTAAGACAGGGCTGTGAAGCAGCTTTGCTATAA

FIGURE 29

```
  1  ANFLGKIWPS  HKGRPGNFLQ  SRPMRVRGIQ  RNWPQWWIWG  ILGFWMLMIC  SGVGNLWVTI
 61  YYGVPVWREA  KTTLFCASDA  KAYDREVHNV  WATHACVPTD  PNPQEIVMGN  VTENFNMWKN
121  DMVDQMHEDI  INLWDQSLKP  CVKLTPLCVT  LKCSTYNGSD  TNDMRNCSFN  TTTEIRDKKQ
181  TVYALFYKPD  IVPINESEYI  LIHCNTSTIT  QACPKVSFDP  IPIHYCAPAG  YAILKCNNKT
241  FNGTGPCQNV  STVQCTHGIK  PVVSTQLLLN  GSIAEGEIII  RSENLTNNVK  TIIVHLNESI
301  GIVCTRPGNN  TRKSIRIGPG  QAFYTNHIIG  DIRQAYCNIS  KQEWNKTLEE  VRKKLQEHFP
361  NKTIKFNSSS  GGDLEITTHS  FNCRGEFFYC  NTSKLFNDSL  VNDTESNSTI  TIPCRIKQII
421  NMWQEVGRAM  YAPPIAGNIT  CKSNITGLLL  TRDGGTDNTT  EIFRPGGGNM  KDNWRSELYK
481  YKVVEIKPLG  IAPTEAKRRV  VEREKRAVGI  GAVLLGFLGA  AGSTMGAASI  TLTVQARQLL
541  SGIVQQQSNL  LRAIEAQQHM  LQLTVWGIKQ  LQTRVLAIER  YLKDQQLLGL  WGCSGKLICT
601  TNVPWNSSWS  NKSQAIWDN   MTWMQWDREI  NNYTNIIYQL  LEDSQIQQEQ  NEKDLLALDK
661  WQNLWSWFSI  TNWLWYIKIF  IMIVGGLIGL  RIIFAVLSIV  NRVRQGYSPL  SFQTLTPNPR
721  GPDRLGEIEE  EGGEQDRDRS  VRLVSGFLPL  AWDDLRSLCL  FSYHRLRDFI  FDCSEDSGTS
781  GTQQSQGTPE  GWEVLKYLGS  LVQYWGLELK  RVLLVCLIPI  AIAVAEGTDR  IIELVLRFCR
841  AIRNIPTRVR  QGCEAALL*
```

FIGURE 30

```
GEKLDKWEKI  RLRPGGKKHY  MLKHLVWASR  ELERFALNPG  LLETSEGCKQ   50
IMKQLQPALQ  TGTEELRSLY  NTVATLYCVH  EKIEVRDTKE  ALDKIEEEQN  100
KSQQ-CQQKT  QQAKAADGG-  KVSQNYPIVQ  NLQGQMVHQA  ISPRTLNAWV  150
KVIEEKAFSP  EVIPMFTALS  EGATPQDLNT  MLNTVGGHQA  AMQMLKDTIN  200
EEAAEWDRLH  PVHAGPIAPG  QMREPRGSDI  AGTTSTLQEQ  IAWMTSNPPI  250
PVGDIYKRWI  ILGLNKIVRM  YSPVSILDIK  QGPKEPFRDY  VDRFFKTLRA  300
EQATQDVKNW  MTD 313
```

FIGURE 31

```
LTEEKIKALT  AICEEMEKEG  KITKIGPENP  YNTPVFAIKK  KDSTKWRKL-   50
VDFRELNKRT  QDFWEVQLGI  PHPAGLKKKK  SVTVLDVGDA  YFSVPLDEGF  100
RKYTAFTIPS  INNETPGIRY  QYNVLPQGWK  GSPAIFQSSM  TKILEPFRAK  150
NPEIVIYQYM  DDLYVGSDLE  IGQHRAKIEE  LREHLLKWGF  TTPDKKHQKE  200
PPFLWMGYEL  HPDKWTVQPI  QLPEKDSWTV  NDIQKLVGKL  NWASQIYPGI  250
KVRQLCKLLR  GAKALTDIVP  LTEEEAELE 278
```

FIGURE 32

```
YCAPAGYAIL  KCNNKTFNGT  GPCNNVSTVQ  CTHGIKPVVS  TQLLLNGSLA   50
EEEIIRSEN   LTNNAKTIIV  HLNESVEIVC  TRPNNNTRKS  IRIGPGQTFY  100
ATGDIIGDIR  QAHCNISEGK  WNKTLQKVKK  KLKEELYKYK  VVEIKPLGIA  150
PTEAKRRVVE  REKRAVGIGA  VFLGFLGAAG  STMGAASITL  TVQARQLLSG  200
IVQQQSNLLR  AIEAQQHMLQ  LTVWGIKQL 229
```

FIGURE 33

| | |
|---|---|
| 1<br>1 | GGGGGATGTGCTGCAAGGCGATTAAGTTGGGTAACGCCAGGGTTTTCCAATCACGACGT<br>G G C A A R R L S W V T P G F S Q S R R |
| 61<br>21 | TGTAAAACGACAGCCAATGAATTGAAGCTTATGGCTGTCGCGCATCTATCCTCAGAGGC<br>C K T T A N E L K L M A A R A S I L R G |
| 121<br>41 | GAAAAGTTGGATAAGTGGGAAAAAATCAGACTCAGGCCAGGAGGTAAAAAACACTACATG<br>E K L D K W E K I R L R P G G K K H Y M |
| 181<br>61 | CTGAAGCATATCGTGTGGGCATCTAGGGAGTTGGAGAGATTTGCACTGAACCCCGGACTG<br>L K H I V W A S R E L E R F A L N P G L |
| 241<br>81 | CTGGAAACCTCAGAGGGCTGTAAGCAAATCATGAAACAGCTCCAACCAGCCTTGCAGACC<br>L E T S E G C K Q I M K Q L Q P A L Q T |
| 301<br>101 | GGAACAGAGAGCTGAAGTCCCTTTACAATACCGTGGCAACCCTCTATTGCGTCCACGAG<br>G T E E L K S L Y N T V A T L Y C V H E |
| 361<br>121 | AAGATCGAGGTGAGAGATACAAAGGAGGCCCTGGACAAAATCGAGGAGGAGCAGAATAAG<br>K I E V R D T K E A L D K I E E E Q N K |
| 421<br>141 | TGCCAGCAGAAGACCCAGCAGGCAAAGGCTGCTGACGGAAAGGTCTCTCAGAACTATCCT<br>C Q Q K T Q Q A K A A D G K V S Q N Y P |
| 481<br>161 | ATCGTTCAGAACCTTCAGGGGCAGATGGTGCACCAAGCAATCAGCCCTAGAACCCTGAAC<br>I V Q N L Q G Q M V H Q A I S P R T L N |
| 541<br>181 | GCATGGGTGAAGGTGATCGAGGAGAAAGCCTTTTCTCCCGAGGTTATCCCCATGTTTACC<br>A W V K V I E E K A F S P E V I P M F T |

FIG. 34A

```
601   GCCCTGAGCGAAGGCGCCACTCCTCAAGACCTGAACACATATGCTGAACACAGTGGGAGGA
201    A   L   S   E   G   A   T   P   Q   D   L   N   T   M   L   N   T   V   G   G

661   CACCAGGCCCGCTATGCAGATGTTGAAGGATACCATCAACGAGGAGGCAGCCGAATGGGAC
221    H   Q   A   A   M   Q   M   L   K   D   T   I   N   E   E   A   A   E   W   D

721   CGCCTCCACCCCGTGCACGCCGGACCTATCGCCCCCGGACAAATGAGAGAACCTCGCGGA
241    R   L   H   P   V   H   A   G   P   I   A   P   G   Q   M   R   E   P   R   G

781   AGTGATATTGCCGGTACTACCAGCACCCTTCAAGAGCAGATTGCTTGGATGACCAGCAAC
261    S   D   I   A   G   T   T   S   T   L   Q   E   Q   I   A   W   M   T   S   N

841   CCACCCATCCCAGTGGGCGATATTTACAAAAGGTGGATTATTCTGGGGCTGAACAAAATT
281    P   P   I   P   V   G   D   I   Y   K   R   W   I   I   L   G   L   N   K   I

901   GTGAGAATGTACTCCCCCGTCTCCATCCTGGACATCCGCCAAGGACCCAAGGAGCCTTTT
301    V   R   M   Y   S   P   V   S   I   L   D   I   R   Q   G   P   K   E   P   F

961   AGGGATTACGTGGACAGATTCTTCAAAACCCTTAGAGCTGAGCAAGCCACTCAGGAGGTT
321    R   D   Y   V   D   R   F   F   K   T   L   R   A   E   Q   A   T   Q   E   V

1021  AAGAACTGGATGACAGATACTCTGCTCGTGCAAAACGCTAACCCCGATTGCAAAACCATC
341    K   N   W   M   T   D   T   L   L   V   Q   N   A   N   P   D   C   K   T   I

1081  TTGAGAGCTCTCGGTCCAGGTGCCACCCTTGAGGAAATGATGACAGCATGTCAAGGCGTG
361    L   R   A   L   G   P   G   A   T   L   E   E   M   M   T   A   C   Q   G   V

1141  GGAGGACCTGGGCACAAGGCCAGAGTTCTGCTGAGGCCATGAGCCAGACAAACTCAGGC
381    G   G   P   G   H   K   A   R   V   L   A   E   A   M   S   Q   T   N   S   G
```

FIG. 34B

```
1201  AATATCATGATGCAGAGAGTAACTTTAAGGGTCCCAGGAGAATCGTCAAGTGCTTCAAT
 401   N  I  M  M  Q  R  S  N  F  K  G  P  R  R  I  V  K  C  F  N

1261  TGTGGCAAGGAGGGTCACATTGCCAGGAACTGCCGCGCCCCCAGGAAGAAGGCTGCTGG
 421   C  G  K  E  G  H  I  A  R  N  C  R  A  P  R  K  K  G  C  W

1321  AAGTGTGGCAAAGAGGGCCACCAGATGAAGGATTGCACCGAGCGCCAAGCAAACTTCCTG
 441   K  C  G  K  E  G  H  Q  M  K  D  C  T  E  R  Q  A  N  F  L

1381  GGAAAGATTTGGCCCAGTCATAAGGGCCGCCCTGCAACTTCCTTCAAAACAGACCCGAG
 461   G  K  I  W  P  S  H  K  G  R  P  G  N  F  L  Q  N  R  P  E

1441  CCTACCGCCCCCCCCGCTGAGTCTTTCAGATTTGAGGAGACCACCCCGCTCCAAAGCAG
 481   P  T  A  P  P  A  E  S  F  R  F  E  E  T  T  P  A  P  K  Q

1501  GAGCCAATTGAGAGAGCCCTCTCACCAGTCTCAAAAGCCTCTTTTGGTAGCGACCCCTC
 501   E  P  I  E  R  E  P  L  T  S  L  K  S  L  F  G  S  D  P  L

1561  AGCCAATAAGAATTCTAGCTTGGCGTAATCATGGTCATAGCTGTTTCCTGTGTGAAATTG
 521   S  Q  *  E  F  *  L  G  V  I  M  V  I  A  V  S  C  V  K  L

1621  TTATCAGCTCACAATTCCACACAACATACGAGCCGGAAGCATAAAGTGTAAAGCCTGGA
 541   L  S  A  H  N  S  T  Q  H  T  S  R  K  H  K  V  *  S  L  G

1681  TGCCTAATGAGTGAGCTAACTCACATTAGTTGCCGTTGCCGCTCACTGCCGCTTTCCAGTC
 561   C  L  M  S  E  L  T  H  I  S  C  V  A  L  T  A  R  F  P  V

1741  GGGAAACCTGTCGTGCCAGCTCCATTAGTGAATCGTCCAACGCACCGGGAGAGGCGGTTT
 581   G  K  P  V  V  P  A  P  L  V  N  R  P  T  H  G  E  R  R  F
```

FIG. 34C

```
1801 GCGTATTGGGGCGCACTTCCGCTTCCTCGCTTCACTGACTCGCTGCGCTCGTTCGTTCGGCT
 601  A   Y   W   G   A   H   F   R   F   L   A   H   *   L   A   A   L   V   R   S   A

1861 GCGGCGAGCCGTATCAGCTCACTCAAAGGCGGTAATACGGTTATC
 621  A   A   S   R   I   S   S   L   K   G   G   N   T   V   I
```

FIG. 34D

|      |            |            |            |            |            |
|------|------------|------------|------------|------------|------------|
|    1 | TCGCGCGTTT | CGGTGATGAC | GGTGAAAACC | TCTGACACAT | GCAGCTCCCG |
|   51 | GAGACGGTCA | CAGCTTGTCT | GTAAGCGGAT | GCCGGGAGCA | GACAAGCCCG |
|  101 | TCAGGGCGCG | TCAGCGGGTG | TTGGCGGGTG | TCGGGGCTGG | CTTAACTATG |
|  151 | CGGCATCAGA | GCAGATTGTA | CTGAGAGTGC | ACCATATGCG | GTGTGAAATA |
|  201 | CCGCACAGAT | GCGTAAGGAG | AAAATACCGC | ATCAGGCGCC | ATTCGCCATT |
|  251 | CAGGCTGCGC | AACTGTTGGG | AAGGGCGATC | GGTGCGGGCC | TCTTCGCTAT |
|  301 | TACGCCAGCT | GGCGAAAGGG | GGATGTGCTG | CAAGGCGATT | AAGTTGGGTA |
|  351 | ACGCCAGGGT | TTTCCCAGTC | ACGACGTTGT | AAAACGACGG | CCAGTGCCAA |
|  401 | GCTTGCATGC | CTGCAGGTCG | ACTCTAGAGG | ATCCCCGGGT | ACCGAGCTCC |
|      |            | BglI (join to Gag for Gag-pol) | | | |
|  451 | TTCCCACAAG | GGCCGGCCAG | GCAATTTCCT | TCAGAACAGA | CCAGAGCCAA |
|  501 | CAGCCCCACC | AGCAGAGAGC | TTCAGGTTCG | AAGAGACAAC | CCCCGCTCCG |
|  551 | AAACAGGAGC | CGAGAGAAAG | GGAACCCTTA | ACTTCCCTCA | AATCACTCTT |
|  601 | TGGCAGCGAC | CCCTTGTCTC | AATAAAAATC | GGGGCCAGA  | CCCGGAGGC  |
|  651 | CCTGCTGGAC | ACCGGCGCCG | ACGACACCGT | GCTGGAGGAC | ATCAACTGC  |
|  701 | CCGGCAAGTG | GAAGCCCAAG | ATGATCGGCG | GCATCGGGCG | CTTCATCAAG |
|  751 | GTGCGGCAGT | ACGACCAGAT | CCTGATCGAG | ATCTGCGGCA | AGAAGGCCAT |
|  801 | CGGCACCGTG | CTGGTGGGCC | CCACCCCCGT | GAACATCATC | GGCCGGAACA |
|  851 | TGCTGACCCA | GCTGGGCTGC | ACCCTGAACT | TCCCCATCAG | CCCCATCGAG |
|  901 | ACCGTGCCCG | TGAAGCTGAA | GCCCGGCATG | GACGGCCCCA | AGTGAAGCA  |
|  951 | GTGGCCCCTG | ACCGAGGTGA | AGATCAAGGC | CCTGACCGCC | ATCTGCGAGG |
| 1001 | AGATGGAGAA | GGAGGGCAAG | ATCACCAAGA | TCGGCCCCGA | GAACCCCTAC |
| 1051 | AACACCCCCA | TCTTCGCCAT | CAAGAAGGAG | GACAGCACCA | AGTGGCGGAA |
| 1101 | GCTGGTGGAC | TTCCGGGAGC | TGAACAAGCG | GACCCAGGAC | TTCTGGGAGG |
| 1151 | TGCAGCTGGG | CATCCCCCAC | CCCGCCGGCC | TGAAGAAGAA | GAAGAGCGTG |
| 1201 | ACCGTGCTGG | ACGTGGGCGA | CGCCTACTTC | AGCGTGCCCC | TGGACGAGGG |
| 1251 | CTTCCGGAAG | TACACCGCCT | TCACCATCCC | CAGCATCAAC | AACGAGACCC |

FIG. 35A

```
1301  CCGGCATCCG  GTACCAGTAC  AACGTGCTGC  CCCAGGGCTG  GAAGGGCAGC
1351  CCCGCCATCT  TCCAGGCCAG  CATGACCAAG  ATCCTGGAGC  CCTTCCGGGC
1401  CAAGAACCCC  GAGATCGTGA  TCTACCAGTA  CATGGCCGCC  CTGTACGTGG
1451  GCAGCGACCT  GGAGATCGGC  CAGCACCGGG  CCAAGATCGA  GGAGCTGCGG
1501  GAGCACCTGC  TGAAGTGGGG  CTTCACCACC  CCCGACAAGA  AGCACCAGAA
1551  GGAGCCCCCC  TTCCTGTGGA  TGGGCTACGA  GCTGCACCCC  GACAAGTGGA
1601  CCGTGCAGCC  CATCCAGCTG  CCCGAGAAGG  ACAGCTGGAC  CGTGAACGAC
1651  ATCCAGAAGC  TGGTGGGCAA  GCTGAACTGG  ACCAGCCAGA  TCTACCCCGG
1701  CATCAAGGTG  CGGCAGCTGT  GCAAGCTGCT  GCGGGGCACC  AAGGCCCTGA
1751  CCGACATCGT  GCCCCTGACC  GAGGAGGCCG  AGCTGGAGCT  GGCCGAGAAC
1801  CGGGAGATCC  TGAAGGAGCC  CGTGCACGGC  GTGTACTACG  ACCCCAGCAA
1851  GGACCTGATC  GCCGAGATCC  AGAAGCAGGG  CGACGACCAG  TGGACCTACC
1901  AGATCTACCA  GGAGCCCTTC  AAGAACCTGA  AAACCGGCAA  GTACGCCAAG
1951  CGGCGGACCA  CCCACACCAA  CGACGTGAAG  CAGCTGACCG  AGGCCGTGCA
2001  GAAGATCAGC  CTGGAGAGCA  TCGTGACCTG  GGGCAAGACC  CCCAAGTTCC
2051  GGCTGCCCAT  CCAGAAGGAG  ACCTGGGAGA  TCTGGTGGAC  CGACTACTGG
2101  CAGGCCACCT  GGATCCCCGA  GTGGGAGTTC  GTGAACACCC  CCCCCCTGGT
2151  GAAGCTGTGG  TACCAGCTGG  AGAAGGAGCC  CATCGCCGGC  GCCGAGACCT
2201  TCTACGTGGA  CGGCGCCGCC  AACCGGGAGA  CCAAGATCGG  CAAGGCCGGC
2251  TACGTGACCG  GCGGGACCA  GCAGAAGATC  GTGACCCTGA  GCGAGACCAC
2301  CAACCAGAAA  ACCGAGCTGC  AGGCCATCCA  GCTGGCCCTG  CAGGACAGCG
2351  AGAGCGAGGT  GAACATCGTG  ACCGACAGCC  AGTACGCCCT  GGGCATCATC
2401  CAGGCCCAGC  CCGACCGGAG  CGAGAGCGAG  CTGGTGAACC  AGATCATCGA
2451  GCAGCTGATC  AAGAAGGAGC  GGGCCTACCT  GAGCTGGGTG  CCCGCCCACA
2501  AGGGCATCGG  CGGCGACGAG  CAGGTGGACA  AGCTGGTGAG  CAGCGGCATC
2551  CGGAAGGTGC  TGTGATCTAG  AGAATTC
```

FIG. 35B

```
  1  SRVSVMTVKT SDTCSSRRRS QLVCKRMPGA DKPVRARQRV LAGVGAGLTM RHQSRLY*EC
 61  TICGVKYRTD A*GENTASGA IRHSGCATVG KGDRCGPLRY YASWRKGDVL QGD*VG*RQG
121  FPSHDVVKRR PVPSLHACRS TLEDPRVPSS FPQGPARQFP SEQTRANSPT SRELQVRRDN
181  PRSETGAERK GTLNFPQITL WQRPLVSIKI GGQTREALLD TGADDTVLED INLPGKWKPK
241  MIGGIGFIK VRQYDQILIE ICGKKAIGTV LVGPTPVNII GRNMLTQLGC TLNFPISPIE
301  TVPVKLKPGM DGPKVKQWPL TEVKIKALTA ICEEMEKEGK ITKIGPENPY NTPIFAIKKE
361  DSTKWRKLVD FRELNKRTQD FWEVQLGIPH PAGLKKKKSV TVLDVGDAYF SVPLDEGFRK
421  YTAFTIPSIN NETPGIRYQY NVLPQGWKGS PAIFQASMTK ILEPFRAKNP EIVIYQYMAA
481  LYVGSDLEIG QHRAKIEELR EHLLKWGFTT PDKKHQKEPP FLWMGYELHP DKWTVQPIQL
541  PEKDSWTVND IQKLVGKLNW TSQIYPGIKV RQLCKLLRGT KALTDIVPLT EEAELELAEN
601  REILKEPVHG VYYDPSKDLI AEIQKQGDDQ WTYQIYQEPF KNLKTGKYAK RRTTHTNDVK
661  QLTEAVQKIS LESIVTWGKT PKFRLPIQKE TWEIWWTDYW QATWIPEWEF VNTPPLVKLW
721  YQLEKEPIAG NRETKIGKAG YVTDRGRQKI VTLSETTNQK TELQAIQLAL
781  QDSESEVNIV TDSQYALGII QAQPDRSESE LVNQIIEQLI KKERAYLSWV PAHKGIGGDE
841  QVDKLVSSGI RKVL*
```

FIGURE 36

SEQUENCE LISTING

```
<160> NUMBER OF SEQ ID NOS: 120

<210> SEQ ID NO 1
<211> LENGTH: 1479
<212> TYPE: DNA
<213> ORGANISM: Human immunodeficiency virus type 1

<400> SEQUENCE: 1
atgggtgcga gagcgtcaat attaagaggg gaaaattag ataaatggga aaaaattagg        60
ttaaggccag ggggaaagaa acattatatg ttaaaacaca tagtatgggc aagcagggag       120
ctggaaagat ttgcacttaa ccctggcctt ttagaaacat cagaaggatg taaacaaata       180
atgaaacagc tacaaccagc tctccagaca ggaacagagg aacttaaatc attatacaac       240
acagtagcaa ctctctattg tgtacatgaa aagatagaag tacgagacac caaggaagcc       300
ttagataaga tagaggaaga acaaaacaaa tgtcagcaaa aaacgcagca ggcaaaagcg       360
gctgacggga aagtcagtca aaattatcct atagtgcaga atctccaagg gcaaatggta       420
catcaagcca tatcacctag aaccttgaat gcatgggtaa aagtaataga agaaaaggct       480
tttagcccag aggtaatacc catgtttaca gcattatcag aaggagccac cccacaagat       540
ttaaacacca tgttaaatac agtggggga catcaagcag ccatgcaaat gttaaaagat       600
actattaatg aagaggctgc agaatgggat agagtacatc cagtccatgc ggggcctatt       660
gcaccaggcc agatgagaga accaagggga agtgacatag caggaactac tagtaccctt       720
caggaacaaa tagcatggat gacaagtaac ccacctattc cagtgggaga catctataaa       780
agatggataa ttctggggtt aaataaaata gtgagaatgt atagccctgt cagcattttg       840
gacataagac aagggccaaa ggaacccttt cgagactatg tagatcggtt ctttaaaact       900
ttaagagctg aacaagctac acaagaagta aaaaattgga tgacagacac cttgttagtc       960
caaaatgcga acccagattg taagaccatt ttgagagcat taggaccagg ggctacatta      1020
gaagaaatga tgacagcatg tcaaggggtg ggaggacctg gtcacaaagc aagagtattg      1080
gctgaggcaa tgagtcaagc aaacagtgga aacataatga tgcagagaag caattttaaa      1140
ggccctagaa gaattgttaa atgttttaac tgtggcaagg aagggcacat agccagaaat      1200
tgcagagccc ctaggaaaaa aggctgttgg aaatgtggaa aggaaggaca ccaaatgaaa      1260
gactgtactg aaaggcaggc taatttttta gggaaaattt ggccttccca caggggagg       1320 ccagggaatt tccttcagaa cagaccagag ccaacagccc caccagcaga gagcttcagg      1380
ttcgaagaga caaccccgc tccgaaacag gagccgatag aaagggaacc cttaacttcc       1440
```
ctcaaatcac tctttggcag cgacccttg tctcaataa            1479

<210> SEQ ID NO 2
<211> LENGTH: 492
<212> TYPE: PRT
<213> ORGANISM: Human immunodeficiency virus type 1

<400> SEQUENCE: 2

```
Met Gly Ala Arg Ala Ser Ile Leu Arg Gly Glu Lys Leu Asp Lys Trp
 1               5                  10                  15

Glu Lys Ile Arg Leu Arg Pro Gly Gly Lys Lys His Tyr Met Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Lys Gln Ile Met Lys Gln Leu
    50                  55                  60

Gln Pro Ala Leu Gln Thr Gly Thr Glu Glu Leu Lys Ser Leu Tyr Asn
65                  70                  75                  80

Thr Val Ala Thr Leu Tyr Cys Val His Glu Lys Ile Glu Val Arg Asp
                85                  90                  95

Thr Lys Glu Ala Leu Asp Lys Ile Glu Glu Glu Gln Asn Lys Cys Gln
            100                 105                 110

Gln Lys Thr Gln Gln Ala Lys Ala Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Val His Pro Val His Ala Gly Pro Ile Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Glu Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Ala Asn
        355                 360                 365
```

```
Ser Gly Asn Ile Met Met Gln Arg Ser Asn Phe Lys Gly Pro Arg Arg
        370                 375                 380

Ile Val Lys Cys Phe Asn Cys Gly Lys Glu Gly His Ile Ala Arg Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Asn Arg
                435                 440                 445

Pro Glu Pro Thr Ala Pro Ala Glu Ser Phe Arg Phe Glu Glu Thr
        450                 455                 460

Thr Pro Ala Pro Lys Gln Glu Pro Ile Glu Arg Glu Pro Leu Thr Ser
465                 470                 475                 480

Leu Lys Ser Leu Phe Gly Ser Asp Pro Leu Ser Gln
                485                 490
```

<210> SEQ ID NO 3
<211> LENGTH: 2997
<212> TYPE: DNA
<213> ORGANISM: Human immunodeficiency virus type 1

<400> SEQUENCE: 3

```
tttagggaaa atttggcctt cccacaaggg gaggccaggg aatttccttc agaacagacc      60
agagccaaca gccccaccag cagagagctt caggttcgaa gaaacaaccc ccgctccgaa     120
acaggagccg agagaaaggg aacccttaac ttccctcaaa tcactctttg gcagcgaccc    180
cttgtctcaa taaaatagg gggccagaca agggaggctc tcttagacac aggagcagat    240
gatacagtat tagaagacat aaatttgcca ggaaaatgga accaaaaat gataggagga    300 attggaggtt ttatcaaagt aagacagtat gatcaaatac ttatagaaat ttgtggaaaa    360
aaggctatag gtacagtatt agtagggcct acacctgtca acataattgg cagaaacatg    420
ttgactcagc ttggatgcac actaaacttt ccaatcagtc ccattgaaac tgtaccagta    480
aaactgaagc caggaatgga tggcccaaag gttaaacaat ggccgttaac agaagagaaa    540
ataaaagcat taacagcaat ttgtgaagaa atggaaaagg aaggaaaaat tacaaaaatt    600
gggcctgaaa atccatataa cactccaata tttgccataa aaaagaaaga cagcactaag    660
tggagaaaat tagtagattt cagggaactc aataaaagaa ctcaagactt tggggaggtt    720
caattaggaa taccacaccc agcagggtta aaaagaaaa atcagtgac agtactggat    780 gtgggagatg catatttttc agttccttta gatgaaggct tcaggaaata tactgcattc    840
accatacctg tataaacaa tgaaacacca gggattagat atcaatataa tgtgcttcca    900
caaggatgga aagggtcacc agcaatattc caggtagca tgacaaaaat cttagagccc    960
tttagagctc aaaatccaga aatagtcatc tatcaatata tggatgactt gtatgtagga    1020
tctgacttag aaatagggca acatagagca aaaatagaag agttaagaga acatctatta    1080
aagtggggat ttaccacacc agacaaaaaa catcagaaag aaccccatt tctttggatg    1140 gggtatgaac tccatcctga caaatggaca gtacagccta tagctgcc agaaaaggat    1200 agctggactg tcaatgatat acagaagtta gtgggaaaat taaactgggc aagtcagatt    1260
tacccaggga ttaaagtaag gcaactttgt aagctcctta gggggaccaa agcactaaca    1320
gacatagtac cactaactga agaagcagaa ttagaattgg cagagaacag ggaaattcta    1380
aaagaaccag tgcatggagt atattatgac ccatcaaaag acttgatagc tgaaatacag    1440
```

-continued

```
aaacagggggg atgaccaatg gacatatcaa atttaccaag aaccattcaa aaacctgaag    1500
acaggaaagt atgcaaaaag gaggactacc cacactaatg atgtaaaaca gttaacagag    1560
gcagtgcaaa aatatccttt ggaaagcata gtaatatggg aaagactcc taaatttaga    1620 ctacccatcc aaaagaaaac atgggaaata tggtggacag actattggca agccacatgg    1680
attcctgagt gggagtttgt aatacccct ccctagtaa aactatggta ccagctagaa    1740
aaagaaccca tagcaggagc agaaactttc tatgtagatg gagcagctaa tagggaaact    1800
aaaataggaa aagcggggta tgttactgac agaggaaggc agaaaattgt aactctaagt    1860
gaaacaacaa atcagaagac tgaattacaa gcaattcagc tagctttgca agattcagaa    1920
tcagaagtaa acataataac agactcacag tacgcattag gaatcattca agcacaacca    1980
gataggagtg aatcagagtt ggtcaatcaa ataatagaac aattaataaa aaaggaaagg    2040
gtctatctgt catgggtacc agcacacaac ggacttgcag gaaatgaaca tgtagataaa    2100
ttagtaagta ggggaatcag gaaagtgctg gttctagatg gaatagataa ggctcatgaa    2160
gagcatgaaa agtatcacag caattggaga gcaatggcta gtgagtttaa tctgccaccc    2220
gtagtagcaa agagaaatagt agccagctgt gataaatgtc agctaaaagg ggaagccata    2280
catggacaag tagattgtag tccggggata tggcaattag attgtacaca tttagaagga    2340
aaaatcatcc tggtagcagt ccatgtagcc agtggctaca tagaagcaga ggttatccca    2400
gcagaaacag gacaagaaac agcatactat atactaaaat tagcaggaag atggccagtc    2460
aaagtaatac atacagacaa tggcagtaat ttcaccagtg ctgcagttaa ggcagcctgt    2520
tggtgggcag gtatccaaca ggaatttggg attccctaca tccccaaag tcagggagta    2580 gtagaatcca tgaataaaga attaagaaa atcataggc aggtaagaga tcaagctgag    2640
caccttaaga cagcagtaca aatggcagta ttcattcaca atttttaaaag aaaaggggggg    2700 attgggggt acagtgcagg ggaaagaata atagacataa tagcaacaga catacaaact    2760
aaagaattac aaaaacaaat tataaaaatt caaaattttc gggtttatta cagagacagc    2820
agagatccta tttggaaagg accagccaag ctactctgga aaggtgaagg ggcagtagta    2880
atacaagaca acagtgacat aaaggtagta ccaaggagga agtaaaaat cattagggac    2940 tatggaaaac agatggcagg tgctgattgt gtggcaggta gacaggatga agattag      2997
```

<210> SEQ ID NO 4
<211> LENGTH: 998
<212> TYPE: PRT
<213> ORGANISM: Human immunodeficiency virus type 1

<400> SEQUENCE: 4

```
Phe Arg Glu Asn Leu Ala Phe Pro Gln Gly Glu Ala Arg Glu Phe Pro
1               5                   10                  15

Ser Glu Gln Thr Arg Ala Asn Ser Pro Thr Ser Arg Glu Leu Gln Val
            20                  25                  30

Arg Arg Asn Asn Pro Arg Ser Glu Thr Gly Ala Glu Arg Lys Gly Thr
        35                  40                  45

Leu Asn Phe Pro Gln Ile Thr Leu Trp Gln Arg Pro Leu Val Ser Ile
    50                  55                  60

Lys Ile Gly Gly Gln Thr Arg Glu Ala Leu Leu Asp Thr Gly Ala Asp
65                  70                  75                  80

Asp Thr Val Leu Glu Asp Ile Asn Leu Pro Gly Lys Trp Lys Pro Lys
                85                  90                  95

Met Ile Gly Gly Ile Gly Gly Phe Ile Lys Val Arg Gln Tyr Asp Gln
            100                 105                 110
```

```
Ile Leu Ile Glu Ile Cys Gly Lys Lys Ala Ile Gly Thr Val Leu Val
            115                 120                 125
Gly Pro Thr Pro Val Asn Ile Ile Gly Arg Asn Met Leu Thr Gln Leu
        130                 135                 140
Gly Cys Thr Leu Asn Phe Pro Ile Ser Pro Ile Glu Thr Val Pro Val
145                 150                 155                 160
Lys Leu Lys Pro Gly Met Asp Gly Pro Lys Val Lys Gln Trp Pro Leu
                165                 170                 175
Thr Glu Glu Lys Ile Lys Ala Leu Thr Ala Ile Cys Glu Glu Met Glu
            180                 185                 190
Lys Glu Gly Lys Ile Thr Lys Ile Gly Pro Glu Asn Pro Tyr Asn Thr
        195                 200                 205
Pro Ile Phe Ala Ile Lys Lys Asp Ser Thr Lys Trp Arg Lys Leu
        210                 215                 220
Val Asp Phe Arg Glu Leu Asn Lys Arg Thr Gln Asp Phe Trp Glu Val
225                 230                 235                 240
Gln Leu Gly Ile Pro His Pro Ala Gly Leu Lys Lys Lys Ser Val
                245                 250                 255
Thr Val Leu Asp Val Gly Asp Ala Tyr Phe Ser Val Pro Leu Asp Glu
            260                 265                 270
Gly Phe Arg Lys Tyr Thr Ala Phe Thr Ile Pro Ser Ile Asn Asn Glu
        275                 280                 285
Thr Pro Gly Ile Arg Tyr Gln Tyr Asn Val Leu Pro Gln Gly Trp Lys
    290                 295                 300
Gly Ser Pro Ala Ile Phe Gln Gly Ser Met Thr Lys Ile Leu Glu Pro
305                 310                 315                 320
Phe Arg Ala Gln Asn Pro Glu Ile Val Ile Tyr Gln Tyr Met Asp Asp
                325                 330                 335
Leu Tyr Val Gly Ser Asp Leu Glu Ile Gly Gln His Arg Ala Lys Ile
            340                 345                 350
Glu Glu Leu Arg Glu His Leu Leu Lys Trp Gly Phe Thr Thr Pro Asp
        355                 360                 365
Lys Lys His Gln Lys Glu Pro Pro Phe Leu Trp Met Gly Tyr Glu Leu
    370                 375                 380
His Pro Asp Lys Trp Thr Val Gln Pro Ile Gln Leu Pro Glu Lys Asp
385                 390                 395                 400
Ser Trp Thr Val Asn Asp Ile Gln Lys Leu Val Gly Lys Leu Asn Trp
                405                 410                 415
Ala Ser Gln Ile Tyr Pro Gly Ile Lys Val Arg Gln Leu Cys Lys Leu
            420                 425                 430
Leu Arg Gly Thr Lys Ala Leu Thr Asp Ile Val Pro Leu Thr Glu Glu
        435                 440                 445
Ala Glu Leu Glu Leu Ala Glu Asn Arg Glu Ile Leu Lys Glu Pro Val
    450                 455                 460
His Gly Val Tyr Tyr Asp Pro Ser Lys Asp Leu Ile Ala Glu Ile Gln
465                 470                 475                 480
Lys Gln Gly Asp Asp Gln Trp Thr Tyr Gln Ile Tyr Gln Glu Pro Phe
                485                 490                 495
Lys Asn Leu Lys Thr Gly Lys Tyr Ala Lys Arg Thr Thr His Thr
            500                 505                 510
Asn Asp Val Lys Gln Leu Thr Glu Ala Val Gln Lys Ile Ser Leu Glu
        515                 520                 525
Ser Ile Val Ile Trp Gly Lys Thr Pro Lys Phe Arg Leu Pro Ile Gln
```

-continued

```
                530                 535                 540
Lys Glu Thr Trp Glu Ile Trp Trp Thr Asp Tyr Trp Gln Ala Thr Trp
545                 550                 555                 560

Ile Pro Glu Trp Glu Phe Val Asn Thr Pro Leu Val Lys Leu Trp
                565                 570                 575

Tyr Gln Leu Glu Lys Glu Pro Ile Ala Gly Ala Glu Thr Phe Tyr Val
                580                 585                 590

Asp Gly Ala Ala Asn Arg Glu Thr Lys Ile Gly Lys Ala Gly Tyr Val
                595                 600                 605

Thr Asp Arg Gly Arg Gln Lys Ile Val Thr Leu Ser Glu Thr Thr Asn
610                 615                 620

Gln Lys Thr Glu Leu Gln Ala Ile Gln Leu Ala Leu Gln Asp Ser Glu
625                 630                 635                 640

Ser Glu Val Asn Ile Ile Thr Asp Ser Gln Tyr Ala Leu Gly Ile Ile
                        645                 650                 655

Gln Ala Gln Pro Asp Arg Ser Glu Ser Glu Leu Val Asn Gln Ile Ile
                660                 665                 670

Glu Gln Leu Ile Lys Lys Glu Arg Val Tyr Leu Ser Trp Val Pro Ala
                675                 680                 685

His Asn Gly Leu Ala Gly Asn Glu His Val Asp Lys Leu Val Ser Arg
690                 695                 700

Gly Ile Arg Lys Val Leu Val Leu Asp Gly Ile Asp Lys Ala His Glu
705                 710                 715                 720

Glu His Glu Lys Tyr His Ser Asn Trp Arg Ala Met Ala Ser Glu Phe
                        725                 730                 735

Asn Leu Pro Pro Val Val Ala Arg Glu Ile Val Ala Ser Cys Asp Lys
                740                 745                 750

Cys Gln Leu Lys Gly Glu Ala Ile His Gly Gln Val Asp Cys Ser Pro
                755                 760                 765

Gly Ile Trp Gln Leu Asp Cys Thr His Leu Glu Gly Lys Ile Ile Leu
770                 775                 780

Val Ala Val His Val Ala Ser Gly Tyr Ile Glu Ala Glu Val Ile Pro
785                 790                 795                 800

Ala Glu Thr Gly Gln Glu Thr Ala Tyr Tyr Ile Leu Lys Leu Ala Gly
                805                 810                 815

Arg Trp Pro Val Lys Val Ile His Thr Asp Asn Gly Ser Asn Phe Thr
                820                 825                 830

Ser Ala Ala Val Lys Ala Ala Cys Trp Trp Ala Gly Ile Gln Gln Glu
                835                 840                 845

Phe Gly Ile Pro Tyr Asn Pro Gln Ser Gln Gly Val Val Glu Ser Met
850                 855                 860

Asn Lys Glu Leu Lys Lys Ile Ile Gly Gln Val Arg Asp Gln Ala Glu
865                 870                 875                 880

His Leu Lys Thr Ala Val Gln Met Ala Val Phe Ile His Asn Phe Lys
                        885                 890                 895

Arg Lys Gly Gly Ile Gly Gly Tyr Ser Ala Gly Glu Arg Ile Ile Asp
                900                 905                 910

Ile Ile Ala Thr Asp Ile Gln Thr Lys Glu Leu Gln Lys Gln Ile Ile
                915                 920                 925

Lys Ile Gln Asn Phe Arg Val Tyr Tyr Arg Asp Ser Arg Asp Pro Ile
                930                 935                 940

Trp Lys Gly Pro Ala Lys Leu Leu Trp Lys Gly Glu Gly Ala Val Val
945                 950                 955                 960
```

```
Ile Gln Asp Asn Ser Asp Ile Lys Val Val Pro Arg Arg Lys Val Lys
                965                 970                 975
Ile Ile Arg Asp Tyr Gly Lys Gln Met Ala Gly Ala Asp Cys Val Ala
            980                 985                 990
Gly Arg Gln Asp Glu Asp
        995

<210> SEQ ID NO 5
<211> LENGTH: 2535
<212> TYPE: DNA
<213> ORGANISM: Human immunodeficiency virus type 1

<400> SEQUENCE: 5
atgagagtga tggggataca gaggaattgg ccacaatggt ggatatgggg caccttaggc      60
ttttggatga taataatttg tagggtggtg gggaacttga acttgtgggt cacagtctat     120
tatggggtac ctgtgtggaa agaagcaaaa actactctat tctgtgcatc agatgctaaa     180
gcatatgata agaagtaca taatgtctgg gctacacatg cctgtgtacc cacagacccc      240
aacccacgag aaatagtttt ggaaaatgta acagaaaatt ttaacatgtg gaaaatgac      300 atggtggatc agatgcatga ggatataatc agtttatggg atcaaagcct aaaaccatgt     360
gtaaagttga ccccactctg tgtcactta aattgtacaa atgcacctgc ctacaataat      420
agcatgcatg gagaaatgaa aaattgctct ttcaatacaa ccacagagat aagagatagg     480
aaacagaaag cgtatgcact tttttataaa cctgatgtag tgccacttaa taggagagaa     540
gagaataatg gacaggaga gtatatatta ataaattgca attcctcaac cataacacaa      600
gcctgtccaa aggtcacttt tgacccaatt cctatacatt attgtgctcc agctggttat     660
gcgattctaa agtgtaataa taagacattc aatgggacag gaccatgcaa taatgtcagc     720
acagtacaat gtacacatgg aattatgcca gtggtatcaa ctcaattact gttaaatggt     780
agcctagcag aagaagagat aataattaga tctgaaaatc tgacaaacaa tatcaaaaca     840
ataatagtcc accttaataa atctgtagaa attgtgtgta agacccaa caataataca       900 agaaaaagta taaggatagg accaggacaa acattctatg caacaggtga ataatagga     960 aacataagag aagcacattg taacattagt aaaagtaact ggaccagtac tttagaacag    1020
gtaaagaaaa aattaaaaga acactacaat aagacaatag aatttaaccc accctcagga    1080
ggggatctag aagttacaac acatagcttt aattgtagag gagaattttt ctattgcaat    1140
acaacaaaac tgttttcaaa caacagtgat tcaaacaacg aaaccatcac actcccatgc    1200
aagataaaac aaattataaa catgtggcag aaggtaggac gagcaatgta tgcccctccc    1260
attgaaggaa acataacatg taaatcaaat atcacaggac tactattgac acgtgatgga    1320
ggaaagaata caacaaatga gatattcaga ccggaggag gaaatatgaa ggacaattgg    1380
agaagtgaat tatataaata taaagtggta gaaattgagc cattgggagt agcacccact    1440
aaatcaaaaa ggagagtggt ggagagagaa aaaagagcag tgggactagg agctgtactc    1500
cttgggttct tgggagcagc aggaagcact atgggcgcgg cgtcaataac gctgacggta    1560
caggccagac aactgttgtc tggtatagtg caacagcaaa gcaatttgct gagagctata    1620
gaggcgcaac agcatatgtt gcaactcacg gtctggggca ttaagcagct ccagacaaga    1680
gtcttggcta tagagagata cctaaaggat caacagctcc tagggctttg gggctgctct    1740
ggaaaaatca tctgcaccac tgctgtgcct tggaactcca gttggagtaa taaatctcaa    1800
gaagatattt gggataacat gacctggatg cagtgggata gagaaattag taattacaca    1860
ggcacaatat ataggttact tgaagactcg caaaaccagc aggagaaaaa tgaaaaagat    1920
```

-continued

```
ttattagcat tggacagttg gaaaaacttg tggaattggt ttaacataac aaattggctg   1980
tggtatataa aaatattcat catgatagta ggaggcttga taggtttgag aataattttt   2040
ggtgtactcg ctatagtgaa aagagttagg cagggatact caccttttgtc gtttcagacc   2100 cttaccccaa gcccgagggg tcccgacagg ctcggaagaa tcgaagaaga aggtggagag   2160
caagacaaag acagatccat tcgattagtg agcggattct tagcacttgc ctgggacgat   2220
ctgcggagcc tgtgcctctt cagctaccac cacttgagag acttcatatt gattgcagcg   2280
agagcagcgg aacttctggg acgcagcagt ctcaggggac tgcagagagg gtgggaagcc   2340
cttaagtatc tgggaaatct tgtgcagtat gggggtctgg agctaaaaag aagtgctatt   2400
aaactgtttg ataccatagc aatagcagta gctgaaggaa cagataggat tcttgaagta   2460
atacagagaa tttgtagagc tatccgccac atacctataa gaataagaca gggctttgaa   2520
gcagctttgc aataa                                                    2535
```

<210> SEQ ID NO 6
<211> LENGTH: 844
<212> TYPE: PRT
<213> ORGANISM: Human immunodeficiency virus type 1

<400> SEQUENCE: 6

```
Met Arg Val Met Gly Ile Gln Arg Asn Trp Pro Gln Trp Trp Ile Trp
1               5                   10                  15

Gly Thr Leu Gly Phe Trp Met Ile Ile Ile Cys Arg Val Val Gly Asn
            20                  25                  30

Leu Asn Leu Trp Val Thr Val Tyr Tyr Gly Val Pro Val Trp Lys Glu
        35                  40                  45

Ala Lys Thr Thr Leu Phe Cys Ala Ser Asp Ala Lys Ala Tyr Asp Lys
    50                  55                  60

Glu Val His Asn Val Trp Ala Thr His Ala Cys Val Pro Thr Asp Pro
65                  70                  75                  80

Asn Pro Arg Glu Ile Val Leu Glu Asn Val Thr Glu Asn Phe Asn Met
                85                  90                  95

Trp Lys Asn Asp Met Val Asp Gln Met His Glu Asp Ile Ile Ser Leu
            100                 105                 110

Trp Asp Gln Ser Leu Lys Pro Cys Val Lys Leu Thr Pro Leu Cys Val
        115                 120                 125

Thr Leu Asn Cys Thr Asn Ala Pro Ala Tyr Asn Asn Ser Met His Gly
    130                 135                 140

Glu Met Lys Asn Cys Ser Phe Asn Thr Thr Thr Glu Ile Arg Asp Arg
145                 150                 155                 160

Lys Gln Lys Ala Tyr Ala Leu Phe Tyr Lys Pro Asp Val Val Pro Leu
                165                 170                 175

Asn Arg Arg Glu Glu Asn Asn Gly Thr Gly Glu Tyr Ile Leu Ile Asn
            180                 185                 190

Cys Asn Ser Ser Thr Ile Thr Gln Ala Cys Pro Lys Val Thr Phe Asp
        195                 200                 205

Pro Ile Pro Ile His Tyr Cys Ala Pro Ala Gly Tyr Ala Ile Leu Lys
    210                 215                 220

Cys Asn Asn Lys Thr Phe Asn Gly Thr Gly Pro Cys Asn Asn Val Ser
225                 230                 235                 240

Thr Val Gln Cys Thr His Gly Ile Met Pro Val Val Ser Thr Gln Leu
                245                 250                 255

Leu Leu Asn Gly Ser Leu Ala Glu Glu Glu Ile Ile Ile Arg Ser Glu
```

```
                260                 265                 270
Asn Leu Thr Asn Asn Ile Lys Thr Ile Ile Val His Leu Asn Lys Ser
            275                 280                 285
Val Glu Ile Val Cys Thr Arg Pro Asn Asn Thr Arg Lys Ser Ile
    290                 295                 300
Arg Ile Gly Pro Gly Gln Thr Phe Tyr Ala Thr Gly Glu Ile Ile Gly
305                 310                 315                 320
Asn Ile Arg Glu Ala His Cys Asn Ile Ser Lys Ser Asn Trp Thr Ser
                325                 330                 335
Thr Leu Glu Gln Val Lys Lys Lys Leu Lys Glu His Tyr Asn Lys Thr
            340                 345                 350
Ile Glu Phe Asn Pro Pro Ser Gly Gly Asp Leu Glu Val Thr Thr His
            355                 360                 365
Ser Phe Asn Cys Arg Gly Glu Phe Phe Tyr Cys Asn Thr Thr Lys Leu
    370                 375                 380
Phe Ser Asn Asn Ser Asp Ser Asn Asn Glu Thr Ile Thr Leu Pro Cys
385                 390                 395                 400
Lys Ile Lys Gln Ile Ile Asn Met Trp Gln Lys Val Gly Arg Ala Met
                405                 410                 415
Tyr Ala Pro Pro Ile Glu Gly Asn Ile Thr Cys Lys Ser Asn Ile Thr
            420                 425                 430
Gly Leu Leu Leu Thr Arg Asp Gly Gly Lys Asn Thr Thr Asn Glu Ile
            435                 440                 445
Phe Arg Pro Gly Gly Gly Asn Met Lys Asp Asn Trp Arg Ser Glu Leu
    450                 455                 460
Tyr Lys Tyr Lys Val Val Glu Ile Glu Pro Leu Gly Val Ala Pro Thr
465                 470                 475                 480
Lys Ser Lys Arg Arg Val Val Glu Arg Glu Lys Arg Ala Val Gly Leu
                485                 490                 495
Gly Ala Val Leu Leu Gly Phe Leu Gly Ala Ala Gly Ser Thr Met Gly
            500                 505                 510
Ala Ala Ser Ile Thr Leu Thr Val Gln Ala Arg Gln Leu Leu Ser Gly
            515                 520                 525
Ile Val Gln Gln Gln Ser Asn Leu Leu Arg Ala Ile Glu Ala Gln Gln
    530                 535                 540
His Met Leu Gln Leu Thr Val Trp Gly Ile Lys Gln Leu Gln Thr Arg
545                 550                 555                 560
Val Leu Ala Ile Glu Arg Tyr Leu Lys Asp Gln Gln Leu Leu Gly Leu
                565                 570                 575
Trp Gly Cys Ser Gly Lys Ile Ile Cys Thr Thr Ala Val Pro Trp Asn
            580                 585                 590
Ser Ser Trp Ser Asn Lys Ser Gln Glu Asp Ile Trp Asp Asn Met Thr
    595                 600                 605
Trp Met Gln Trp Asp Arg Glu Ile Ser Asn Tyr Thr Gly Thr Ile Tyr
    610                 615                 620
Arg Leu Leu Glu Asp Ser Gln Asn Gln Gln Glu Lys Asn Glu Lys Asp
625                 630                 635                 640
Leu Leu Ala Leu Asp Ser Trp Lys Asn Leu Trp Asn Trp Phe Asn Ile
                645                 650                 655
Thr Asn Trp Leu Trp Tyr Ile Lys Ile Phe Ile Met Ile Val Gly Gly
            660                 665                 670
Leu Ile Gly Leu Arg Ile Ile Phe Gly Val Leu Ala Ile Val Lys Arg
            675                 680                 685
```

| | | | | | | | | | | | |
|---|---|---|---|---|---|---|---|---|---|---|---|
|Val|Arg|Gln|Gly|Tyr|Ser|Pro|Leu|Ser|Phe|Gln|Thr|Leu|Thr|Pro|Ser|
| |690| | | |695| | | |700| | | | | | |

Val Arg Gln Gly Tyr Ser Pro Leu Ser Phe Gln Thr Leu Thr Pro Ser
    690             695             700

Pro Arg Gly Pro Asp Arg Leu Gly Arg Ile Glu Glu Gly Gly Glu
705             710             715             720

Gln Asp Lys Asp Arg Ser Ile Arg Leu Val Ser Gly Phe Leu Ala Leu
                725             730             735

Ala Trp Asp Asp Leu Arg Ser Leu Cys Leu Phe Ser Tyr His His Leu
            740             745             750

Arg Asp Phe Ile Leu Ile Ala Ala Arg Ala Ala Glu Leu Leu Gly Arg
            755             760             765

Ser Ser Leu Arg Gly Leu Gln Arg Gly Trp Glu Ala Leu Lys Tyr Leu
770             775             780

Gly Asn Leu Val Gln Tyr Gly Gly Leu Glu Leu Lys Arg Ser Ala Ile
785             790             795             800

Lys Leu Phe Asp Thr Ile Ala Ile Ala Val Ala Glu Gly Thr Asp Arg
                805             810             815

Ile Leu Glu Val Ile Gln Arg Ile Cys Arg Ala Ile Arg His Ile Pro
            820             825             830

Ile Arg Ile Arg Gln Gly Phe Glu Ala Ala Leu Gln
        835             840

<210> SEQ ID NO 7
<211> LENGTH: 1479
<212> TYPE: DNA
<213> ORGANISM: Human immunodeficiency virus type 1

<400> SEQUENCE: 7

```
atggctgctc gcgcatctat cctcagaggc gaaaagttgg ataagtggga aaaaatcaga      60
ctcaggccag gaggtaaaaa acactacatg ctgaagcata tcgtgtgggc atctagggag     120
ttggagagat ttgcactgaa ccccggactg ctggaaacct cagagggctg taagcaaatc     180
atgaaacagc tccaaccagc cttgcagacc ggaacagaag agctgaagtc cctttacaat     240
accgtggcaa ccctctattg cgtccacgag aagatcgagg tgagagacac aaaggaggcc     300
ctggacaaaa tcgaggagga gcagaataag tgccagcaga agacccagca ggcaaaggct     360
gctgacggaa aggtctctca gaactatcct atcgttcaga accttcaggg gcagatggtg     420
caccaagcaa tcagccctag aaccctgaac gcatgggtga aggtgatcga ggagaaagcc     480
tttctcccg aggttatccc catgtttacc gccctgagcg aaggcgccac tcctcaagac     540
ctgaacacta tgctgaacac agtgggagga caccaggccg ctatgcagat gttgaaggat     600
accatcaacg aggaggcagc cgaatgggac cgcctccacc ccgtgcacgc cggacctatc     660
gcccccggac aaatgagaga acctcgcgga agtgatattg ccggtactac cagcacccct     720
caagagcaga ttgcttggat gaccagcaac ccacccatcc cagtgggcga tatttacaaa     780
aggtggatta ttctggggct gaacaaaatt gtgagaatgt actcccccgt ctccatcctc     840
gacatccgcc aaggacccaa ggagcctttt agggattacg tggacagatt cttcaaaacc     900
cttagagctg agcaagccac tcaggaggtt aagaactgga tgacagatac tctgctcgtg     960
caaaacgcta accccgattg caaaaccatc ttgagagctc tcggtccagg tgccaccctt    1020
gaggaaatga tgacagcatg tcaaggcgtg gaggacctg gcacaaggc cagagttctc    1080
gctgaggcca tgagccagac aaactcaggc aatatcatga tgcagaggag taactttaag    1140
ggtcccagga gaatcgtcaa gtgcttcaat tgtggcaagg agggtcacat tgccaggaac    1200
tgccgcgccc ccaggaagaa aggctgctgg aagtgtggca agagggggcca ccagatgaag    1260
```

```
gattgcaccg agcgccaagc aaacttcctg ggaaagattt ggcccagtca taagggccgc    1320
cctggcaact tccttcaaaa cagacccgag cctaccgccc ccccgctga gtctttcaga     1380 tttgaggaga ccaccccgc tccaaagcag gagccaattg agagagagcc tctcaccagt     1440
ctcaaaagcc tctttggtag cgaccccctc agccaataa                          1479

<210> SEQ ID NO 8
<211> LENGTH: 492
<212> TYPE: PRT
<213> ORGANISM: Human immunodeficiency virus type 1

<400> SEQUENCE: 8

Met Ala Ala Arg Ala Ser Ile Leu Arg Gly Glu Lys Leu Asp Lys Trp
1               5                   10                  15

Glu Lys Ile Arg Leu Arg Pro Gly Gly Lys Lys His Tyr Met Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Lys Gln Ile Met Lys Gln Leu
    50                  55                  60

Gln Pro Ala Leu Gln Thr Gly Thr Glu Glu Leu Lys Ser Leu Tyr Asn
65                  70                  75                  80

Thr Val Ala Thr Leu Tyr Cys Val His Glu Lys Ile Glu Val Arg Asp
                85                  90                  95

Thr Lys Glu Ala Leu Asp Lys Ile Glu Glu Glu Gln Asn Lys Cys Gln
            100                 105                 110

Gln Lys Thr Gln Gln Ala Lys Ala Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Ile Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Glu Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
```

```
                     340              345                350
Pro Gly His Lys Ala Arg Val Leu Ala Glu Ala Met Ser Gln Thr Asn
            355                 360                365

Ser Gly Asn Ile Met Met Gln Arg Ser Asn Phe Lys Gly Pro Arg Arg
        370                 375                380

Ile Val Lys Cys Phe Asn Cys Gly Lys Glu Gly His Ile Ala Arg Asn
385                 390                395                400

Cys Arg Ala Pro Arg Lys Lys Gly Cys Trp Lys Cys Gly Lys Glu Gly
                405                410                415

His Gln Met Lys Asp Cys Thr Glu Arg Gln Ala Asn Phe Leu Gly Lys
            420                 425                430

Ile Trp Pro Ser His Lys Gly Arg Pro Gly Asn Phe Leu Gln Asn Arg
        435                 440                445

Pro Glu Pro Thr Ala Pro Pro Ala Glu Ser Phe Arg Phe Glu Glu Thr
    450                 455                460

Thr Pro Ala Pro Lys Gln Glu Pro Ile Glu Arg Glu Pro Leu Thr Ser
465                 470                475                480

Leu Lys Ser Leu Phe Gly Ser Asp Pro Leu Ser Gln
                485                 490

<210> SEQ ID NO 9
<211> LENGTH: 2117
<212> TYPE: DNA
<213> ORGANISM: Human immunodeficiency virus type 1

<400> SEQUENCE: 9
ccttcccaca agggccggcc aggcaatttc cttcagaaca gaccagagcc aacagcccca      60
ccagcagaga gcttcaggtt cgaagagaca ccccccgctc cgaaacagga gccgagagaa     120
agggaaccct taacttccct caaatcactc tttggcagcg accccttgtc tcaataaaaa     180
tcggcggcca gacccgggag gccctgctgg acaccggcgc cgacgacacc gtgctggagg     240
acatcaacct gcccggcaag tggaagccca agatgatcgg cggcatcggc ggcttcatca     300
aggtgcggca gtacgaccag atcctgatcg agatctgcgg caagaaggcc atcggcaccg     360
tgctggtggg ccccaccccc gtgaacatca tcggccggaa catgctgacc cagctgggct     420
gcaccctgaa cttccccatc agccccatcg agaccgtgcc cgtgaagctg aagcccggca     480
tggacggccc caaggtgaag cagtggcccc tgaccgaggt gaagatcaag gccctgaccg     540
ccatctgcga ggagatggag aaggagggca gatcaccaa gatcggcccc gagaacccct     600
acaacacccc catcttcgcc atcaagaagg aggacagcac caagtggcgg aagctggtgg     660
acttccggga gctgaacaag cggacccagg acttctggga ggtgcagctg ggcatccccc     720
accccgccgg cctgaagaag aagaagagcg tgaccgtgct ggacgtgggc gacgcctact     780
tcagcgtgcc cctggacgag ggcttccgga gtacaccgc cttcaccatc cccagcatca     840
acaacgagac ccccggcatc cggtaccagt acaacgtgct gccccagggc tggaagggca     900
gccccgccat cttccaggcc agcatgacca gatcctgga gccctttccgg gccaagaacc     960
ccgagatcgt gatctaccag tacatggccg ccctgtacgt gggcagcgac ctggagatcg    1020
gccagcaccg ggccaagatc gaggagctgc gggagcacct gctgaagtgg ggcttcacca    1080
cccccgacaa gaagcaccag aaggagcccc cttcctgtg gatgggctac gagctgcacc    1140
ccgacaagtg gaccgtgcag cccatccagc tgcccgagaa ggacagctgg accgtgaacg    1200
acatccagaa gctggtgggc aagctgaact ggaccagcca gatctacccc ggcatcaagg    1260
tgcggcagct gtgcaagctg ctgcggggca ccaaggccct gaccgacatc gtgcccctga    1320
```

```
ccgaggaggc cgagctggag ctggccgaga accgggagat cctgaaggag cccgtgcacg      1380
gcgtgtacta cgaccccagc aaggacctga tcgccgagat ccagaagcag ggcgacgacc      1440
agtggaccta ccagatctac caggagccct tcaagaacct gaaaaccggc aagtacgcca      1500
agcggcggac cacccacacc aacgacgtga agcagctgac cgaggccgtg cagaagatca      1560
gcctggagag catcgtgacc tggggcaaga ccccccaagtt ccggctgccc atccagaagg      1620
agacctggga gatctggtgg accgactact ggcaggccac ctggatcccc gagtgggagt      1680
tcgtgaacac ccccccccctg gtgaagctgt ggtaccagct ggagaaggag cccatcgccg      1740
gcgccgagac cttctacgtg gacggcgccg ccaaccggga gaccaagatc ggcaaggccg      1800
gctacgtgac cgaccggggc cggcagaaga tcgtgaccct gagcgagacc accaaccaga      1860
aaaccgagct gcaggccatc cagctggccc tgcaggacag cgagagcgag gtgaacatcg      1920
tgaccgacag ccagtacgcc ctgggcatca tccaggccca gcccgaccgg agcgagagcg      1980
agctggtgaa ccagatcatc gagcagctga tcaagaagga gcgggcctac ctgagctggg      2040
tgcccgccca aagggcatc ggcggcgacg agcaggtgga caagctggtg agcagcggca      2100
tccggaaggt gctgtga                                                    2117
```

<210> SEQ ID NO 10
<211> LENGTH: 696
<212> TYPE: PRT
<213> ORGANISM: Human immunodeficiency virus type 1

<400> SEQUENCE: 10

```
Phe Pro Ser Glu Gln Thr Arg Ala Asn Ser Pro Thr Ser Arg Glu Leu
1               5                   10                  15

Gln Val Arg Arg Asp Asn Pro Arg Ser Glu Thr Gly Ala Glu Arg Lys
            20                  25                  30

Gly Thr Leu Asn Phe Pro Gln Ile Thr Leu Trp Gln Arg Pro Leu Val
        35                  40                  45

Ser Ile Lys Ile Gly Gly Gln Thr Arg Glu Ala Leu Leu Asp Thr Gly
    50                  55                  60

Ala Asp Asp Thr Val Leu Glu Asp Ile Asn Leu Pro Gly Lys Trp Lys
65                  70                  75                  80

Pro Lys Met Ile Gly Gly Ile Gly Gly Phe Ile Lys Val Arg Gln Tyr
                85                  90                  95

Asp Gln Ile Leu Ile Glu Ile Cys Gly Lys Lys Ala Ile Gly Thr Val
            100                 105                 110

Leu Val Gly Pro Thr Pro Val Asn Ile Ile Gly Arg Asn Met Leu Thr
        115                 120                 125

Gln Leu Gly Cys Thr Leu Asn Phe Pro Ile Ser Pro Ile Glu Thr Val
    130                 135                 140

Pro Val Lys Leu Lys Pro Gly Met Asp Gly Pro Lys Val Lys Gln Trp
145                 150                 155                 160

Pro Leu Thr Glu Val Lys Ile Lys Ala Leu Thr Ala Ile Cys Glu Glu
                165                 170                 175

Met Glu Lys Glu Gly Lys Ile Thr Lys Ile Gly Pro Glu Asn Pro Tyr
            180                 185                 190

Asn Thr Pro Ile Phe Ala Ile Lys Lys Glu Asp Ser Thr Lys Trp Arg
        195                 200                 205

Lys Leu Val Asp Phe Arg Glu Leu Asn Lys Arg Thr Gln Asp Phe Trp
    210                 215                 220

Glu Val Gln Leu Gly Ile Pro His Pro Ala Gly Leu Lys Lys Lys Lys
```

```
                    225                 230                 235                 240
Ser Val Thr Val Leu Asp Val Gly Asp Ala Tyr Phe Ser Val Pro Leu
                245                 250                 255

Asp Glu Gly Phe Arg Lys Tyr Thr Ala Phe Thr Ile Pro Ser Ile Asn
                260                 265                 270

Asn Glu Thr Pro Gly Ile Arg Tyr Gln Tyr Asn Val Leu Pro Gln Gly
                275                 280                 285

Trp Lys Gly Ser Pro Ala Ile Phe Gln Ala Ser Met Thr Lys Ile Leu
                290                 295                 300

Glu Pro Phe Arg Ala Lys Asn Pro Glu Ile Val Ile Tyr Gln Tyr Met
305                 310                 315                 320

Ala Ala Leu Tyr Val Gly Ser Asp Leu Glu Ile Gly Gln His Arg Ala
                325                 330                 335

Lys Ile Glu Glu Leu Arg Glu His Leu Leu Lys Trp Gly Phe Thr Thr
                340                 345                 350

Pro Asp Lys Lys His Gln Lys Glu Pro Pro Phe Leu Trp Met Gly Tyr
                355                 360                 365

Glu Leu His Pro Asp Lys Trp Thr Val Gln Pro Ile Gln Leu Pro Glu
370                 375                 380

Lys Asp Ser Trp Thr Val Asn Asp Ile Gln Lys Leu Val Gly Lys Leu
385                 390                 395                 400

Asn Trp Thr Ser Gln Ile Tyr Pro Gly Ile Lys Val Arg Gln Leu Cys
                405                 410                 415

Lys Leu Leu Arg Gly Thr Lys Ala Leu Thr Asp Ile Val Pro Leu Thr
                420                 425                 430

Glu Glu Ala Glu Leu Glu Leu Ala Glu Asn Arg Glu Ile Leu Lys Glu
                435                 440                 445

Pro Val His Gly Val Tyr Tyr Asp Pro Ser Lys Asp Leu Ile Ala Glu
                450                 455                 460

Ile Gln Lys Gln Gly Asp Asp Gln Trp Thr Tyr Gln Ile Tyr Gln Glu
465                 470                 475                 480

Pro Phe Lys Asn Leu Lys Thr Gly Lys Tyr Ala Lys Arg Arg Thr Thr
                485                 490                 495

His Thr Asn Asp Val Lys Gln Leu Thr Glu Ala Val Gln Lys Ile Ser
                500                 505                 510

Leu Glu Ser Ile Val Thr Trp Gly Lys Thr Pro Lys Phe Arg Leu Pro
                515                 520                 525

Ile Gln Lys Glu Thr Trp Glu Ile Trp Trp Thr Asp Tyr Trp Gln Ala
                530                 535                 540

Thr Trp Ile Pro Glu Trp Glu Phe Val Asn Thr Pro Pro Leu Val Lys
545                 550                 555                 560

Leu Trp Tyr Gln Leu Glu Lys Glu Pro Ile Ala Gly Ala Glu Thr Phe
                565                 570                 575

Tyr Val Asp Gly Ala Ala Asn Arg Glu Thr Lys Ile Gly Lys Ala Gly
                580                 585                 590

Tyr Val Thr Asp Arg Gly Arg Gln Lys Ile Val Thr Leu Ser Glu Thr
                595                 600                 605

Thr Asn Gln Lys Thr Glu Leu Gln Ala Ile Gln Leu Ala Leu Gln Asp
                610                 615                 620

Ser Glu Ser Glu Val Asn Ile Val Thr Asp Ser Gln Tyr Ala Leu Gly
625                 630                 635                 640

Ile Ile Gln Ala Gln Pro Asp Arg Ser Glu Ser Glu Leu Val Asn Gln
                645                 650                 655
```

```
                   Ile Ile Glu Gln Leu Ile Lys Lys Glu Arg Ala Tyr Leu Ser Trp Val
                                   660                 665                 670

Pro Ala His Lys Gly Ile Gly Asp Glu Gln Val Asp Lys Leu Val
                               675                 680                 685

Ser Ser Gly Ile Arg Lys Val Leu
                       690                 695

<210> SEQ ID NO 11
<211> LENGTH: 2564
<212> TYPE: DNA
<213> ORGANISM: Human immunodeficiency virus type 1

<400> SEQUENCE: 11
aagcttatga gggttatggg gattcagaga aactggcctc agtggtggat ttggggggaca    60 ttgggatttt ggatgatcat catctgtcgc gtcgtgggca acctgaacct gtgggtcact    120
gtctactatg gagtgccagt ttggaaggaa gccaagacaa ctctgttttg cgccagcgac    180
gccaaggctt atgacaagga agtccacaac gtgtgggcca cccacgcatg tgtcccaacc    240
gaccccaacc cacgcgaaat cgtgctggaa aacgtcacag aaaatttcaa catgtggaaa    300
aacgatatgg tggatcagat gcatgaggat attattagcc tctgggacca gtctctgaag    360
ccatgtgtga agttgacacc tctctgtgtg acccttaact gtactaacgc ccccgcctat    420
aacaactcta tgcacgggga gatgaaaaac tgttccttca acaccaccac cgaaatcagg    480
gacagaaaac agaaagccta tgccctgttc tataagcccg atgtggtgcc acttaaccgc    540
cgcgaagaaa taatggtac tggcgaatat attctgatta actgtaacag ctctacaatt    600
actcaggctt gccctaaagt caccttgac ccaatcccaa tccactactg cgcccctgca    660
ggatacgcta tcctgaaatg caataataag accttcaacg gaactggacc ctgcaataac    720
gtgtctacag tgcaatgtac ccacggcatt atgcccgtcg tctccaccca actgctgctc    780
aatggcagct ggcagaagaa ggagatcatt attaggagcg aaaacctcac caacaatatc    840
aagacaatca tcgtgcacct gaacaagtct gtggaaattg tgtgtaccag cccaataac    900 aacaccagga gagcatccg catcggacct ggacaaactt tctacgccac cggcgaaatc    960
atcgggaaca ttagagaagc ccactgcaac atctctaaga gcaattggac atctacattg   1020
gagcaagtga aaaaaaagct gaaagagcac tacaataaga ccatcgagtt caaccctcct   1080
tccggcggcg atctggaggt cacaacacac tccttaact gtaggggga gttctttac    1140 tgcaacacaa caaagctgtt tagcaacaac tccgacagca ataatgagac tatcaccctg   1200
ccttgcaaga tcaagcaaat cattaacatg tggcagaaag tgggaagggc aatgtatgca   1260
cctcccatcg agggcaacat cacatgcaag tctaatatca ccggcctgtt gctgactaga   1320
gacggtggca agaatactac taacgaaatc ttcaggccag gtggagggaa catgaaagat   1380
aattggcgct ccgaactgta taagtacaag gtggtggaga ttgagcccct cggcgtcgcc   1440
cccacaaagt ctaagcgccg cgtggtggaa agagagaaga gggctgtcgg cctcggcgca   1500
gtgctgctgg ggttcttggg tgccgctggg tctacaatgg cgctgcctc tattacactc   1560 accgtgcaag ctaggcagct gctgtccggt attgtgcaac aacagagcaa tctcttgaga   1620
gctatcgagg cccagcagca tatgctgcaa cttacagtgt ggggtattaa gcagctgcaa   1680
actcgcgtcc tggcaatcga acgctacctg aaagaccagc aactcctggg tctgtggggc   1740
tgctccggta agatcatctg taccacagcc gtgccctgga acagcagctg gtccaataag   1800
agccaagagg atatttggga taatatgacc tggatgcaat gggatagaga gatcagcaac   1860
tacacaggaa ccatttatag gctcctggaa gattctcaga accagcagga agaacgag     1920
```

```
aaggacttgc tcgccctgga tagctggaaa aacctgtgga attggtttaa catcaccaac    1980
tggctttggt acattaagat tttcatcatg attgtgggag gcttgatcgg cctgaggatt    2040
atcttcgggg tgcttgccat tgtgaaaagg gtcagacaag gatactcccc attgtccttt    2100
cagaccttga ctccaagccc acgcggaccc gacaggttgg gcaggatcga ggaggaagga    2160
ggcgaacagg ataaggaccg ctccatcaga cttgttagcg ggtttctggc cctggcctgg    2220
gatgatctga ggagcctgtg cctcttctcc tatcaccacc tccgcgattt catcctcatt    2280
gcagctaggg ctgctgagtt gctgggacgc tcctccctga gaggtctcca gagaggctgg    2340
gaggcactga agtacctcgg gaaccttgtg caatacggcg ggctggagct gaaaagatcc    2400
gccatcaagc tgttcgacac catcgcaatc gccgttgcag agggcaccga caggatcttg    2460
gaggtcattc agaggatctg tcgcgccatc cgccacatcc ccatcaggat cagacaagga    2520
ttcgaggcag cactgcaatg atagttaatt aaacgcgtgg atcc                     2564
```

<210> SEQ ID NO 12
<211> LENGTH: 852
<212> TYPE: PRT
<213> ORGANISM: Human immunodeficiency virus type 1

<400> SEQUENCE: 12

```
Lys Leu Met Arg Val Met Gly Ile Gln Arg Asn Trp Pro Gln Trp Trp
1               5                   10                  15

Ile Trp Gly Thr Leu Gly Phe Trp Met Ile Ile Cys Arg Val Val
            20                  25                  30

Gly Asn Leu Asn Leu Trp Val Thr Val Tyr Tyr Gly Val Pro Val Trp
        35                  40                  45

Lys Glu Ala Lys Thr Thr Leu Phe Cys Ala Ser Asp Ala Lys Ala Tyr
    50                  55                  60

Asp Lys Glu Val His Asn Val Trp Ala Thr His Ala Cys Val Pro Thr
65                  70                  75                  80

Asp Pro Asn Pro Arg Glu Ile Val Leu Glu Asn Val Thr Glu Asn Phe
                85                  90                  95

Asn Met Trp Lys Asn Asp Met Val Asp Gln Met His Glu Asp Ile Ile
            100                 105                 110

Ser Leu Trp Asp Gln Ser Leu Lys Pro Cys Val Lys Leu Thr Pro Leu
        115                 120                 125

Cys Val Thr Leu Asn Cys Thr Asn Ala Pro Ala Tyr Asn Asn Ser Met
    130                 135                 140

His Gly Glu Met Lys Asn Cys Ser Phe Asn Thr Thr Glu Ile Arg
145                 150                 155                 160

Asp Arg Lys Gln Lys Ala Tyr Ala Leu Phe Tyr Lys Pro Asp Val Val
                165                 170                 175

Pro Leu Asn Arg Arg Glu Glu Asn Asn Gly Thr Gly Glu Tyr Ile Leu
            180                 185                 190

Ile Asn Cys Asn Ser Ser Thr Ile Thr Gln Ala Cys Pro Lys Val Thr
        195                 200                 205

Phe Asp Pro Ile Pro Ile His Tyr Cys Ala Pro Ala Gly Tyr Ala Ile
    210                 215                 220

Leu Lys Cys Asn Asn Lys Thr Phe Asn Gly Thr Gly Pro Cys Asn Asn
225                 230                 235                 240

Val Ser Thr Val Gln Cys Thr His Gly Ile Met Pro Val Val Ser Thr
                245                 250                 255

Gln Leu Leu Leu Asn Gly Ser Leu Ala Glu Glu Glu Ile Ile Ile Arg
```

```
                260                 265                 270
Ser Glu Asn Leu Thr Asn Asn Ile Lys Thr Ile Ile Val His Leu Asn
        275                 280                 285
Lys Ser Val Glu Ile Val Cys Thr Arg Pro Asn Asn Asn Thr Arg Lys
        290                 295                 300
Ser Ile Arg Ile Gly Pro Gly Gln Thr Phe Tyr Ala Thr Gly Glu Ile
305                 310                 315                 320
Ile Gly Asn Ile Arg Glu Ala His Cys Asn Ile Ser Lys Ser Asn Trp
                325                 330                 335
Thr Ser Thr Leu Glu Gln Val Lys Lys Lys Leu Lys Glu His Tyr Asn
            340                 345                 350
Lys Thr Ile Glu Phe Asn Pro Pro Ser Gly Gly Asp Leu Glu Val Thr
            355                 360                 365
Thr His Ser Phe Asn Cys Arg Gly Glu Phe Phe Tyr Cys Asn Thr Thr
        370                 375                 380
Lys Leu Phe Ser Asn Asn Ser Asp Ser Asn Asn Glu Thr Ile Thr Leu
385                 390                 395                 400
Pro Cys Lys Ile Lys Gln Ile Ile Asn Met Trp Gln Lys Val Gly Arg
                405                 410                 415
Ala Met Tyr Ala Pro Pro Ile Glu Gly Asn Ile Thr Cys Lys Ser Asn
            420                 425                 430
Ile Thr Gly Leu Leu Leu Thr Arg Asp Gly Gly Lys Asn Thr Thr Asn
            435                 440                 445
Glu Ile Phe Arg Pro Gly Gly Gly Asn Met Lys Asp Asn Trp Arg Ser
        450                 455                 460
Glu Leu Tyr Lys Tyr Lys Val Val Glu Ile Glu Pro Leu Gly Val Ala
465                 470                 475                 480
Pro Thr Lys Ser Lys Arg Arg Val Val Glu Arg Glu Lys Arg Ala Val
                485                 490                 495
Gly Leu Gly Ala Val Leu Leu Gly Phe Leu Gly Ala Ala Gly Ser Thr
            500                 505                 510
Met Gly Ala Ala Ser Ile Thr Leu Thr Val Gln Ala Arg Gln Leu Leu
            515                 520                 525
Ser Gly Ile Val Gln Gln Gln Ser Asn Leu Leu Arg Ala Ile Glu Ala
        530                 535                 540
Gln Gln His Met Leu Gln Leu Thr Val Trp Gly Ile Lys Gln Leu Gln
545                 550                 555                 560
Thr Arg Val Leu Ala Ile Glu Arg Tyr Leu Lys Asp Gln Gln Leu Leu
                565                 570                 575
Gly Leu Trp Gly Cys Ser Gly Lys Ile Ile Cys Thr Thr Ala Val Pro
            580                 585                 590
Trp Asn Ser Ser Trp Ser Asn Lys Ser Gln Glu Asp Ile Trp Asp Asn
        595                 600                 605
Met Thr Trp Met Gln Trp Asp Arg Glu Ile Ser Asn Tyr Thr Gly Thr
        610                 615                 620
Ile Tyr Arg Leu Leu Glu Asp Ser Gln Asn Gln Gln Glu Lys Asn Glu
625                 630                 635                 640
Lys Asp Leu Leu Ala Leu Asp Ser Trp Lys Asn Leu Trp Asn Trp Phe
                645                 650                 655
Asn Ile Thr Asn Trp Leu Trp Tyr Ile Lys Ile Phe Ile Met Ile Val
            660                 665                 670
Gly Gly Leu Ile Gly Leu Arg Ile Ile Phe Gly Val Leu Ala Ile Val
            675                 680                 685
```

```
Lys Arg Val Arg Gln Gly Tyr Ser Pro Leu Ser Phe Gln Thr Leu Thr
    690                 695                 700

Pro Ser Pro Arg Gly Pro Asp Arg Leu Gly Arg Ile Glu Glu Glu Gly
705                 710                 715                 720

Gly Glu Gln Asp Lys Asp Arg Ser Ile Arg Leu Val Ser Gly Phe Leu
                725                 730                 735

Ala Leu Ala Trp Asp Asp Leu Arg Ser Leu Cys Leu Phe Ser Tyr His
            740                 745                 750

His Leu Arg Asp Phe Ile Leu Ile Ala Ala Arg Ala Ala Glu Leu Leu
        755                 760                 765

Gly Arg Ser Ser Leu Arg Gly Leu Gln Arg Gly Trp Glu Ala Leu Lys
    770                 775                 780

Tyr Leu Gly Asn Leu Val Gln Tyr Gly Gly Leu Glu Leu Lys Arg Ser
785                 790                 795                 800

Ala Ile Lys Leu Phe Asp Thr Ile Ala Ile Ala Val Ala Glu Gly Thr
                805                 810                 815

Asp Arg Ile Leu Glu Val Ile Gln Arg Ile Cys Arg Ala Ile Arg His
            820                 825                 830

Ile Pro Ile Arg Ile Arg Gln Gly Phe Glu Ala Ala Leu Gln Leu Ile
        835                 840                 845

Lys Arg Val Asp
    850

<210> SEQ ID NO 13
<211> LENGTH: 2579
<212> TYPE: DNA
<213> ORGANISM: Human immunodeficiency virus type 1

<400> SEQUENCE: 13
aggctaattt tttagggaaa atttggcctt cccacaaggg gaggccaggg aatttccttc     60
agagcaggcc aatgagagtg aggggggatac agaggaattg ccacaatgg tggatatggg    120 gcatcttagg cttttggatg ttaatgattt gtagtggggt gggaaacttg tgggtcacaa    180
tctattatgg ggtacctgtg tggagagaag caaaaactac tctattctgt gcatcagatg    240
ctaaagcata tgatagagaa gtgcataatg tctgggctac acatgcctgt gtacccacag    300
accccaaccc acaagaaata gttatgggaa atgtaacaga aaattttaac atgtggaaaa    360
atgacatggt ggatcagatg catgaggata taatcaattt atgggatcaa agcctaaagc    420
catgtgtaaa gttaaccccca ctctgtgtca ctttaaaatg tagtacctat aatggtagtg    480
ataccaacga tatgagaaat tgctctttca atacaactac agaaataagg acaagaaac    540 agacagtgta tgcactttttt tataaacctg atatagtacc aattaatgag agtgagtata    600
tattaataca ttgcaatacc tcaaccataa cacaagcctg tccaaaggtc tcttttgacc    660
caattcctat acattattgt gctccagctg gttatgcgat tctaaagtgt aataataaga    720
cattcaatgg gacgggacca tgccaaaatg tcagcacagt acaatgcaca catggaatta    780
agccagtagt atcaactcaa ctactgttaa atggtagcat agcagaagga gagataataa    840
ttagatctga aaatctgaca aacaatgtta aaacaataat agtacacctt aatgaatcta    900
taggaattgt gtgtacaaga cccggcaata tacaagaaa agtataagg ataggaccag    960 gacaagcatt ctatacaaat cacataatag gagatataag acaagcatat tgtaacatta   1020
gtaaacaaga atggaacaaa actttagaag aggtgagaaa aaaattgcaa gaacacttcc   1080
caaataaaac aataaaattt aactcatcct caggagggga cctagaaatt acaacacata   1140
gctttaattg cagaggagaa ttttctctatt gcaatacatc aaaactattt aatgatagtc   1200
```

```
tagtaaatga tacagaaagt aattcaacca tcactattcc atgcagaata aaacaaatta    1260
taaacatgtg gcaggaggta ggacgagcaa tgtatgcccc tcccattgca ggaaacataa    1320
catgtaaatc aaatatcaca ggactactat tgacacgtga tggaggaaca gataacacaa    1380
cagagatatt cagacctgga ggaggaaata tgaaggacaa ttggagaagt gaattatata    1440
aatataaagt agtagaaatt aagccattgg gaatagcacc cactgaagca aaaaggagag    1500
tggtggagag agaaaaaaga gcagtgggaa taggagctgt gctccttggg ttcttgggag    1560
cagcaggaag cactatgggc gcggcgtcaa taacgctgac ggtacaggcc agacaactgt    1620
tgtctggtat agtgcaacag caaagcaatt tgctgagagc tatagaggcg caacagcata    1680
tgttgcaact cacagtctgg ggcattaagc agctccagac aagagtcctg gctatagaaa    1740
gatacctaaa ggatcaacag ctcctaggac tttggggctg ctctggaaaa ctcatctgca    1800
ccactaatgt gccttggaac tccagttgga gcaataaatc tcaacaagct atttgggata    1860
acatgacatg gatgcagtgg gatagagaaa ttaataatta cacaaacata atataccagt    1920
tgcttgagga ctcgcaaatc cagcaggaac agaatgaaaa agatttatta gcattggaca    1980
agtggcaaaa tctgtggagt tggttagca taacaaattg gctatggtat ataaaaatat    2040
tcataatgat agtaggaggc ttaataggtt taagaataat ttttgctgtg ctatctatag    2100
taaatagagt taggcaggga tactcacctt tgtcgtttca gacccttacc ccaaacccga    2160
ggggacccga caggctcgga gaaatcgaag aagaaggtgg agagcaagac agagacagat    2220
ccgttcgatt agtgagcgga ttcttaccac ttgcctggga cgatctgcgg agcctgtgcc    2280
tcttcagcta ccaccgattg agagacttca tattcgattg cagcgaggac agtggaactt    2340
ctgggacgca gcagtctcag gggactccag aggggtggga agtccttaaa tatctgggaa    2400
gccttgtgca gtattggggt ctggagctaa aaagagtgct attagtctgc ttgatcccca    2460
tagcaatagc agtagctgaa ggaacagata ggattattga attagtacta agatttgta    2520 gagctatccg caacatacct acaagagtaa gacagggctg tgaagcagct ttgctataa    2579
```

<210> SEQ ID NO 14
<211> LENGTH: 858
<212> TYPE: PRT
<213> ORGANISM: Human immunodeficiency virus type 1

<400> SEQUENCE: 14

```
Ala Asn Phe Leu Gly Lys Ile Trp Pro Ser His Lys Gly Arg Pro Gly
1               5                   10                  15

Asn Phe Leu Gln Ser Arg Pro Met Arg Val Arg Gly Ile Gln Arg Asn
            20                  25                  30

Trp Pro Gln Trp Trp Ile Trp Gly Ile Leu Gly Phe Trp Met Leu Met
        35                  40                  45

Ile Cys Ser Gly Val Gly Asn Leu Trp Val Thr Ile Tyr Tyr Gly Val
    50                  55                  60

Pro Val Trp Arg Glu Ala Lys Thr Thr Leu Phe Cys Ala Ser Asp Ala
65                  70                  75                  80

Lys Ala Tyr Asp Arg Glu Val His Asn Val Trp Ala Thr His Ala Cys
                85                  90                  95

Val Pro Thr Asp Pro Asn Pro Gln Glu Ile Val Met Gly Asn Val Thr
            100                 105                 110

Glu Asn Phe Asn Met Trp Lys Asn Asp Met Val Asp Gln Met His Glu
        115                 120                 125

Asp Ile Ile Asn Leu Trp Asp Gln Ser Leu Lys Pro Cys Val Lys Leu
```

```
            130                 135                 140
Thr Pro Leu Cys Val Thr Leu Lys Cys Ser Thr Tyr Asn Gly Ser Asp
145                 150                 155                 160

Thr Asn Asp Met Arg Asn Cys Ser Phe Asn Thr Thr Glu Ile Arg
                165                 170                 175

Asp Lys Lys Gln Thr Val Tyr Ala Leu Phe Tyr Lys Pro Asp Ile Val
                180                 185                 190

Pro Ile Asn Glu Ser Glu Tyr Ile Leu Ile His Cys Asn Thr Ser Thr
                195                 200                 205

Ile Thr Gln Ala Cys Pro Lys Val Ser Phe Asp Pro Ile Pro Ile His
210                 215                 220

Tyr Cys Ala Pro Ala Gly Tyr Ala Ile Leu Lys Cys Asn Asn Lys Thr
225                 230                 235                 240

Phe Asn Gly Thr Gly Pro Cys Gln Asn Val Ser Thr Val Gln Cys Thr
                245                 250                 255

His Gly Ile Lys Pro Val Val Ser Thr Gln Leu Leu Leu Asn Gly Ser
                260                 265                 270

Ile Ala Glu Gly Glu Ile Ile Ile Arg Ser Glu Asn Leu Thr Asn Asn
                275                 280                 285

Val Lys Thr Ile Ile Val His Leu Asn Glu Ser Ile Gly Ile Val Cys
                290                 295                 300

Thr Arg Pro Gly Asn Asn Thr Arg Lys Ser Ile Arg Ile Gly Pro Gly
305                 310                 315                 320

Gln Ala Phe Tyr Thr Asn His Ile Ile Gly Asp Ile Arg Gln Ala Tyr
                325                 330                 335

Cys Asn Ile Ser Lys Gln Glu Trp Asn Lys Thr Leu Glu Glu Val Arg
                340                 345                 350

Lys Lys Leu Gln Glu His Phe Pro Asn Lys Thr Ile Lys Phe Asn Ser
                355                 360                 365

Ser Ser Gly Gly Asp Leu Glu Ile Thr Thr His Ser Phe Asn Cys Arg
                370                 375                 380

Gly Glu Phe Phe Tyr Cys Asn Thr Ser Lys Leu Phe Asn Asp Ser Leu
385                 390                 395                 400

Val Asn Asp Thr Glu Ser Asn Ser Thr Ile Thr Ile Pro Cys Arg Ile
                405                 410                 415

Lys Gln Ile Ile Asn Met Trp Gln Glu Val Gly Arg Ala Met Tyr Ala
                420                 425                 430

Pro Pro Ile Ala Gly Asn Ile Thr Cys Lys Ser Asn Ile Thr Gly Leu
                435                 440                 445

Leu Leu Thr Arg Asp Gly Gly Thr Asp Asn Thr Thr Glu Ile Phe Arg
450                 455                 460

Pro Gly Gly Gly Asn Met Lys Asp Asn Trp Arg Ser Glu Leu Tyr Lys
465                 470                 475                 480

Tyr Lys Val Val Glu Ile Lys Pro Leu Gly Ile Ala Pro Thr Glu Ala
                485                 490                 495

Lys Arg Arg Val Val Glu Arg Glu Lys Arg Ala Val Gly Ile Gly Ala
                500                 505                 510

Val Leu Leu Gly Phe Leu Gly Ala Ala Gly Ser Thr Met Gly Ala Ala
                515                 520                 525

Ser Ile Thr Leu Thr Val Gln Ala Arg Gln Leu Leu Ser Gly Ile Val
                530                 535                 540

Gln Gln Gln Ser Asn Leu Leu Arg Ala Ile Glu Ala Gln Gln His Met
545                 550                 555                 560
```

Leu Gln Leu Thr Val Trp Gly Ile Lys Gln Leu Gln Thr Arg Val Leu
            565                 570                 575

Ala Ile Glu Arg Tyr Leu Lys Asp Gln Gln Leu Leu Gly Leu Trp Gly
            580                 585                 590

Cys Ser Gly Lys Leu Ile Cys Thr Thr Asn Val Pro Trp Asn Ser Ser
            595                 600                 605

Trp Ser Asn Lys Ser Gln Gln Ala Ile Trp Asp Asn Met Thr Trp Met
        610                 615                 620

Gln Trp Asp Arg Glu Ile Asn Asn Tyr Thr Asn Ile Ile Tyr Gln Leu
625                 630                 635                 640

Leu Glu Asp Ser Gln Ile Gln Gln Glu Gln Asn Glu Lys Asp Leu Leu
            645                 650                 655

Ala Leu Asp Lys Trp Gln Asn Leu Trp Ser Trp Phe Ser Ile Thr Asn
            660                 665                 670

Trp Leu Trp Tyr Ile Lys Ile Phe Ile Met Ile Val Gly Gly Leu Ile
            675                 680                 685

Gly Leu Arg Ile Ile Phe Ala Val Leu Ser Ile Val Asn Arg Val Arg
            690                 695                 700

Gln Gly Tyr Ser Pro Leu Ser Phe Gln Thr Leu Thr Pro Asn Pro Arg
705                 710                 715                 720

Gly Pro Asp Arg Leu Gly Glu Ile Glu Glu Gly Gly Glu Gln Asp
            725                 730                 735

Arg Asp Arg Ser Val Arg Leu Val Ser Gly Phe Leu Pro Leu Ala Trp
            740                 745                 750

Asp Asp Leu Arg Ser Leu Cys Leu Phe Ser Tyr His Arg Leu Arg Asp
            755                 760                 765

Phe Ile Phe Asp Cys Ser Glu Asp Ser Gly Thr Ser Gly Thr Gln Gln
770                 775                 780

Ser Gln Gly Thr Pro Glu Gly Trp Glu Val Leu Lys Tyr Leu Gly Ser
785                 790                 795                 800

Leu Val Gln Tyr Trp Gly Leu Glu Leu Lys Arg Val Leu Leu Val Cys
            805                 810                 815

Leu Ile Pro Ile Ala Ile Ala Val Ala Glu Gly Thr Asp Arg Ile Ile
            820                 825                 830

Glu Leu Val Leu Arg Phe Cys Arg Ala Ile Arg Asn Ile Pro Thr Arg
            835                 840                 845

Val Arg Gln Gly Cys Glu Ala Ala Leu Leu
850                 855

<210> SEQ ID NO 15
<211> LENGTH: 311
<212> TYPE: PRT
<213> ORGANISM: Human immunodeficiency virus type 1

<400> SEQUENCE: 15

Gly Glu Lys Leu Asp Lys Trp Glu Lys Ile Arg Leu Arg Pro Gly Gly
1               5                   10                  15

Lys Lys His Tyr Met Leu Lys His Leu Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Lys Gln Leu Gln Pro Ala Leu Gln Thr Gly Thr Glu
    50                  55                  60

Glu Leu Arg Ser Leu Tyr Asn Thr Val Ala Thr Leu Tyr Cys Val His
65                  70                  75                  80

-continued

```
Glu Lys Ile Glu Val Arg Asp Thr Lys Glu Ala Leu Asp Lys Ile Glu
                85                  90                  95
Glu Glu Gln Asn Lys Ser Gln Gln Cys Gln Gln Lys Thr Gln Gln Ala
            100                 105                 110
Lys Ala Ala Asp Gly Lys Val Ser Gln Asn Tyr Pro Ile Val Gln
        115                 120                 125
Asn Leu Gln Gly Gln Met Val His Gln Ala Ile Ser Pro Arg Thr Leu
    130                 135                 140
Asn Ala Trp Val Lys Val Ile Glu Glu Lys Ala Phe Ser Pro Glu Val
145                 150                 155                 160
Ile Pro Met Phe Thr Ala Leu Ser Glu Gly Ala Thr Pro Gln Asp Leu
                165                 170                 175
Asn Thr Met Leu Asn Thr Val Gly Gly His Gln Ala Ala Met Gln Met
            180                 185                 190
Leu Lys Asp Thr Ile Asn Glu Glu Ala Ala Glu Trp Asp Arg Leu His
        195                 200                 205
Pro Val His Ala Gly Pro Ile Ala Pro Gly Gln Met Arg Glu Pro Arg
    210                 215                 220
Gly Ser Asp Ile Ala Gly Thr Thr Ser Thr Leu Gln Glu Gln Ile Ala
225                 230                 235                 240
Trp Met Thr Ser Asn Pro Pro Ile Pro Val Gly Asp Ile Tyr Lys Arg
                245                 250                 255
Trp Ile Ile Leu Gly Leu Asn Lys Ile Val Arg Met Tyr Ser Pro Val
            260                 265                 270
Ser Ile Leu Asp Ile Lys Gln Gly Pro Lys Glu Pro Phe Arg Asp Tyr
        275                 280                 285
Val Asp Arg Phe Phe Lys Thr Leu Arg Ala Glu Gln Ala Thr Gln Asp
    290                 295                 300
Val Lys Asn Trp Met Thr Asp
305                 310

<210> SEQ ID NO 16
<211> LENGTH: 277
<212> TYPE: PRT
<213> ORGANISM: Human immunodeficiency virus type 1

<400> SEQUENCE: 16

Leu Thr Glu Glu Lys Ile Lys Ala Leu Thr Ala Ile Cys Glu Glu Met
1               5                   10                  15
Glu Lys Glu Gly Lys Ile Thr Lys Ile Gly Pro Glu Asn Pro Tyr Asn
            20                  25                  30
Thr Pro Val Phe Ala Ile Lys Lys Lys Asp Ser Thr Lys Trp Arg Lys
        35                  40                  45
Leu Val Asp Phe Arg Glu Leu Asn Lys Arg Thr Gln Asp Phe Trp Glu
    50                  55                  60
Val Gln Leu Gly Ile Pro His Pro Ala Gly Leu Lys Lys Lys Lys Ser
65                  70                  75                  80
Val Thr Val Leu Asp Val Gly Asp Ala Tyr Phe Ser Val Pro Leu Asp
                85                  90                  95
Glu Gly Phe Arg Lys Tyr Thr Ala Phe Thr Ile Pro Ser Ile Asn Asn
            100                 105                 110
Glu Thr Pro Gly Ile Arg Tyr Gln Tyr Asn Val Leu Pro Gln Gly Trp
        115                 120                 125
Lys Gly Ser Pro Ala Ile Phe Gln Ser Ser Met Thr Lys Ile Leu Glu
    130                 135                 140
```

```
Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
            165                 170                 175

Ile Glu Glu Leu Arg Glu His Leu Leu Lys Trp Gly Phe Thr Thr Pro
        180                 185                 190

Asp Lys Lys His Gln Lys Glu Pro Pro Phe Leu Trp Met Gly Tyr Glu
    195                 200                 205

Leu His Pro Asp Lys Trp Thr Val Gln Pro Ile Gln Leu Pro Glu Lys
210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
            245                 250                 255

Leu Leu Arg Gly Ala Lys Ala Leu Thr Asp Ile Val Pro Leu Thr Glu
        260                 265                 270

Glu Ala Glu Leu Glu
        275

<210> SEQ ID NO 17
<211> LENGTH: 229
<212> TYPE: PRT
<213> ORGANISM: Human immunodeficiency virus type 1

<400> SEQUENCE: 17

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Glu Ile Ile Arg Ser Glu Asn Leu Thr Asn Asn
    50                  55                  60

Ala Lys Thr Ile Ile Val His Leu Asn Glu Ser Val Glu Ile Val Cys
65                  70                  75                  80

Thr Arg Pro Asn Asn Asn Thr Arg Lys Ser Ile Arg Ile Gly Pro Gly
                85                  90                  95

Gln Thr Phe Tyr Ala Thr Gly Asp Ile Gly Asp Ile Arg Gln Ala
            100                 105                 110

His Cys Asn Ile Ser Glu Gly Lys Trp Asn Lys Thr Leu Gln Lys Val
        115                 120                 125

Lys Lys Lys Leu Lys Glu Glu Leu Tyr Lys Tyr Lys Val Val Glu Ile
    130                 135                 140

Lys Pro Leu Gly Ile Ala Pro Thr Glu Ala Lys Arg Arg Val Val Glu
145                 150                 155                 160

Arg Glu Lys Arg Ala Val Gly Ile Gly Ala Val Phe Leu Gly Phe Leu
            165                 170                 175

Gly Ala Ala Gly Ser Thr Met Gly Ala Ala Ser Ile Thr Leu Thr Val
        180                 185                 190

Gln Ala Arg Gln Leu Leu Ser Gly Ile Val Gln Gln Ser Asn Leu
    195                 200                 205

Leu Arg Ala Ile Glu Ala Gln Gln His Met Leu Gln Leu Thr Val Trp
210                 215                 220

Gly Ile Lys Gln Leu
225
```

```
<210> SEQ ID NO 18
<211> LENGTH: 311
<212> TYPE: PRT
<213> ORGANISM: Human immunodeficiency virus type 1

<400> SEQUENCE: 18

Gly Glu Lys Leu Asp Lys Trp Glu Lys Ile Arg Leu Arg Pro Gly Gly
1               5                   10                  15

Lys Lys His Tyr Met Leu Lys His Leu Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Lys Gln Leu Gln Pro Ala Leu Gln Thr Gly Thr Glu
    50                  55                  60

Glu Leu Arg Ser Leu Tyr Asn Thr Val Ala Thr Leu Tyr Cys Val His
65                  70                  75                  80

Glu Lys Ile Glu Val Arg Asp Thr Lys Glu Ala Leu Asp Lys Ile Glu
                85                  90                  95

Glu Glu Gln Asn Lys Ser Gln Gln Cys Gln Gln Lys Thr Gln Gln Ala
            100                 105                 110

Lys Ala Ala Asp Gly Gly Lys Val Ser Gln Asn Tyr Pro Ile Val Gln
        115                 120                 125

Asn Leu Gln Gly Gln Met Val His Gln Ala Ile Ser Pro Arg Thr Leu
    130                 135                 140

Asn Ala Trp Val Lys Val Ile Glu Glu Lys Ala Phe Ser Pro Glu Val
145                 150                 155                 160

Ile Pro Met Phe Thr Ala Leu Ser Glu Gly Ala Thr Pro Gln Asp Leu
                165                 170                 175

Asn Thr Met Leu Asn Thr Val Gly Gly His Gln Ala Ala Met Gln Met
            180                 185                 190

Leu Lys Asp Thr Ile Asn Glu Glu Ala Ala Glu Trp Asp Arg Leu His
        195                 200                 205

Pro Val His Ala Gly Pro Ile Ala Pro Gly Gln Met Arg Glu Pro Arg
    210                 215                 220

Gly Ser Asp Ile Ala Gly Thr Thr Ser Thr Leu Gln Glu Gln Ile Ala
225                 230                 235                 240

Trp Met Thr Ser Asn Pro Pro Ile Pro Val Gly Asp Ile Tyr Lys Arg
                245                 250                 255

Trp Ile Ile Leu Gly Leu Asn Lys Ile Val Arg Met Tyr Ser Pro Val
            260                 265                 270

Ser Ile Leu Asp Ile Lys Gln Gly Pro Lys Glu Pro Phe Arg Asp Tyr
        275                 280                 285

Val Asp Arg Phe Phe Lys Thr Leu Arg Ala Glu Gln Ala Thr Gln Asp
    290                 295                 300

Val Lys Asn Trp Met Thr Asp
305                 310

<210> SEQ ID NO 19
<211> LENGTH: 308
<212> TYPE: PRT
<213> ORGANISM: Human immunodeficiency virus type 1

<400> SEQUENCE: 19

Gly Gly Lys Leu Asp Ala Trp Glu Arg Ile Arg Leu Arg Pro Gly Gly
1               5                   10                  15

Lys Lys Gln Tyr Met Ile Lys His Leu Val Trp Ala Ser Arg Glu Leu
```

```
                    20                  25                  30
Glu Arg Phe Ala Leu Asn Pro Gly Leu Leu Glu Thr Gly Gly Cys
             35                  40                  45
Lys Gln Ile Met Lys Gln Leu Gln Pro Ala Leu Gln Thr Gly Thr Lys
 50                  55                  60
Glu Leu Arg Ser Leu Tyr Asn Thr Val Ala Thr Leu Tyr Cys Val His
 65                  70                  75                  80
Glu Lys Ile Glu Val Arg Asp Thr Lys Glu Ala Leu Asp Lys Ile Glu
                 85                  90                  95
Glu Glu Gln Lys Lys Cys Gln Gln Ile Gln Gln Ala Glu Ala Ala
                100                 105                 110
Asp Lys Gly Lys Val Ser Gln Asn Tyr Pro Ile Val Gln Asn Leu Gln
             115                 120                 125
Gly Gln Met Val His Gln Ala Ile Ser Pro Arg Thr Leu Asn Ala Trp
         130                 135                 140
Val Lys Val Ile Glu Lys Ala Phe Ser Pro Glu Val Ile Pro Met
145                 150                 155                 160
Phe Thr Ala Leu Ser Glu Gly Ala Thr Pro Gln Asp Leu Asn Thr Met
                 165                 170                 175
Leu Asn Thr Val Gly Gly His Gln Ala Ala Met Gln Met Leu Lys Asp
             180                 185                 190
Thr Ile Asn Glu Glu Ala Ala Glu Trp Asp Arg Leu His Pro Val His
             195                 200                 205
Ala Gly Pro Ile Ala Pro Gly Gln Met Arg Glu Pro Arg Gly Ser Asp
         210                 215                 220
Ile Ala Gly Thr Thr Ser Thr Leu Gln Glu Gln Ile Ala Trp Met Thr
225                 230                 235                 240
Ser Asn Pro Pro Ile Pro Val Gly Asp Ile Tyr Lys Arg Trp Ile Ile
                 245                 250                 255
Leu Gly Leu Asn Lys Ile Val Arg Met Tyr Ser Pro Val Ser Ile Leu
             260                 265                 270
Asp Ile Lys Gln Gly Pro Lys Glu Pro Phe Arg Asp Tyr Val Asp Arg
         275                 280                 285
Phe Phe Lys Thr Leu Arg Ala Glu Gln Ser Thr Gln Glu Val Lys Asn
    290                 295                 300
Trp Met Thr Asp
305

<210> SEQ ID NO 20
<211> LENGTH: 308
<212> TYPE: PRT
<213> ORGANISM: Human immunodeficiency virus type 1

<400> SEQUENCE: 20

Gly Gly Lys Leu Asp Lys Trp Glu Lys Ile Lys Leu Arg Pro Gly Gly
 1               5                  10                  15
Lys Lys His Tyr Met Leu Lys His Leu Val Trp Ala Ser Arg Glu Leu
                 20                  25                  30
Glu Arg Phe Ala Leu Asn Pro Gly Leu Leu Glu Thr Ala Asp Gly Cys
             35                  40                  45
Lys Gln Ile Ile Lys Gln Leu Gln Pro Ala Leu Gln Thr Gly Thr Glu
         50                  55                  60
Glu Leu Arg Ser Leu Phe Asn Thr Val Ala Thr Leu Tyr Cys Val His
 65                  70                  75                  80
Lys Glu Ile Glu Val Arg Asp Thr Lys Glu Ala Leu Asp Lys Ile Glu
```

```
                        85                  90                  95
Glu Glu Gln Asn Lys Cys Gln Gln Lys Ala Gln Gln Ala Glu Ala Ser
                    100                 105                 110
Asp Lys Gly Lys Val Ser Gln Asn Tyr Pro Ile Val Gln Asn Leu Gln
                115                 120                 125
Gly Gln Met Val His Gln Pro Leu Ser Pro Arg Thr Leu Asn Ala Trp
            130                 135                 140
Val Lys Val Ile Glu Lys Ala Phe Ser Pro Glu Val Ile Pro Met
145                 150                 155                 160
Phe Thr Ala Leu Ser Glu Gly Ala Thr Pro Gln Asp Leu Asn Thr Met
                165                 170                 175
Leu Asn Thr Val Gly Gly His Gln Ala Ala Met Gln Met Leu Lys Asp
                180                 185                 190
Thr Ile Asn Glu Glu Ala Ala Glu Trp Asp Arg Leu His Pro Val His
                195                 200                 205
Ala Gly Pro Asn Ala Pro Gly Gln Met Arg Glu Pro Arg Gly Ser Asp
            210                 215                 220
Ile Ala Gly Thr Thr Ser Thr Leu Gln Glu Gln Ile Thr Trp Met Thr
225                 230                 235                 240
Asn Asn Pro Pro Ile Pro Val Gly Asp Ile Tyr Lys Arg Trp Ile Ile
                245                 250                 255
Leu Gly Leu Asn Lys Ile Val Arg Met Tyr Ser Pro Val Ser Ile Leu
                260                 265                 270
Asp Ile Lys Gln Gly Pro Lys Glu Pro Phe Arg Asp Tyr Val Asp Arg
                275                 280                 285
Phe Phe Lys Thr Leu Arg Ala Glu Gln Ala Thr Gln Asp Val Lys Asn
                290                 295                 300
Trp Met Thr Asp
305

<210> SEQ ID NO 21
<211> LENGTH: 307
<212> TYPE: PRT
<213> ORGANISM: Human immunodeficiency virus type 1
<220> FEATURE:
<221> NAME/KEY: misc_feature
<222> LOCATION: (133)..(133)
<223> OTHER INFORMATION: Xaa can be any naturally occurring amino
      acid

<400> SEQUENCE: 21

Gly Gly Lys Leu Asp Lys Trp Glu Lys Ile Arg Leu Arg Pro Gly Gly
1               5                   10                  15
Lys Lys His Tyr Met Ile Lys His Leu Val Trp Ala Ser Arg Glu Leu
                20                  25                  30
Glu Arg Phe Ala Leu Asn Pro Gly Leu Leu Glu Thr Ser Glu Gly Cys
            35                  40                  45
Arg Gln Ile Ile Arg Gln Leu Gln Pro Ala Leu Gln Thr Gly Thr Glu
        50                  55                  60
Glu Leu Arg Ser Leu Phe Asn Thr Val Ala Thr Leu Tyr Cys Val His
65                  70                  75                  80
Glu Glu Ile Glu Val Arg Asp Thr Lys Glu Ala Leu Asp Arg Ile Glu
                85                  90                  95
Glu Glu Gln Lys Lys Ser Gln Gln Lys Thr Gln Gln Ala Lys Glu Ala
                100                 105                 110
Asp Lys Lys Val Ser Gln Asn Tyr Pro Ile Val Gln Asn Leu Gln Gly
            115                 120                 125
```

Gln Met Val His Xaa Ala Leu Ser Pro Arg Thr Leu Asn Ala Trp Val
            130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
        195                 200                 205

Gly Pro Asn Pro Pro Gly Gln Ile Arg Glu Pro Arg Gly Ser Asp Ile
210                 215                 220

Ala Gly Thr Thr Ser Thr Leu Gln Glu Gln Ile Ala Trp Met Thr Gly
225                 230                 235                 240

Asn Pro Pro Val Pro Val Gly Glu Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Arg Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
290                 295                 300

Met Thr Asp
305

<210> SEQ ID NO 22
<211> LENGTH: 305
<212> TYPE: PRT
<213> ORGANISM: Human immunodeficiency virus type 1

<400> SEQUENCE: 22

Gly Gly Lys Leu Asp Ala Trp Glu Lys Ile Arg Leu Arg Pro Gly Gly
1               5                   10                  15

Lys Lys His Tyr Met Ile Lys His Leu Val Trp Ala Ser Arg Glu Leu
            20                  25                  30

Glu Arg Phe Ala Leu Asn Pro Gly Leu Leu Glu Thr Ser Ala Gly Cys
        35                  40                  45

Lys Gln Ile Ile Arg Gln Leu Gln Pro Ala Leu Gln Thr Gly Thr Glu
    50                  55                  60

Glu Leu Arg Ser Leu Tyr Asn Thr Val Ala Thr Leu Tyr Cys Val His
65                  70                  75                  80

Glu Arg Ile Glu Val Arg Asp Thr Lys Glu Ala Leu Asp Lys Ile Glu
                85                  90                  95

Glu Glu Gln Lys Lys Cys Gln Gln Lys Thr Gln Gln Ala Ala Asp Glu
            100                 105                 110

Lys Val Ser Gln Asn Tyr Pro Ile Val Gln Asn Ala Gln Gly Gln Met
        115                 120                 125

Val His Gln Ala Ile Ser Pro Arg Thr Leu Asn Ala Trp Val Lys Val
    130                 135                 140

Ile Glu Glu Lys Ala Phe Ser Pro Glu Val Ile Pro Met Phe Thr Ala
145                 150                 155                 160

Leu Ser Glu Gly Ala Thr Pro Gln Asp Leu Asn Thr Met Leu Asn Thr
                165                 170                 175

Val Gly Gly His Gln Ala Ala Met Gln Met Leu Lys Asp Thr Ile Asn
            180                 185                 190

Glu Glu Ala Ala Glu Trp Asp Arg Leu His Pro Val His Ala Gly Pro
            195                 200                 205

Val Ala Pro Gly Gln Met Arg Glu Pro Arg Gly Ser Asp Ile Ala Gly
210                 215                 220

Thr Thr Ser Thr Leu Gln Glu Gln Ile Ala Trp Met Thr Asn Asn Pro
225                 230                 235                 240

Pro Ile Pro Val Gly Asp Ile Tyr Lys Arg Trp Ile Ile Met Gly Leu
            245                 250                 255

Asn Lys Ile Val Arg Met Tyr Ser Pro Val Ser Ile Leu Asp Ile Lys
            260                 265                 270

Gln Gly Pro Lys Glu Pro Phe Arg Asp Tyr Val Asp Arg Phe Phe Lys
            275                 280                 285

Thr Leu Arg Ala Glu Gln Ala Thr Gln Asp Val Lys Asn Trp Met Thr
            290                 295                 300

Asp
305

<210> SEQ ID NO 23
<211> LENGTH: 307
<212> TYPE: PRT
<213> ORGANISM: Human immunodeficiency virus type 1

<400> SEQUENCE: 23

Gly Glu Lys Leu Asp Lys Trp Glu Lys Ile Arg Leu Arg Pro Gly Gly
1               5                   10                  15

Lys Lys His Tyr Met Leu Lys His Leu Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Ser Gln Leu Gln Ser Ala Leu Gln Thr Gly Thr Glu
    50                  55                  60

Glu Leu Arg Ser Leu Tyr Asn Thr Val Ala Val Leu Trp Cys Val His
65                  70                  75                  80

Asn Asn Ile Glu Val Arg Asp Thr Lys Glu Ala Leu Asp Lys Ile Glu
            85                  90                  95

Glu Glu Gln Lys Lys Ser Gln Gln Lys Thr Gln Gln Ala Lys Ala Ala
            100                 105                 110

Asp Gly Asn Val Ser Gln Asn Tyr Pro Ile Val Gln Asn Leu Gln Gly
            115                 120                 125

Ala Met Val His Gln Ala Leu Ser Pro Arg Thr Leu Asn Ala Trp Val
130                 135                 140

Lys Val Ile Glu Glu Lys Ala Phe Asn Pro Glu Ile Ile Pro Met Phe
145                 150                 155                 160

Thr Ala Leu Ser Glu Gly Ala Thr Pro Gln Asp Leu Asn Thr Met Leu
            165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
            195                 200                 205

Gly Pro Val Ala Pro Gly Gln Met Arg Glu Pro Arg Gly Ser Asp Ile
        210                 215                 220

Ala Gly Thr Thr Ser Thr Leu Gln Glu Gln Ile Ala Trp Met Thr Ser
225                 230                 235                 240

Asn Pro Pro Val Pro Val Gly Asp Ile Tyr Lys Arg Trp Ile Ile Leu
            245                 250                 255

Gly Leu Asn Lys Ile Val Arg Met Tyr Ser Pro Val Ser Ile Leu Asp
            260                 265                 270

Ile Lys Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
290                 295                 300

Met Thr Asp
305

<210> SEQ ID NO 24
<211> LENGTH: 307
<212> TYPE: PRT
<213> ORGANISM: Human immunodeficiency virus type 1

<400> SEQUENCE: 24

Gly Glu Lys Leu Asp Lys Trp Glu Lys Ile Arg Leu Arg Pro Gly Gly
1               5                   10                  15

Lys Lys Gln Tyr Met Leu Lys His Leu Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Lys Gln Leu Gln Pro Ala Leu Gln Thr Gly Thr Glu
    50                  55                  60

Glu Leu Arg Ser Leu Tyr Asn Thr Val Ala Thr Leu Tyr Cys Val His
65                  70                  75                  80

Ser Asn Ile Glu Val Arg Asp Thr Lys Glu Ala Leu Asp Lys Ile Glu
                85                  90                  95

Glu Glu Gln Asn Lys Ser Gln Gln Lys Thr Gln Gln Ala Gly Ala Ala
            100                 105                 110

Asp Gly Lys Val Ser Gln Asn Tyr Pro Ile Val Gln Asn Leu Gln Gly
        115                 120                 125

Gln Met Val His Gln Pro Leu Ser Pro Arg Thr Leu Asn Ala Trp Val
    130                 135                 140

Lys Val Ile Glu Glu Lys Ala Phe Asn Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
        195                 200                 205

Gly Pro Ile Ala Pro Gly Gln Met Arg Glu Pro Arg Gly Ser Asp Ile
    210                 215                 220

Ala Gly Thr Thr Ser Asn Leu Gln Glu Gln Ile Ala Trp Met Thr Ser
225                 230                 235                 240

Asn Pro Pro Val Pro Val Gly Glu Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Lys Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
    290                 295                 300

Met Thr Asp
305

<210> SEQ ID NO 25
<211> LENGTH: 307
<212> TYPE: PRT
<213> ORGANISM: Human immunodeficiency virus type 1

<400> SEQUENCE: 25

```
Gly Glu Lys Leu Asp Thr Trp Glu Lys Ile Arg Leu Arg Pro Gly Gly
1               5                   10                  15

Lys Lys Arg Tyr Met Leu Lys His Ile Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Glu Gln Leu Gln Pro Ala Leu Gln Thr Gly Thr Glu
    50                  55                  60

Glu Leu Lys Ser Leu Phe Asn Thr Val Ala Thr Leu Tyr Cys Val His
65                  70                  75                  80

Lys Arg Ile Asp Val Arg Asp Thr Lys Glu Ala Leu Asp Lys Val Glu
                85                  90                  95

Glu Glu Gln Lys Arg Ser Gln Gln Lys Thr Gln Gln Ala Lys Ala Ala
            100                 105                 110

Asp Glu Lys Val Ser Gln Asn Tyr Pro Ile Val Gln Asn Leu Gln Gly
        115                 120                 125

Gln Met Val His Gln Ala Ile Ser Pro Arg Thr Leu Asn Ala Trp Val
    130                 135                 140

Lys Val Ile Glu Glu Lys Ala Phe Ser Pro Glu Ile Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
        195                 200                 205

Gly Pro Ile Ala Pro Gly Gln Met Arg Glu Pro Arg Gly Ser Asp Ile
    210                 215                 220

Ala Gly Thr Thr Ser Thr Leu Gln Glu Gln Ile Thr Trp Met Thr Asn
225                 230                 235                 240

Asn Pro Pro Val Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Arg Gln Gly Pro Lys Glu Pro Phe Arg Asp Tyr Val Asp Arg Phe
        275                 280                 285

Phe Lys Thr Leu Arg Ala Glu Gln Ala Thr Gln Glu Val Lys Asn Trp
    290                 295                 300

Met Thr Asp
305
```

<210> SEQ ID NO 26
<211> LENGTH: 309
<212> TYPE: PRT
<213> ORGANISM: Human immunodeficiency virus type 1

<400> SEQUENCE: 26

```
Gly Glu Lys Leu Asp Ala Trp Glu Lys Ile Arg Leu Arg Pro Gly Gly
1               5                   10                  15
```

```
Lys Lys His Tyr Met Leu Lys His Ile Val Trp Ala Ser Arg Glu Leu
             20                  25                  30

Glu Arg Phe Ala Leu Asn Pro Gly Leu Leu Glu Thr Ser Glu Gly Cys
         35                  40                  45

Lys Gln Ile Met Asn Gln Leu Gln Pro Ala Leu Gln Thr Gly Thr Glu
     50                  55                  60

Glu Leu Arg Ser Leu Tyr Asn Thr Val Ala Thr Leu Tyr Cys Val His
 65                  70                  75                  80

Lys Arg Ile Asp Val Arg Asp Thr Lys Glu Ala Leu Asp Lys Ile Glu
                 85                  90                  95

Glu Glu Gln Asn Lys Ser Gln Gln Lys Thr Gln Gln Ala Lys Ala Ala
            100                 105                 110

Asp Glu Lys Val Lys Val Ser Gln Asn Tyr Pro Ile Val Gln Asn Leu
        115                 120                 125

Gln Gly Gln Met Val His Gln Pro Ile Ser Pro Arg Thr Leu Asn Ala
    130                 135                 140

Trp Val Lys Val Ile Glu Gly Lys Ala Phe Ser Pro Glu Val Ile Pro
145                 150                 155                 160

Met Phe Thr Ala Leu Ser Glu Gly Ala Thr Pro Gln Asp Leu Asn Thr
                165                 170                 175

Met Leu Asn Thr Val Gly Gly His Gln Ala Ala Met Gln Met Leu Lys
            180                 185                 190

Asp Thr Ile Asn Glu Glu Ala Ala Glu Trp Asp Arg Leu His Pro Val
        195                 200                 205

His Ser Gly Pro Val Ala Pro Gly Gln Val Arg Glu Pro Arg Gly Ser
    210                 215                 220

Asp Ile Ala Gly Thr Thr Ser Thr Leu Gln Glu Gln Ile Thr Trp Met
225                 230                 235                 240

Thr Ser Asn Pro Pro Ile Pro Val Gly Asp Ile Tyr Lys Arg Trp Ile
                245                 250                 255

Ile Leu Gly Leu Asn Lys Ile Val Arg Met Tyr Ser Pro Val Ser Ile
            260                 265                 270

Leu Asp Ile Arg Gln Gly Pro Lys Glu Pro Phe Arg Asp Tyr Val Asp
        275                 280                 285

Arg Phe Phe Lys Thr Leu Arg Ala Glu Gln Ala Thr Gln Asp Val Lys
    290                 295                 300

Asn Trp Met Thr Glu
305

<210> SEQ ID NO 27
<211> LENGTH: 307
<212> TYPE: PRT
<213> ORGANISM: Human immunodeficiency virus type 1

<400> SEQUENCE: 27

Gly Glu Lys Leu Asp Lys Trp Glu Arg Ile Arg Leu Arg Pro Gly Gly
 1               5                  10                  15

Lys Lys Cys Tyr Met Leu Lys His Ile Val Trp Ala Ser Arg Glu Leu
             20                  25                  30

Glu Arg Phe Ala Leu Asn Pro Gly Leu Leu Glu Thr Ser Glu Gly Cys
         35                  40                  45

Lys Gln Ile Met Gln Gln Leu Gln Pro Ala Leu Gln Thr Gly Thr Glu
     50                  55                  60

Glu Leu Lys Ser Leu Tyr Asn Thr Ile Ala Thr Leu Tyr Cys Val His
 65                  70                  75                  80
```

```
Lys Gly Ile Glu Val Arg Asp Thr Lys Glu Ala Leu Asp Lys Ile Glu
                85                  90                  95

Glu Glu Gln Asn Lys Ser Gln Gln Lys Thr Gln Gln Thr Lys Ala Ala
            100                 105                 110

Asp Gly Lys Val Ser Gln Asn Tyr Pro Ile Val Gln Asn Leu Gln Gly
        115                 120                 125

Gln Met Val His Gln Ala Ile Ser Pro Arg Thr Leu Asn Ala Trp Val
    130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Asp Glu Ala Ala Glu Trp Asp Arg Leu His Pro Val His Ala
        195                 200                 205

Gly Pro Ile Gln Pro Gly Gln Met Arg Glu Pro Arg Gly Ser Asp Ile
    210                 215                 220

Ala Gly Thr Thr Ser Thr Leu Gln Glu Gln Ile Ala Trp Met Thr Ser
225                 230                 235                 240

Asn Pro Pro Ile Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Arg Gln Gly Pro Lys Glu Pro Phe Arg Asp Tyr Val Asp Arg Phe
        275                 280                 285

Phe Lys Thr Leu Arg Ala Glu Gln Ala Thr Gln Glu Val Lys Asn Trp
    290                 295                 300

Met Thr Asp
305

<210> SEQ ID NO 28
<211> LENGTH: 307
<212> TYPE: PRT
<213> ORGANISM: Human immunodeficiency virus type 1

<400> SEQUENCE: 28

Gly Glu Lys Leu Asp Arg Trp Glu Arg Ile Arg Leu Arg Pro Gly Gly
1               5                   10                  15

Lys Lys His Tyr Met Leu Lys His Ile Val Trp Ala Ser Arg Glu Leu
            20                  25                  30

Glu Arg Phe Ala Leu Asn Pro Gly Leu Leu Glu Thr Ser Glu Gly Cys
        35                  40                  45

Arg Gln Ile Met Asn Gln Leu Gln Pro Ala Leu Gln Thr Gly Thr Glu
    50                  55                  60

Glu Leu Lys Ser Leu Tyr Asn Thr Val Ala Thr Leu Tyr Cys Val His
65                  70                  75                  80

Glu Lys Ile Asp Val Arg Asp Thr Lys Glu Ala Leu Asp Lys Ile Glu
                85                  90                  95

Glu Glu Gln Asn Lys Ser Gln Gln Lys Thr Gln Gln Glu Lys Ala Ala
            100                 105                 110

Gly Gly Lys Val Ser Gln Asn Tyr Pro Ile Val Gln Asn Leu Gln Gly
        115                 120                 125

Gln Met Val His Gln Ala Ile Ser Pro Arg Thr Leu Asn Ala Trp Val
    130                 135                 140
```

```
Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
        195                 200                 205

Gly Pro Ile Ala Pro Gly Gln Met Arg Glu Pro Arg Gly Ser Asp Ile
    210                 215                 220

Ala Gly Thr Thr Ser Thr Leu Gln Glu Gln Ile Ala Trp Met Thr Asn
225                 230                 235                 240

Asn Pro Pro Val Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Arg Gln Gly Pro Lys Glu Pro Phe Arg Asp Tyr Val Asp Arg Phe
        275                 280                 285

Phe Lys Val Leu Arg Ala Glu Gln Ala Thr Gln Glu Val Lys Asn Trp
290                 295                 300

Met Thr Glu
305

<210> SEQ ID NO 29
<211> LENGTH: 310
<212> TYPE: PRT
<213> ORGANISM: Human immunodeficiency virus type 1

<400> SEQUENCE: 29

Gly Glu Lys Leu Asp Arg Trp Glu Lys Ile Arg Leu Arg Pro Gly Gly
1               5                   10                  15

Lys Lys His Tyr Met Leu Lys His Ile Val Trp Ala Ser Arg Glu Leu
                20                  25                  30

Glu Arg Phe Ala Leu Asn Pro Gly Leu Leu Glu Thr Ser Glu Gly Cys
            35                  40                  45

Lys Gln Ile Ile Thr Gln Leu Gln Pro Ala Leu Gln Thr Gly Thr Glu
    50                  55                  60

Glu Leu Lys Ser Leu Phe Asn Thr Val Ala Thr Leu Tyr Cys Val His
65                  70                  75                  80

Lys Lys Ile Asp Val Arg Asp Thr Lys Glu Ala Leu Asp Lys Ile Glu
                85                  90                  95

Glu Glu Gln Asn Lys Ser Gln Gln Val Gln Gln Lys Thr Gln Gln Ala
            100                 105                 110

Lys Thr Ala Asp Gly Lys Val Ser Gln Asn Tyr Pro Ile Val Gln Asn
    115                 120                 125

Leu Gln Gly Gln Met Val His Gln Ala Ile Ser Pro Arg Thr Leu Asn
130                 135                 140

Ala Trp Val Lys Val Ile Lys Glu Lys Ala Phe Ser Pro Glu Val Ile
145                 150                 155                 160

Pro Met Phe Thr Ala Leu Ser Glu Gly Ala Thr Pro Gln Asp Leu Asn
                165                 170                 175

Thr Met Leu Asn Thr Val Gly Gly His Gln Ala Ala Met Gln Met Leu
            180                 185                 190

Lys Asp Thr Ile Asn Asp Glu Ala Ala Glu Trp Asp Arg Leu His Pro
    195                 200                 205
```

```
Val His Ala Gly Pro Ile Ala Pro Gly Gln Met Arg Glu Pro Arg Gly
    210                 215                 220
Ser Asp Ile Ala Gly Thr Thr Ser Thr Leu Gln Glu Gln Ile Ala Trp
225                 230                 235                 240
Met Thr Ser Asn Pro Pro Ile Pro Val Gly Asp Ile Tyr Lys Arg Trp
                245                 250                 255
Ile Ile Leu Gly Leu Asn Lys Ile Val Arg Met Tyr Ser Pro Val Ser
            260                 265                 270
Ile Leu Asp Ile Arg Gln Gly Pro Lys Glu Pro Phe Arg Asp Tyr Val
        275                 280                 285
Asp Arg Phe Phe Lys Thr Leu Arg Ala Glu Gln Ala Thr Gln Glu Val
    290                 295                 300
Lys Asn Trp Met Thr Asp
305                 310

<210> SEQ ID NO 30
<211> LENGTH: 307
<212> TYPE: PRT
<213> ORGANISM: Human immunodeficiency virus type 1

<400> SEQUENCE: 30

Gly Gly Lys Leu Asp Ala Trp Glu Lys Ile Arg Leu Arg Pro Gly Gly
1               5                   10                  15
Lys Lys Cys Tyr Met Ile Lys His Leu Ile Trp Ala Ser Arg Glu Leu
                20                  25                  30
Glu Arg Phe Ala Leu Asn Pro Gly Leu Leu Glu Thr Ser Glu Gly Cys
            35                  40                  45
Lys Gln Ile Met Lys Gln Leu Gln Pro Ala Leu Gln Thr Gly Thr Glu
        50                  55                  60
Glu Leu Arg Ser Leu Tyr Asn Thr Val Ala Thr Leu Tyr Cys Val His
65                  70                  75                  80
Glu Lys Ile Glu Val Arg Asp Thr Lys Glu Ala Leu Asp Lys Ile Glu
                85                  90                  95
Glu Glu Gln Asn Lys Ser Gln Gln Lys Thr Gln Gln Ala Gln Ala Ala
            100                 105                 110
Asp Gly Lys Val Ser Gln Asn Tyr Pro Ile Val Gln Asn Val Gln Gly
        115                 120                 125
Gln Met Val His Gln Ala Leu Ser Pro Arg Thr Leu Asn Ala Trp Val
    130                 135                 140
Lys Val Ile Glu Glu Lys Ala Phe Ser Pro Glu Val Ile Pro Met Phe
145                 150                 155                 160
Thr Ala Leu Ser Glu Gly Ala Thr Pro Gln Asp Leu Asn Thr Met Leu
                165                 170                 175
Asn Thr Val Gly Gly His Gln Ala Ala Met Gln Met Leu Lys Asp Thr
            180                 185                 190
Ile Asn Glu Glu Ala Ala Glu Trp Asp Arg Leu His Pro Val His Ala
        195                 200                 205
Gly Pro Val Ala Pro Gly Gln Leu Arg Glu Pro Arg Gly Ser Asp Ile
    210                 215                 220
Ala Gly Thr Thr Ser Thr Leu Gln Glu Gln Ile Ala Trp Met Thr Asn
225                 230                 235                 240
Asn Pro Pro Val Pro Val Gly Glu Ile Tyr Lys Arg Trp Ile Ile Leu
                245                 250                 255
Gly Leu Asn Lys Ile Val Arg Met Tyr Ser Pro Val Ser Ile Leu Asp
            260                 265                 270
```

```
Ile Lys Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
290                 295                 300

Met Thr Asp
305

<210> SEQ ID NO 31
<211> LENGTH: 307
<212> TYPE: PRT
<213> ORGANISM: Human immunodeficiency virus type 1

<400> SEQUENCE: 31

Gly Glu Lys Leu Asp Ala Trp Glu Lys Ile Lys Leu Arg Pro Gly Gly
1               5                   10                  15

Lys Lys Cys Tyr Met Ile Lys His Leu Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Lys Gln Leu Gln Pro Ala Leu Gln Thr Gly Thr Glu
50                  55                  60

Glu Leu Arg Ser Leu Tyr Asn Thr Val Ala Thr Leu Tyr Cys Val His
65                  70                  75                  80

Glu Lys Ile Glu Val Gln Asp Thr Lys Glu Ala Leu Asp Lys Ile Glu
                85                  90                  95

Glu Glu Gln Asn Lys Ser Gln Gln Lys Thr Gln Gln Ala Gln Ala Ala
            100                 105                 110

Asp Gly Lys Val Ser Gln Asn Tyr Pro Ile Val Gln Asn Val Gln Gly
        115                 120                 125

Gln Met Val His Gln Ala Leu Ser Pro Arg Thr Leu Asn Ala Trp Val
130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
        195                 200                 205

Gly Pro Val Ala Pro Gly Gln Leu Arg Glu Pro Arg Gly Ser Asp Ile
210                 215                 220

Ala Gly Thr Thr Ser Thr Leu Gln Glu Gln Ile Ala Trp Met Thr Asn
225                 230                 235                 240

Asn Pro Pro Val Pro Val Gly Glu Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Lys Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
290                 295                 300

Met Thr Asp
305

<210> SEQ ID NO 32
<211> LENGTH: 308
```

-continued

```
<212> TYPE: PRT
<213> ORGANISM: Human immunodeficiency virus type 1

<400> SEQUENCE: 32

Gly Gly Lys Leu Asp Ala Trp Glu Lys Ile Arg Leu Arg Pro Gly Gly
1               5                   10                  15

Lys Lys His Tyr Met Ile Lys His Leu Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Ile Lys Gln Leu Gln Pro Ala Leu Gln Thr Gly Thr Glu
    50                  55                  60

Glu Leu Arg Ser Leu Tyr Asn Thr Val Ala Thr Leu Tyr Cys Val His
65                  70                  75                  80

Glu Lys Ile Asp Val Arg Asp Thr Lys Glu Ala Leu Asp Lys Ile Glu
                85                  90                  95

Glu Glu Gln Asn Lys Ile Gln Gln Lys Thr Gln Gln Ala Glu Ala Ala
            100                 105                 110

Asp Lys Gly Lys Val Ser Gln Asn Tyr Pro Ile Val Gln Asn Leu Gln
        115                 120                 125

Gly Gln Met Val His Gln Ala Ile Ser Pro Arg Thr Leu Asn Ala Trp
    130                 135                 140

Val Lys Val Ile Glu Glu Lys Ala Phe Ser Pro Glu Val Ile Pro Met
145                 150                 155                 160

Phe Thr Ala Leu Ser Glu Gly Ala Thr Pro Gln Asp Leu Asn Thr Met
                165                 170                 175

Leu Asn Thr Val Gly Gly His Gln Ala Ala Met Gln Met Leu Lys Asp
            180                 185                 190

Thr Ile Asn Glu Glu Ala Ala Glu Trp Asp Arg Leu His Pro Val His
        195                 200                 205

Ala Gly Pro Val Ala Pro Gly Gln Met Arg Glu Pro Arg Gly Ser Asp
    210                 215                 220

Ile Ala Gly Thr Thr Ser Thr Leu Gln Glu Gln Ile Ala Trp Met Thr
225                 230                 235                 240

Ser Asn Pro Pro Ile Pro Val Gly Asp Ile Tyr Lys Arg Trp Ile Ile
                245                 250                 255

Leu Gly Leu Asn Lys Ile Val Arg Met Tyr Ser Pro Val Ser Ile Leu
            260                 265                 270

Asp Ile Lys Gln Gly Pro Lys Glu Pro Phe Arg Asp Tyr Val Asp Arg
        275                 280                 285

Phe Phe Lys Thr Leu Arg Ala Glu Gln Ser Thr Gln Glu Val Lys Asn
    290                 295                 300

Trp Met Thr Asp
305

<210> SEQ ID NO 33
<211> LENGTH: 308
<212> TYPE: PRT
<213> ORGANISM: Human immunodeficiency virus type 1

<400> SEQUENCE: 33

Gly Gly Gln Leu Asp Lys Trp Glu Lys Ile Arg Leu Arg Pro Gly Gly
1               5                   10                  15

Lys Lys His Tyr Met Leu Lys His Leu Val Trp Ala Ser Arg Glu Leu
            20                  25                  30

Glu Arg Phe Ala Leu Asn Pro Gly Leu Leu Glu Thr Ser Glu Gly Cys
```

```
                35                  40                  45
Lys Gln Ile Ile Lys Gln Leu Gln Pro Ala Leu Gln Thr Gly Thr Glu
         50                  55                  60

Glu Leu Arg Ser Leu Tyr Asn Thr Val Ala Thr Leu Tyr Cys Val His
 65                  70                  75                  80

Glu Lys Ile Glu Val Arg Asp Thr Lys Glu Ala Leu Asp Lys Ile Glu
                 85                  90                  95

Glu Glu Gln Asn Lys Ser Gln Gln Lys Thr Gln Gln Ala Glu Ala Ala
                100                 105                 110

Asp Lys Gly Lys Val Ser Gln Asn Tyr Pro Ile Val Gln Asn Leu Gln
            115                 120                 125

Gly Gln Met Val His Gln Ala Leu Ser Pro Arg Thr Leu Asn Ala Trp
        130                 135                 140

Val Lys Val Ile Glu Glu Lys Ala Phe Ser Pro Glu Val Ile Pro Met
145                 150                 155                 160

Phe Thr Ala Leu Ser Glu Gly Ala Thr Pro Gln Asp Leu Asn Thr Met
                165                 170                 175

Leu Asn Thr Val Gly Gly His Gln Ala Ala Met Gln Met Leu Lys Asp
            180                 185                 190

Thr Ile Asn Glu Glu Ala Ala Glu Trp Asp Arg Leu His Pro Val His
        195                 200                 205

Ala Gly Pro Ile Ala Pro Gly Gln Met Arg Glu Pro Arg Gly Ser Asp
    210                 215                 220

Ile Ala Gly Thr Thr Ser Thr Leu Gln Glu Gln Ile Ala Trp Met Thr
225                 230                 235                 240

Ser Asn Pro Pro Ile Pro Val Gly Asp Ile Tyr Lys Arg Trp Ile Ile
                245                 250                 255

Leu Gly Leu Asn Lys Ile Val Arg Met Tyr Ser Pro Val Ser Ile Leu
            260                 265                 270

Asp Ile Lys Gln Gly Pro Lys Glu Pro Phe Arg Asp Tyr Val Asp Arg
        275                 280                 285

Phe Phe Lys Thr Leu Arg Ala Glu Gln Ala Thr Gln Asp Val Lys Asn
    290                 295                 300

Trp Met Thr Asp
305

<210> SEQ ID NO 34
<211> LENGTH: 307
<212> TYPE: PRT
<213> ORGANISM: Human immunodeficiency virus type 1

<400> SEQUENCE: 34

Gly Glu Lys Leu Asp Thr Trp Glu Lys Ile Arg Leu Arg Pro Gly Gly
 1               5                  10                  15

Lys Lys His Tyr Met Leu Lys His Ile Val Trp Ala Ser Arg Glu Leu
                20                  25                  30

Glu Arg Phe Ala Leu Asn Pro Gly Leu Leu Glu Thr Ser Glu Gly Cys
            35                  40                  45

Lys Gln Ile Met Lys Gln Leu Gln Pro Ala Leu Gln Thr Gly Thr Glu
        50                  55                  60

Glu Leu Lys Ser Leu Tyr Asn Thr Val Ala Thr Leu Tyr Cys Val His
 65                  70                  75                  80

Glu Lys Ile Glu Val Arg Asp Thr Lys Glu Ala Leu Asp Lys Ile Glu
                 85                  90                  95

Glu Glu Gln Asn Lys Cys Gln Gln Lys Thr Gln Gln Ala Lys Ala Ala
```

-continued

```
                100                 105                 110
Asp Gly Lys Val Ser Gln Asn Tyr Pro Ile Val Gln Asn Leu Gln Gly
            115                 120                 125
Gln Met Val His Gln Ala Ile Ser Pro Arg Thr Leu Asn Ala Trp Val
        130                 135                 140
Lys Val Ile Glu Glu Lys Ala Phe Ser Pro Glu Val Ile Pro Met Phe
145                 150                 155                 160
Thr Ala Leu Ser Glu Gly Ala Thr Pro Gln Asp Leu Asn Thr Met Leu
                165                 170                 175
Asn Thr Val Gly Gly His Gln Ala Ala Met Gln Met Leu Lys Asp Thr
            180                 185                 190
Ile Asn Glu Glu Ala Ala Glu Trp Asp Arg Leu His Pro Val His Ala
        195                 200                 205
Gly Pro Ile Ala Pro Gly Gln Met Arg Glu Pro Arg Gly Ser Asp Ile
210                 215                 220
Ala Gly Thr Thr Ser Thr Leu Gln Glu Gln Ile Ala Trp Met Thr Ser
225                 230                 235                 240
Asn Pro Pro Ile Pro Val Gly Asp Ile Tyr Lys Arg Trp Ile Ile Leu
                245                 250                 255
Gly Leu Asn Lys Ile Val Arg Met Tyr Ser Pro Val Ser Ile Leu Asp
            260                 265                 270
Ile Arg Gln Gly Pro Lys Glu Pro Phe Arg Asp Tyr Val Asp Arg Phe
        275                 280                 285
Phe Lys Thr Leu Arg Ala Glu Gln Ala Thr Gln Glu Val Lys Asn Trp
    290                 295                 300
Met Thr Asp
305

<210> SEQ ID NO 35
<211> LENGTH: 307
<212> TYPE: PRT
<213> ORGANISM: Human immunodeficiency virus type 1

<400> SEQUENCE: 35

Gly Glu Lys Leu Asp Thr Trp Glu Arg Ile Arg Leu Arg Pro Gly Gly
1               5                   10                  15
Lys Lys His Tyr Met Leu Lys His Ile Val Trp Ala Ser Arg Glu Leu
            20                  25                  30
Glu Arg Phe Ala Leu Asn Pro Gly Leu Leu Glu Thr Ser Glu Gly Cys
        35                  40                  45
Lys Gln Ile Ile Arg Gln Leu Gln Pro Ala Leu Gln Thr Gly Thr Glu
    50                  55                  60
Glu Leu Lys Ser Leu Phe Asn Thr Val Ala Thr Leu Tyr Cys Val His
65                  70                  75                  80
Glu Lys Ile Lys Val Arg Asp Thr Lys Glu Ala Leu Asp Lys Ile Glu
                85                  90                  95
Glu Glu Gln Asn Lys Ser Gln Gln Lys Thr Gln Gln Ala Lys Ala Ala
            100                 105                 110
Asp Glu Lys Ile Ser Gln Asn Tyr Pro Ile Val Gln Asn Leu Gln Gly
        115                 120                 125
Gln Met Val His Gln Ala Ile Ser Pro Arg Thr Leu Asn Ala Trp Val
    130                 135                 140
Lys Val Ile Glu Glu Lys Ala Phe Ser Pro Glu Val Ile Pro Met Phe
145                 150                 155                 160
Thr Ala Leu Ser Glu Gly Ala Thr Pro Gln Asp Leu Asn Thr Met Leu
```

```
                    165                 170                 175
Asn Thr Val Gly Gly His Gln Ala Ala Met Gln Met Leu Lys Asp Thr
            180                 185                 190

Ile Asn Asp Glu Ala Ala Glu Trp Asp Arg Leu His Pro Val His Ala
        195                 200                 205

Gly Pro Ile Ala Pro Gly Gln Met Arg Glu Pro Arg Gly Ser Asp Ile
    210                 215                 220

Ala Gly Thr Thr Ser Thr Leu Gln Glu Gln Ile Ala Trp Met Thr Ser
225                 230                 235                 240

Asn Pro Pro Ile Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Arg Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
    290                 295                 300

Met Thr Asp
305

<210> SEQ ID NO 36
<211> LENGTH: 257
<212> TYPE: PRT
<213> ORGANISM: Human immunodeficiency virus type 1

<400> SEQUENCE: 36

Gly Glu Asn Leu Asp Arg Trp Glu Lys Ile Arg Leu Arg Pro Gly Gly
1               5                   10                  15

Lys Lys Arg Tyr Met Leu Lys His Ile Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Lys Gln Leu Gln Pro Ala Leu Gln Thr Gly Thr Glu
    50                  55                  60

Glu Leu Lys Ser Leu Tyr Asn Thr Val Ala Thr Leu Tyr Cys Val His
65                  70                  75                  80

Lys Lys Ile Asp Val Gln Asp Thr Lys Glu Ala Leu Asp Lys Val Glu
                85                  90                  95

Glu Glu Gln Asn Lys Ser Gln Gln Lys Thr Gln Gln Ala Glu Ala Ala
            100                 105                 110

Asp Gly Lys Val Ser Gln Asn Tyr Pro Ile Val Gln Asn Leu Gln Gly
        115                 120                 125

Gln Met Val His Gln Ala Ile Ser Pro Arg Thr Leu Asn Ala Trp Val
    130                 135                 140

Glu Glu Ala Ala Glu Trp Asp Arg Met His Pro Val His Ala Gly Pro
145                 150                 155                 160

Ile Ala Pro Gly Gln Met Arg Glu Pro Arg Gly Ser Asp Ile Ala Gly
                165                 170                 175

Thr Thr Ser Thr Leu Gln Glu Gln Ile Ala Trp Met Thr Ser Asn Pro
            180                 185                 190

Pro Val Pro Val Gly Asp Ile Tyr Lys Arg Trp Ile Ile Leu Gly Leu
        195                 200                 205

Asn Lys Ile Val Arg Met Tyr Ser Pro Val Ser Ile Leu Asp Ile Arg
    210                 215                 220

Gln Gly Pro Lys Glu Pro Phe Arg Asp Tyr Val Asp Arg Phe Phe Lys
```

```
            225                 230                 235                 240
Thr Leu Arg Ala Glu Gln Ala Thr Gln Asp Val Lys Asn Trp Met Thr
                245                 250                 255

Asp

<210> SEQ ID NO 37
<211> LENGTH: 307
<212> TYPE: PRT
<213> ORGANISM: Human immunodeficiency virus type 1

<400> SEQUENCE: 37

Gly Lys Lys Leu Asp Ser Trp Glu Arg Ile Arg Leu Arg Pro Gly Gly
1               5                   10                  15

Lys Lys His Tyr Met Ile Lys His Leu Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Lys Gln Leu Gln Pro Ala Leu Gln Thr Gly Thr Glu
    50                  55                  60

Glu Leu Arg Ser Leu Phe Asn Thr Val Ala Thr Leu Tyr Cys Val His
65                  70                  75                  80

Glu Lys Ile Glu Val Arg Asp Thr Lys Glu Ala Leu Asp Lys Ile Glu
                85                  90                  95

Glu Glu Gln Asn Lys Ser Gln Gln Lys Thr Gln Gln Ala Lys Glu Ala
            100                 105                 110

Asp Gly Lys Thr Ser Gln Asn Tyr Pro Ile Val Gln Asn Leu Gln Gly
        115                 120                 125

Gln Met Val His Gln Ala Leu Ser Pro Arg Thr Leu Asn Ala Trp Val
    130                 135                 140

Lys Val Val Glu Glu Lys Ala Phe Ser Pro Glu Val Ile Pro Met Phe
145                 150                 155                 160

Thr Ala Leu Ser Glu Gly Ala Thr Pro Gln Asp Leu Asn Ser Met Leu
                165                 170                 175

Asn Thr Val Gly Gly His Gln Ala Ala Met Gln Ile Leu Lys Asp Thr
            180                 185                 190

Ile Asn Glu Glu Val Ala Glu Trp Asp Arg Leu His Pro Val His Ala
        195                 200                 205

Gly Pro Ile Ala Pro Gly Gln Met Arg Glu Pro Arg Gly Ser Asp Ser
    210                 215                 220

Ala Gly Thr Thr Ser Thr Leu Gln Glu Gln Ile Ala Trp Ile Thr Asn
225                 230                 235                 240

Asn Pro Pro Ile Pro Val Gly Glu Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Lys Gln Gly Pro Lys Glu Pro Phe Arg Asp Tyr Val Asp Arg Phe
        275                 280                 285

Phe Lys Thr Leu Arg Ala Glu Gln Ala Thr Gln Glu Val Lys Asn Trp
    290                 295                 300

Met Thr Asp
305

<210> SEQ ID NO 38
<211> LENGTH: 307
<212> TYPE: PRT
<213> ORGANISM: Human immunodeficiency virus type 1
```

<400> SEQUENCE: 38

Gly Gly Lys Leu Asp Thr Trp Glu Lys Ile Arg Leu Arg Pro Gly Gly
1               5                   10                  15

Lys Lys Gln Tyr Met Ile Lys His Leu Val Trp Ala Ser Arg Glu Leu
            20                  25                  30

Glu Arg Phe Ala Leu Asn Pro Gly Leu Leu Glu Thr Ser Glu Gly Cys
        35                  40                  45

Arg Gln Ile Met Lys Gln Leu Gln Pro Ala Leu Gln Thr Gly Thr Glu
    50                  55                  60

Glu Leu Arg Ser Leu Phe Asn Thr Val Ala Thr Leu Tyr Cys Val His
65                  70                  75                  80

Glu Lys Ile Glu Val Arg Asp Thr Lys Glu Ala Leu Asp Lys Ile Glu
                85                  90                  95

Glu Glu Gln Asn Lys Ser Gln Gln Lys Thr Gln Gln Ala Lys Gly Ala
            100                 105                 110

Asp Gly Lys Ile Ser Gln Asn Tyr Pro Ile Val Gln Asn Leu Gln Gly
        115                 120                 125

Gln Met Val His Gln Ala Ile Ser Pro Arg Thr Leu Asn Ala Trp Val
    130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Ile Leu Lys Asp Thr
            180                 185                 190

Ile Asn Glu Glu Ala Ala Glu Trp Asp Arg Leu His Pro Ile His Ala
        195                 200                 205

Gly Pro Ile Ala Pro Gly Gln Val Arg Glu Pro Arg Gly Ser Asp Ile
    210                 215                 220

Ala Gly Thr Thr Ser Thr Leu Gln Glu Gln Ile Thr Trp Ile Thr Ala
225                 230                 235                 240

Asn Pro Pro Val Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Arg Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
    290                 295                 300

Met Thr Asp
305

<210> SEQ ID NO 39
<211> LENGTH: 307
<212> TYPE: PRT
<213> ORGANISM: Human immunodeficiency virus type 1

<400> SEQUENCE: 39

Gly Glu Lys Leu Asp Lys Trp Glu Lys Ile Arg Leu Arg Pro Gly Gly
1               5                   10                  15

Lys Lys Lys Tyr Met Leu Lys His Leu Ile Trp Ala Ser Arg Glu Leu
            20                  25                  30

Glu Arg Phe Ala Leu Asn Pro Gly Leu Leu Glu Thr Ala Glu Gly Cys
        35                  40                  45

-continued

```
Lys Gln Ile Met Gln Gln Ile Gln Pro Ala Leu Gln Thr Gly Thr Glu
            50                  55                  60

Glu Leu Arg Ser Leu Phe Asn Thr Val Ala Thr Leu Tyr Cys Val His
 65                  70                  75                  80

Ala Lys Ile Glu Val Arg Asp Thr Lys Glu Ala Leu Asp Lys Ile Glu
                    85                  90                  95

Glu Glu Gln Asn Lys Ser Gln Gln Lys Thr Gln Gln Ala Lys Ala Ala
                100                 105                 110

Gly Gly Gln Val Ser Gln Asn Tyr Pro Ile Val Gln Asn Leu Gln Gly
            115                 120                 125

Gln Met Val His Gln Ala Ile Ser Pro Arg Thr Leu Asn Ala Trp Val
    130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
        195                 200                 205

Gly Pro Ala Ala Pro Gly Gln Met Arg Glu Pro Arg Gly Ser Asp Ile
    210                 215                 220

Ala Gly Thr Thr Ser Thr Leu Gln Glu Gln Ile Ala Trp Met Thr Ser
225                 230                 235                 240

Asn Pro Pro Val Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Arg Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
    290                 295                 300

Met Thr Asp
305

<210> SEQ ID NO 40
<211> LENGTH: 307
<212> TYPE: PRT
<213> ORGANISM: Human immunodeficiency virus type 1

<400> SEQUENCE: 40

Gly Gly Lys Leu Asp Lys Trp Glu Lys Ile Arg Leu Arg Pro Gly Gly
1               5                   10                  15

Lys Lys Cys Tyr Met Leu Lys His Ile Ile Trp Ala Ser Arg Glu Leu
                20                  25                  30

Glu Arg Phe Ala Leu Asn Pro Gly Leu Leu Glu Thr Lys Glu Gly Cys
            35                  40                  45

Lys Gln Ile Ile Asn Gln Leu His Pro Ala Leu Gln Thr Gly Thr Glu
        50                  55                  60

Glu Leu Arg Ser Leu Phe Asn Thr Val Ala Thr Leu Tyr Cys Val His
 65                 70                  75                  80

Ala Glu Ile Glu Val Arg Asp Thr Lys Glu Ala Leu Asp Lys Ile Glu
                    85                  90                  95

Glu Glu Gln Asn Asn Ile Gln Gln Lys Thr Gln Gln Ala Lys Ala Ala
                100                 105                 110
```

```
Asp Gly Lys Val Ser Gln Asn Tyr Pro Ile Val Gln Asn Leu Gln Gly
            115                 120                 125

Gln Met Val His Gln Ala Ile Ser Pro Arg Thr Leu Asn Ala Trp Val
    130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
        195                 200                 205

Gly Pro Val Ala Pro Gly Gln Met Arg Glu Pro Arg Gly Ser Asp Ile
    210                 215                 220

Ala Gly Thr Thr Ser Thr Leu Gln Glu Gln Ile Ala Trp Met Thr Ala
225                 230                 235                 240

Asn Pro Pro Ile Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Arg Gln Gly Pro Lys Glu Pro Phe Arg Asp Tyr Val Asp Arg Phe
        275                 280                 285

Phe Lys Thr Leu Arg Ala Glu Gln Ala Thr Gln Asp Val Lys Asn Trp
    290                 295                 300

Met Thr Glu
305

<210> SEQ ID NO 41
<211> LENGTH: 307
<212> TYPE: PRT
<213> ORGANISM: Human immunodeficiency virus type 1

<400> SEQUENCE: 41

Gly Glu Lys Leu Asp Arg Trp Glu Arg Ile Arg Leu Arg Pro Gly Gly
1               5                   10                  15

Lys Lys Thr Tyr Met Leu Lys His Ile Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Asn Gln Leu Gln Pro Ala Val Gln Thr Gly Thr Glu
    50                  55                  60

Glu Leu Lys Ser Leu Phe Asn Thr Val Ala Thr Leu Tyr Cys Val His
65                  70                  75                  80

Glu Lys Ile Asp Val Arg Asp Thr Lys Glu Ala Leu Asp Lys Ile Glu
                85                  90                  95

Glu Glu Gln Asn Lys Ser Gln Gln Lys Thr Pro Gln Ala Lys Ala Ala
            100                 105                 110

Asp Gly Lys Val Ser Gln Asn Tyr Pro Ile Val Gln Asn Leu Gln Gly
        115                 120                 125

Gln Met Val His Gln Ala Ile Ser Pro Arg Thr Leu Asn Ala Trp Val
    130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175
```

```
Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val Gln Ala
        195                 200                 205

Gly Pro Ile Ala Pro Gly Gln Ile Arg Glu Pro Arg Gly Ser Asp Ile
    210                 215                 220

Ala Gly Ser Thr Ser Asn Leu Gln Glu Gln Ile Thr Trp Met Thr Ser
225                 230                 235                 240

Asn Pro Pro Ile Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Lys Gln Gly Pro Lys Glu Pro Phe Arg Asp Tyr Val Asp Arg Phe
        275                 280                 285

Phe Lys Ala Leu Arg Ala Glu Gln Ala Thr Gln Asp Val Lys Asn Trp
    290                 295                 300

Met Thr Asp
305

<210> SEQ ID NO 42
<211> LENGTH: 307
<212> TYPE: PRT
<213> ORGANISM: Human immunodeficiency virus type 1

<400> SEQUENCE: 42

Gly Glu Lys Leu Asp Lys Trp Glu Lys Ile Arg Leu Arg Pro Gly Gly
1               5                   10                  15

Lys Lys His Tyr Met Leu Lys His Leu Val Trp Ala Ser Arg Glu Leu
            20                  25                  30

Glu Arg Phe Ala Leu Asn Pro Asp Leu Leu Glu Thr Ser Glu Gly Cys
        35                  40                  45

Lys Gln Ile Met Lys Gln Leu Gln Pro Ala Leu Gln Thr Gly Thr Glu
    50                  55                  60

Glu Leu Arg Ser Leu Phe Asn Thr Val Ala Thr Leu Tyr Cys Val His
65                  70                  75                  80

Glu Lys Ile Glu Ile Arg Asp Thr Lys Glu Ala Leu Asp Lys Ile Glu
                85                  90                  95

Glu Glu Gln Asn Lys Cys Gln Gln Lys Thr Gln Gln Ala Lys Glu Ala
            100                 105                 110

Asp Gly Lys Val Ser Gln Asn Tyr Pro Ile Val Gln Asn Leu Gln Gly
        115                 120                 125

Gln Met Val His Gln Ala Ile Ser Pro Arg Thr Leu Asn Ala Trp Val
    130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Ala Gln Ala
        195                 200                 205

Gly Pro His Pro Ala Gly Gln Met Arg Asp Pro Arg Gly Ser Asp Ile
    210                 215                 220

Ala Gly Thr Thr Ser Thr Leu Gln Glu Gln Ile Ala Trp Met Thr Ser
225                 230                 235                 240
```

-continued

```
Asn Pro Pro Ile Pro Val Gly Glu Ile Tyr Lys Arg Trp Ile Ile Leu
            245                 250                 255

Gly Leu Asn Lys Ile Val Arg Met Tyr Ser Pro Val Ser Ile Leu Asp
            260                 265                 270

Ile Lys Gln Gly Pro Lys Glu Pro Phe Arg Asp Tyr Val Asp Arg Phe
            275                 280                 285

Phe Lys Thr Leu Arg Ala Glu Gln Ala Thr Gln Asp Val Lys Asn Trp
            290                 295                 300

Met Thr Asp
305

<210> SEQ ID NO 43
<211> LENGTH: 299
<212> TYPE: PRT
<213> ORGANISM: Human immunodeficiency virus type 1

<400> SEQUENCE: 43

Gly Glu Lys Leu Asp Lys Trp Glu Arg Ile Lys Leu Arg Pro Gly Gly
1               5                   10                  15

Lys Lys His Tyr Arg Leu Lys His Ile Val Trp Ala Ser Arg Glu Leu
            20                  25                  30

Glu Arg Phe Ala Leu Asn Pro Gly Leu Leu Glu Thr Ser Glu Gly Cys
        35                  40                  45

Lys Gln Ile Met Asn Gln Leu Gln Pro Ala Leu Gln Thr Gly Thr Glu
    50                  55                  60

Glu Leu Arg Ser Leu Phe Asn Thr Val Ala Thr Leu Tyr Cys Val His
65                  70                  75                  80

Ala Lys Ile Asp Val Arg Asp Thr Lys Glu Ala Leu Asp Lys Ile Glu
                85                  90                  95

Glu Glu Gln Asn Lys Ser Gln Gln Lys Thr Gln Val Ser Gln Asn Tyr
            100                 105                 110

Pro Ile Val Gln Asn Leu Gln Gly Gln Met Val His Gln Pro Ile Thr
        115                 120                 125

Pro Arg Thr Leu Asn Ala Trp Val Lys Val Ile Glu Glu Lys Gly Phe
    130                 135                 140

Asn Pro Glu Val Ile Pro Met Phe Thr Ala Leu Ser Glu Gly Ala Thr
145                 150                 155                 160

Pro Gln Asp Leu Asn Thr Met Leu Asn Thr Val Gly Gly His Gln Ala
                165                 170                 175

Ala Met Gln Met Leu Lys Asp Thr Ile Asn Glu Glu Ala Ala Glu Trp
            180                 185                 190

Asp Arg Leu His Pro Val His Ala Gly Pro Ile Ala Pro Gly Gln Met
        195                 200                 205

Arg Glu Pro Arg Gly Ser Asp Ile Ala Gly Thr Thr Ser Thr Leu Gln
    210                 215                 220

Glu Gln Ile Ala Trp Ile Thr Gly Asn Pro Pro Ile Pro Val Gly Glu
225                 230                 235                 240

Ile Tyr Lys Arg Trp Ile Ile Leu Gly Leu Asn Lys Ile Val Arg Met
                245                 250                 255

Tyr Ser Pro Val Ser Ile Leu Asp Ile Lys Gln Gly Pro Lys Glu Pro
            260                 265                 270

Phe Arg Asp Tyr Val Asp Arg Phe Phe Lys Thr Leu Arg Ala Glu Gln
        275                 280                 285

Ala Thr Gln Asp Val Lys Asn Trp Met Thr Asp
    290                 295
```

```
<210> SEQ ID NO 44
<211> LENGTH: 308
<212> TYPE: PRT
<213> ORGANISM: Human immunodeficiency virus type 1

<400> SEQUENCE: 44

Gly Gly Lys Leu Asp Thr Trp Glu Lys Ile Arg Leu Arg Pro Gly Gly
1               5                   10                  15

Lys Lys Arg Tyr Lys Met Lys His Ile Val Trp Ala Ser Arg Glu Leu
            20                  25                  30

Glu Arg Phe Ala Leu Asn Pro Gly Leu Leu Glu Thr Ala Glu Gly Cys
        35                  40                  45

Lys Gln Ile Ile Gln Gln Leu Gln Pro Ala Leu Lys Thr Gly Thr Glu
    50                  55                  60

Glu Leu Lys Ser Leu Phe Asn Thr Val Ala Thr Leu Tyr Cys Val His
65                  70                  75                  80

Lys Arg Ile Glu Val Arg Asp Thr Lys Glu Ala Leu Asp Lys Val Glu
                85                  90                  95

Glu Glu Gln Asn Lys Ser Gln Gln Lys Thr Gln Gln Ala Asp Ala Ala
            100                 105                 110

Asp Lys Gly Lys Val Ser Gln Asn Phe Pro Ile Val Gln Asn Val Gln
        115                 120                 125

Gly Gln Met Val His Gln Ala Ile Ser Pro Arg Thr Leu Asn Ala Trp
    130                 135                 140

Val Lys Val Ile Glu Glu Lys Ala Phe Ser Pro Glu Val Ile Pro Met
145                 150                 155                 160

Phe Thr Ala Leu Ser Glu Gly Ala Thr Pro Gln Asp Leu Asn Thr Met
                165                 170                 175

Leu Asn Thr Val Gly Gly His Gln Ala Ala Met Gln Met Leu Lys Asp
            180                 185                 190

Thr Ile Asn Glu Glu Ala Ala Glu Trp Asp Arg Leu His Pro Val Gln
        195                 200                 205

Ala Gly Pro Val Ala Pro Gly Gln Ile Arg Glu Pro Arg Gly Ser Asp
    210                 215                 220

Ile Ala Gly Thr Thr Ser Thr Leu Gln Glu Gln Ile Ala Trp Met Thr
225                 230                 235                 240

Arg Asn Pro Pro Val Pro Val Gly Asp Ile Tyr Lys Arg Trp Ile Ile
                245                 250                 255

Met Gly Leu Asn Lys Ile Val Arg Met Tyr Ser Pro Val Ser Ile Leu
            260                 265                 270

Asp Ile Lys Gln Gly Pro Lys Glu Pro Phe Arg Asp Tyr Val Asp Arg
        275                 280                 285

Phe Phe Lys Thr Leu Arg Ala Glu Gln Ala Thr Gln Glu Val Lys Asn
    290                 295                 300

Trp Met Thr Asp
305

<210> SEQ ID NO 45
<211> LENGTH: 311
<212> TYPE: PRT
<213> ORGANISM: Human immunodeficiency virus type 1

<400> SEQUENCE: 45

Gly Gly Lys Leu Asp Lys Trp Glu Arg Ile Arg Leu Arg Pro Gly Gly
1               5                   10                  15

Lys Lys His Tyr Met Leu Lys His Leu Ile Trp Ala Ser Arg Glu Leu
```

```
                 20                  25                  30
Glu Arg Phe Ala Leu Asn Pro Gly Leu Leu Glu Thr Ser Glu Gly Cys
             35                  40                  45
Lys Gln Ile Ile Lys Gln Leu His Pro Ala Leu Gln Thr Gly Thr Glu
         50                  55                  60
Glu Leu Arg Ser Leu Tyr Asn Thr Ile Ala Val Leu Tyr Cys Val His
 65                  70                  75                  80
Lys Asp Ile Ala Val Gln Asp Thr Lys Glu Ala Leu Asp Lys Ile Glu
                 85                  90                  95
Glu Glu Gln Asn Lys Cys Gln Gln Lys Ser Gln Gln Lys Thr Gln Gln
             100                 105                 110
Thr Ala Ala Ala Asp Gly Ala Ala Ser Gln Asn Tyr Pro Ile Val Gln
         115                 120                 125
Asn Leu Gln Gly Gln Met Val His Gln Ser Leu Ser Pro Arg Thr Leu
         130                 135                 140
Asn Ala Trp Val Lys Val Ile Glu Glu Lys Ala Phe Ser Pro Glu Val
145                 150                 155                 160
Ile Pro Met Phe Thr Ala Leu Ser Glu Gly Ala Thr Pro Gln Asp Leu
                 165                 170                 175
Asn Thr Met Leu Asn Thr Val Gly Gly His Gln Ala Ala Met Gln Met
             180                 185                 190
Leu Lys Asp Thr Ile Asn Glu Glu Ala Ala Glu Trp Asp Arg Leu His
         195                 200                 205
Pro Val His Ala Gly Pro Ile Ala Pro Gly Gln Met Arg Glu Pro Arg
         210                 215                 220
Gly Ser Asp Ile Ala Gly Thr Thr Ser Thr Leu Gln Glu Gln Ile Thr
225                 230                 235                 240
Trp Met Thr Ser Asn Pro Pro Val Pro Val Gly Glu Ile Tyr Lys Arg
                 245                 250                 255
Trp Ile Ile Leu Gly Leu Asn Lys Ile Val Arg Met Tyr Ser Pro Val
             260                 265                 270
Ser Ile Leu Asp Ile Lys Gln Gly Pro Lys Glu Pro Phe Arg Asp Tyr
         275                 280                 285
Val Asp Arg Phe Phe Lys Thr Leu Arg Ala Glu Gln Ala Thr Gln Asp
         290                 295                 300
Val Lys Asn Trp Met Thr Glu
305                 310

<210> SEQ ID NO 46
<211> LENGTH: 307
<212> TYPE: PRT
<213> ORGANISM: Human immunodeficiency virus type 1

<400> SEQUENCE: 46

Gly Gly Lys Leu Asp Lys Trp Glu Lys Ile Arg Leu Arg Pro Gly Gly
  1               5                  10                  15
Lys Lys Arg Tyr Met Ile Lys His Leu Val Trp Ala Ser Arg Glu Leu
             20                  25                  30
Glu Arg Phe Ala Leu Asn Pro Gly Leu Leu Glu Thr Ala Glu Gly Cys
             35                  40                  45
Lys Gln Ile Ile Gln Gln Leu Gln Pro Ala Leu Lys Thr Gly Thr Glu
         50                  55                  60
Glu Leu Lys Ser Leu Tyr Asn Thr Val Ala Thr Leu Tyr Cys Val His
 65                  70                  75                  80
Ala Glu Ile Glu Val Arg Asp Thr Lys Glu Ala Leu Asp Lys Ile Glu
```

```
                      85                  90                  95
Glu Glu Gln Asn Lys Cys Gln Gln Lys Thr Lys Gln Thr Lys Glu Asp
                100                 105                 110
Asp Gly Lys Ala Ser Gln Asn Tyr Pro Ile Val Gln Asn Ala Gln Gly
            115                 120                 125
Ala Met Val His Gln Pro Ile Ser Pro Arg Thr Leu Asn Ala Trp Val
        130                 135                 140
Lys Val Ile Glu Glu Lys Gly Phe Asn Pro Glu Val Ile Pro Met Phe
145                 150                 155                 160
Thr Ala Leu Ser Glu Gly Ala Thr Pro Gln Asp Leu Asn Thr Met Leu
                165                 170                 175
Asn Thr Val Gly Gly His Gln Ala Ala Met Gln Met Leu Lys Asp Thr
                180                 185                 190
Ile Asn Glu Glu Ala Ala Glu Trp Asp Arg Val His Pro Val His Ala
            195                 200                 205
Gly Pro Ile Ala Pro Gly Gln Met Arg Glu Pro Arg Gly Ser Asp Ile
        210                 215                 220
Ala Gly Thr Thr Ser Asn Leu Gln Glu Gln Ile Ala Trp Met Thr Asn
225                 230                 235                 240
Asn Pro Pro Ile Pro Val Gly Glu Ile Tyr Lys Arg Trp Ile Val Leu
                245                 250                 255
Gly Leu Asn Lys Ile Val Arg Met Tyr Ser Pro Val Ser Ile Leu Asp
                260                 265                 270
Ile Lys Gln Gly Pro Lys Glu Pro Phe Arg Asp Tyr Val Asp Arg Phe
            275                 280                 285
Phe Lys Thr Leu Arg Ala Glu Gln Ala Thr Gln Asp Val Lys Asn Trp
        290                 295                 300
Met Thr Glu
305

<210> SEQ ID NO 47
<211> LENGTH: 309
<212> TYPE: PRT
<213> ORGANISM: Human immunodeficiency virus type 1

<400> SEQUENCE: 47

Gly Gly Asn Leu Asp Thr Trp Glu Lys Ile Arg Leu Arg Pro Gly Gly
1               5                   10                  15
Lys Lys Gln Tyr Lys Leu Lys His Leu Val Trp Ala Ser Arg Glu Leu
                20                  25                  30
Glu Arg Phe Ala Leu Asn Pro Gly Leu Leu Glu Ser Ala Glu Gly Cys
            35                  40                  45
Lys Gln Ile Ile Lys Gln Leu Gln Pro Ala Leu Gln Thr Gly Thr Glu
        50                  55                  60
Glu Leu Arg Ser Leu Tyr Asn Thr Val Ala Thr Leu Tyr Cys Val His
65                  70                  75                  80
Glu Arg Ile Glu Val Gln Asp Thr Lys Glu Ala Leu Asp Lys Ile Glu
                85                  90                  95
Glu Glu Gln Asn Lys Ile Gln Gln Lys Thr Gln Gln Ala Lys Ala Lys
                100                 105                 110
Glu Ala Asp Gly Lys Thr Ser Gln Asn Tyr Pro Ile Val Gln Asn Ile
            115                 120                 125
Gln Gly Gln Met Val His Gln Ala Leu Ser Pro Arg Thr Leu Asn Ala
        130                 135                 140
Trp Val Lys Val Val Glu Glu Lys Ala Phe Ser Gln Glu Val Ile Pro
```

```
                145                 150                 155                 160
Met Phe Thr Ala Leu Ser Glu Gly Ala Thr Pro Gln Asp Leu Asn Thr
                    165                 170                 175

Met Leu Asn Thr Val Gly Gly His Gln Ala Ala Met Gln Ile Leu Lys
                180                 185                 190

Asp Thr Ile Asn Glu Glu Ala Ala Glu Trp Asp Arg Val His Pro Val
            195                 200                 205

Gln Ala Gly Pro Ile Ala Pro Gly Gln Ile Arg Glu Pro Arg Gly Ser
        210                 215                 220

Asp Ile Ala Gly Thr Thr Ser Thr Leu Gln Glu Gln Ile Thr Trp Met
225                 230                 235                 240

Thr Asn Asn Pro Pro Ile Pro Val Gly Glu Ile Tyr Lys Arg Trp Ile
                245                 250                 255

Ile Leu Gly Leu Asn Lys Ile Val Arg Met Tyr Ser Pro Val Ser Ile
                260                 265                 270

Leu Asp Ile Arg Gln Gly Pro Lys Glu Pro Phe Arg Asp Tyr Val Asp
            275                 280                 285

Arg Phe Phe Lys Thr Leu Arg Ala Glu Gln Ala Thr Gln Asp Val Lys
        290                 295                 300

Asn Trp Met Thr Asp
305

<210> SEQ ID NO 48
<211> LENGTH: 308
<212> TYPE: PRT
<213> ORGANISM: Human immunodeficiency virus type 1

<400> SEQUENCE: 48

Gly Gly Lys Leu Asp Ala Trp Glu Arg Ile Arg Leu Arg Pro Gly Gly
1               5                   10                  15

Lys Lys His Tyr Met Leu Lys His Leu Ile Trp Ala Ser Lys Glu Leu
            20                  25                  30

Glu Arg Phe Ala Leu Asn Pro Gly Leu Leu Glu Asn Ser Glu Gly Cys
        35                  40                  45

Lys Gln Ile Met Lys Gln Leu His Pro Ala Leu Gln Thr Gly Thr Glu
    50                  55                  60

Glu Leu Lys Ser Leu Tyr Asn Thr Val Ala Thr Leu Tyr Cys Val His
65                  70                  75                  80

Glu Lys Ile Glu Val Arg Asp Thr Lys Glu Ala Leu Asp Lys Ile Glu
                85                  90                  95

Glu Glu Gln Asn Lys Cys Gln His Lys Ala Gln Gln Ala Glu Thr Asp
            100                 105                 110

Asp Lys Gly Lys Val Ser Gln Asn Tyr Pro Ile Val Gln Asn Leu Gln
        115                 120                 125

Gly Gln Met Val His Gln Ala Leu Ser Pro Arg Thr Leu Asn Ala Trp
    130                 135                 140

Val Lys Val Ile Glu Glu Lys Asn Phe Ser Pro Glu Val Ile Pro Met
145                 150                 155                 160

Phe Thr Ala Leu Ser Glu Gly Ala Thr Pro Gln Asp Leu Asn Thr Met
                165                 170                 175

Leu Asn Thr Val Gly Gly His Gln Ala Ala Met Gln Met Leu Lys Glu
            180                 185                 190

Thr Ile Asn Glu Arg Ala Ala Glu Trp Asp Arg Leu His Pro Val His
        195                 200                 205

Ala Gly Pro Ile Ala Pro Gly Gln Met Arg Glu Pro Arg Gly Ser Asp
```

-continued

```
                210                 215                 220
Ile Ala Gly Thr Thr Ser Thr Leu Gln Glu Gln Ile Ala Trp Met Thr
225                 230                 235                 240

Ser Asn Pro Pro Ile Pro Val Gly Glu Ile Tyr Lys Arg Trp Ile Ile
                245                 250                 255

Leu Gly Leu Asn Lys Ile Val Arg Met Tyr Ser Pro Val Ser Ile Leu
                260                 265                 270

Asp Ile Arg Gln Gly Pro Lys Arg Ala Phe Arg Asp Tyr Val Asp Arg
                275                 280                 285

Phe Phe Lys Thr Leu Arg Ala Asp Gln Ser Thr Gln Glu Val Lys Asn
                290                 295                 300

Trp Met Thr Asp
305

<210> SEQ ID NO 49
<211> LENGTH: 307
<212> TYPE: PRT
<213> ORGANISM: Human immunodeficiency virus type 1

<400> SEQUENCE: 49

Gly Gly Lys Leu Asp Thr Trp Glu Lys Ile Arg Leu Arg Pro Gly Gly
1               5                   10                  15

Lys Lys His Tyr Met Ile Lys His Leu Val Trp Ala Ser Arg Glu Leu
                20                  25                  30

Glu Arg Phe Ala Leu Asn Pro Gly Leu Leu Glu Thr Ser Glu Gly Cys
            35                  40                  45

Lys Gln Ile Ile Lys Gln Leu Gln Pro Ala Leu Gln Thr Gly Thr Glu
50                  55                  60

Glu Leu Arg Ser Leu Tyr Asn Thr Val Ala Thr Leu Tyr Cys Val His
65                  70                  75                  80

Glu Lys Ile Glu Val Arg Asp Thr Lys Glu Ala Leu Asp Lys Ile Glu
                85                  90                  95

Glu Glu Gln Asn Lys Ser Gln Gln Lys Thr Gln Gln Ala Lys Ala Ala
            100                 105                 110

Asp Gly Lys Val Ser Gln Asn Tyr Pro Ile Val Gln Asn Leu Gln Gly
            115                 120                 125

Gln Met Val His Gln Ala Ile Ser Pro Arg Thr Leu Asn Ala Trp Val
        130                 135                 140

Lys Val Ile Glu Glu Lys Ala Phe Ser Pro Glu Val Ile Pro Met Phe
145                 150                 155                 160

Thr Ala Leu Ser Glu Gly Ala Thr Pro Gln Asp Leu Asn Thr Met Leu
                165                 170                 175

Asn Thr Val Gly Gly His Gln Ala Ala Met Gln Met Leu Lys Asp Thr
            180                 185                 190

Ile Asn Glu Glu Ala Ala Glu Trp Asp Arg Leu His Pro Val His Ala
        195                 200                 205

Gly Pro Val Ala Pro Gly Gln Met Arg Glu Pro Arg Gly Ser Asp Ile
    210                 215                 220

Ala Gly Thr Thr Ser Thr Leu Gln Glu Gln Ile Ala Trp Met Thr Ser
225                 230                 235                 240

Asn Pro Pro Ile Pro Val Gly Asp Ile Tyr Lys Arg Trp Ile Ile Leu
                245                 250                 255

Gly Leu Asn Lys Ile Val Arg Met Tyr Ser Pro Val Ser Ile Leu Asp
            260                 265                 270

Ile Lys Gln Gly Pro Lys Glu Pro Phe Arg Asp Tyr Val Asp Arg Phe
```

```
                275                 280                 285
Phe Lys Thr Leu Arg Ala Glu Gln Ala Thr Gln Asp Val Lys Asn Trp
290                 295                 300

Met Thr Asp
305

<210> SEQ ID NO 50
<211> LENGTH: 277
<212> TYPE: PRT
<213> ORGANISM: Human immunodeficiency virus type 1

<400> SEQUENCE: 50

Leu Thr Glu Glu Lys Ile Lys Ala Leu Thr Ala Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Gly Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ser Ser Met Thr Lys Ile Leu Glu
    130                 135                 140

Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Lys Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Ala Lys Ala Leu Thr Asp Ile Val Pro Leu Thr Glu
            260                 265                 270

Glu Ala Glu Leu Glu
        275

<210> SEQ ID NO 51
<211> LENGTH: 277
<212> TYPE: PRT
<213> ORGANISM: Human immunodeficiency virus type 1

<400> SEQUENCE: 51

Leu Thr Glu Glu Lys Ile Lys Ala Leu Thr Glu Ile Cys Glu Glu Met
1               5                   10                  15
```

```
Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
            35                  40                  45

Leu Val Asp Phe Arg Glu Leu Asn Lys Arg Thr Gln Asp Phe Trp Glu
        50                  55                  60

Val Gln Leu Gly Ile Pro His Pro Ala Gly Leu Lys Lys Lys Ser
65                  70                  75                  80

Val Thr Val Leu Asp Val Gly Asp Ala Tyr Phe Ser Val Pro Leu His
                85                  90                  95

Glu Asp Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
            115                 120                 125

Lys Gly Ser Pro Ala Ile Phe Gln Ser Ser Met Thr Lys Ile Leu Glu
            130                 135                 140

Pro Phe Arg Thr Asn Asn Pro Glu Leu Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Arg Trp Gly Phe Thr Thr Pro
            180                 185                 190

Asp Lys Lys His Gln Lys Glu Pro Pro Phe Leu Trp Met Gly Tyr Glu
            195                 200                 205

Leu His Pro Asp Lys Trp Thr Val Gln Pro Ile Gln Leu Pro Glu Lys
        210                 215                 220

Glu Asp Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Thr Lys Ala Leu Thr Asp Ile Val Pro Leu Thr Glu
            260                 265                 270

Glu Ala Glu Leu Glu
            275

<210> SEQ ID NO 52
<211> LENGTH: 277
<212> TYPE: PRT
<213> ORGANISM: Human immunodeficiency virus type 1

<400> SEQUENCE: 52

Leu Thr Glu Glu Lys Ile Lys Ala Leu Thr Ala Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Ile Phe Ala Ile Lys Lys Lys Asp Ser Thr Lys Trp Arg Lys
            35                  40                  45

Leu Val Asp Phe Arg Glu Leu Asn Lys Arg Thr Gln Asp Phe Trp Glu
        50                  55                  60

Val Gln Leu Gly Ile Pro His Pro Ala Gly Leu Lys Lys Lys Ser
65                  70                  75                  80

Val Thr Val Leu Asp Val Gly Asp Ala Tyr Phe Ser Val Pro Leu Asp
                85                  90                  95

Glu Gly Phe Arg Lys Tyr Thr Ala Phe Thr Ile Pro Ser Ile Asn Asn
            100                 105                 110
```

Glu Thr Pro Gly Ile Arg Tyr Gln Tyr Asn Val Leu Pro Gln Gly Trp
            115                 120                 125

Lys Gly Ser Pro Ala Ile Phe Gln Ser Arg His Ala Lys Ile Leu Glu
        130                 135                 140

Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Lys His Leu Leu Arg Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Lys Gln Leu Cys Lys
                245                 250                 255

Leu Leu Arg Gly Ala Lys Ala Leu Thr Asp Ile Val Pro Leu Thr Glu
            260                 265                 270

Glu Ala Glu Leu Glu
        275

<210> SEQ ID NO 53
<211> LENGTH: 277
<212> TYPE: PRT
<213> ORGANISM: Human immunodeficiency virus type 1

<400> SEQUENCE: 53

Leu Thr Glu Glu Lys Ile Lys Ala Leu Thr Glu Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Gly Phe Arg Lys Tyr Thr Ala Phe Thr Ile Pro Ser Ile Asn Asn
            100                 105                 110

Glu Thr Pro Gly Ile Arg Tyr Gln Tyr Asn Gly Leu Pro Gln Gly Trp
            115                 120                 125

Lys Gly Ser Pro Ala Ile Phe Gln Ser Arg His Ala Lys Ile Leu Glu
        130                 135                 140

Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Lys Trp Gly Phe Thr Thr Pro
            180                 185                 190

Asp Lys Lys His Gln Lys Glu Pro Pro Phe Leu Trp Met Gly Tyr Glu
        195                 200                 205

```
Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Ala Lys Ala Leu Thr Asp Ile Val Pro Leu Thr Glu
            260                 265                 270

Glu Ala Glu Leu Glu
        275

<210> SEQ ID NO 54
<211> LENGTH: 277
<212> TYPE: PRT
<213> ORGANISM: Human immunodeficiency virus type 1

<400> SEQUENCE: 54

Leu Thr Glu Glu Lys Ile Lys Ala Leu Thr Ala Ile Cys Glu Asp Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Asn Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ser Ser Met Thr Lys Ile Leu Glu
    130                 135                 140

Pro Phe Arg Ala Gln Asn Pro Gly Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Lys Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Asp Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Ala Gly Ile Lys Val Arg Gln Leu Cys Lys
                245                 250                 255

Leu Leu Arg Gly Ala Lys Ala Leu Thr Asp Val Ile Pro Leu Thr Glu
            260                 265                 270

Glu Ala Glu Leu Glu
        275

<210> SEQ ID NO 55
```

```
<211> LENGTH: 277
<212> TYPE: PRT
<213> ORGANISM: Human immunodeficiency virus type 1

<400> SEQUENCE: 55

Leu Thr Glu Glu Lys Ile Lys Ala Leu Thr Ala Ile Cys Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
                35                  40                  45

Leu Val Asp Phe Arg Glu Leu Asn Lys Arg Thr Gln Asp Phe Trp Glu
50                  55                  60

Val Gln Leu Gly Ile Pro His Pro Ala Gly Leu Lys Lys Lys Ser
65                  70                  75                  80

Val Thr Val Leu Asp Val Gly Asp Ala Tyr Phe Ser Val Pro Leu Asp
                85                  90                  95

Glu Asn Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ser Ser Met Thr Lys Ile Leu Glu
    130                 135                 140

Pro Phe Arg Ala Gln Asn Pro Gly Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Arg Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Glu Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Ser Gly Ile Lys Val Arg Gln Leu Cys Lys
                245                 250                 255

Leu Ile Arg Gly Ala Lys Ala Leu Thr Asp Ile Val Pro Leu Thr Glu
            260                 265                 270

Glu Ala Glu Leu Glu
        275

<210> SEQ ID NO 56
<211> LENGTH: 277
<212> TYPE: PRT
<213> ORGANISM: Human immunodeficiency virus type 1

<400> SEQUENCE: 56

Leu Ser Glu Glu Lys Ile Lys Ala Leu Thr Ala Ile Cys Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
                35                  40                  45

Leu Val Asp Phe Arg Glu Leu Asn Lys Arg Thr Gln Asp Phe Trp Glu
50                  55                  60
```

```
Val Gln Leu Gly Ile Pro His Pro Ala Gly Leu Lys Lys Lys Ser
 65                  70                  75                  80

Val Thr Val Leu Asp Val Gly Asp Ala Tyr Phe Ser Val Pro Leu Asp
                 85                  90                  95

Glu Asn Phe Arg Lys Tyr Thr Ala Phe Thr Ile Pro Ser Val Asn Asn
                100                 105                 110

Glu Thr Pro Gly Leu Arg Tyr Gln Tyr Asn Val Leu Pro Gln Gly Trp
                115                 120                 125

Lys Gly Ser Pro Ala Ile Phe Gln Ser Ser Met Thr Lys Ile Leu Glu
            130                 135                 140

Pro Phe Arg Ala Gln Asn Pro Gly Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Asp His Leu Leu Lys Trp Gly Phe Thr Thr Pro
                180                 185                 190

Asp Lys Lys His Gln Lys Glu Pro Pro Phe Leu Trp Met Gly Tyr Glu
                195                 200                 205

Leu His Pro Asp Lys Trp Thr Val Gln Pro Ile Gln Leu Pro Glu Lys
            210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Lys Gln Leu Cys Lys
                245                 250                 255

Leu Leu Arg Gly Ala Lys Ala Leu Thr Asp Ile Ile Pro Leu Thr Glu
                260                 265                 270

Glu Ala Glu Leu Glu
            275

<210> SEQ ID NO 57
<211> LENGTH: 277
<212> TYPE: PRT
<213> ORGANISM: Human immunodeficiency virus type 1

<400> SEQUENCE: 57

Leu Thr Glu Glu Lys Ile Lys Ala Leu Thr Ala Ile Cys Glu Glu Met
 1               5                  10                  15

Glu Lys Glu Gly Lys Ile Thr Lys Ile Gly Pro Glu Asn Pro Tyr Asn
                20                  25                  30

Thr Pro Ile Phe Ala Ile Lys Lys Lys Asp Ser Thr Lys Trp Arg Lys
            35                  40                  45

Leu Val Asp Phe Arg Glu Leu Asn Lys Arg Thr Gln Asp Phe Trp Glu
 50                  55                  60

Val Gln Leu Gly Ile Pro His Pro Ala Gly Leu Lys Lys Lys Ser
 65                  70                  75                  80

Val Thr Val Leu Asp Val Gly Asp Ala Tyr Phe Ser Val Pro Leu Asp
                 85                  90                  95

Glu Gly Phe Arg Lys Tyr Thr Ala Phe Thr Ile Pro Ser Ile Asn Asn
                100                 105                 110

Glu Thr Pro Gly Ile Arg Tyr Gln Tyr Asn Val Leu Pro Gln Gly Trp
                115                 120                 125

Lys Gly Ser Pro Ala Ile Phe Gln Ala Ser Met Thr Lys Ile Leu Glu
            130                 135                 140

Pro Phe Arg Ala Lys Asn Pro Glu Ile Val Ile Tyr Gln Tyr Met Asp
145                 150                 155                 160
```

```
Asp Leu Tyr Val Gly Ser Asp Leu Glu Ile Gly Gln His Arg Ala Lys
            165                 170                 175

Ile Glu Glu Leu Arg Gly His Leu Leu Lys Trp Gly Phe Thr Thr Pro
        180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Ala Lys Ala Leu Thr Asp Ile Val Pro Leu Thr Glu
            260                 265                 270

Glu Ala Glu Leu Glu
            275

<210> SEQ ID NO 58
<211> LENGTH: 277
<212> TYPE: PRT
<213> ORGANISM: Human immunodeficiency virus type 1

<400> SEQUENCE: 58

Leu Thr Glu Glu Lys Ile Lys Ala Leu Thr Ala Ile Cys Asp Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Gly Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ser Ser Met Thr Arg Ile Leu Glu
    130                 135                 140

Pro Phe Arg Thr Gln Asn Pro Asp Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Lys Leu Arg Glu His Leu Leu Arg Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255
```

```
Leu Leu Arg Gly Ala Lys Ala Leu Thr Asp Ile Ile Pro Leu Thr Glu
            260                 265                 270

Glu Ala Glu Leu Glu
        275

<210> SEQ ID NO 59
<211> LENGTH: 277
<212> TYPE: PRT
<213> ORGANISM: Human immunodeficiency virus type 1

<400> SEQUENCE: 59

Leu Thr Glu Glu Lys Ile Lys Ala Leu Thr Glu Ile Cys Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Ser
65              70                  75                  80

Val Thr Val Leu Asp Val Gly Asp Ala Tyr Phe Ser Val Pro Leu Asp
                85                  90                  95

Glu Gly Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ser Ser Met Thr Lys Ile Leu Glu
    130                 135                 140

Pro Phe Arg Thr Lys Asn Pro Asp Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Arg Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Ala Lys Ala Leu Thr Asp Ile Val Pro Leu Thr Glu
            260                 265                 270

Glu Ala Glu Leu Glu
        275

<210> SEQ ID NO 60
<211> LENGTH: 277
<212> TYPE: PRT
<213> ORGANISM: Human immunodeficiency virus type 1

<400> SEQUENCE: 60

Leu Thr Glu Glu Lys Ile Lys Ala Leu Thr Ala Ile Cys Glu Met
1               5                   10                  15

Glu Lys Glu Gly Lys Ile Thr Lys Ile Gly Pro Glu Asn Pro Tyr Asn
```

-continued

```
                    20                  25                  30
Thr Pro Val Phe Ala Ile Lys Lys Lys Asp Ser Thr Lys Trp Arg Lys
                35                  40                  45

Leu Val Asp Phe Arg Glu Leu Asn Lys Arg Thr Gln Asp Phe Trp Glu
             50                  55                  60

Val Gln Leu Gly Ile Pro His Pro Ala Gly Leu Lys Lys Lys Lys Ser
 65                  70                  75                  80

Val Thr Val Leu Asp Val Gly Asp Ala Tyr Phe Ser Val Pro Leu Asp
                 85                  90                  95

Glu Gly Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
            115                 120                 125

Lys Gly Ser Pro Ala Ile Phe Gln Ala Ser Met Thr Lys Ile Leu Glu
            130                 135                 140

Pro Phe Arg Thr Gln Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Val Glu Glu Leu Arg Glu His Leu Leu Arg Trp Gly Phe Thr Thr Pro
            180                 185                 190

Asp Lys Lys His Gln Lys Glu Pro Pro Phe Leu Trp Met Gly Tyr Glu
            195                 200                 205

Leu His Pro Asp Lys Trp Thr Val Gln Pro Ile Lys Leu Pro Glu Lys
            210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Lys Gln Leu Cys Lys
                245                 250                 255

Leu Leu Arg Gly Ala Lys Ala Leu Thr Asp Ile Ile Pro Leu Thr Glu
            260                 265                 270

Glu Ala Glu Leu Glu
            275

<210> SEQ ID NO 61
<211> LENGTH: 277
<212> TYPE: PRT
<213> ORGANISM: Human immunodeficiency virus type 1

<400> SEQUENCE: 61

Leu Thr Glu Glu Lys Ile Lys Ala Leu Thr Ala Ile Cys Glu Glu Met
 1               5                  10                  15

Glu Lys Glu Gly Lys Ile Thr Lys Ile Gly Pro Glu Asn Pro Tyr Asn
                 20                  25                  30

Thr Pro Ile Phe Ala Ile Lys Lys Lys Asp Ser Thr Lys Trp Arg Lys
                35                  40                  45

Leu Val Asp Phe Arg Glu Leu Asn Lys Arg Thr Gln Asp Phe Trp Glu
             50                  55                  60

Val Gln Leu Gly Ile Pro His Pro Ala Gly Leu Lys Lys Lys Lys Ser
 65                  70                  75                  80

Val Thr Val Leu Asp Val Gly Asp Ala Tyr Phe Ser Val Pro Leu Asp
                 85                  90                  95

Pro Asp Phe Arg Lys Tyr Thr Ala Phe Thr Ile Pro Ser Val Asn Asn
            100                 105                 110

Glu Thr Pro Gly Ile Arg Tyr Gln Tyr Asn Val Leu Pro Gln Gly Trp
```

```
                115                 120                 125
Lys Gly Ser Pro Ala Ile Phe Gln Ser Ser Met Thr Lys Ile Leu Glu
    130                 135                 140

Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Arg Trp Gly Phe Thr Thr Pro
                180                 185                 190

Asp Lys Lys His Gln Lys Glu Pro Pro Phe Leu Trp Met Gly Tyr Glu
                195                 200                 205

Leu His Pro Asp Lys Trp Thr Val Gln Pro Ile Gln Leu Pro Glu Lys
        210                 215                 220

Asp Asp Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Ala Lys Ala Leu Thr Asp Ile Val Pro Leu Thr Glu
                260                 265                 270

Glu Ala Glu Leu Glu
        275

<210> SEQ ID NO 62
<211> LENGTH: 277
<212> TYPE: PRT
<213> ORGANISM: Human immunodeficiency virus type 1

<400> SEQUENCE: 62

Leu Thr Glu Glu Lys Ile Lys Ala Leu Thr Ala Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Asp Ser Thr Lys Trp Arg Lys
        35                  40                  45

Leu Val Asp Phe Arg Glu Leu Asn Lys Arg Thr Gln Asp Phe Trp Glu
50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Asp Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ser Ser Met Thr Lys Ile Leu Glu
    130                 135                 140

Pro Phe Arg Ala Gln Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Lys Trp Gly Phe Thr Thr Pro
                180                 185                 190

Asp Lys Lys His Gln Lys Glu Pro Pro Phe Leu Trp Met Gly Tyr Glu
                195                 200                 205

Leu His Pro Asp Lys Trp Thr Val Gln Pro Ile Asn Leu Pro Asp Lys
```

```
                     210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Gln Val Arg Gln Leu Cys Lys
                245                 250                 255

Leu Leu Arg Gly Ala Lys Ala Leu Thr Asp Ile Val Pro Leu Thr Glu
            260                 265                 270

Glu Ala Glu Leu Glu
        275

<210> SEQ ID NO 63
<211> LENGTH: 277
<212> TYPE: PRT
<213> ORGANISM: Human immunodeficiency virus type 1
<220> FEATURE:
<221> NAME/KEY: misc_feature
<222> LOCATION: (6)..(6)
<223> OTHER INFORMATION: Xaa can be any naturally occurring amino
      acid
<220> FEATURE:
<221> NAME/KEY: misc_feature
<222> LOCATION: (118)..(118)
<223> OTHER INFORMATION: Xaa can be any naturally occurring amino
      acid

<400> SEQUENCE: 63

Leu Thr Glu Glu Lys Xaa Lys Ala Leu Thr Ala Ile Cys Asp Glu Met
1               5                   10                  15

Glu Lys Glu Gly Lys Ile Thr Lys Ile Gly Pro Glu Asn Pro Tyr Asn
            20                  25                  30

Thr Pro Ile Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Asn Phe Arg Lys Tyr Thr Ala Phe Thr Ile Pro Ser Ile Asn Asn
            100                 105                 110

Glu Thr Pro Gly Ile Xaa Tyr Gln Tyr Asn Val Leu Pro Gln Gly Trp
        115                 120                 125

Lys Gly Ser Pro Ala Ile Phe Gln Ala Ser Met Thr Lys Ile Leu Glu
    130                 135                 140

Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Arg Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Arg
                245                 250                 255
```

```
Leu Leu Arg Gly Ala Lys Ala Leu Thr Asp Ile Val Pro Leu Thr Glu
        260                 265                 270

Glu Ala Glu Leu Glu
        275

<210> SEQ ID NO 64
<211> LENGTH: 277
<212> TYPE: PRT
<213> ORGANISM: Human immunodeficiency virus type 1
<220> FEATURE:
<221> NAME/KEY: misc_feature
<222> LOCATION: (100)..(100)
<223> OTHER INFORMATION: Xaa can be any naturally occurring amino
      acid

<400> SEQUENCE: 64

Leu Thr Glu Glu Lys Ile Lys Ala Leu Thr Glu Ile Cys Lys Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Asp Ser Thr Lys Trp Arg Lys
        35                  40                  45

Leu Val Asp Phe Arg Glu Leu Asn Lys Arg Thr Gln Asp Phe Trp Glu
 50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Gly Phe Xaa Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Cys Ser Met Thr Lys Ile Leu Glu
130                 135                 140

Pro Phe Arg Ala Gln Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Lys Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Thr Lys Ala Leu Thr Asp Ile Val Pro Leu Thr Glu
            260                 265                 270

Glu Ala Glu Leu Glu
        275

<210> SEQ ID NO 65
<211> LENGTH: 277
<212> TYPE: PRT
<213> ORGANISM: Human immunodeficiency virus type 1

<400> SEQUENCE: 65
```

```
Leu Thr Glu Glu Lys Ile Lys Ala Leu Lys Glu Ile Cys Glu Met
1               5                   10                  15

Glu Lys Glu Gly Lys Ile Thr Lys Ile Gly Pro Glu Asn Pro Tyr Asn
                20                  25                  30

Thr Pro Ile Phe Ala Ile Lys Lys Lys Asp Ser Thr Lys Trp Arg Lys
                35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Ser
65              70                  75                  80

Val Thr Val Leu Asp Val Gly Asp Ala Tyr Phe Ser Val Pro Leu Asp
                85                  90                  95

Glu Gly Phe Arg Lys Tyr Thr Ala Phe Thr Ile Pro Ser Ile Asn Asn
                100                 105                 110

Glu Thr Pro Gly Ile Arg Tyr Gln Tyr Asn Val Leu Pro Gln Gly Trp
                115                 120                 125

Lys Gly Ser Pro Ala Ile Phe Gln Ser Ser Met Thr Lys Ile Leu Glu
                130                 135                 140

Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Arg Gln His Arg Ala Lys
                165                 170                 175

Ile Glu Glu Leu Arg Glu His Leu Leu Lys Trp Gly Phe Thr Thr Pro
                180                 185                 190

Asp Lys Lys His Gln Lys Glu Pro Pro Phe Leu Trp Met Gly Tyr Glu
                195                 200                 205

Leu His Pro Asp Lys Trp Thr Val Gln Pro Ile Gln Leu Pro Glu Lys
                210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Lys Gln Met Cys Lys
                245                 250                 255

Leu Leu Arg Gly Ala Lys Ala Leu Thr Asp Val Ile Pro Leu Thr Glu
                260                 265                 270

Glu Ala Glu Leu Glu
            275

<210> SEQ ID NO 66
<211> LENGTH: 277
<212> TYPE: PRT
<213> ORGANISM: Human immunodeficiency virus type 1
<220> FEATURE:
<221> NAME/KEY: misc_feature
<222> LOCATION: (7)..(7)
<223> OTHER INFORMATION: Xaa can be any naturally occurring amino
      acid

<400> SEQUENCE: 66

Leu Arg Glu Glu Lys Ile Xaa Ala Leu Thr Ala Ile Cys Glu Met
1               5                   10                  15

Glu Lys Glu Gly Lys Ile Thr Lys Ile Gly Pro Glu Asn Pro Tyr Asn
                20                  25                  30

Thr Pro Ile Phe Ala Ile Lys Lys Lys Asp Ser Thr Lys Trp Arg Lys
                35                  40                  45

Leu Val Asp Phe Arg Glu Leu Asn Lys Arg Thr Gln Asp Phe Trp Glu
    50                  55                  60
```

```
Val Gln Leu Gly Ile Pro His Pro Ala Gly Leu Lys Lys Lys Ser
 65                  70                  75                  80

Val Thr Val Leu Asp Val Gly Asp Ala Tyr Phe Ser Val Pro Leu Asp
                 85                  90                  95

Lys Asp Phe Arg Lys Tyr Thr Ala Phe Thr Ile Pro Ser Val Asn Asn
            100                 105                 110

Glu Thr Pro Gly Val Arg Tyr Gln Tyr Asn Val Leu Pro Gln Gly Trp
        115                 120                 125

Lys Gly Ser Pro Ala Ile Phe Gln Ser Ser Met Thr Arg Ile Leu Glu
    130                 135                 140

Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Ala His Leu Leu Lys Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Ala Lys Ala Leu Thr Asp Ile Val Pro Leu Thr Glu
            260                 265                 270

Glu Ala Glu Leu Glu
        275

<210> SEQ ID NO 67
<211> LENGTH: 277
<212> TYPE: PRT
<213> ORGANISM: Human immunodeficiency virus type 1

<400> SEQUENCE: 67

Leu Thr Glu Glu Lys Ile Lys Ala Leu Thr Ala Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Arg Ser
 65                  70                  75                  80

Val Thr Val Leu Asp Val Gly Asp Ala Tyr Phe Ser Val Pro Leu Asp
                 85                  90                  95

Glu Ser Phe Arg Lys Tyr Thr Ala Phe Thr Ile Pro Ser Thr Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ala Ser Met Thr Arg Ile Leu Glu
    130                 135                 140

Pro Phe Arg Thr Lys Asn Pro Asp Ile Val Ile Tyr Gln Tyr Met Asp
145                 150                 155                 160
```

```
Asp Leu Tyr Val Gly Ser Asp Leu Glu Ile Gly Gln His Arg Ala Lys
                165                 170                 175

Ile Glu Glu Leu Arg Glu His Leu Leu Lys Trp Gly Leu Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Asn Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Ser Gly Ile Lys Val Arg Gln Leu Cys Lys
                245                 250                 255

Leu Leu Arg Gly Thr Lys Ala Leu Thr Asp Ile Val Pro Leu Thr Glu
            260                 265                 270

Glu Ala Glu Leu Glu
        275

<210> SEQ ID NO 68
<211> LENGTH: 277
<212> TYPE: PRT
<213> ORGANISM: Human immunodeficiency virus type 1

<400> SEQUENCE: 68

Leu Thr Glu Glu Lys Ile Lys Ala Leu Thr Ala Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Arg Ser
65                  70                  75                  80

Val Thr Val Leu Asp Val Gly Asp Ala Tyr Phe Ser Val Pro Leu Asp
                85                  90                  95

Glu Ser Phe Arg Lys Tyr Thr Ala Phe Thr Ile Pro Ser Thr Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Cys Ser Met Thr Arg Ile Leu Glu
    130                 135                 140

Pro Phe Arg Thr Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Lys Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255
```

Leu Leu Arg Gly Thr Lys Ala Leu Thr Asp Val Val Pro Leu Thr Glu
            260                 265                 270

Glu Ala Glu Leu Glu
        275

<210> SEQ ID NO 69
<211> LENGTH: 277
<212> TYPE: PRT
<213> ORGANISM: Human immunodeficiency virus type 1

<400> SEQUENCE: 69

Leu Ser Glu Glu Lys Ile Lys Ala Leu Thr Glu Ile Cys Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
            35                  40                  45

Leu Val Asp Phe Arg Glu Leu Asn Lys Arg Thr Gln Asp Phe Trp Glu
        50                  55                  60

Val Gln Leu Gly Ile Pro His Pro Ala Gly Leu Lys Lys Lys Ser
65              70                  75                  80

Val Thr Val Leu Asp Val Gly Asp Ala Tyr Phe Ser Val Pro Leu Asp
            85                  90                  95

Glu Ser Phe Arg Lys Tyr Thr Ala Phe Thr Ile Pro Ser Thr Asn Asn
            100                 105                 110

Glu Thr Pro Gly Thr Arg Tyr Gln Tyr Asn Val Leu Pro Gln Gly Trp
        115                 120                 125

Lys Gly Ser Pro Ala Ile Phe Gln Ser Ser Met Thr Arg Ile Leu Glu
    130                 135                 140

Pro Phe Arg Thr Gln Asn Pro Glu Ile Val Ile Tyr Gln Tyr Met Asp
145                 150                 155                 160

Asp Leu Tyr Val Gly Ser Asp Leu Glu Ile Lys Gln His Arg Ala Lys
            165                 170                 175

Ile Glu Glu Leu Arg Ala His Leu Leu Lys Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg His Leu Cys Lys
            245                 250                 255

Leu Leu Arg Gly Thr Lys Ala Leu Thr Asp Ile Val Pro Leu Thr Glu
            260                 265                 270

Glu Ala Glu Leu Glu
        275

<210> SEQ ID NO 70
<211> LENGTH: 277
<212> TYPE: PRT
<213> ORGANISM: Human immunodeficiency virus type 1
<220> FEATURE:
<221> NAME/KEY: misc_feature
<222> LOCATION: (32)..(32)
<223> OTHER INFORMATION: Xaa can be any naturally occurring amino
      acid

<400> SEQUENCE: 70

Leu Thr Glu Glu Lys Ile Lys Ala Leu Thr Glu Ile Cys Glu Met
1               5                   10                  15

Glu Lys Glu Gly Lys Ile Thr Lys Ile Gly Pro Glu Asn Pro Tyr Xaa
                20                  25                  30

Thr Pro Val Phe Ala Ile Lys Lys Lys Asp Ser Thr Lys Trp Arg Lys
            35                  40                  45

Leu Val Asp Phe Arg Glu Leu Asn Lys Arg Thr Gln Asp Phe Trp Glu
50                  55                  60

Val Gln Leu Gly Ile Pro His Pro Ala Gly Leu Lys Lys Lys Ser
65              70                  75                  80

Val Thr Val Leu Asp Val Gly Asp Ala Tyr Phe Ser Val Pro Leu Asp
                85                  90                  95

Glu Ser Phe Arg Lys Tyr Thr Ala Phe Thr Ile Pro Ser Ile Asn Asn
                100                 105                 110

Ala Thr Pro Gly Ile Arg Tyr Gln Tyr Asn Val Leu Pro Gln Gly Trp
            115                 120                 125

Lys Gly Ser Pro Ala Ile Phe Gln Ser Ser Met Thr Lys Ile Leu Glu
130                 135                 140

Pro Phe Arg Thr Gln Asn Pro Asp Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Arg Trp Gly Phe Thr Thr Pro
                180                 185                 190

Asp Lys Lys His Gln Lys Glu Pro Pro Phe Gln Trp Met Gly Tyr Glu
            195                 200                 205

Leu His Pro Asp Lys Trp Thr Val Gln Pro Ile Cys Leu Pro Glu Lys
210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg His Leu Cys Lys
                245                 250                 255

Leu Leu Arg Gly Ala Lys Ala Leu Thr Asp Ile Val Pro Leu Thr Glu
                260                 265                 270

Glu Ala Glu Leu Glu
        275

<210> SEQ ID NO 71
<211> LENGTH: 277
<212> TYPE: PRT
<213> ORGANISM: Human immunodeficiency virus type 1
<220> FEATURE:
<221> NAME/KEY: misc_feature
<222> LOCATION: (98)..(98)
<223> OTHER INFORMATION: Xaa can be any naturally occurring amino
      acid

<400> SEQUENCE: 71

Leu Thr Glu Glu Lys Ile Lys Ala Leu Thr Ala Ile Cys Glu Met
1               5                   10                  15

Glu Lys Glu Gly Lys Ile Thr Lys Ile Gly Pro Glu Asn Pro Tyr Asn
                20                  25                  30

Thr Pro Val Phe Ala Ile Lys Lys Lys Asp Ser Thr Lys Trp Arg Lys
            35                  40                  45

Leu Val Asp Phe Arg Glu Leu Asn Lys Arg Thr Gln Asp Phe Trp Glu
50                  55                  60

-continued

```
Val Gln Leu Gly Ile Pro His Pro Ala Gly Leu Lys Lys Lys Ser
 65                  70                  75                  80

Val Thr Val Leu Asp Val Gly Asp Ala Tyr Phe Ser Ile Pro Leu Tyr
                 85                  90                  95

Glu Xaa Phe Arg Lys Tyr Thr Ala Phe Thr Ile Pro Ser Phe Asn Asn
            100                 105                 110

Glu Thr Pro Gly Ile Arg Phe Gln Tyr Asn Val Leu Pro Gln Gly Trp
        115                 120                 125

Lys Gly Ser Pro Ala Ile Phe Gln Ser Ser Met Thr Lys Ile Leu Glu
    130                 135                 140

Pro Phe Arg Ala Gln Asn Pro Glu Leu Val Ile Tyr Gln Tyr Met Asp
145                 150                 155                 160

Asp Leu Tyr Val Gly Ser Asp Leu Glu Ile Gly Gln His Arg Ala Arg
                165                 170                 175

Ile Glu Lys Leu Arg Glu His Leu Leu Arg Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Glu Ser Trp Thr Val Asn Asp Ile Gln Lys Leu Val Gly Lys Leu Asn
225                 230                 235                 240

Trp Ala Ser Gln Ile Tyr Pro Gly Ile Lys Val Lys Arg Met Cys Lys
                245                 250                 255

Leu Leu Arg Gly Ala Lys Ala Leu Thr Asp Val Val Pro Leu Thr Glu
            260                 265                 270

Glu Ala Glu Leu Glu
        275

<210> SEQ ID NO 72
<211> LENGTH: 277
<212> TYPE: PRT
<213> ORGANISM: Human immunodeficiency virus type 1

<400> SEQUENCE: 72

Leu Ser Glu Glu Lys Ile Lys Ala Leu Thr Glu Ile Cys Glu Glu Met
 1               5                  10                  15

Glu Lys Glu Gly Lys Ile Thr Lys Ile Gly Pro Glu Asn Pro Tyr Asn
             20                  25                  30

Thr Pro Val Phe Ala Ile Lys Lys Lys Asp Ser Thr Lys Trp Arg Lys
         35                  40                  45

Leu Val Asp Phe Arg Glu Leu Asn Lys Arg Thr Gln Asp Phe Trp Glu
     50                  55                  60

Val Gln Leu Gly Ile Pro His Pro Ala Gly Leu Lys Lys Lys Ser
 65                  70                  75                  80

Val Thr Val Leu Asp Val Gly Asp Ala Tyr Phe Ser Val Pro Leu Asp
                 85                  90                  95

Lys Asp Phe Arg Lys Tyr Thr Ala Phe Thr Ile Pro Ser Ile Asn Asn
            100                 105                 110

Glu Thr Pro Gly Ile Arg Tyr Gln Tyr Asn Gly Ser Pro Gln Gly Trp
        115                 120                 125

Lys Gly Ser Pro Ser Ile Phe Gln Ser Ser Met Thr Lys Ile Leu Glu
    130                 135                 140

Pro Phe Arg Ala Lys Asn Pro Asp Ile Val Phe Tyr Gln Tyr Met Asp
145                 150                 155                 160
```

```
Asp Leu Tyr Val Gly Ser Asp Leu Glu Ile Met Gln His Arg Ala Lys
            165                 170                 175

Ile Glu Asp Leu Arg Glu His Leu Leu Lys Trp Gly Phe Thr Thr Pro
        180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
        210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Met Cys Lys
                245                 250                 255

Leu Leu Arg Gly Ala Lys Ala Leu Thr Asp Ile Val Pro Leu Thr Glu
            260                 265                 270

Glu Ala Glu Leu Glu
            275

<210> SEQ ID NO 73
<211> LENGTH: 277
<212> TYPE: PRT
<213> ORGANISM: Human immunodeficiency virus type 1

<400> SEQUENCE: 73

Leu Thr Glu Glu Lys Ile Lys Ala Leu Thr Ala Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Asn Phe Arg Lys Tyr Thr Ala Phe Thr Ile Pro Ser Ile Asn Asn
            100                 105                 110

Ala Ala Pro Gly Thr Arg Tyr Gln Tyr Asn Val Leu Pro Gln Gly Trp
        115                 120                 125

Lys Gly Ser Pro Ala Ile Phe Gln Ser Ser Met Ile Lys Ile Leu Glu
    130                 135                 140

Pro Phe Arg Lys Asn Asn Pro Asp Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Ile Glu Glu Leu Arg Glu His Leu Leu Lys Trp Gly Leu Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Asp Lys
        210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Lys His Leu Cys Arg
                245                 250                 255
```

```
Leu Leu Arg Gly Ala Lys Ala Leu Thr Asp Ile Val Pro Leu Thr Glu
            260                 265                 270

Glu Ala Glu Leu Glu
        275

<210> SEQ ID NO 74
<211> LENGTH: 277
<212> TYPE: PRT
<213> ORGANISM: Human immunodeficiency virus type 1

<400> SEQUENCE: 74

Pro Ala Val Phe Gln Ile Ser Val Leu Thr Ala Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Gly Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ala Ser Met Thr Arg Ile Leu Glu
    130                 135                 140

Pro Phe Arg Thr Gln Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Val Glu Glu Leu Arg Glu His Leu Leu Arg Trp Gly Phe Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Lys Gln Leu Cys Lys
                245                 250                 255

Leu Leu Arg Gly Ala Lys Ala Leu Thr Asp Ile Ile Pro Leu Thr Glu
            260                 265                 270

Glu Ala Glu Leu Glu
        275

<210> SEQ ID NO 75
<211> LENGTH: 277
<212> TYPE: PRT
<213> ORGANISM: Human immunodeficiency virus type 1

<400> SEQUENCE: 75

Leu Thr Glu Glu Lys Ile Lys Ala Leu Pro Ala Phe Cys Asp Glu Met
1               5                   10                  15

Glu Lys Glu Gly Lys Ile Thr Lys Ile Gly Pro Glu Asn Pro Tyr Asn
```

```
                  20                  25                  30
Thr Pro Ile Phe Ala Ile Lys Lys Lys Asp Ser Thr Lys Trp Arg Lys
            35                  40                  45

Leu Val Asp Phe Arg Glu Leu Asn Lys Arg Thr Gln Asp Phe Trp Glu
        50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Gly Phe Arg Lys Tyr Thr Ala Phe Thr Ile Pro Ser Ile Asn Asn
            100                 105                 110

Glu Pro Pro Gly Ile Arg Tyr Gln Tyr Asn Val Leu Pro Gln Gly Trp
        115                 120                 125

Lys Gly Ser Pro Ala Ile Phe Gln Ser Arg His Val Arg Ile Leu Glu
    130                 135                 140

Pro Phe Arg Ala Lys Asn Pro Glu Ile Val Ile Tyr Gln Tyr Met Asp
145                 150                 155                 160

Asp Leu Tyr Val Gly Ser Asp Leu Glu Ile Gly Gln His Arg Ala Lys
                165                 170                 175

Val Glu Glu Leu Arg Lys His Leu Leu Lys Trp Gly Leu Thr Thr Pro
            180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
                245                 250                 255

Leu Leu Arg Gly Ala Lys Ala Leu Thr Asp Ile Val Ala Leu Thr Glu
            260                 265                 270

Glu Ala Glu Arg Glu
        275

<210> SEQ ID NO 76
<211> LENGTH: 120
<212> TYPE: PRT
<213> ORGANISM: Human immunodeficiency virus type 1

<400> SEQUENCE: 76

Leu Thr Glu Glu Lys Ile Lys Ala Leu Thr Ala Ile Cys Glu Glu Met
1               5                   10                  15

Glu Lys Glu Gly Lys Ile Thr Lys Ile Gly Pro Glu Asn Pro Tyr Asn
            20                  25                  30

Thr Pro Val Phe Ala Ile Lys Lys Lys Asp Ser Thr Lys Trp Arg Lys
        35                  40                  45

Val Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Asp
                85                  90                  95

Glu Ser Phe Arg Lys Tyr Thr Ala Phe Thr Ile Pro Ser Val Asn Asn
            100                 105                 110

Glu Thr Pro Gly Asn Arg Tyr Gln
```

<210> SEQ ID NO 77
<211> LENGTH: 156
<212> TYPE: PRT
<213> ORGANISM: Human immunodeficiency virus type 1
<220> FEATURE:
<221> NAME/KEY: misc_feature
<222> LOCATION: (107)..(107)
<223> OTHER INFORMATION: Xaa can be any naturally occurring amino acid

<400> SEQUENCE: 77

```
Asn Val Leu Pro Gln Gly Trp Lys Gly Ser Pro Ala Ile Phe Gln Ser
 1               5                  10                  15

Arg His Ala Lys Ile Leu Glu Pro Phe Arg Ala Gln Asn Pro Glu Ile
            20                  25                  30

Val Ile Tyr Gln Tyr Met Asp Asp Leu Tyr Val Gly Ser Asp Leu Glu
        35                  40                  45

Ile Gly Gln His Arg Ala Lys Ile Glu Lys Leu Arg Asp His Leu Leu
    50                  55                  60

Lys Trp Gly Leu Thr Thr Pro Asp Lys Lys His Gln Lys Glu Pro Pro
65                  70                  75                  80

Phe Leu Trp Met Gly Tyr Glu Leu His Pro Asp Lys Trp Thr Val Gln
                85                  90                  95

Pro Ile Gln Leu Pro Glu Lys Asp Ser Trp Xaa Val Asn Asp Ile Gln
            100                 105                 110

Lys Leu Val Gly Lys Leu Asn Trp Ala Ser Gln Ile Tyr Pro Gly Ile
        115                 120                 125

Lys Val Arg Gln Leu Cys Lys Leu Leu Arg Gly Ala Lys Ala Leu Thr
    130                 135                 140

Asp Ile Val Pro Leu Thr Glu Glu Pro Glu Leu Glu
145                 150                 155
```

<210> SEQ ID NO 78
<211> LENGTH: 277
<212> TYPE: PRT
<213> ORGANISM: Human immunodeficiency virus type 1

<400> SEQUENCE: 78

```
Leu Thr Glu Glu Lys Ile Lys Ala Leu Thr Ala Ile Cys Asp Glu Met
 1               5                  10                  15

Glu Lys Glu Gly Lys Ile Thr Lys Ile Gly Pro Glu Asn Pro Tyr Asn
            20                  25                  30

Thr Pro Ile Phe Ala Ile Lys Lys Lys Asp Ser Thr Lys Trp Arg Lys
        35                  40                  45

Leu Val Asp Phe Arg Glu Leu Asn Lys Arg Thr Gln Asp Phe Trp Glu
    50                  55                  60

Val Gln Leu Gly Ile Pro His Pro Ala Gly Leu Lys Lys Lys Lys Ser
65                  70                  75                  80

Val Thr Val Leu Asp Val Gly Asp Ala Tyr Phe Ser Val Pro Leu Tyr
                85                  90                  95

Glu Asp Phe Arg Lys Tyr Thr Ala Phe Thr Ile Pro Ser Ile Asn Asn
            100                 105                 110

Glu Thr Pro Gly Ile Arg Tyr Gln Tyr Asn Val Leu Pro Gln Gly Trp
        115                 120                 125

Lys Gly Ser Pro Ala Ile Phe Gln Ser Ser Met Thr Lys Ile Leu Glu
    130                 135                 140
```

```
Pro Phe Arg Asp Arg Asn Pro Glu Leu Val Ile Tyr Gln Tyr Met Asp
145                 150                 155                 160

Asp Leu Tyr Val Gly Ser Asp Leu Glu Ile Gly Gln His Arg Ala Lys
            165                 170                 175

Ile Glu Glu Leu Arg Glu His Leu Leu Lys Trp Gly Phe Thr Thr Pro
        180                 185                 190

Asp Lys Lys His Gln Lys Glu Pro Pro Phe Leu Trp Met Gly Tyr Glu
        195                 200                 205

Leu His Pro Asp Lys Trp Thr Val Gln Pro Ile Gln Leu Pro Glu Lys
    210                 215                 220

Asp Ser Trp Thr Val Asn Asp Ile Gln Lys Leu Val Gly Lys Leu Asn
225                 230                 235                 240

Trp Ala Ser Gln Ile Tyr Pro Gly Ile Lys Val Arg Gln Leu Cys Lys
            245                 250                 255

Leu Leu Arg Gly Ala Lys Ala Leu Thr Asp Ile Val Pro Leu Thr Glu
        260                 265                 270

Glu Ala Glu Leu Glu
        275

<210> SEQ ID NO 79
<211> LENGTH: 229
<212> TYPE: PRT
<213> ORGANISM: Human immunodeficiency virus type 1

<400> SEQUENCE: 79

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Glu Ile Ile Ile Arg Ser Glu Asn Leu Thr Asn Asn
    50                  55                  60

Ala Lys Thr Ile Ile Val His Leu Asn Glu Ser Val Glu Ile Val Cys
65                  70                  75                  80

Thr Arg Pro Asn Asn Asn Thr Arg Lys Ser Ile Arg Ile Gly Pro Gly
                85                  90                  95

Gln Thr Phe Tyr Ala Thr Gly Asp Ile Ile Gly Asp Ile Arg Gln Ala
            100                 105                 110

His Cys Asn Ile Ser Glu Gly Lys Trp Asn Lys Thr Leu Gln Lys Val
        115                 120                 125

Lys Lys Lys Leu Lys Glu Glu Leu Tyr Lys Tyr Lys Val Val Glu Ile
    130                 135                 140

Lys Pro Leu Gly Ile Ala Pro Thr Glu Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
    210                 215                 220

Gly Ile Lys Gln Leu
225
```

<210> SEQ ID NO 80
<211> LENGTH: 229
<212> TYPE: PRT
<213> ORGANISM: Human immunodeficiency virus type 1

<400> SEQUENCE: 80

```
Tyr Cys Ala Pro Ala Gly Phe Ala Ile Leu Lys Cys Lys Asp Lys Thr
 1               5                  10                  15

Phe Asn Gly Thr Gly Pro Cys Asn Asn Val Ser Thr Val Gln Cys Thr
             20                  25                  30

His Gly Ile Lys Pro Val Val Ser Thr Gln Leu Leu Leu Asn Gly Ser
         35                  40                  45

Leu Ala Lys Gly Glu Ile Ile Ile Ser Ser Gln Asn Leu Thr Asp Asn
 50                  55                  60

Ala Lys Thr Ile Ile Val His Leu Asn Glu Ser Ile Glu Ile Thr Cys
 65                  70                  75                  80

Ile Arg Pro Asn Asn Thr Arg Gln Ser Ile Arg Ile Gly Pro Gly
                 85                  90                  95

Gln Thr Phe Tyr Ala Thr Lys Asp Ile Ile Gly Asp Ile Arg Gln Ala
                100                 105                 110

His Cys Thr Ile Ser Glu Gly Lys Trp Asn Lys Thr Leu Gln Lys Val
            115                 120                 125

Ile Gly Lys Leu Lys Glu Leu Tyr Lys Tyr Lys Val Val Glu Ile
        130                 135                 140

Lys Pro Leu Gly Ile Ala Pro Thr Gly Ala Asn Arg Arg Val Val Glu
145                 150                 155                 160

Arg Glu Lys Arg Ala Val Gly Ile Gly Ala Met Phe Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
    210                 215                 220

Gly Ile Lys Gln Leu
225
```

<210> SEQ ID NO 81
<211> LENGTH: 229
<212> TYPE: PRT
<213> ORGANISM: Human immunodeficiency virus type 1

<400> SEQUENCE: 81

```
Tyr Cys Ala Pro Ala Gly Phe Ala Ile Leu Lys Cys Asn Asp Lys Thr
 1               5                  10                  15

Phe Asn Gly Thr Gly Pro Cys Asn Asn Val Ser Thr Val Gln Cys Thr
             20                  25                  30

His Gly Ile Lys Pro Val Val Ser Thr Gln Leu Leu Leu Asn Gly Ser
         35                  40                  45

Leu Ala Glu Gly Gly Ile Ile Ile Arg Ser Lys Asn Leu Thr Asp Asn
 50                  55                  60

Ser Lys Thr Ile Ile Val His Leu Asn Glu Thr Ile Glu Ile Val Cys
 65                  70                  75                  80

Thr Arg Pro Gly Asn Asn Thr Arg Gln Ser Ile Arg Ile Gly Pro Gly
                 85                  90                  95

Gln Ala Phe Phe Ala Thr Lys Glu Ile Ile Gly Asp Ile Arg Gln Ala
```

-continued

```
                100             105             110
His Cys Asn Ile Ser Glu Gly Gln Trp Asn Lys Thr Leu Gln Lys Val
            115                 120                 125

Ala Glu Lys Leu Lys Glu Lys Leu Tyr Lys Tyr Lys Val Val Glu Ile
130                 135                 140

Lys Pro Leu Gly Ile Ala Pro Thr Gly Thr Lys Trp Arg Val Val Glu
145                 150                 155                 160

Arg Glu Lys Arg Ala Val Thr Leu Gly Ala Val Phe Leu Gly Phe Leu
                165                 170                 175

Gly Met Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
            195                 200                 205

Leu Arg Ala Ile Glu Ala Gln Gln His Met Leu Gln Leu Thr Val Trp
210                 215                 220

Gly Ile Lys Gln Leu
225

<210> SEQ ID NO 82
<211> LENGTH: 228
<212> TYPE: PRT
<213> ORGANISM: Human immunodeficiency virus type 1

<400> SEQUENCE: 82

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
                20                  25                  30

His Gly Ile Lys Pro Val Val Ser Thr Gln Phe Leu Leu Asn Gly Ser
            35                  40                  45

Leu Ala Glu Glu Glu Ile Ile Ile Arg Ser Lys Asn Leu Thr Asp Asn
        50                  55                  60

Ala Arg Thr Ile Ile Val His Leu Asn Glu Ser Val Glu Ile Val Cys
65                  70                  75                  80

Thr Arg Pro Asn Asn Asn Thr Arg Gln Ser Ile Arg Ile Gly Pro Gly
                85                  90                  95

Ala Thr Phe Phe Ala Thr Lys Gly Ile Ile Gly Asp Ile Arg Gln Ala
            100                 105                 110

Tyr Cys Asn Ile Ser Lys Gly Lys Trp Asn Glu Thr Leu Gln Lys Val
            115                 120                 125

Lys Gln Lys Leu Gly Glu Glu Leu Tyr Lys Tyr Lys Val Val Glu Ile
130                 135                 140

Lys Pro Leu Gly Ile Ala Pro Thr Thr Ala Lys Arg Arg Val Val Glu
145                 150                 155                 160

Arg Glu Lys Arg Ala Val Ile Gly Ala Met Phe Leu Gly Phe Leu Gly
                165                 170                 175

Val Ala Gly Ser Thr Met Gly Ala Ala Ser Leu Thr Leu Thr Val Gln
            180                 185                 190

Ala Arg Gln Val Leu Ser Gly Ile Val Gln Gln Ser Asn Leu Leu
            195                 200                 205

Lys Ala Ile Glu Ala Gln Gln His Met Leu Gln Leu Thr Val Trp Gly
210                 215                 220

Ile Lys Gln Leu
225
```

```
<210> SEQ ID NO 83
<211> LENGTH: 229
<212> TYPE: PRT
<213> ORGANISM: Human immunodeficiency virus type 1

<400> SEQUENCE: 83

Tyr Cys Ala Pro Ala Gly Tyr Ala Ile Leu Lys Cys Asn Asn Lys Thr
1               5                   10                  15

Phe Asn Gly Thr Gly Pro Cys His Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Gly Lys Val Ile Ile Arg Ser Lys Asn Leu Thr Asn Asn
    50                  55                  60

Val Lys Thr Ile Ile Val His Leu Asn Lys Ser Val Asn Ile Val Cys
65                  70                  75                  80

Ile Arg Pro Asn Asn Asn Thr Arg Lys Gly Ile Arg Ile Gly Pro Gly
                85                  90                  95

Gln Thr Phe Tyr Ala Thr Asn Ala Ile Ile Gly Asp Ile Arg Gln Ala
            100                 105                 110

His Cys Asn Ile Ser Gln Ala Lys Trp Asn Thr Ala Leu Lys Asn Val
        115                 120                 125

Lys Arg Lys Leu Gly Glu Lys Leu Tyr Lys Tyr Lys Val Val Glu Ile
    130                 135                 140

Lys Pro Leu Gly Val Ala Pro Thr Lys Ala Lys Arg Arg Val Val Lys
145                 150                 155                 160

Arg Glu Lys Arg Ala Val Gly Ile Gly Ala Val Leu Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Leu Leu Gln Leu Thr Val Trp
    210                 215                 220

Gly Ile Lys Gln Leu
225

<210> SEQ ID NO 84
<211> LENGTH: 229
<212> TYPE: PRT
<213> ORGANISM: Human immunodeficiency virus type 1

<400> SEQUENCE: 84

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Trp Thr
            20                  25                  30

His Gly Ile Lys Pro Val Val Ser Thr Gln Leu Leu Leu Asn Gly Ser
        35                  40                  45

Leu Ala Glu Glu Glu Ile Val Arg Ser Glu Asn Leu Thr Asn Ser
    50                  55                  60

Ile Lys Thr Ile Ile Val His Leu Asn Lys Ser Val Glu Ile Lys Cys
65                  70                  75                  80

Thr Arg Pro Asn Asn Asn Thr Arg Lys Ser Val Arg Ile Gly Pro Gly
                85                  90                  95

Gln Thr Phe Tyr Ala Thr Gly Ala Ile Ile Gly Asp Ile Arg Glu Ala
            100                 105                 110
```

His Cys Asn Ile Ser Arg Glu Thr Trp Asn Ser Thr Leu Lys Gln Val
            115                 120                 125

Lys Gly Lys Leu Gly Glu Glu Leu Tyr Lys Tyr Lys Val Val Glu Ile
130             135                 140

Lys Pro Leu Gly Val Ala Pro Thr Lys Ser Lys Arg Lys Val Val Gly
145                 150                 155                 160

Arg Glu Lys Arg Ala Val Gly Leu Gly Ala Val Leu Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Leu Leu Gln Leu Thr Val Trp
        210                 215                 220

Gly Ile Lys Gln Leu
225

<210> SEQ ID NO 85
<211> LENGTH: 229
<212> TYPE: PRT
<213> ORGANISM: Human immunodeficiency virus type 1

<400> SEQUENCE: 85

Tyr Cys Ala Pro Ala Gly Tyr Ala Ile Leu Lys Cys Asn Asn Lys Thr
1               5                   10                  15

Phe Asn Gly Thr Gly Pro Cys His Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Arg Asp Ile Ile Ile Arg Ser Glu Asn Leu Thr Asp Asn
    50                  55                  60

Ala Lys Thr Ile Ile Val His Leu Asn Glu Ser Val Glu Ile Val Cys
65                  70                  75                  80

Thr Arg Pro Asn Asn Asn Thr Arg Pro Ser Ile Arg Ile Gly Pro Gly
                85                  90                  95

Gln Ala Phe Tyr Ala Thr His Asp Ile Ile Gly Asp Ile Arg Glu Ala
            100                 105                 110

His Cys Asn Ile Ser Glu Gly Asn Trp Thr Lys Thr Leu Gln Arg Val
        115                 120                 125

Gly Lys Thr Leu Glu Glu Leu Phe Lys Tyr Lys Val Val Glu Ile
130             135                 140

Lys Pro Leu Gly Ile Ala Pro Thr Glu Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
        210                 215                 220

Gly Ile Lys Gln Leu
225

<210> SEQ ID NO 86

-continued

```
<211> LENGTH: 229
<212> TYPE: PRT
<213> ORGANISM: Human immunodeficiency virus type 1

<400> SEQUENCE: 86

Tyr Cys Ala Pro Ala Gly Tyr Ala Ile Leu Lys Cys Asn Asn Lys Thr
1               5                   10                  15

Phe Asn Gly Thr Gly Pro Cys Tyr Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Arg Asp Ile Ile Ile Arg Ser Glu Asn Leu Thr Asp Asn
    50                  55                  60

Ala Lys Thr Ile Ile Val His Leu Asn Glu Ser Val Glu Ile Val Cys
65                  70                  75                  80

Thr Arg Pro Asn Asn Asn Thr Arg Gln Ser Ile Arg Ile Gly Pro Gly
                85                  90                  95

Gln Ala Phe Tyr Ala Thr His Asp Ile Ile Gly Asn Ile Arg Glu Ala
            100                 105                 110

His Cys Asn Ile Ser Glu Gly Asn Trp Thr Lys Thr Leu Gln Arg Val
        115                 120                 125

Gly Lys Thr Leu Glu Glu Glu Leu Tyr Lys Tyr Lys Val Val Glu Ile
    130                 135                 140

Lys Pro Leu Gly Ile Ala Pro Thr Glu Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
    210                 215                 220

Gly Ile Lys Gln Leu
225

<210> SEQ ID NO 87
<211> LENGTH: 229
<212> TYPE: PRT
<213> ORGANISM: Human immunodeficiency virus type 1

<400> SEQUENCE: 87

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Glu Ile Ile Ile Arg Ser Glu Asn Leu Thr Asn Asn
    50                  55                  60

Val Lys Thr Ile Ile Val His Leu Asn Glu Ser Val Glu Ile Val Cys
65                  70                  75                  80

Thr Arg Pro Gly Asn Asn Thr Arg Lys Ser Val Arg Ile Gly Pro Gly
                85                  90                  95

Gln Thr Phe Tyr Ala Thr Gly Asp Ile Ile Gly Asp Ile Arg Gln Ala
            100                 105                 110
```

-continued

His Cys Asn Ile Ser Ser Asp Lys Trp Asn Gln Thr Leu Gln Gln Val
        115                 120                 125

Gly Lys Lys Leu Ala Glu Glu Leu Tyr Lys Tyr Lys Val Val Glu Val
130                 135                 140

Lys Pro Leu Gly Val Ala Pro Thr Ala Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
                180                 185                 190

Gln Ala Arg Gln Leu Leu Ser Gly Ile Val Gln Gln Ser Asn Leu
        195                 200                 205

Leu Arg Ala Ile Glu Val Gln Gln His Met Leu Gln Leu Thr Val Trp
210                 215                 220

Gly Ile Lys Gln Leu
225

<210> SEQ ID NO 88
<211> LENGTH: 229
<212> TYPE: PRT
<213> ORGANISM: Human immunodeficiency virus type 1

<400> SEQUENCE: 88

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
                20                  25                  30

His Gly Ile Lys Pro Val Val Ser Thr Gln Leu Leu Leu Asn Gly Ser
        35                  40                  45

Leu Ala Glu Glu Glu Ile Ile Ile Arg Ser Glu Asn Leu Thr Asn Asn
    50                  55                  60

Val Lys Thr Ile Ile Val His Phe Asn Glu Ser Val Glu Ile Val Cys
65                  70                  75                  80

Thr Arg Pro Gly Asn Asn Thr Arg Lys Ser Ile Arg Ile Gly Pro Gly
                85                  90                  95

Gln Thr Phe Tyr Ala Thr Gly Glu Ile Ile Gly Asp Ile Arg Gln Ala
            100                 105                 110

His Cys Asn Ile Ser Gly Ala Asn Trp Thr Lys Thr Met Gln Arg Val
        115                 120                 125

Ser Lys Lys Leu Lys Glu Glu Leu Tyr Lys Tyr Lys Val Val Glu Ile
130                 135                 140

Lys Pro Leu Gly Leu Ala Pro Thr Glu Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
                180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
210                 215                 220

Gly Ile Lys Gln Leu
225

<210> SEQ ID NO 89
<211> LENGTH: 229

```
<212> TYPE: PRT
<213> ORGANISM: Human immunodeficiency virus type 1

<400> SEQUENCE: 89

Tyr Cys Ala Pro Ala Gly Tyr Ala Ile Leu Lys Cys Asn Asn Lys Thr
1               5                   10                  15

Phe Asn Gly Thr Gly Pro Cys His Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Glu Ile Ile Ile Arg Ser Glu Asn Leu Thr Asn Asn
    50                  55                  60

Ala Lys Thr Ile Ile Val His Leu Asn Glu Ser Ile Glu Ile Val Cys
65                  70                  75                  80

Ile Arg Pro Asn Asn Asn Thr Arg Lys Ser Ile Arg Ile Gly Pro Gly
                85                  90                  95

Gln Thr Phe Tyr Ala Thr Asn Asp Ile Ile Gly Asp Ile Arg Gln Ala
            100                 105                 110

His Cys Asn Ile Ser Lys Thr Lys Trp Asn Thr Thr Leu Glu Lys Val
        115                 120                 125

Lys Glu Lys Leu Lys Asp Glu Leu Tyr Lys Tyr Lys Val Val Glu Ile
    130                 135                 140

Lys Pro Leu Gly Val Ala Pro Thr Lys Ala Lys Arg Arg Val Val Glu
145                 150                 155                 160

Arg Glu Lys Arg Ala Val Gly Ile Gly Ala Val Leu Phe Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
    210                 215                 220

Gly Ile Lys Gln Leu
225

<210> SEQ ID NO 90
<211> LENGTH: 229
<212> TYPE: PRT
<213> ORGANISM: Human immunodeficiency virus type 1

<400> SEQUENCE: 90

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Glu Val Val Ile Arg Phe Glu Asn Leu Thr Asn Asn
    50                  55                  60

Ala Lys Ile Ile Ile Val His Leu Asn Glu Ser Val Glu Ile Asn Cys
65                  70                  75                  80

Thr Arg Pro Ser Asn Asn Thr Arg Lys Ser Val Arg Ile Gly Pro Gly
                85                  90                  95

Gln Thr Phe Phe Ala Thr Gly Asp Ile Ile Gly Asp Ile Arg Gln Ala
            100                 105                 110

His Cys Asn Ile Ser Arg Glu Lys Trp Asn Thr Thr Leu Gln Arg Val
```

```
            115                 120                 125
Lys Glu Lys Leu Lys Glu Leu Tyr Lys Tyr Lys Val Val Glu Ile
130                 135                 140

Lys Pro Leu Gly Ile Ala Pro Asp Lys Ala Lys Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Met Thr Leu Thr Val
                180                 185                 190

Gln Ala Arg Gln Leu Leu Ser Gly Ile Val Gln Gln Gln Ser Asn Leu
                195                 200                 205

Leu Arg Ala Ile Glu Ala Gln Gln His Met Leu Gln Leu Thr Val Trp
        210                 215                 220

Gly Ile Lys Gln Leu
225

<210> SEQ ID NO 91
<211> LENGTH: 229
<212> TYPE: PRT
<213> ORGANISM: Human immunodeficiency virus type 1

<400> SEQUENCE: 91

Tyr Cys Ala Pro Ala Gly Tyr Ala Ile Leu Lys Cys Asn Asn Lys Thr
1               5                   10                  15

Phe Asn Gly Thr Gly Pro Cys His Asn Val Ser Thr Val Gln Cys Thr
                20                  25                  30

His Gly Ile Lys Pro Val Val Ser Thr Gln Leu Leu Leu Asn Gly Ser
            35                  40                  45

Leu Ala Glu Glu Asp Ile Ile Ile Arg Ser Glu Asn Leu Thr Asn Asn
        50                  55                  60

Ala Lys Thr Ile Ile Val Gln Leu Asn Lys Ser Val Glu Ile Val Cys
65                  70                  75                  80

Thr Arg Pro Asn Asn Asn Thr Arg Lys Ser Ile Arg Ile Gly Pro Gly
                85                  90                  95

Gln Thr Phe Tyr Ala Thr Asn Ala Ile Ile Gly Asp Ile Arg Gln Ala
                100                 105                 110

Tyr Cys Asn Ile Ser Gly Ala Asp Trp Asn Lys Thr Leu Glu Ser Val
            115                 120                 125

Lys Lys Lys Leu Gly Glu Glu Leu Tyr Lys Tyr Lys Val Val Glu Ile
130                 135                 140

Lys Pro Leu Gly Val Ala Pro Thr Lys Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
                180                 185                 190

Gln Ala Arg Gln Leu Leu Ser Gly Ile Val Gln Gln Gln Ser Asn Leu
                195                 200                 205

Leu Arg Ala Ile Glu Ala Gln Gln His Met Leu Gln Leu Thr Val Trp
        210                 215                 220

Gly Ile Lys Gln Leu
225

<210> SEQ ID NO 92
<211> LENGTH: 229
<212> TYPE: PRT
```

<213> ORGANISM: Human immunodeficiency virus type 1

<400> SEQUENCE: 92

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Glu Ile Ile Ile Arg Ser Glu Asn Leu Thr Asn Asn
    50                  55                  60

Ile Lys Thr Ile Ile Val His Leu Asn Lys Ser Val Glu Ile Val Cys
65                  70                  75                  80

Thr Arg Pro Asn Asn Thr Arg Lys Ser Ile Arg Ile Gly Pro Gly
                85                  90                  95

Gln Thr Phe Tyr Ala Thr Asp Ala Ile Ile Gly Asn Ile Arg Glu Ala
            100                 105                 110

His Cys Asn Ile Ser Lys Ser Asn Trp Thr Ser Thr Leu Glu Gln Val
        115                 120                 125

Lys Lys Lys Leu Lys Glu Glu Leu Tyr Lys Tyr Lys Val Val Glu Ile
    130                 135                 140

Lys Pro Leu Gly Ile Ala Pro Thr Glu Thr Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Glu Gly Ser Thr Met Gly Ala Ala Ser Leu Thr Leu Thr Val
            180                 185                 190

Gln Ala Arg Gln Leu Leu Ser Gly Ile Val Gln Gln Ser Asn Leu
    195                 200                 205

Leu Arg Ala Ile Glu Ala Gln Gln His Met Leu Gln Leu Thr Gly Trp
210                 215                 220

Gly Ile Lys Gln Leu
225

<210> SEQ ID NO 93
<211> LENGTH: 229
<212> TYPE: PRT
<213> ORGANISM: Human immunodeficiency virus type 1

<400> SEQUENCE: 93

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Gly Lys Ile Ile Ile Arg Ser Glu Asn Leu Thr Asn Asn
    50                  55                  60

Ala Lys Thr Ile Ile Val His Leu Asn Thr Ser Val Ala Ile Val Cys
65                  70                  75                  80

Thr Arg Pro Asn Asn Thr Arg Lys Ser Ile Arg Ile Gly Pro Gly
                85                  90                  95

Gln Thr Phe Tyr Ala Thr Asn Asp Ile Ile Gly Asn Ile Arg Gln Ala
            100                 105                 110

His Cys Asn Ile Ser Glu Glu Gln Trp Ser Thr Thr Val Ala Gln Val
        115                 120                 125

```
Lys Lys Lys Leu Arg Ala Glu Leu Tyr Lys Tyr Lys Val Val Glu Ile
    130                 135                 140

Lys Pro Leu Gly Val Ala Pro Thr Glu Ser Lys Arg Val Val Glu
145                 150                 155                 160

Arg Glu Lys Arg Ala Val Gly Ile Gly Ala Val Leu Leu Gly Phe Leu
                165                 170                 175

Gly Ala Ala Gly Ser Thr Met Gly Ala Ala Ser Val Thr Leu Thr Val
                180                 185                 190

Gln Ala Arg Gln Leu Leu Ser Gly Ile Val Gln Gln Gln Ser Asn Leu
            195                 200                 205

Leu Arg Ala Ile Glu Ala Gln Gln His Met Leu Gln Leu Thr Val Trp
    210                 215                 220

Gly Ile Lys Gln Leu
225

<210> SEQ ID NO 94
<211> LENGTH: 228
<212> TYPE: PRT
<213> ORGANISM: Human immunodeficiency virus type 1

<400> SEQUENCE: 94

Tyr Cys Ala Pro Ala Gly Tyr Ala Ile Leu Lys Cys Asn Asn Lys Thr
1               5                   10                  15

Phe Asn Gly Thr Gly Pro Cys Gln Asn Val Ser Thr Val Gln Cys Thr
                20                  25                  30

His Gly Ile Lys Pro Val Val Ser Thr Gln Leu Leu Leu Asn Gly Ser
            35                  40                  45

Ile Ala Glu Gly Glu Ile Ile Ile Arg Ser Glu Asn Leu Thr Asn Asn
        50                  55                  60

Val Lys Thr Ile Ile Val His Leu Asn Glu Ser Ile Gly Ile Val Cys
65                  70                  75                  80

Thr Arg Pro Gly Asn Asn Thr Arg Lys Ser Ile Arg Ile Gly Pro Gly
                85                  90                  95

Gln Ala Phe Tyr Thr Asn His Ile Ile Gly Asp Ile Arg Gln Ala Tyr
            100                 105                 110

Cys Asn Ile Ser Lys Gln Glu Trp Asn Lys Thr Leu Glu Glu Val Arg
        115                 120                 125

Lys Lys Leu Gln Glu Glu Leu Tyr Lys Tyr Lys Val Val Glu Ile Lys
    130                 135                 140

Pro Leu Gly Ile Ala Pro Thr Glu Ala Lys Arg Arg Val Val Glu Arg
145                 150                 155                 160

Glu Lys Arg Ala Val Gly Ile Gly Ala Val Leu Leu Gly Phe Leu Gly
                165                 170                 175

Ala Ala Gly Ser Thr Met Gly Ala Ala Ser Ile Thr Leu Thr Val Gln
            180                 185                 190

Ala Arg Gln Leu Leu Ser Gly Ile Val Gln Gln Gln Ser Asn Leu Leu
        195                 200                 205

Arg Ala Ile Glu Ala Gln Gln His Met Leu Gln Leu Thr Val Trp Gly
    210                 215                 220

Ile Lys Gln Leu
225

<210> SEQ ID NO 95
<211> LENGTH: 227
<212> TYPE: PRT
<213> ORGANISM: Human immunodeficiency virus type 1
```

-continued

```
<400> SEQUENCE: 95

Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Gly Ile Ile Ile Arg Ser Glu Asn Leu Thr Asn Asn
    50                  55                  60

Ala Lys Thr Ile Ile Val Gln Leu Asn Glu Ser Val Pro Ile Val Cys
65                  70                  75                  80

Ile Arg Pro Asn Asn Asn Thr Arg Gln Ser Ile Arg Ile Gly Pro Gly
                85                  90                  95

Gln Ala Phe Phe Ala Thr Lys Asp Ile Ile Gly Asp Ile Arg Gln Ala
            100                 105                 110

Tyr Cys Asn Ile Ser Lys Trp Asn Thr Thr Leu Glu Lys Val Lys Glu
        115                 120                 125

Arg Leu Lys Glu Glu Leu Tyr Lys Tyr Lys Val Val Glu Ile Lys Pro
    130                 135                 140

Leu Gly Val Ala Pro Thr Lys Ala Lys Arg Arg Val Val Glu Arg Glu
145                 150                 155                 160

Lys Arg Ala Val Gly Ile Gly Ala Val Phe Leu Gly Phe Leu Gly Ala
                165                 170                 175

Ala Gly Ser Thr Met Gly Ala Ala Ser Ile Thr Leu Pro Val Gln Ala
            180                 185                 190

Arg Gln Leu Leu Ser Gly Ile Val Gln Gln Gln Ser Asn Leu Leu Arg
        195                 200                 205

Ala Ile Glu Ala Gln Gln His Leu Leu Gln Leu Thr Val Trp Gly Ile
    210                 215                 220

Lys Gln Leu
225

<210> SEQ ID NO 96
<211> LENGTH: 229
<212> TYPE: PRT
<213> ORGANISM: Human immunodeficiency virus type 1

<400> SEQUENCE: 96

Tyr Cys Ala Pro Ala Gly Tyr Ala Ile Leu Lys Cys Asn Asn Lys Thr
1               5                   10                  15

Phe Asp Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Glu Ile Ile Ile Arg Ser Glu Asn Leu Thr Asn Asn
    50                  55                  60

Val Lys Ile Ile Ile Val His Leu Asn Gln Ser Val Pro Ile Glu Cys
65                  70                  75                  80

Thr Arg Pro Gly Asn Asn Thr Arg Lys Ser Val Arg Ile Gly Pro Gly
                85                  90                  95

Gln Thr Phe Tyr Ala Thr Gly Asp Ile Ile Gly Asp Ile Arg Gln Ala
            100                 105                 110

Tyr Cys Asn Val Thr Glu Glu Arg Trp Asn Ile Thr Leu Gln Lys Ile
        115                 120                 125
```

-continued

```
Ala Lys Lys Leu Leu Gly Glu Leu Tyr Lys Tyr Lys Val Val Glu Ile
            130                 135                 140

Lys Pro Leu Gly Ile Ala Pro Thr Glu Ala Lys Arg Arg Val Val Glu
145                 150                 155                 160

Arg Glu Lys Arg Ala Val Gly Ile Gly Ala Val Phe Leu Gly Phe Leu
                165                 170                 175

Ala Ala Ala Gly Ser Thr Met Gly Ala Ala Ser Ile Thr Leu Thr Val
            180                 185                 190

Gln Ala Arg Gln Leu Leu Ser Gly Ile Val Gln Gln Asn Asn Leu
        195                 200                 205

Leu Arg Ala Ile Glu Ala Gln Gln His Met Leu Gln Leu Thr Val Trp
    210                 215                 220

Gly Ile Lys Gln Leu
225
```

<210> SEQ ID NO 97
<211> LENGTH: 229
<212> TYPE: PRT
<213> ORGANISM: Human immunodeficiency virus type 1

<400> SEQUENCE: 97

```
Tyr Cys Ala Pro Ala Gly Tyr Ala Ile Leu Lys Cys Asn Asn Asn Thr
1               5                   10                  15

Phe Asn Gly Lys Gly Pro Cys Thr Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Lys Glu Ile Val Ile Arg Ser Glu Asn Leu Thr Asn Asn
    50                  55                  60

Ala Lys Thr Ile Ile Val Gln Leu Glu Asn Pro Ile Glu Ile Val Cys
65                  70                  75                  80

Thr Arg Pro Gly Asn Asn Thr Arg Lys Ser Val Arg Ile Gly Pro Gly
                85                  90                  95

Gln Thr Phe Tyr Ala Thr Gly Asp Ile Ile Gly Asp Ile Arg Gln Ala
            100                 105                 110

His Cys Thr Ile Ser Glu Glu Lys Trp Asn Thr Thr Leu Gln Lys Val
        115                 120                 125

Gly Glu Lys Leu Ile Lys Glu Leu Tyr Lys Tyr Lys Val Val Glu Ile
    130                 135                 140

Lys Pro Leu Gly Ile Ala Pro Thr Thr Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
    210                 215                 220

Gly Ile Lys Gln Leu
225
```

<210> SEQ ID NO 98
<211> LENGTH: 229
<212> TYPE: PRT
<213> ORGANISM: Human immunodeficiency virus type 1

```
<400> SEQUENCE: 98

Tyr Cys Ala Pro Ala Gly Tyr Ala Ile Leu Lys Cys Asn Asn Glu Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Asn Gly Ser
        35                  40                  45

Leu Ala Glu Glu Gly Ile Ile Ile Lys Ser Glu Asn Met Thr Asp Asn
50                  55                  60

Ile Lys Thr Ile Ile Val His Leu Asn Lys Leu Val Lys Ile Glu Cys
65                  70                  75                  80

Thr Arg Pro Ser Asn Asn Thr Arg Lys Ser Ile Arg Ile Gly Pro Gly
                85                  90                  95

Gln Ala Phe Phe Ala Thr Asn Ala Ile Ile Gly Asp Ile Arg Gln Ala
            100                 105                 110

His Cys Asn Ile Ser Arg Asp His Trp Asn Lys Thr Leu Glu Lys Ile
        115                 120                 125

Lys Gly Lys Phe Lys Glu Glu Leu Tyr Lys Tyr Lys Val Val Glu Ile
130                 135                 140

Lys Pro Leu Gly Val Ala Pro Thr Glu Ala Lys Arg Arg Val Val Glu
145                 150                 155                 160

Arg Glu Lys Arg Ala Val Gly Ile Gly Ala Val Leu Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
            195                 200                 205

Leu Arg Ala Ile Glu Ala Gln Gln His Met Leu Gln Leu Thr Val Trp
210                 215                 220

Gly Ile Lys Gln Leu
225

<210> SEQ ID NO 99
<211> LENGTH: 129
<212> TYPE: PRT
<213> ORGANISM: Human immunodeficiency virus type 1

<400> SEQUENCE: 99

Tyr Cys Ala Pro Ala Gly Tyr Ala Ile Leu Lys Cys Asn Asp Lys Lys
1               5                   10                  15

Phe Asn Gly Thr Gly Pro Cys Tyr Asn Val Ser Thr Val Gln Cys Thr
            20                  25                  30

His Gly Ile Lys Pro Val Val Ser Thr Gln Leu Leu Asn Gly Ser
        35                  40                  45

Leu Ala Glu Glu Glu Ile Ile Ile Lys Ser Glu Asp Leu Thr Asn Asn
50                  55                  60

Val Lys Thr Ile Ile Val His Leu Asn Glu Ser Ile Pro Ile Val Cys
65                  70                  75                  80

Ile Arg Pro Gly Asn Asn Thr Arg Lys Ser Ile Arg Ile Gly Pro Gly
                85                  90                  95

Gln Thr Phe Tyr Ala Asn Asn Asp Ile Ile Gly Asp Ile Arg Gln Ala
            100                 105                 110

His Cys Asn Ile Ser Lys Cys Asn Trp Lys Leu Thr Leu Val Lys Val
        115                 120                 125

Lys
```

```
<210> SEQ ID NO 100
<211> LENGTH: 99
<212> TYPE: PRT
<213> ORGANISM: Human immunodeficiency virus type 1

<400> SEQUENCE: 100

Lys Leu His Tyr Glu Leu Tyr Lys Tyr Lys Val Val Glu Ile Lys Pro
1               5                   10                  15

Leu Gly Val Ala Pro Thr Glu Ala Lys Arg Arg Val Val Glu Arg Glu
            20                  25                  30

Lys Arg Ala Val Gly Met Gly Ala Val Phe Leu Gly Phe Leu Gly Ala
        35                  40                  45

Ala Gly Ser Thr Met Gly Ala Ala Ser Ile Thr Leu Thr Val Gln Ala
    50                  55                  60

Arg Gln Leu Leu Ser Gly Ile Val Gln Gln Gln Ser Asn Leu Leu Arg
65                  70                  75                  80

Ala Ile Glu Ala Gln Gln His Met Leu Gln Leu Thr Val Trp Gly Ile
                85                  90                  95

Lys Gln Leu

<210> SEQ ID NO 101
<211> LENGTH: 228
<212> TYPE: PRT
<213> ORGANISM: Human immunodeficiency virus type 1

<400> SEQUENCE: 101

Tyr Cys Ala Pro Ala Gly Tyr Ala Ile Leu Lys Cys Asn Asn Glu Thr
1               5                   10                  15

Phe Asn Gly Thr Gly Pro Cys Asn Asn Val Ser Thr Val Leu Cys Thr
            20                  25                  30

His Gly Ile Lys Pro Val Val Ser Thr Gln Leu Leu Leu Asn Gly Ser
        35                  40                  45

Leu Ala Lys Glu Thr Ile Ile Arg Ser Glu Asn Leu Thr Asn Asn Ala
    50                  55                  60

Lys Ile Ile Ile Val His Leu Asn Glu Ser Val Gln Ile Val Cys Thr
65                  70                  75                  80

Arg Pro Asn Asn Asn Thr Arg Glu Ser Val Arg Ile Gly Pro Gly Gln
                85                  90                  95

Thr Phe Tyr Ala Thr Gly Asp Ile Ile Gly Asp Leu Arg Gln Ala Pro
            100                 105                 110

Cys Ser Ile Ser Ile Asn Lys Trp Asn Lys Thr Leu Gln Glu Val Ser
        115                 120                 125

Lys Lys Leu Gln Lys Glu Leu Tyr Lys Tyr Lys Val Ile Glu Ile Lys
    130                 135                 140

Pro Leu Gly Ile Ala Pro Thr Thr Ala Lys Arg Arg Val Val Glu Arg
145                 150                 155                 160

Glu Lys Arg Ala Val Gly Ile Gly Ala Met Phe Leu Gly Phe Leu Gly
                165                 170                 175

Ala Ala Gly Ser Thr Met Gly Ala Ala Ser Ile Thr Leu Thr Val Gln
            180                 185                 190

Ala Arg Gln Leu Leu Ser Gly Ile Val Gln Gln Gln Asn Asn Leu Leu
        195                 200                 205

Arg Ala Ile Glu Ala Gln Gln His Met Leu Gln Leu Thr Val Trp Gly
    210                 215                 220

Ile Lys Gln Leu
```

<210> SEQ ID NO 102
<211> LENGTH: 229
<212> TYPE: PRT
<213> ORGANISM: Human immunodeficiency virus type 1

<400> SEQUENCE: 102

```
Tyr Cys Ala Pro Ala Gly Tyr Ala Ile Leu Lys Cys Asn Asn Lys Thr
  1               5                  10                  15

Phe Asn Gly Ser Gly Pro Cys Asn Asn Val Ser Thr Val Gln Cys Thr
             20                  25                  30

His Gly Ile Lys Pro Val Val Ser Thr Gln Leu Leu Leu Asn Gly Ser
         35                  40                  45

Leu Ala Glu Glu Lys Ile Ile Ile Arg Ser Glu Asn Leu Thr Asp Asn
 50                  55                  60

Thr Lys Thr Ile Ile Ile His Leu Thr Glu Ser Val Glu Ile Leu Cys
 65                  70                  75                  80

Ile Arg Pro Gly Asn Asn Thr Arg Lys Ser Ile Arg Ile Gly Pro Gly
                 85                  90                  95

Gln Ile Phe Tyr Ala Thr Gly Gly Ile Ile Gly Asp Ile Arg Gln Ala
            100                 105                 110

Tyr Cys Asn Ile Asn Glu Tyr Ser Trp Asn Lys Thr Leu Lys Arg Val
        115                 120                 125

Ser Glu Lys Phe Arg Glu Leu Tyr Lys Tyr Lys Val Val Glu Val
    130                 135                 140

Arg Pro Leu Gly Ile Ala Pro Thr Arg Ala Lys Arg Arg Val Val Glu
145                 150                 155                 160

Arg Glu Lys Arg Ala Val Gly Ala Gly Ala Val Ile Phe Gly Phe Leu
                165                 170                 175

Ala Ala Ala Gly Ser Thr Met Gly Ala Ala Ser Leu Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
210                 215                 220

Gly Ile Lys Gln Leu
225
```

<210> SEQ ID NO 103
<211> LENGTH: 229
<212> TYPE: PRT
<213> ORGANISM: Human immunodeficiency virus type 1

<400> SEQUENCE: 103

```
Tyr Cys Ala Pro Ala Gly Tyr Ala Ile Leu Lys Cys Thr Asp Lys Lys
  1               5                  10                  15

Phe Asn Gly Thr Gly Ser Cys Asn Asn Val Ser Thr Val Gln Cys Thr
             20                  25                  30

His Gly Ile Lys Pro Val Val Ser Thr Gln Leu Leu Leu Asn Gly Ser
         35                  40                  45

Leu Ala Glu Glu Glu Ile Ile Ile Lys Ser Glu Asn Leu Thr Asp Asn
 50                  55                  60

Ile Lys Thr Ile Ile Val Ala Leu Asn Ala Ser Ile Gly Ile Asn Cys
 65                  70                  75                  80

Thr Arg Pro Asn Asn Asn Thr Arg Lys Ser Val Arg Ile Gly Pro Gly
                 85                  90                  95
```

Gln Thr Phe Tyr Ala Thr Gly Asp Ile Ile Gly Asp Ile Arg Gln Ala
                100                 105                 110

His Cys Asn Ile Ser Arg Asn Gln Trp Asn Glu Thr Leu Glu Gln Val
            115                 120                 125

Lys Lys Lys Leu Gly Glu Leu Tyr Lys Tyr Lys Val Val Glu Ile
130                 135                 140

Lys Pro Leu Gly Val Ala Pro Thr Gly Ala Lys Arg Met Val Val Lys
145                 150                 155                 160

Arg Glu Lys Arg Ala Val Gly Leu Gly Ala Val Leu Phe Gly Phe Leu
                165                 170                 175

Gly Ala Ala Gly Ser Thr Met Gly Ala Ala Ser Ile Thr Leu Thr Ala
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
210                 215                 220

Gly Ile Lys Gln Leu
225

<210> SEQ ID NO 104
<211> LENGTH: 229
<212> TYPE: PRT
<213> ORGANISM: Human immunodeficiency virus type 1
<220> FEATURE:
<221> NAME/KEY: misc_feature
<222> LOCATION: (222)..(222)
<223> OTHER INFORMATION: Xaa can be any naturally occurring amino
      acid

<400> SEQUENCE: 104

Tyr Cys Ala Pro Ala Gly Tyr Ala Ile Leu Lys Cys Asp Asn Glu Thr
1               5                   10                  15

Phe Asn Gly Thr Gly Pro Cys Asn Asn Val Ser Thr Val Gln Cys Thr
                20                  25                  30

His Gly Ile Lys Pro Val Val Ser Thr Gln Leu Leu Leu Asn Gly Ser
            35                  40                  45

Leu Ala Glu Lys Glu Ile Ile Ile Arg Ser Glu Asn Met Thr Asp Asn
50                  55                  60

Gly Lys Thr Ile Ile Val His Leu Asn Glu Ser Val Arg Ile Glu Cys
65                  70                  75                  80

Ile Arg Pro Asn Asn Asn Thr Arg Lys Ser Val Arg Ile Gly Pro Gly
                85                  90                  95

Gln Thr Phe Tyr Ala Thr Gly Gln Val Ile Gly Asp Ile Arg Gln Ala
                100                 105                 110

His Cys Asn Ile Ser Glu Arg Asp Trp Asn Thr Thr Leu Gln Arg Val
            115                 120                 125

Ser Lys Lys Leu Lys Glu Glu Leu Tyr Lys Tyr Lys Val Val Glu Ile
130                 135                 140

Gln Pro Leu Gly Val Ala Pro Thr Arg Ala Lys Arg Arg Val Val Glu
145                 150                 155                 160

Arg Glu Lys Arg Ala Val Gly Ile Gly Ala Ala Leu Leu Gly Phe Leu
                165                 170                 175

Gly Ala Ala Gly Ser Thr Met Gly Ala Ala Ser Met Ala Leu Thr Val
            180                 185                 190

Gln Ala Arg Gln Leu Leu Ser Gly Ile Val Gln Gln Ser Asn Leu
        195                 200                 205

```
Leu Arg Ala Ile Glu Ala Pro Gln His Met Leu Gln Leu Xaa Val Ser
    210                 215                 220

Gly Ile Lys Gln Leu
225
```

<210> SEQ ID NO 105
<211> LENGTH: 228
<212> TYPE: PRT
<213> ORGANISM: Human immunodeficiency virus type 1

<400> SEQUENCE: 105

```
Tyr Cys Ala Pro Ala Gly Tyr Ala Ile Leu Lys Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Gly Glu Ile Ile Arg Ser Glu Asn Leu Thr Asn Asn
    50                  55                  60

Ile Lys Thr Ile Ile Val His Leu Asn Glu Ser Val Thr Ile Asn Cys
65                  70                  75                  80

Thr Arg Pro Asn Asn Asn Thr Arg Arg Ser Ile Arg Ile Gly Pro Gly
                85                  90                  95

Gln Thr Phe Tyr Thr Asn Asp Ile Ile Gly Asp Ile Arg Gln Ala His
            100                 105                 110

Cys Asn Ile Ser Arg Thr Glu Trp Asn Asn Thr Leu Glu Arg Val Arg
        115                 120                 125

Lys Lys Leu Glu Glu Glu Leu Tyr Leu Tyr Lys Val Val Glu Ile Lys
    130                 135                 140

Pro Leu Glu Ile Ala Pro Ile Lys Ala Lys Arg Arg Val Val Glu Arg
145                 150                 155                 160

Glu Ile Arg Ala Val Gly Ile Gly Ala Val Leu Leu Gly Phe Leu Gly
                165                 170                 175

Ala Ala Gly Ser Thr Met Gly Ala Ala Ser Ile Thr Leu Thr Val Gln
            180                 185                 190

Ala Arg Gln Leu Leu Ser Gly Val Val Gln Gln Ser Asn Glu Leu
        195                 200                 205

Arg Ala Ile Gln Ala Gln Gln His Met Met Gln Leu Thr Val Trp Gly
    210                 215                 220

Val Lys Gln Leu
225
```

<210> SEQ ID NO 106
<211> LENGTH: 122
<212> TYPE: PRT
<213> ORGANISM: Human immunodeficiency virus type 1
<220> FEATURE:
<221> NAME/KEY: misc_feature
<222> LOCATION: (57)..(57)
<223> OTHER INFORMATION: Xaa can be any naturally occurring amino
      acid
<220> FEATURE:
<221> NAME/KEY: misc_feature
<222> LOCATION: (119)..(119)
<223> OTHER INFORMATION: Xaa can be any naturally occurring amino
      acid

<400> SEQUENCE: 106

```
Tyr Cys Ala Pro Ala Gly Phe Ala Ile Leu Lys Cys Asn Asn Gln Thr
1               5                   10                  15
```

```
Phe Asn Gly Thr Gly Pro Cys Thr Asn Val Ser Thr Val Gln Cys Thr
                20                  25                  30

His Gly Ile Lys Pro Val Val Ser Thr Gln Leu Leu Leu Asn Gly Ser
            35                  40                  45

Leu Ala Glu Gly Glu Ile Ile Ile Xaa Ser Glu Asn Leu Thr Asp Asn
 50                  55                  60

Thr Lys Thr Ile Ile Val His Leu Asn Glu Pro Val Ala Ile Asn Cys
 65                  70                  75                  80

Thr Arg Pro Gly Asn Asn Thr Arg Lys Ser Val Arg Ile Gly Pro Gly
                85                  90                  95

Gln Thr Phe Tyr Ala Thr Asp Val Ile Gly Val Ile Arg Ala Ala
                100                 105                 110

Arg Cys Asp Val Ser Arg Xaa Asn Trp Asn
            115                 120
```

<210> SEQ ID NO 107
<211> LENGTH: 6
<212> TYPE: PRT
<213> ORGANISM: Human immunodeficiency virus type 1
<220> FEATURE:
<221> NAME/KEY: misc_feature
<222> LOCATION: (2)..(2)
<223> OTHER INFORMATION: Xaa can be any naturally occurring amino acid

<400> SEQUENCE: 107

```
Thr Xaa Glu Gly Val Lys
1               5
```

<210> SEQ ID NO 108
<211> LENGTH: 99
<212> TYPE: PRT
<213> ORGANISM: Human immunodeficiency virus type 1

<400> SEQUENCE: 108

```
Lys Leu Leu Glu Glu Leu Tyr Lys Tyr Lys Val Val Glu Val Lys Pro
1               5                   10                  15

Leu Gly Ile Ala Pro Thr Lys Ser Lys Arg Arg Val Val Glu Arg Glu
            20                  25                  30

Lys Arg Ala Val Gly Met Gly Ala Val Ile Phe Gly Phe Leu Gly Ala
        35                  40                  45

Ala Gly Ser Thr Met Gly Ala Ala Ser Val Ala Leu Thr Val Gln Ala
 50                  55                  60

Arg Gln Leu Leu Ser Gly Ile Val Gln Gln Asn Asn Leu Leu Arg
 65                  70                  75                  80

Ala Ile Glu Ala Gln Gln His Met Leu Gln Leu Thr Val Trp Gly Ile
                85                  90                  95

Lys Gln Leu
```

<210> SEQ ID NO 109
<211> LENGTH: 229
<212> TYPE: PRT
<213> ORGANISM: Human immunodeficiency virus type 1
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid

<400> SEQUENCE: 109

```
Tyr Cys Ala Pro Ala Gly Tyr Ala Ile Leu Gln Cys Asn Asn Lys Thr
1               5                   10                  15

Phe Asn Gly Thr Gly Pro Cys Asn Asn Val Ser Thr Val Gln Cys Thr
            20                  25                  30

His Gly Ile Xaa Pro Val Val Ser Thr Gln Leu Leu Leu Asn Gly Ser
        35                  40                  45

Leu Ala Glu Lys Glu Ile Ile Ile Arg Ser Glu Asn Ile Thr Asn Asn
    50                  55                  60

Val Lys Thr Ile Ile Val His Leu Asn Glu Ser Val Gln Ile Thr Cys
65                  70                  75                  80

Thr Arg Pro His Asn Asn Thr Arg Lys Ser Met Arg Ile Gly Pro Gly
                85                  90                  95

Gln Thr Phe Tyr Ala Thr Gly Val Ile Ile Gly Ile Ile Gln Pro Pro
            100                 105                 110

Cys Cys Ile Ile Asn Glu Arg Xaa Trp Trp Thr Thr Phe Leu His Val
            115                 120                 125

Gly Gly Glu Leu Leu Glu Leu Tyr Lys Tyr Lys Val Val Glu Ile
130                 135                 140

Lys Pro Leu Gly Val Val Pro Thr Glu Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
            195                 200                 205

Leu Lys Ala Ile Glu Ala Gln Gln His Leu Leu Gln Leu Thr Val Trp
    210                 215                 220

Gly Ile Lys Gln Leu
225
```

<210> SEQ ID NO 110
<211> LENGTH: 229
<212> TYPE: PRT
<213> ORGANISM: Human immunodeficiency virus type 1

<400> SEQUENCE: 110

```
Tyr Cys Ala Pro Ala Gly Tyr Ala Ile Leu Lys Cys Asn Asn Lys Thr
1               5                   10                  15

Phe Asn Gly Thr Gly Pro Cys His Asn Val Ser Thr Val Gln Cys Thr
            20                  25                  30

His Gly Ile Lys Pro Val Val Ser Thr Gln Leu Leu Leu Asn Gly Ser
        35                  40                  45

Leu Ala Glu Glu Glu Ile Ile Ile Arg Ser Glu Asn Leu Thr Asn Asn
    50                  55                  60

Val Lys Thr Ile Ile Val His Leu Asn Glu Ser Val Glu Ile Val Cys
65                  70                  75                  80

Thr Arg Pro Asn Asn Asn Thr Arg Lys Ser Ile Arg Ile Gly Pro Gly
                85                  90                  95

Gln Thr Phe Tyr Ala Thr Gly Asp Ile Ile Gly Asp Ile Arg Gln Ala
            100                 105                 110

His Cys Asn Ile Ser Lys Asp Lys Trp Asn Lys Thr Leu Gln Lys Val
            115                 120                 125
```

```
Ser Lys Lys Leu Ala Glu Glu Leu Tyr Lys Tyr Lys Val Val Glu Ile
    130                 135                 140

Lys Pro Leu Gly Val Ala Pro Thr Lys Ala Lys Arg Arg Val Val Glu
145                 150                 155                 160

Arg Glu Lys Arg Ala Val Gly Ile Gly Ala Val Phe Leu Gly Phe Leu
                165                 170                 175

Gly Ala Ala Gly Ser Thr Met Gly Ala Ala Ser Ile Thr Leu Thr Val
            180                 185                 190

Gln Ala Arg Gln Leu Leu Ser Gly Ile Val Gln Gln Ser Asn Leu
        195                 200                 205

Leu Arg Ala Ile Glu Ala Gln Gln His Met Leu Gln Leu Thr Val Trp
    210                 215                 220

Gly Ile Lys Gln Leu
225

<210> SEQ ID NO 111
<211> LENGTH: 1905
<212> TYPE: DNA
<213> ORGANISM: Human immunodeficiency virus type 1

<400> SEQUENCE: 111
gggggatgtg ctgcaaggcg attaagttgg gtaacgccag ggttttccca atcacgacgt    60
tgtaaaacga cagccaatga attgaagctt atgctgctc cgcatctat cctcagaggc    120 gaaaagttgg ataagtggga aaaaatcaga ctcaggccag gaggtaaaaa acactacatg    180
ctgaagcata tcgtgtgggc atctagggag ttggagagat ttgcactgaa ccccggactg    240
ctggaaacct cagagggctg taagcaaatc atgaaacagc tccaaccagc cttgcagacc    300
ggaacagaag agctgaagtc cctttacaat accgtggcaa ccctctattg cgtccacgag    360
aagatcgagg tgagagacac aaaggaggcc ctggacaaaa tcgaggagga gcagaataag    420
tgccagcaga gacccagca ggcaaaggct gctgacggaa aggtctctca gaactatcct    480
atcgttcaga accttcaggg gcagatggtg caccaagcaa tcagccctag aaccctgaac    540
gcatgggtga aggtgatcga ggagaaagcc ttttctcccg aggttatccc catgtttacc    600
gccctgagcg aaggcgccac tcctcaagac ctgaacacta tgctgaacac agtgggagga    660
caccaggccg ctatgcagat gttgaaggat accatcaacg aggaggcagc cgaatgggac    720
cgcctccacc ccgtgcacgc cggacctatc gccccggac aaatgagaga acctcgcgga    780
agtgatattg ccggtactac cagcacccct caagagcaga ttgcttggat gaccagcaac    840
ccacccatcc cagtgggcga tatttacaaa aggtggatta ttctggggct gaacaaaatt    900
gtgagaatgt actcccccgt ctccatcctc gacatccgcc aaggacccaa ggagcctttt    960
agggattacg tggacagatt cttcaaaacc cttagagctg agcaagccac tcaggaggtt   1020
aagaactgga tgacagatac tctgctcgtg caaaacgcta accccgattg caaaaccatc   1080
ttgagagctc tcggtccagg tgccacccct gaggaaatga tgacagcatg tcaaggcgtg   1140
ggaggacctg gcacaaggc cagagttctc gctgaggcca tgagccagac aaactcaggc   1200
aatatcatga tgcagaggag taactttaag ggtcccagga gaatcgtcaa gtgcttcaat   1260
tgtggcaagg agggtcacat tgccaggaac tgccgcgccc ccaggaagaa aggctgctgg   1320
aagtgtggca agagggcca ccagatgaag gattgcaccg agcgcaagc aaacttcctg   1380 ggaaagattt ggccccagtca taagggccgc cctggcaact tccttcaaaa cagacccgag   1440
cctaccgccc ccccgctga gtctttcaga tttgaggaga ccaccccgc tccaaagcag   1500 gagccaattg agagagagcc tctcaccagt ctcaaaagcc tctttggtag cgaccccctc   1560
```

```
agccaataag aattctagct tggcgtaatc atggtcatag ctgtttcctg tgtgaaattg    1620
ttatcagctc acaattccac acaacatacg agccggaagc ataaagtgta aagcctggga    1680
tgcctaatga gtgagctaac tcacattagt tgcgttgcgc tcactgcccg ctttccagtc    1740
gggaaacctg tcgtgccagc tccattagtg aatcgtccaa cgcacgggga gaggcggttt    1800
gcgtattggg cgcacttccg cttcctcgct cactgactcg ctgcgctcgt tcgttcggct    1860
gcggcgagcc gtatcagctc actcaaaggc ggtaatacgg ttatc                   1905
```

<210> SEQ ID NO 112
<211> LENGTH: 522
<212> TYPE: PRT
<213> ORGANISM: Human immunodeficiency virus type 1

<400> SEQUENCE: 112

```
Gly Gly Cys Ala Ala Arg Arg Leu Ser Trp Val Thr Pro Gly Phe Ser
1               5                   10                  15

Gln Ser Arg Arg Cys Lys Thr Thr Ala Asn Glu Leu Lys Leu Met Ala
            20                  25                  30

Ala Arg Ala Ser Ile Leu Arg Gly Glu Lys Leu Asp Lys Trp Glu Lys
        35                  40                  45

Ile Arg Leu Arg Pro Gly Gly Lys Lys His Tyr Met Leu Lys His Ile
    50                  55                  60

Val Trp Ala Ser Arg Glu Leu Glu Arg Phe Ala Leu Asn Pro Gly Leu
65                  70                  75                  80

Leu Glu Thr Ser Glu Gly Cys Lys Gln Ile Met Lys Gln Leu Gln Pro
                85                  90                  95

Ala Leu Gln Thr Gly Thr Glu Glu Leu Lys Ser Leu Tyr Asn Thr Val
            100                 105                 110

Ala Thr Leu Tyr Cys Val His Glu Lys Ile Glu Val Arg Asp Thr Lys
        115                 120                 125

Glu Ala Leu Asp Lys Ile Glu Glu Gln Asn Lys Cys Gln Gln Lys
    130                 135                 140

Thr Gln Gln Ala Lys Ala Ala Asp Gly Lys Val Ser Gln Asn Tyr Pro
145                 150                 155                 160

Ile Val Gln Asn Leu Gln Gly Gln Met Val His Gln Ala Ile Ser Pro
                165                 170                 175

Arg Thr Leu Asn Ala Trp Val Lys Val Ile Glu Glu Lys Ala Phe Ser
            180                 185                 190

Pro Glu Val Ile Pro Met Phe Thr Ala Leu Ser Glu Gly Ala Thr Pro
        195                 200                 205

Gln Asp Leu Asn Thr Met Leu Asn Thr Val Gly Gly His Gln Ala Ala
    210                 215                 220

Met Gln Met Leu Lys Asp Thr Ile Asn Glu Glu Ala Ala Glu Trp Asp
225                 230                 235                 240

Arg Leu His Pro Val His Ala Gly Pro Ile Ala Pro Gly Gln Met Arg
                245                 250                 255

Glu Pro Arg Gly Ser Asp Ile Ala Gly Thr Thr Ser Thr Leu Gln Glu
            260                 265                 270

Gln Ile Ala Trp Met Thr Ser Asn Pro Pro Ile Pro Val Gly Asp Ile
        275                 280                 285

Tyr Lys Arg Trp Ile Ile Leu Gly Leu Asn Lys Ile Val Arg Met Tyr
    290                 295                 300

Ser Pro Val Ser Ile Leu Asp Ile Arg Gln Gly Pro Lys Glu Pro Phe
305                 310                 315                 320
```

```
Arg Asp Tyr Val Asp Arg Phe Phe Lys Thr Leu Arg Ala Glu Gln Ala
            325                 330                 335

Thr Gln Glu Val Lys Asn Trp Met Thr Asp Thr Leu Leu Val Gln Asn
            340                 345                 350

Ala Asn Pro Asp Cys Lys Thr Ile Leu Arg Ala Leu Gly Pro Gly Ala
            355                 360                 365

Thr Leu Glu Glu Met Met Thr Ala Cys Gln Gly Val Gly Gly Pro Gly
        370                 375                 380

His Lys Ala Arg Val Leu Ala Glu Ala Met Ser Gln Thr Asn Ser Gly
385                 390                 395                 400

Asn Ile Met Met Gln Arg Ser Asn Phe Lys Gly Pro Arg Arg Ile Val
                405                 410                 415

Lys Cys Phe Asn Cys Gly Lys Glu Gly His Ile Ala Arg Asn Cys Arg
                420                 425                 430

Ala Pro Arg Lys Lys Gly Cys Trp Lys Cys Gly Lys Glu Gly His Gln
            435                 440                 445

Met Lys Asp Cys Thr Glu Arg Gln Ala Asn Phe Leu Gly Lys Ile Trp
        450                 455                 460

Pro Ser His Lys Gly Arg Pro Gly Asn Phe Leu Gln Asn Arg Pro Glu
465                 470                 475                 480

Pro Thr Ala Pro Pro Ala Glu Ser Phe Arg Phe Glu Glu Thr Thr Pro
                485                 490                 495

Ala Pro Lys Gln Glu Pro Ile Glu Arg Glu Pro Leu Thr Ser Leu Lys
            500                 505                 510

Ser Leu Phe Gly Ser Asp Pro Leu Ser Gln
            515                 520

<210> SEQ ID NO 113
<211> LENGTH: 30
<212> TYPE: PRT
<213> ORGANISM: Human immunodeficiency virus type 1

<400> SEQUENCE: 113

Leu Gly Val Ile Met Val Ile Ala Val Ser Cys Val Lys Leu Leu Ser
1               5                   10                  15

Ala His Asn Ser Thr Gln His Thr Ser Arg Lys His Lys Val
            20                  25                  30

<210> SEQ ID NO 114
<211> LENGTH: 54
<212> TYPE: PRT
<213> ORGANISM: Human immunodeficiency virus type 1

<400> SEQUENCE: 114

Ser Leu Gly Cys Leu Met Ser Glu Leu Thr His Ile Ser Cys Val Ala
1               5                   10                  15

Leu Thr Ala Arg Phe Pro Val Gly Lys Pro Val Val Pro Ala Pro Leu
            20                  25                  30

Val Asn Arg Pro Thr His Gly Glu Arg Arg Phe Ala Tyr Trp Ala His
                35                  40                  45

Phe Arg Phe Leu Ala His
            50

<210> SEQ ID NO 115
<211> LENGTH: 23
<212> TYPE: PRT
<213> ORGANISM: Human immunodeficiency virus type 1
```

<400> SEQUENCE: 115

Leu Ala Ala Leu Val Arg Ser Ala Ala Ala Ser Arg Ile Ser Ser Leu
1               5                   10                  15

Lys Gly Gly Asn Thr Val Ile
            20

<210> SEQ ID NO 116
<211> LENGTH: 2577
<212> TYPE: DNA
<213> ORGANISM: Human immunodeficiency virus type 1

<400> SEQUENCE: 116

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgccaa gcttgcatgc ctgcaggtcg      420
actctagagg atccccgggt accgagctcc ttcccacaag gccggccag gcaatttcct      480
tcagaacaga ccagagccaa cagccccacc agcagagagc ttcaggttcg aagagacaac      540
ccccgctccg aaacaggagc cgagagaaag ggaacccta acttccctca aatcactctt      600
tggcagcgac cccttgtctc aataaaaatc ggcggccaga cccgggaggc cctgctggac      660
accggcgccg acgaccgt gctggaggac atcaacctgc cggcaagtg aagcccaag      720
atgatcggcg gcatcggcgg cttcatcaag gtgcggcagt acgaccagat cctgatcgag      780
atctgcggca gaaggccat cggcaccgtg ctggtgggcc ccacccccgt gaacatcatc      840
ggccggaaca tgctgaccca gctgggctgc accctgaact tccccatcag ccccatcgag      900
accgtgcccg tgaagctgaa gcccggcatg gacggcccca ggtgaagca gtggcccctg      960
accgaggtga agatcaaggc cctgaccgcc atctgcgagg atgagaa ggagggcaag      1020
atcaccaaga tcggccccga gaaccctac aacacccca tcttcgccat caagaaggag      1080
gacagcacca gtggcggaa gctggtggac ttccgggagc tgaacaagcg acccaggac      1140
ttctgggagg tgcagctgg catcccccac ccgccggcc tgaagaagaa gaagagcgtg      1200
accgtgctgg acgtgggga cgcctacttc agcgtgccccc tggacgaggg cttccggaag      1260
tacaccgcct tcaccatccc cagcatcaac aacgagaccc ccggcatccg gtaccagtac      1320
aacgtgctgc ccagggctg gaagggcagc ccgccatct tccaggccag catgaccaag      1380
atcctggagc ccttccgggc caagaaccc gagatcgtga tctaccagta catggccgcc      1440
ctgtacgtgg gcagcgacct ggagatcggc cagcaccggg ccaagatcga ggagctgcgg      1500
gagcacctgc tgaagtgggg cttcaccacc cccgacaaga gcaccagaa ggagcccccc      1560
ttcctgtgga tgggctacga gctgcacccc gacaagtgga ccgtcagcc catccagctg      1620
cccgagaagg acagctggac cgtgaacgac atccagaagc tggtgggcaa gctgaactgg      1680
accagccaga tctaccccgg catcaaggtg cggcagctgt gcaagctgct gcggggcacc      1740
aaggccctga ccgacatcgt gccctgacc gaggaggccg agctggagct ggccgagaac      1800
cgggagatcc tgaaggagcc cgtgcacggc gtgtactacg accccagcaa ggacctgatc      1860
gccgagatcc agaagcaggg cgacgaccag tggacctacc agatctacca ggagcccttc      1920
```

-continued

```
aagaacctga aaaccggcaa gtacgccaag cggcggacca cccacaccaa cgacgtgaag    1980
cagctgaccg aggccgtgca gaagatcagc ctggagagca tcgtgacctg gggcaagacc    2040
cccaagttcc ggctgcccat ccagaaggag acctgggaga tctggtggac cgactactgg    2100
caggccacct ggatccccga gtgggagttc gtgaacaccc cccccctggt gaagctgtgg    2160
taccagctgg agaaggagcc catcgccggc gccgagacct tctacgtgga cggcgccgcc    2220
aaccgggaga ccaagatcgg caaggccggc tacgtgaccg accggggccg gcagaagatc    2280
gtgaccctga gcgagaccac caaccagaaa accgagctgc aggccatcca gctggccctg    2340
caggacagcg agagcgaggt gaacatcgtg accgacagcc agtacgccct gggcatcatc    2400
caggcccagc ccgaccggag cgagagcgag ctggtgaacc agatcatcga gcagctgatc    2460
aagaaggagc gggcctacct gagctggtg cccgcccaca agggcatcgg cggcgacgag    2520
caggtggaca gctggtgag cagcggcatc cggaaggtgc tgtgatctag agaattc       2577
```

```
<210> SEQ ID NO 117
<211> LENGTH: 57
<212> TYPE: PRT
<213> ORGANISM: Human immunodeficiency virus type 1

<400> SEQUENCE: 117

Ser Arg Val Ser Val Met Thr Val Lys Thr Ser Asp Thr Cys Ser Ser
1               5                   10                  15

Arg Arg Arg Ser Gln Leu Val Cys Lys Arg Met Pro Gly Ala Asp Lys
            20                  25                  30

Pro Val Arg Ala Arg Gln Arg Val Leu Ala Gly Val Gly Ala Gly Leu
        35                  40                  45

Thr Met Arg His Gln Ser Arg Leu Tyr
    50                  55

<210> SEQ ID NO 118
<211> LENGTH: 13
<212> TYPE: PRT
<213> ORGANISM: Human immunodeficiency virus type 1

<400> SEQUENCE: 118

Glu Cys Thr Ile Cys Gly Val Lys Tyr Arg Thr Asp Ala
1               5                   10

<210> SEQ ID NO 119
<211> LENGTH: 41
<212> TYPE: PRT
<213> ORGANISM: Human immunodeficiency virus type 1

<400> SEQUENCE: 119

Gly Glu Asn Thr Ala Ser Gly Ala Ile Arg His Ser Gly Cys Ala Thr
1               5                   10                  15

Val Gly Lys Gly Asp Arg Cys Gly Pro Leu Arg Tyr Tyr Ala Ser Trp
            20                  25                  30

Arg Lys Gly Asp Val Leu Gln Gly Asp
        35                  40

<210> SEQ ID NO 120
<211> LENGTH: 737
<212> TYPE: PRT
<213> ORGANISM: Human immunodeficiency virus type 1
```

```
<400> SEQUENCE: 120

Arg Gln Gly Phe Pro Ser His Asp Val Lys Arg Arg Pro Val Pro
1               5                   10                  15

Ser Leu His Ala Cys Arg Ser Thr Leu Glu Asp Pro Arg Val Pro Ser
            20                  25                  30

Ser Phe Pro Gln Gly Pro Ala Arg Gln Phe Pro Ser Glu Gln Thr Arg
            35                  40                  45

Ala Asn Ser Pro Thr Ser Arg Glu Leu Gln Val Arg Arg Asp Asn Pro
        50                  55                  60

Arg Ser Glu Thr Gly Ala Glu Arg Lys Gly Thr Leu Asn Phe Pro Gln
65                  70                  75                  80

Ile Thr Leu Trp Gln Arg Pro Leu Val Ser Ile Lys Ile Gly Gly Gln
                85                  90                  95

Thr Arg Glu Ala Leu Leu Asp Thr Gly Ala Asp Asp Thr Val Leu Glu
            100                 105                 110

Asp Ile Asn Leu Pro Gly Lys Trp Lys Pro Lys Met Ile Gly Gly Ile
            115                 120                 125

Gly Gly Phe Ile Lys Val Arg Gln Tyr Asp Gln Ile Leu Ile Glu Ile
        130                 135                 140

Cys Gly Lys Lys Ala Ile Gly Thr Val Leu Val Gly Pro Thr Pro Val
145                 150                 155                 160

Asn Ile Ile Gly Arg Asn Met Leu Thr Gln Leu Gly Cys Thr Leu Asn
                165                 170                 175

Phe Pro Ile Ser Pro Ile Glu Thr Val Pro Val Lys Leu Lys Pro Gly
            180                 185                 190

Met Asp Gly Pro Lys Val Lys Gln Trp Pro Leu Thr Glu Val Lys Ile
            195                 200                 205

Lys Ala Leu Thr Ala Ile Cys Glu Glu Met Glu Lys Glu Gly Lys Ile
        210                 215                 220

Thr Lys Ile Gly Pro Glu Asn Pro Tyr Asn Thr Pro Ile Phe Ala Ile
225                 230                 235                 240

Lys Lys Glu Asp Ser Thr Lys Trp Arg Lys Leu Val Asp Phe Arg Glu
                245                 250                 255

Leu Asn Lys Arg Thr Gln Asp Phe Trp Glu Val Gln Leu Gly Ile Pro
            260                 265                 270

His Pro Ala Gly Leu Lys Lys Lys Ser Val Thr Val Leu Asp Val
            275                 280                 285

Gly Asp Ala Tyr Phe Ser Val Pro Leu Asp Glu Gly Phe Arg Lys Tyr
        290                 295                 300

Thr Ala Phe Thr Ile Pro Ser Ile Asn Asn Glu Thr Pro Gly Ile Arg
305                 310                 315                 320

Tyr Gln Tyr Asn Val Leu Pro Gln Gly Trp Lys Gly Ser Pro Ala Ile
                325                 330                 335

Phe Gln Ala Ser Met Thr Lys Ile Leu Glu Pro Phe Arg Ala Lys Asn
            340                 345                 350

Pro Glu Ile Val Ile Tyr Gln Tyr Met Ala Ala Leu Tyr Val Gly Ser
            355                 360                 365

Asp Leu Glu Ile Gly Gln His Arg Ala Lys Ile Glu Glu Leu Arg Glu
        370                 375                 380

His Leu Leu Lys Trp Gly Phe Thr Thr Pro Asp Lys Lys His Gln Lys
385                 390                 395                 400
```

```
Glu Pro Pro Phe Leu Trp Met Gly Tyr Glu Leu His Pro Asp Lys Trp
                405                 410                 415

Thr Val Gln Pro Ile Gln Leu Pro Glu Lys Asp Ser Trp Thr Val Asn
            420                 425                 430

Asp Ile Gln Lys Leu Val Gly Lys Leu Asn Trp Thr Ser Gln Ile Tyr
        435                 440                 445

Pro Gly Ile Lys Val Arg Gln Leu Cys Lys Leu Leu Arg Gly Thr Lys
    450                 455                 460

Ala Leu Thr Asp Ile Val Pro Leu Thr Glu Glu Ala Glu Leu Glu Leu
465                 470                 475                 480

Ala Glu Asn Arg Glu Ile Leu Lys Glu Pro Val His Gly Val Tyr Tyr
            485                 490                 495

Asp Pro Ser Lys Asp Leu Ile Ala Glu Ile Gln Lys Gln Gly Asp Asp
        500                 505                 510

Gln Trp Thr Tyr Gln Ile Tyr Gln Glu Pro Phe Lys Asn Leu Lys Thr
    515                 520                 525

Gly Lys Tyr Ala Lys Arg Arg Thr Thr His Thr Asn Asp Val Lys Gln
530                 535                 540

Leu Thr Glu Ala Val Gln Lys Ile Ser Leu Glu Ser Ile Val Thr Trp
545                 550                 555                 560

Gly Lys Thr Pro Lys Phe Arg Leu Pro Ile Gln Lys Glu Thr Trp Glu
            565                 570                 575

Ile Trp Trp Thr Asp Tyr Trp Gln Ala Thr Trp Ile Pro Glu Trp Glu
            580                 585                 590

Phe Val Asn Thr Pro Pro Leu Val Lys Leu Trp Tyr Gln Leu Glu Lys
        595                 600                 605

Glu Pro Ile Ala Gly Ala Glu Thr Phe Tyr Val Asp Gly Ala Ala Asn
    610                 615                 620

Arg Glu Thr Lys Ile Gly Lys Ala Gly Tyr Val Thr Asp Arg Gly Arg
625                 630                 635                 640

Gln Lys Ile Val Thr Leu Ser Glu Thr Thr Asn Gln Lys Thr Glu Leu
            645                 650                 655

Gln Ala Ile Gln Leu Ala Leu Gln Asp Ser Glu Ser Glu Val Asn Ile
        660                 665                 670

Val Thr Asp Ser Gln Tyr Ala Leu Gly Ile Ile Gln Ala Gln Pro Asp
    675                 680                 685

Arg Ser Glu Ser Glu Leu Val Asn Gln Ile Ile Glu Gln Leu Ile Lys
    690                 695                 700

Lys Glu Arg Ala Tyr Leu Ser Trp Val Pro Ala His Lys Gly Ile Gly
705                 710                 715                 720

Gly Asp Glu Gln Val Asp Lys Leu Val Ser Ser Gly Ile Arg Lys Val
            725                 730                 735

Leu
```

NUCLEIC ACIDS ENCODING MODIFIED SOUTH AFRICAN HIV-1 SUBTYPE C GAG PROTEINS

PRIORITY

This application is a continuation-in-part application of U.S. patent application Ser. No. 11/724,551, filed Mar. 15, 2007, now abandoned, which is a continuation application of U.S. patent application Ser. No. 10/332,413, filed Sep. 12, 2003, now abandoned, which is a 371 application of PCT/IB01/01208, filed Jul. 9, 2001, which claims the benefit of U.S. Provisional Patent Application 60/216,995, filed Jul. 7, 2000, and provisional South African Patent Application 2000/3437, filed Jul. 10, 2000, and provisional South African Patent Application 2000/4924, filed Sep. 15, 2000.

BACKGROUND TO THE INVENTION

This invention relates to a process for the selection of HIV-1 subtype (clade) C isolates, selected HIV-1 subtype C isolates, their genes and modifications and derivatives thereof for use in prophylactic and therapeutic vaccines to produce proteins and polypeptides for the purpose of eliciting protection against HIV infection or disease.

The disease acquired immunodeficiency syndrome (AIDS) is caused by human immunodeficiency virus (HIV). Over 34 million people worldwide are thought to be living with HIV/AIDS, with over 90% of infected people living in developing countries (UNAIDS, 1999). It is estimated that 24 million infected people reside in sub-Saharan Africa and that South Africa currently has one of the world's fastest growing HIV-1 epidemics. At the end of 1999, over 22% of pregnant women attending government antenatal clinics in South Africa were HIV positive (Department of Health, 2000). A preventative vaccine is considered to be the only feasible way to control this epidemic in the long term.

HIV shows remarkable genetic diversity that has confounded the development of a vaccine. The molecular basis of variation resides in the viral enzyme reverse transcriptase which not only introduces an error every round of replication, but also promotes recombination between viral RNAs. Based on phylogenetic analysis of sequences, HIV has been classified into a number of groups: the M (major group) which comprises subtypes A to H and K, the 0 (outlier group) and the N (non-M, non-O group). Recently recombinant viruses have been more frequently identified and there are a number which have spread significantly and established epidemics (circulating recombinant forms or CRF) such as subtype A/G recombinant in West Africa, and CRF AIE recombinant in Thailand (Robertson et al, 2000).

Subtype C predominates in the Southern African region which includes Botswana, Zimbabwe, Zambia, Malawi, Mozambique and South Africa. In addition, increasing numbers of subtype C infections are being detected in the Southern region of Tanzania. This subtype also predominates in Ethiopia and India and is becoming more important in China.

A possible further obstacle to vaccine development is that the biological properties of HIV change as disease progresses. HIV requires two receptors to infect cells, the CD4 and co-receptors of which CCR5 and CXCR4 are the major co-receptors used by HIV-1 strains. The most commonly transmitted phenotype is non-syncytium inducing (NSI), macrophage-tropic viruses that utilize the CCR5 co-receptor for entry (R5 viruses). Langerhans cells in the mucosa are thought to selectively pick up R5 variants at the portal of entry and transport them to the lymph nodes where they undergo replication and expansion. As the infection progresses, viruses evolve that have increased replicative capacity and the ability to grow in T cell lines. These syncytium-inducing (SI) T-tropic viruses use CXCR4 in conjunction with or in preference to CCR5, and in some cases also use other minor co-receptors (Connor et al., 1997, Richman & Bozzette, 1994). However HIV-1 subtype C viruses appear to be unusual in that they do not readily undergo this phenotypic switch, as R5 viruses are also predominant in patients with advanced AIDS (Bjorndal et al., 1999, Peeters et al., 1999, Ping et al., 1999, Tscherning et al., 1998, Scarlatti et al., 1997).

SUMMARY OF THE INVENTION

According to one aspect of the invention a process for the selection of HIV subtype isolates for use in the development of prophylactic and/or therapeutic pharmaceutical composition comprises the following steps:
  isolating viruses from recently infected subjects;
  generating a consensus sequence for at least part of at least one HIV gene by identifying the most common codon or amino acid among the isolated viruses at each position along at least part of the gene; and
  selecting the isolated virus or viruses with a high sequence identity to the consensus sequence, a phenotype which is associated with transmission for the particular HIV subtype.

The isolated virus may be of the same subtype as a likely challenge strain.

The HIV subtype is preferably HIV-1 subtype C.

For HIV-1 subtype C, the phenotype which is associated with transmission is typically a virus that utilizes the CCR5 co-receptor and is non syncitium inducing (NSI).

According to another aspect of the invention an HIV-1 subtype C isolate, designated Du422 and assigned Provisional Accession Number 01032114 by the European Collection of Cell Cultures, is provided.

According to another aspect of the invention an HIV-1 subtype C isolate, designated Du151 and assigned Accession Number 00072724 by the European Collection of Cell Cultures, is provided.

According to another aspect of the invention an HIV-1 subtype C isolate, designated Du179 and assigned Accession Number 00072725 by the European Collection of Cell Cultures, is provided.

According to another aspect of the invention a molecule is provided, the molecule having:
  (i) the nucleotide sequence set out in sequence as set out in SEQ ID NO: 1 (FIG. 17);
  (ii) an RNA sequence corresponding to the nucleotide sequence set out in SEQ NO: 1;
  (iii) a sequence which will hybridize to the nucleotide sequence set out in SEQ ID NO: 1 or an RNA sequence corresponding to it, under strict hybridisation conditions;
  (iv) a sequence which has at least 80%, or 85%, or 90%, or 95%, or 99% nucleotide identity to the nucleotide sequence set out in SEQ ID NO: 1 or an RNA sequence corresponding to it; or
  (v) a sequence which is a modification or derivative of the sequence of any one of (i) to (iv).

The modified sequence is preferably that set out in SEQ ID NO: 7 (FIG. 23).

According to another aspect of the invention a molecule is provided, the molecule having:
(i) the nucleotide sequence set out in SEQ ID NO: 3 (FIG. 19);
(ii) an RNA sequence corresponding to the nucleotide sequence set out in SEQ ID NO: 3;
(iii) a sequence which will hybridize to the nucleotide sequence set out in SEQ ID NO: 3 or an RNA sequence corresponding to it, under strict hybridisation conditions;
(iv) a sequence which has at least 80%, or 85%, or 90%, or 95%, or 99% nucleotide identity to the nucleotide sequence set out in SEQ ID NO. 3 or an RNA sequence corresponding to it; or
(v) a sequence which is a modification or derivative of the sequence of any one of (i) to (iv).

The modified sequence is preferably that set out in SEQ ID NO: 9 (FIG. 25).

According to another aspect of the invention a molecule is provided, the molecule having:
(i) the nucleotide sequence set out in SEQ ID NO: 5 (FIG. 21);
(ii) an RNA sequence corresponding to the nucleotide sequence set out in SEQ ID NO: 5;
(iii) a sequence which will hybridize to the nucleotide sequence set out in SEQ ID NO: 5 or an RNA sequence corresponding to it, under strict hybridisation conditions;
(iv) a sequence which has at least 80%, or 85%, or 90%, or 95%, or 99% nucleotide identity to the nucleotide sequence set out in SEQ ID NO: 5 or an RNA sequence corresponding to it; or
(v) a sequence which is a modification or derivative of the sequence of any one of (i) to (iv).

The modified sequence is preferably that set out in nucleotides 7 to 2552 of SEQ ID NO: 11 (FIG. 27).

According to another aspect of the invention a molecule is provided, the molecule having:
(i) the nucleotide sequence set out in nucleotides 72 to 2579 of SEQ ID NO: 13 (FIG. 29);
(ii) an RNA sequence corresponding to the nucleotide sequence set out in nucleotides 72 to 2579 of SEQ ID NO: 13;
(iii) a sequence which will hybridize to the nucleotide sequence set out in nucleotides 72 to 2579 of SEQ ID NO: 13 or an RNA sequence corresponding to it, under strict hybridisation conditions;
(iv) a sequence which has at least 80%, or 85%, or 90%, or 95%, or 99% nucleotide identity to the nucleotide sequence set out in nucleotides 72 to 2579 of SEQ ID NO: 13 or an RNA sequence corresponding to it; or
(v) a sequence which is a modification or derivative of the sequence of any one of (i) to (iv).

The modified sequence preferably has similar or the same modifications as those set out in nucleotides 7 to 2552 of SEQ. ID NO: 11 (FIG. 27) for the env gene of the isolate DU151.

According to another aspect of the invention a polypeptide is provided, the polypeptide having:
(i) the amino acid sequence set out in SEQ ID NO: 2 (FIG. 18); or
(ii) a sequence which is a modification or derivative of the amino acid sequence set out in SEQ ID NO: 2.

The modified sequence is preferably that set out in SEQ ID NO: 8 (FIG. 24).

According to another aspect of the invention a polypeptide is provided, the polypeptide having:
(i) the amino acid sequence set out in SEQ ID NO: 4 (FIG. 20); or
(ii) a sequence which is a modification or derivative of the amino acid sequence set out in SEQ ID NO: 4.

The modified sequence is preferably that set out in SEQ ID NO: 10 (FIG. 26).

According to another aspect of the invention a polypeptide is provided, the polypeptide having:
(i) the amino acid sequence set out in SEQ ID NO: 6 (FIG. 22); or
(ii) a sequence which is a modification or derivative of the amino acid sequence set out in SEQ ID NO: 6.

The modified sequence is preferably that set out in amino acids 3 to 852 of SEQ ID NO: 12 (FIG. 28).

According to another aspect of the invention a polypeptide is provided, the polypeptide having:
(i) the amino acid sequence set out in amino acids 24 to 858 of SEQ ID NO: 14 (FIG. 30);
(ii) a sequence which is a modification or derivative of the amino acid sequence set out in amino acids 24 to 858 of SEQ ID NO: 14.

The modified sequence preferably has similar or the same modifications as those set out in amino acids 3 to 852 of SEQ ID NO: 12 (FIG. 28) for the amino acid sequence of the env gene of the isolate Du151.

According to another aspect of the invention a consensus amino acid sequence for the partial gag gene of HIV-1 subtype C is the following:

```
                                                     (SEQ ID NO: 15)
GEKLDKWEKI  RLRPGGKKHY  MLKHLVWASR  ELERFALNPG  LLETSEGCKQ50

IMKQLQPALQ  TGTEELRSLY  NTVATLYCVH  EKIEVRDTKE  ALDKIEEEQN100

KSQQ-CQQKT  QQAKAADGG-  KVSQNYPIVQ  NLQGQMVHQA  ISPRTLNAWV150

KVIEEKAFSP  EVIPMFTALS  EGATPQDLNT  MLNTVGGHQA  AMQMLKDTIN200

EEAAEWDRLH  PVHAGPIAPG  QMREPRGSDI  AGTTSTLQEQ  IAWMTSNPPI250

PVGDIYKRW1  ILGLNKIVRM  YSPVSILDIK  QGPKEPFRDY  VDRFFKTLRA300

EQATQDVKNW  MTD 313
```

According to another aspect of the invention a consensus amino acid sequence for the partial pol gene of HIV-1 subtype C is the following:

```
                                                  (SEQ ID NO: 16)
LTEEKIKALT AICEEMEKEG KITKIGPENP YNTPVFAIKK KDSTKWRKL-50

VDFRELNKRT QDFWEVQLGI PHPAGLKKKK SVTVLDVGDA YFSVPLDEGF100

RKYTAFTIPS INNETPGIRY QYNVLPQGWK GSPAIFQSSM TKILEPFRAK150

NPEIVIYQYM DDLYVGSDLE IGQHRAKIEE LREHLLKWGF TTPDKKHQKE200

PPFLWMGYEL HPDKWTVQPI QLPEKDSWTV NDIQKLVGKL NWASQIYPGI250

KVRQLCKLLR GAKALTDIVP LTEEAELE278
```

According to another aspect of the invention a consensus amino acid sequence for the partial env gene of HIV-1 subtype C is the following:

```
                                                  (SEQ ID NO: 17)
YCAPAGYAIL KCNNKTFNGT GPCNNVSTVQ CTHGIKPVVS TQLLLNGSLA50

EEEIIIRSEN LTNNAKTIIV HLNESVEIVC TRPNNNTRKS IRIGPGQTFY100

ATGDIIGDIR QAHCNISEGK WNKTLQKVKK KLKEELYKYK VVEIKPLGIA150

PTEAKRRWE  REKRAVGIGA VFLGFLGAAG STMGAASITL TVQARQLLSG200

IVQQQSNLLR AIEAQQHMLQ LTVWGIKQL229
```

Thus, in some embodiments, the present invention comprises an isolated nucleic acid molecule comprising a sequence that encodes an HIV Gag polypeptide as set forth SEQ ID NO: 8, or a sequence at least 80%, 85%, 90%, 95%, or 99% identical thereto. In one embodiment, the HIV gag polypeptide is as set forth in SEQ ID NO: 2. In certain embodiments, the present invention comprises (i) the sequence as set forth in SEQ ID NO: 1 or a sequence at least 80%, 85%, 90%, 95%, or 99% identical thereto;
(ii) the sequence as set forth in SEQ ID NO: 1 modified to remove a myristylation site and to reflect human codon usage;
(iii) the sequence as set forth in SEQ ID NO: 7 or a sequence at least 80%, 85%, 90%, 95%, or 99% identical thereto;
(iv) a sequence which is complementary to (i)-(iii);
(v) a sequence that hybridizes to SEQ ID NO: 1 or SEQ ID NO: 7 under strict hybridization conditions; or
(vi) an RNA sequence encoded by (i)-(v).

In yet other embodiments, the present invention comprises a polypeptide comprising the Gag sequence as set forth in SEQ ID NO: 2 or as set forth in SEQ ID NO: 8, or a sequence at least 80%, 85%, 90%, 95%, or 99% identical thereto.

In some embodiments, the present invention comprises a composition comprising a nucleic acid molecule comprising a sequence that encodes an HIV Gag polypeptide as set forth in SEQ ID NO: 2 or as set forth in SEQ ID NO: 8, or a sequence at least 80%, 85%, 90%, 95%, or 99% identical thereto, in a pharmaceutical carrier. In some embodiments, the nucleic acid molecule comprises:

(i) the sequence as set forth in SEQ ID NO: 1 or a sequence at least 80%, 85%, 90%, 95%, or 99% identical thereto;
(ii) the sequence as set forth in SEQ ID NO: 1 modified to remove a myristylation site and to reflect human codon usage;
(iii) the sequence as set forth in SEQ ID NO: 7 or a sequence at least 80%, 85%, 90%, 95%, or 99% identical thereto;
(iv) a sequence which is complementary to (i)-(iii);
(v) a sequence that hybridizes to SEQ ID NO: 1 or SEQ ID NO: 7 under strict hybridization conditions; or
(vi) an RNA sequence encoded by (i)-(v).

In certain embodiments, the present invention comprises a composition comprising a polypeptide comprising the Gag sequence as set forth in SEQ ID NO: 2 or as set forth in SEQ ID NO: 8, or a sequence at least 80%, 85%, 90%, 95%, or 99% identical thereto, in a pharmaceutical carrier.

In yet other embodiments, the present invention comprises a method to treat or prevent HIV-1 infection in a subject comprising administering a nucleic acid molecule that encodes an HIV Gag polypeptide as set forth in SEQ ID NO: 2 or as set forth in SEQ ID NO: 8 or a sequence at least 80%, 85%, 90%, 95%, or 99% identical thereto, to the subject. In certain embodiments, the nucleic acid molecule comprises:

(i) the sequence as set forth in SEQ ID NO: 1 or a sequence at least 80%, 85%, 90%, 95%, or 99% identical thereto;
(ii) the sequence as set forth in SEQ ID NO: 1 modified to remove a myristylation site and to reflect human codon usage;
(iii) the sequence as set forth in SEQ ID NO: 7 or a sequence at least 80%, 85%, 90%, 95%, or 99% identical thereto;
(iv) a sequence which is complementary to (i)-(iii);
(v) a sequence that hybridizes to SEQ ID NO: 1 or SEQ ID NO: 7 under strict hybridization conditions; or
(vi) an RNA sequence encoded by (i)-(v).

In other embodiments, the present invention comprises a method to treat or prevent HIV-1 infection in a subject. For example, in certain embodiments, the method may comprise administering a polypeptide having the sequence as set forth in SEQ ID NO: 2 or SEQ ID NO: 8, or a sequence at least 80%, 85%, 90%, 95%, or 99% identical thereto, to the subject.

DESCRIPTION OF THE DRAWINGS

FIG. 1 shows a schematic representation of the HIV-1 genome and illustrates the location of overlapping fragments that were sequenced having been generated by reverse transcriptase followed by polymerase chain reaction, in order to generate the South African consensus sequence;

Figure 4:
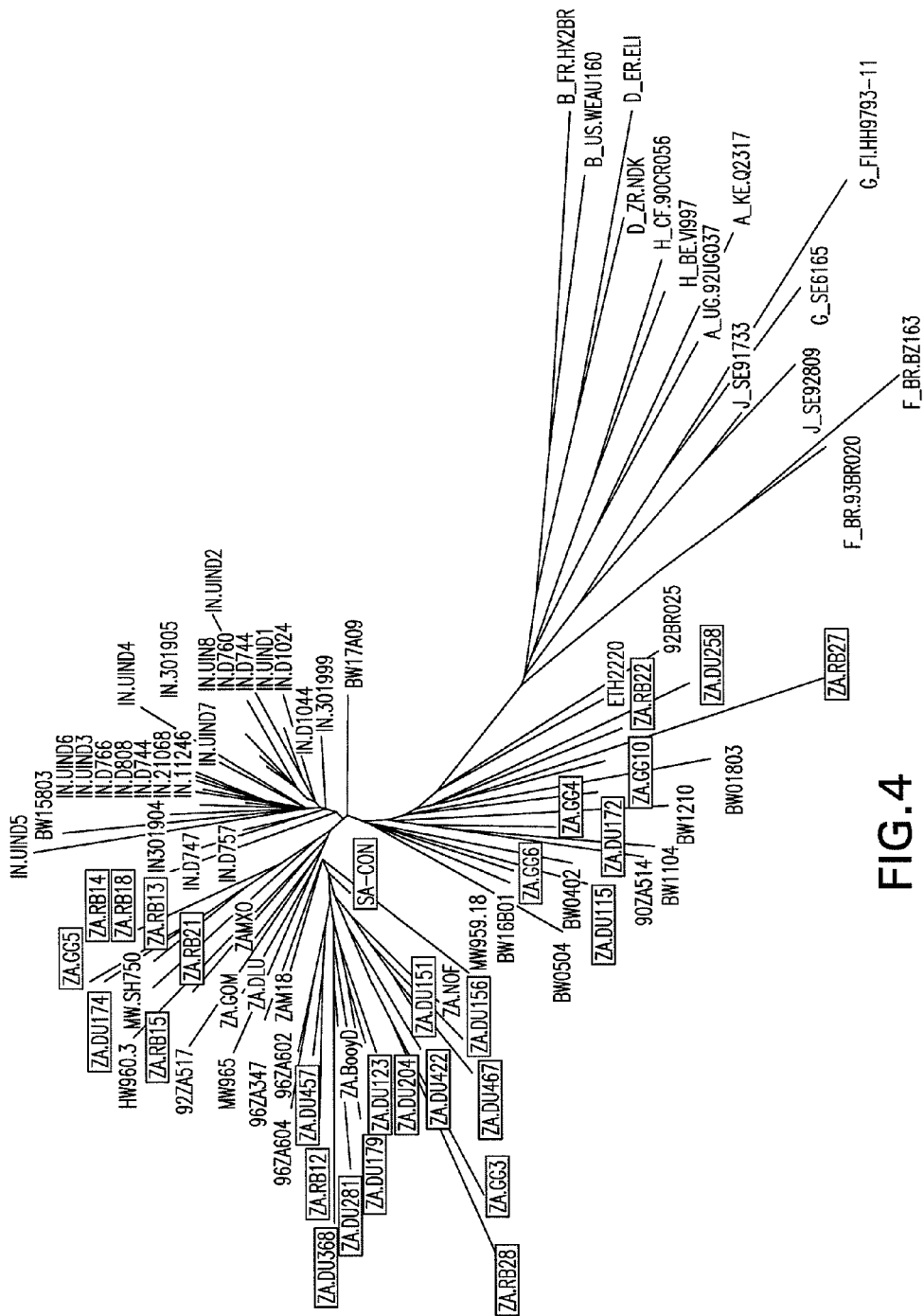
Figure 9:
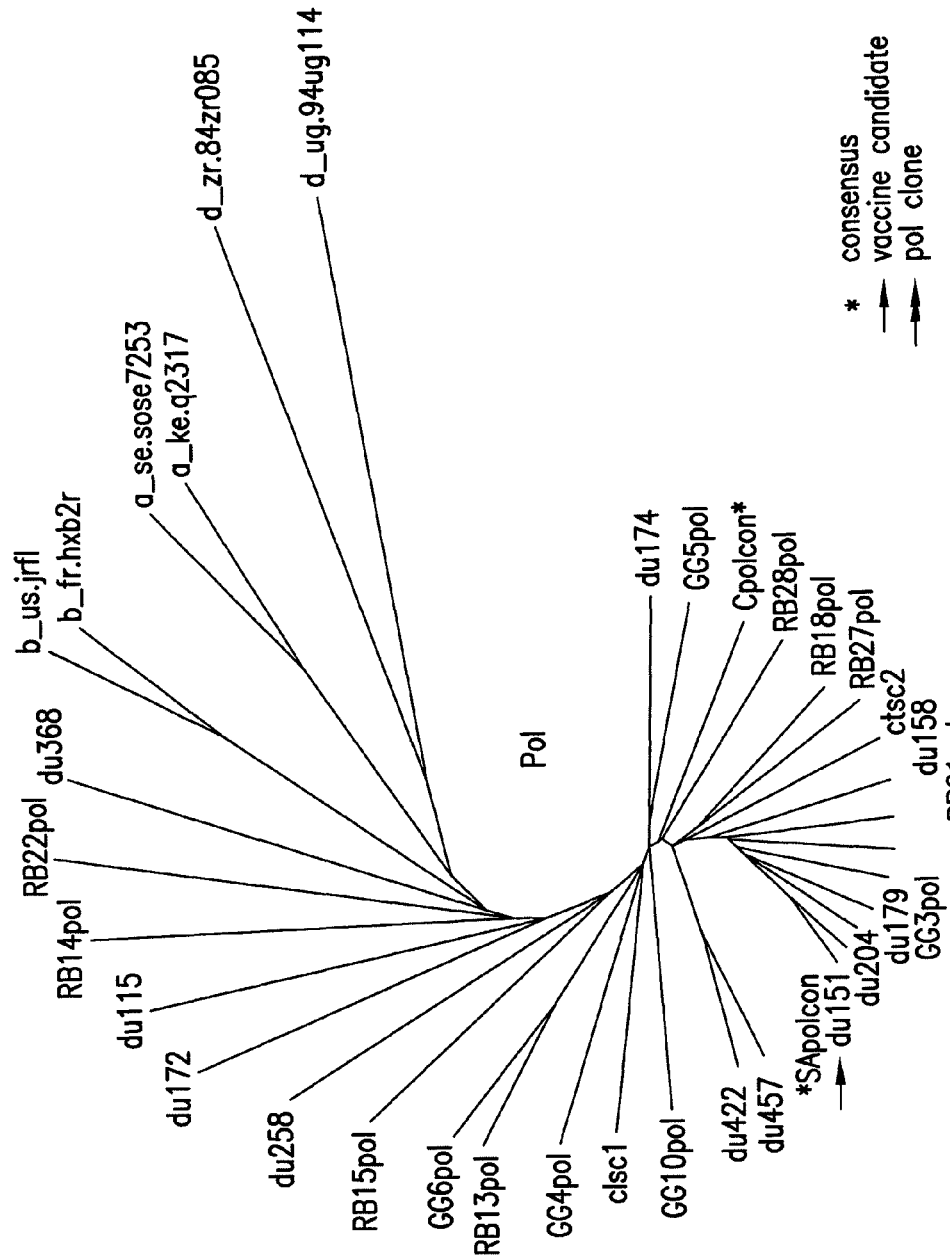
Figure 10:
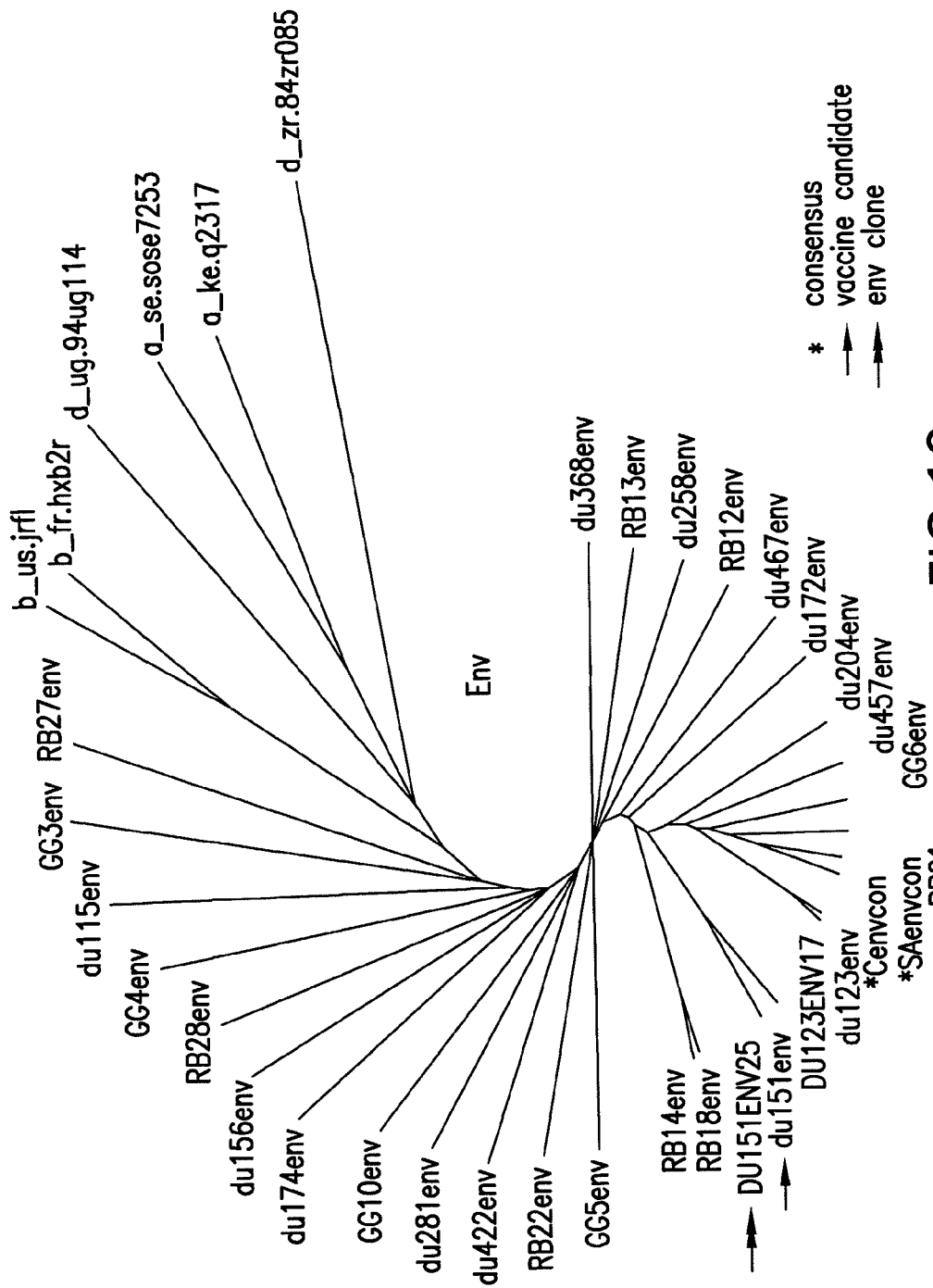
Figure 14:
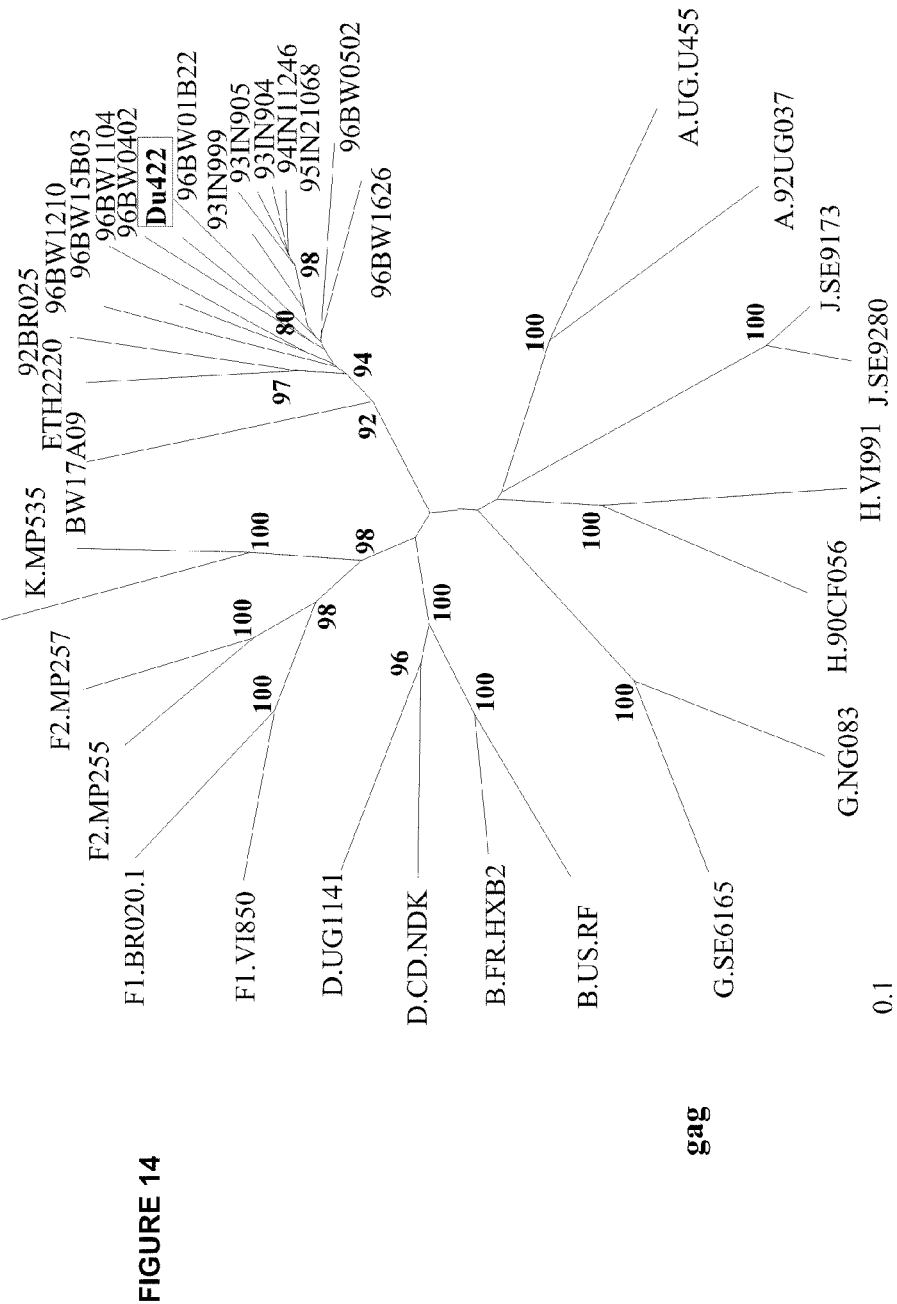
Figure 15:
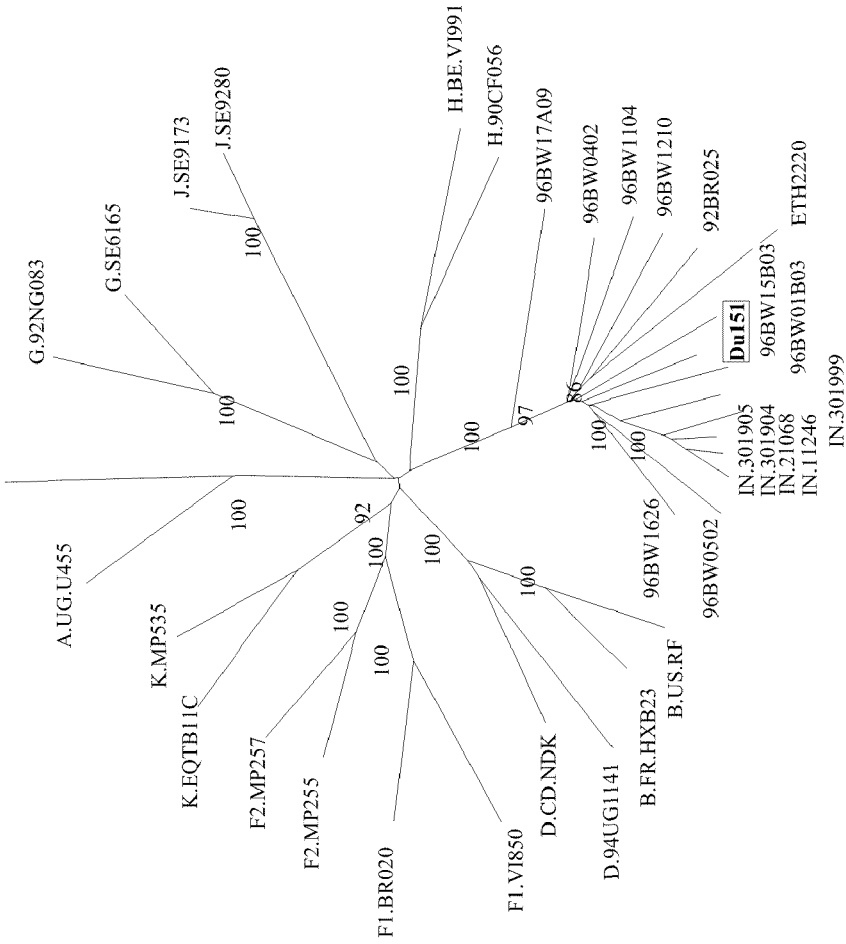
Figure 16:
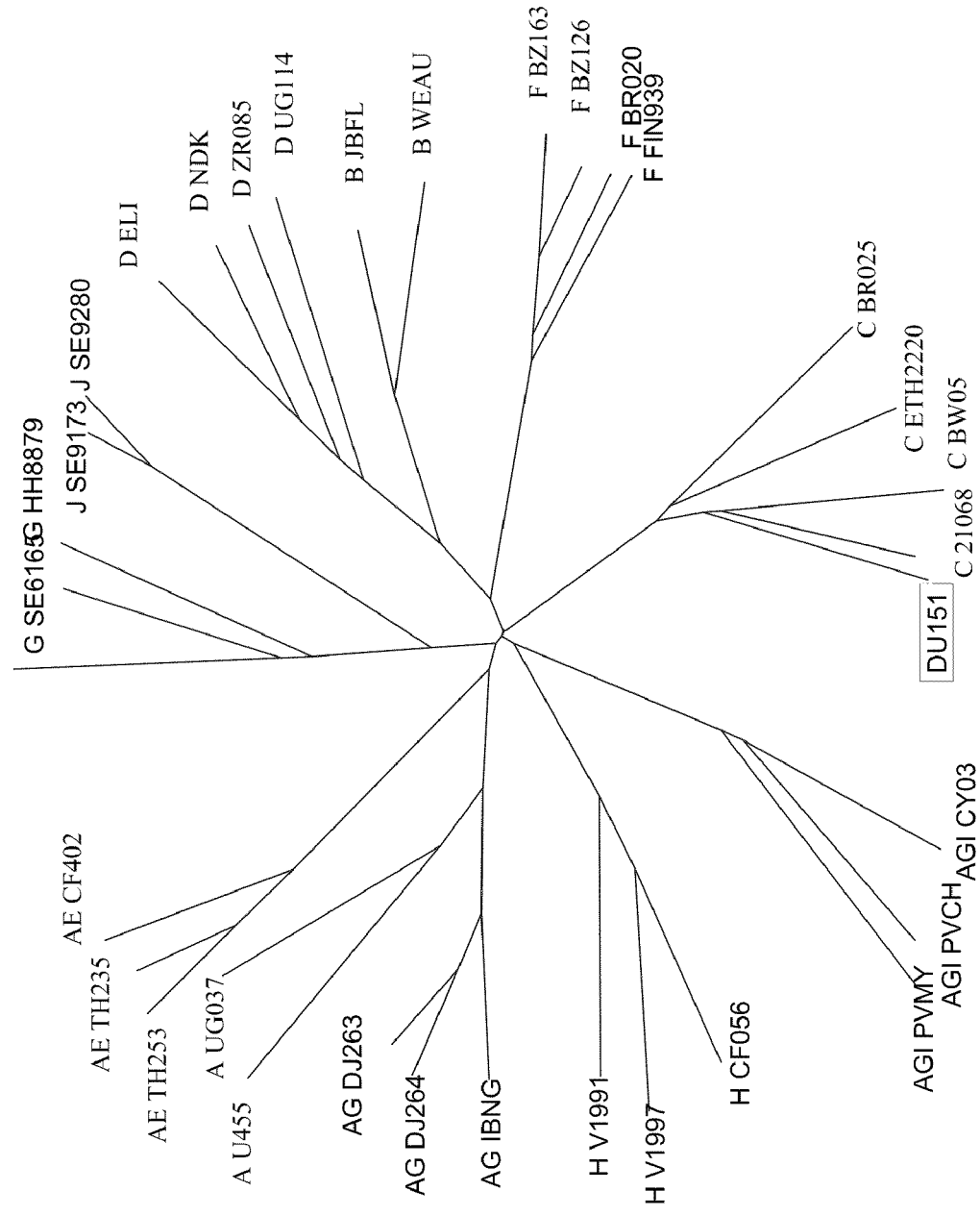

FIG. 4 shows a phylogenetic tree of nucleic acid sequences of various HIV-1 subtype C isolates based on the (partial) sequences of the env gene of the various isolates and includes a number of consensus sequences as well as the South African consensus sequence of the present invention and a selected isolate, Du151, of the present invention FIG. 5 (panels A-D) shows how the sequences of the gag genes of each of a number of isolates varies from the South African consensus sequence for the gag gene which was developed according to the present invention—the SEQ ID NOs for each of the sequences (i.e., SEQ ID NOs: 18-49) are provided as the left most column for the first 50 amino acids of each isolate, where a period signifies no amino acid at that position, an asterisk signifies a stop codon has terminated the peptide, and an "x" represents that the amino acid was not determined;

FIG. 6 (panels A-D) shows how the sequences of the pol genes of each of a number of isolates varies from the South African consensus sequence for the pol gene which was developed according to the present invention—the SEQ ID NOs for each of the sequences (i.e., SEQ ID NOS: 50-78) are provided as the left most column for the first 50 amino acids of each isolate, where a period signifies no amino acid at that position, an asterisk signifies a stop codon has terminated the peptide, and an "x" represents that the amino acid was not determined;

FIG. 7 (panels A-C) shows how the sequences of the env genes of each of a number of isolates varies from the South African consensus sequence for the env gene which was developed according to the present invention—the SEQ ID NOs for each of the sequences (i.e., SEQ ID NOS: 79-110) are provided as the left most column for the first 50 amino acids of each isolate, where a period signifies no amino acid at that position, an asterisk signifies a stop codon has terminated the peptide, and an "x" represents that the amino acid was not determined;

FIG. 8 shows a phylogenetic tree of amino acid sequences of various HIV-1 subtype C isolates based on the sequences of the (partial) gag gene of the various isolates and includes a number of consensus sequences as well as the South African consensus sequence of the present invention and a selected isolate, Du422, of the present invention;

FIG. 9 shows a phylogenetic tree of amino acid sequences of various HIV-1 subtype C isolates based on the sequences of the (partial) pol gene of the various isolates and includes a Cpol consensus sequence as well as a South African consensus sequence of the present invention and a selected isolate, Du151, of the present invention;

FIG. 10 shows a phylogenetic tree of amino acid sequences of various HIV-1 subtype C isolates based on the sequences of the (partial) env gene of the various isolates and includes a Cenv consensus sequence as well as a South African consensus sequence of the present invention and a selected isolate, Du151, of the present invention;

FIG. 11 shows the percentage amino acid sequence identity of the sequenced gag genes of the various isolates in relation to one another, to the gag clone and to the South African consensus sequence for the gag gene and is based on a pair-wise comparison of the gag genes of the isolates;

FIG. 12 shows the percentage amino acid sequence identity of the sequenced pol genes of the various isolates in relation to one another, to the pol clone and to the South African consensus sequence for the pol gene and is based on a pair-wise comparison of the pol genes of the isolates;

FIG. 13 shows the percentage amino acid sequence identity of the sequenced env genes of the various isolates in relation to one another, to the env clone and to the South African consensus sequence for the env gene and is based on a pair-wise comparison of the env genes of the isolates;

FIG. 14 shows a phylogenetic tree analysis of nucleic acid sequences of various HIV-1 subtype C isolates (or vaccine strains) based on the complete sequences of the gag genes of the various isolates and shows the gag gene from a selected isolate, Du422, of the present invention compared to the other subtype C sequences;

FIG. 15 shows a phylogenetic tree analysis of nucleic acid sequences of various HIV-1 subtype C isolates (or vaccine strains) based on the complete sequences of the pol genes of the various isolates and shows the pol gene from a selected isolate, Du151, of the present invention compared to the other subtype C sequences;

FIG. 16 shows a phylogenetic tree analysis of nucleic acid sequences of various HIV-1 subtype C isolates (or vaccine strains) based on the complete sequences of the env gene of the various isolates and shows the env gene from a selected isolate, Du151, of the present invention compared to the other subtype C sequences; and FIG. 17 (SEQ ID NO: 1) shows the nucleic acid sequence (cDNA) of the sequenced gag gene of the isolate Du422;

FIG. 18 (SEQ ID NO: 2) shows the amino acid sequence of the sequenced gag gene of the isolate Du422, derived from the nucleic acid sequence;

FIG. 19 (SEQ ID NO: 3) (panels A and B) shows the nucleic acid sequence (cDNA) of the sequenced pol gene of the isolate Du151;

FIG. 20 (SEQ ID NO: 4) shows the amino acid sequence of the sequenced pol gene of the isolate Du151, derived from the nucleic acid sequence;

FIG. 21 (SEQ ID NO: 5) shows the nucleic acid sequence (cDNA) of the sequenced env gene of the isolate Du151;

FIG. 22 (SEQ ID NO: 6) shows the amino acid sequence of the sequenced env gene of the isolate Du151, derived from the nucleic acid sequence;

FIG. 23 (SEQ ID NO: 7) shows the nucleic acid sequence (DNA) of the resynthesized sequenced gag gene of the isolate Du422 modified to reflect human codon usage for the purposes of increased expression;

Figure 24:
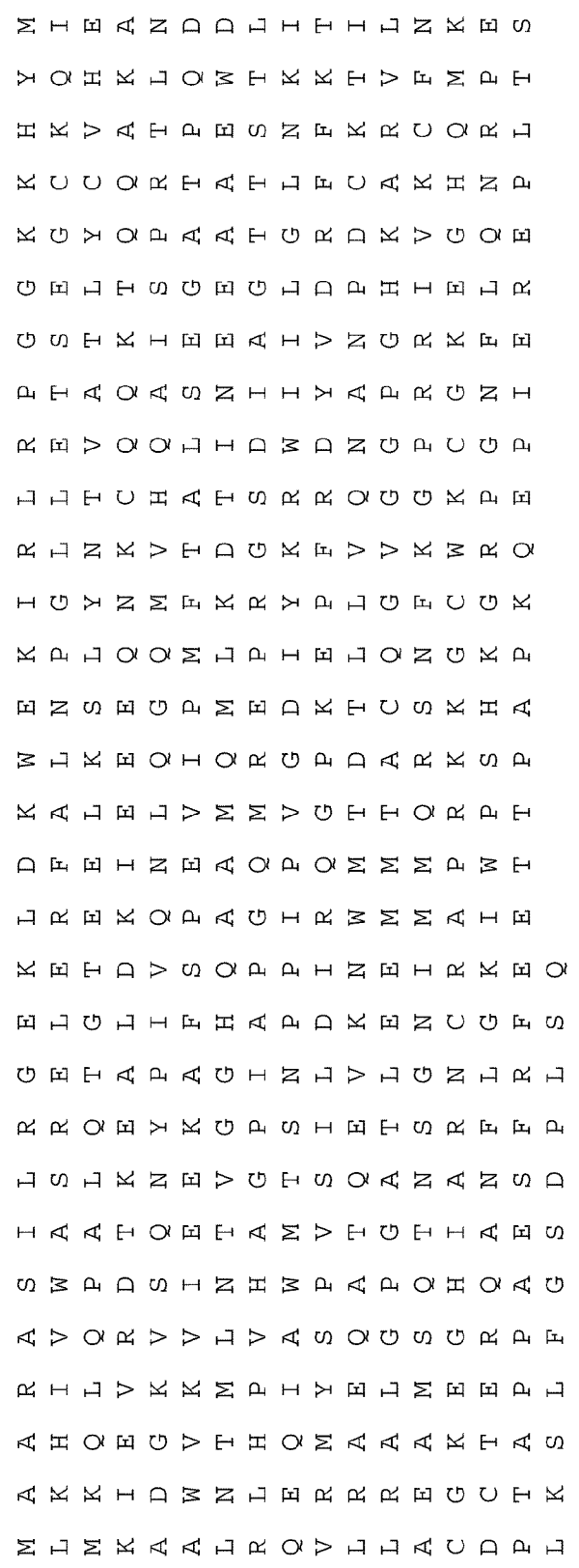

FIG. 24 (SEQ ID NO: 8) shows the amino acid sequence of the resynthesized sequenced gag gene of the isolate Du422 modified to reflect human codon usage for the purposes of increased expression;

FIG. 25 (SEQ ID NO: 9) (panels A and B) shows the nucleic acid sequence (DNA) of the resynthesized sequenced pol gene of the isolate Du151 modified to reflect human codon usage for the purposes of increased expression;

FIG. 26 (SEQ ID NO: 10) shows the amino acid sequence of the resynthesized sequenced pol gene of the isolate Du151 modified to reflect human codon usage for the purposes of increased expression;

FIG. 27 (SEQ ID NO: 11) nucleotides 7 to 2552 of SEQ ID NO: 11 shows the nucleic acid sequence (DNA) of the resynthesized sequenced env gene of the isolate Du151 modified to reflect human codon usage for the purposes of increased expression;

FIG. 28 (SEQ ID NO: 12) amino acids 3 to 852 of SEQ ID NO: 12 shows the amino acid sequence of the resynthesized sequenced env gene of the isolate Du151 modified to reflect human codon usage for the purposes of increased expression;

FIG. 29 (SEQ ID NO: 13) nucleotides 72 to 2579 of SEQ. ID NO: 13 shows the nucleic acid sequence (cDNA) of the sequenced env gene of the isolate Du179;

FIG. 30 (SEQ ID NO: 14) amino acids 24 to 858 shows the amino acid sequence of the sequenced env gene of the isolate Du179;

FIG. 31 (SEQ ID NO: 15) shows a consensus amino acid sequence for the partial gag gene of HIV-1 subtype C;

FIG. 32 (SEQ ID NO: 16) shows a consensus amino acid sequence for the partial pol gene of HIV-1 subtype C;

FIG. 33 (SEQ ID NO: 17) shows a consensus amino acid sequence for the partial env gene of HIV-1 subtype C;

FIG. 34 (SEQ ID NOS: 111-115) (panels A-D) shows the nucleic acid sequence and amino acid sequence of the resynthesized sequenced gag gene of the isolate Du422 modified to reflect human codon usage for the purposes of increased expression as well as flanking vector sequences, where nucleic acids sequence is SEQ ID NO: 111 and peptides are SEQ ID NO: 112 (amino acids 1-522), SEQ ID NO: 113 (amino acids 527-556), SEQ ID NO: 114 (amino acids 558-611), and SEQ ID NO: 115 (amino acids 613-635) as indicated in the figure;

FIG. 35 (SEQ ID NO: 116) (panels A and B) shows the nucleic acid sequence (DNA) of the resynthesized sequenced pol gene of the isolate Du151 modified to reflect human codon usage for the purposes of increased expression as well as flanking vector sequences; and FIG. 36 (SEQ ID NOS: 117-120) shows the amino acid sequence of the resynthesized sequenced pol gene of the isolate Du151 modified to reflect human codon usage for the purposes of increased expression as well as flanking vector sequences and peptides are SEQ ID NO: 117 (amino acids 1-57), SEQ ID NO: 118 (amino acids 59-71), SEQ ID NO: 119 (amino acids 73-113), and SEQ ID NO: 120 (amino acids 118-854) as indicated in the figure.

DETAILED DESCRIPTION OF THE INVENTION

This invention relates to the selection of HIV-1 subtype isolates and the use of their genes and modifications and derivatives thereof in making prophylactic and therapeutic pharmaceutical compositions and formulations, and in particular vaccines against HIV-1 subtype C. The compositions could therefore be used either prophylactically to prevent infection or therapeutically to prevent or modify disease. A number of factors must be taken into consideration in the development of an HIV vaccine and one aspect of the present invention relates to a process for the selection of suitable HIV isolates for the development of a vaccine.

The applicant envisages that the vaccine developed according to the above method could be used against one or more HIV subtypes other than HIV-1 subtype C.

An HIV vaccine aims to elicit both a CD8+ cytotoxic T lymphocyte (CTL) immune response as well as a neutralizing antibody response. Many current vaccine approaches have primarily focused on inducing a CTL response. It is thought that the CTL response may be more important as it is associated with the initial control of viral replication after infection, as well as control of replication during disease, and is inversely correlated with disease progression (Koup et al., 1994, Ogg et al., 1999 Schmitz et al., 1999). The importance of CTL in protecting individuals from infection is demonstrated by their presence in highly exposed seronegative individuals such as sex-workers (Rowland-Jones et al., 1998).

Knowledge of genetic diversity is highly relevant to the design of vaccines aiming at eliciting a cytotoxic T-lymphocyte (CTL) response. There are many CTL epitopes in common between viruses, particularly in the gag and pol region of the genome (HIV Molecular Immunology Database, 1998). In addition, several studies have now shown that there is a cross-reactive CTL response: individuals vaccinated with a subtype B-based vaccine could lyse autologous targets infected with a diverse group of isolates (Ferrari et al., 1997); and CTLs from non-B infected individuals could lyse subtype B-primed targets (Betts et al. 1997; Durali et al., 1998). A comparison of CTL epitopes in the HIV-1 sequence database shows about 40% of gp41 and 84% of p24 epitopes are identical or have only one amino acid difference between subtypes. Although this is a very crude analysis and does not take into consideration populations or dominant responses to certain epitopes, it does however indicate that there is a greater conservation of cytotoxic T epitopes within a subtype compared to between subtypes and that there will be a greater chance of a CTL response if the challenge virus is the same subtype as the vaccine strain.

The importance of genetic diversity in inducing a neutralizing antibody response appears to be less crucial. In general, neutralization serotypes are not related to genetic subtype, Some individuals elicit antibodies that can neutralize a broad range of viruses, including viruses of different subtypes while others fail to elicit effective neutralizing antibodies at all (Wyatt and Sodroski, 1998; Kostrikis et al., 1996; Moore et al., 1996), As neutralizing antibodies are largely evoked against functional domains of the virus which are essentially conserved, it is probable that HIV-1 genetic diversity may not be relevant in producing a vaccine designed to elicit neutralizing antibodies.

Viral strains used in the design of a vaccine need to be shown by genotypic analysis to be representative of the circulating strains and not an unusual or outlier strain. In addition, it is important that a vaccine strain also has the phenotype of a recently transmitted virus, which is NSI and uses the CCR5 co-receptor.

A process was developed to identify appropriate strains for use in developing a vaccine for HIV-1 subtype C. Viral isolates from acutely infected individuals were collected. They were sequenced in the env, gag and pol regions and the amino acid sequences for the env, gag and pol genes from these isolates were compared. A consensus sequence, the South African consensus sequence, was then formed by selecting the most frequently appearing amino acid at each position. The consensus sequence for each of the gag, pol and env genes of HIV-1 subtype C also forms an aspect of the invention. Appropriate strains for vaccine development were then selected from these isolates by comparing them with the consensus sequence and characterising them phenotypically. The isolates also form an aspect of the invention.

In order to select for NSI strains which use the CCR5 co-receptor, a well established sex worker cohort was used to identify the appropriate strains. Appropriate strains were identified from acutely infected individuals by comparing them with the consensus sequence which had been formed. Viral isolates from fifteen acutely infected individuals were sequenced in the env, gag and pol and phenotypically characterized. These sequences were compared with viral isolates from fifteen asymptomatic individuals from another region having more than 500 CD4 cells and other published subtype C sequences located in the Los Alamos Database (http://www.hiv-web.lanl.gov/).

Figure 1:
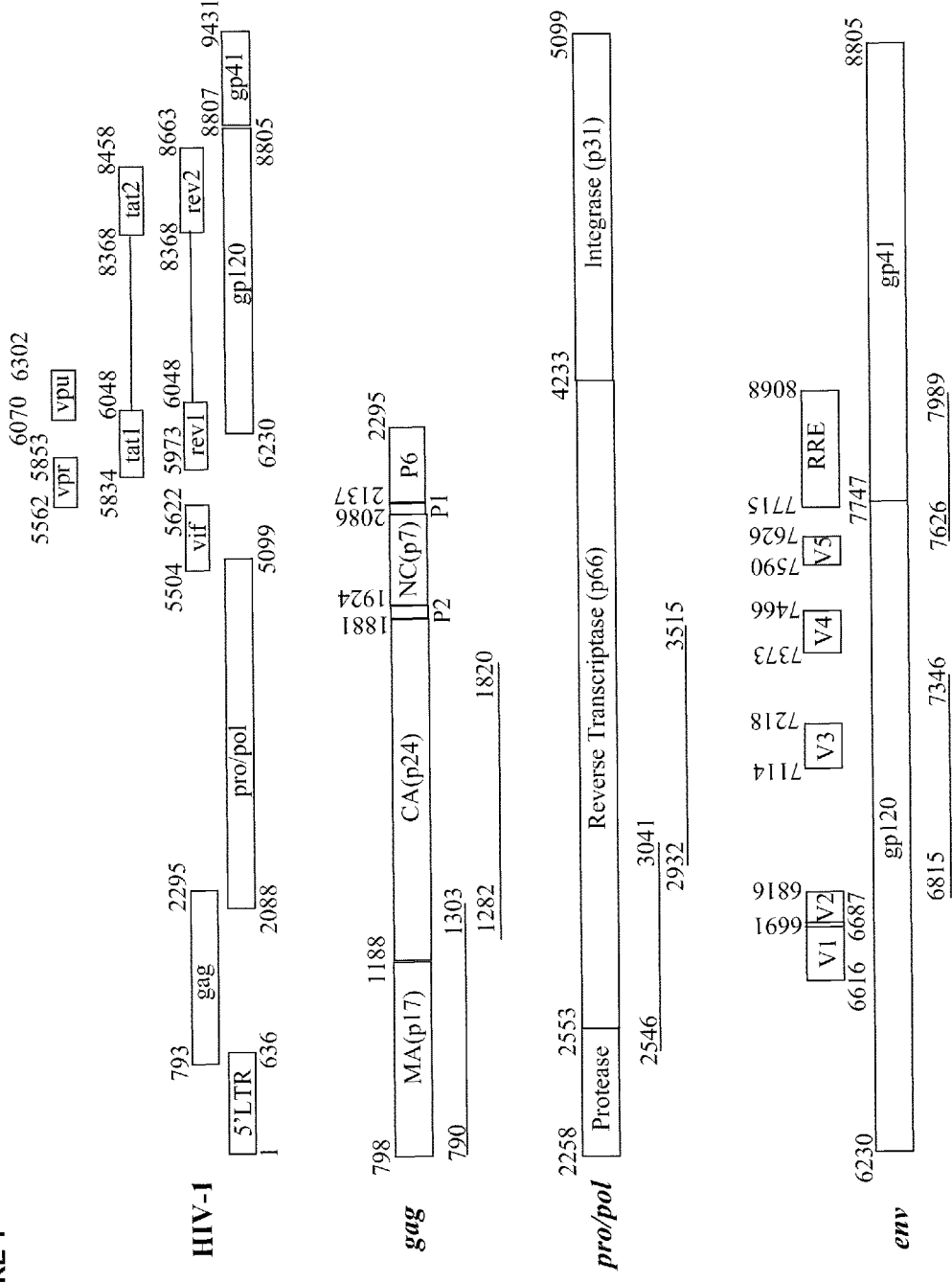

Three potential vaccine strains, designated Du151, Du422 and Du179, were selected. Du151 and Du 422 were selected based on amino acid homology to the consensus sequence in all three gene regions env, gag and pol, CCR5 tropism and ability to grow and replicate in tissue culture. Du179 is a R5X4 virus and was selected because the patient in which this strain was found showed a high level of neutralising antibodies. The nucleotide and amino acid sequences of the three gene regions of the three isolates and modifications and derivatives thereof also form aspects of the invention.

The vaccines of the invention will be formulated in a number of different ways using a variety of different vectors. They involve encapsulating RNA or transcribed DNA sequences from the viruses in a variety of different vectors. The vaccines will contain at least part of the gag gene from the Du422 isolate, and at least part of the pol and env genes from the Du 151 isolate of the present invention and/or at least part of the env gene from the Du179 isolate of the present invention or derivatives or modifications thereof.

Genes for use in DNA vaccines have been resynthesized to reflect human codon usage. The gag Du422 gene was designed so that the myristylation site and inhibitory sequences were removed. Similarly resynthesized gp 160 (the complete env gene consisting of gp 120 and gp 41) and pol genes will be expressed by DNA vaccines. The gp160 gene sequence has also been changed as described above for the gag gene to reflect human codon usage and the rev responsive element removed. The protease, inactivated reverse transcriptase and start of the RNAse H genes from Du151 pol are optimised for increased expression and will be joined with gag at an inserted Bgl1 site. The gag-pol frameshift will be maintained to keep the natural balance of gag to pol protein expression.

Another vaccine will contain DNA transcribed from the RNA for the gag gene from the Du422 isolate and RNA from the pol and env genes from the Du151 isolate and/or RNA from the env gene from the Du 179 isolate. These genes could also be expressed as oligomeric envelope glycoprotein complexes (Progenics, USA) as published in J Virol 2000 January; 74(2):627-43 (Binley, J. L. et al.), the adeno associated virus (AAV) (Target Genetics) and the Venezuelan equine encephalitus virus (U.S. Ser. No. 60/216,995, which is incorporated herein by reference).

The Isolation and Selection of Viral Strains for the Design of a Vaccine

The following criteria were used to select appropriate strains for inclusion into HIV-1 vaccines for Southern Africa:

- that the strains be genotypically representative of circulating strains;
- that the strain not be an outlier strain;
- that the strain be as close as possible (having at least 80%, and preferably at least 90%, more preferably at least 95% amino acid homology) to the consensus amino acid sequence developed according to the invention for the env, gag and pol genes of HIV-1 subtype C;
- that the strain have an R5 phenotype, i.e. a phenotype associated with transmission for selection of the RNA or cDNA to be included for the env region; and
- that the vaccine be able to be grown in tissue culture.

The following procedure was followed in the selection of viral strains for the design of a vaccine. A well-established sex worker cohort in Kwazulu Natal, South Africa was used to identify the appropriate strains for use in an HIV vaccine. Viral isolates from 15 acutely infected individuals were sequenced in env, gag and pol and were also isolated and phenotypically characterized. These sequences were compared with a similar collection from asymptomatic individuals from the Gauteng region in South Africa as well as other published subtype C sequences.

Patients

Individuals with HIV infection were recruited from 4 regions in South Africa. Blood samples were obtained from recently infected sex workers from Kwazulu-Natal (n=13). Recent infection was defined as individuals who were previously seronegative and had became seropositive within the previous year. Samples were also collected from individuals attending out-patients clinics in Cape Town (n=2), women attending ante-natal clinics in Johannesburg (n=7) and men attending a STD clinic on a gold mine outside Johannesburg (n=8). The latter 2 groups were clinically stable and were classified as asymptomatic infections. Blood samples were collected in EDTA and used to determine the CD4 T cell count and genetic analysis of the virus. In the case of recent infections a branched chain (bDNA) assay (Chiron) to measure plasma viral load was done, and the virus was isolated. HIV-1 serostatus was determined by ELISA. The results of the CD4 T cell counts and the viral loads on the sex workers were established and information on the clinical status as at date of seroconversion, CD4, and data on the co-receptor usage is set out in Table 1 below.

Virus Isolation

HIV was isolated from peripheral blood mononuclear cells (PBMC) using standard co-culture techniques with mitogen-activated donor PBMC. $2\times10^6$ patient PBMC were co-cultured with $2\times10^6$ donor PBMC in 12 well plates with 2 ml RPMI 1640 with 20% FCS, antibiotics and 5% IL-2 (Boehringer). Cultures were replenished twice weekly with fresh medium containing IL-2 and once with 5×1051 ml donor PBMC. Virus growth was monitored weekly using a commercial p24 antigen assay (Coulter). Antigen positive cultures were expanded and cultured for a further 2 weeks to obtain 40 mls of virus containing supernatant which was stored at −70° C. until use. The results of the isolation of the viruses from the commercial sex workers is also shown in Table 1 below.

Viral Phenotypes

Virus-containing supernatant was used to assess the biological phenotype of viral isolates on MT-2 and co-receptor transfected cell lines. For the MT-2 assay, 500 μl of supernatant was incubated with $5\times10^4$ MT-2 cells in PRMI plus 10% FCS and antibiotics. Cultures were monitored daily for syncitia formation over 6 days. U87.CD4 cells expressing either the CCR5 or CXCR4 co-receptor were grown in DMEM with 10% FCS, antibiotics, 500 μg/ml G418 and 1 μg/ml puromycin. GHOST cells expressing minor co-receptors were grown in DMEM with 10% FCS, 500 μg/ml G418, 1 μg/ml puromycin and 100 μg/ml hygromycin. Cell lines were passaged twice weekly by trypsination. Co-receptor assays were done in 12 well plates; $5\times10^4$ cells were plated in each well and allowed to adhere overnight. The following day 500 μl of virus containing supernatant was added and incubated overnight to allow viral attachment and infection and washed three times the following day. Cultures were monitored on days 4, 8 and 12 for syncitia formation and p24 antigen production. Cultures that showed evidence of syncitia and increasing concentrations of p24 antigen were considered positive for viral growth. The results of co-receptor usage of the viruses from the commercial sex workers is also shown in Table 1.

Sequencing

RNA was isolated from plasma and the gene fragments were amplified from RNA using reverse transcriptase to generate a cDNA followed by PCR to generate amplified DNA segments. The positions of the PCR primers are as follows, with the second of each primer pair being used as the reverse transcriptase primer in the cDNA synthesis step (numbering using the HIV-1 HXBr sequence): gag1 (790-813, 1282-1303), gag2 (1232-1253, 1797-1820), pol1 (2546-2573, 3012-3041), pol2 (2932-2957, 3492-3515), env1 (6815-6838, 7322-7349), env2 (7626-7653, 7963-7986). The amplified DNA fragments were purified using the QIAQUICK PCR Purification Kit (Qiagen, Germany). The DNA fragments were then sequenced using the upstream PCR primers as sequencing primers. Sequencing was done using the Sanger dideoxyterminator strategy with fluorescent dyes attached to the dideoxynucleotides. The sequence determination was made by electrophoresis using an ABI 377 Sequencer. A mapped illustration of an HIV-1 proviral genome showing the pol, gag and env regions sequenced as described above, is shown in FIG. 1. The following regions were sequenced (numbering according to HXBr, Los Alamos database); 813-1282 (gag1); 1253-1797 (gag2); 2583-3012 (pol1); 2957-3515 (pol2); 6938-7322 (env1); 7653-7963 (env2), as illustrated in FIG. 1.

TABLE 1

COHORT OF ACUTE INFECTIONS FOR SELECTION OF VACCINE CANDIDATES

| Sample ID | Sero date | Sample date | Duration of Infection | CD4 count | Viral load | Co-culture p24 pos | MT-2 assay | Biotype |
|---|---|---|---|---|---|---|---|---|
| Du115 | 15 May 1998 | 20 May. 1999 | 1 year | 437* | 7,597* | — | No isolate | — |
| Du123 | 17 Aug. 1998 | 17 Nov. 1998 | 3 mon | 841 | 19,331 | d6 (50 pg) | NSI | R5 |
| Du151 | 12 Oct. 1998 | 24 Nov. 1998 | 1.5 mon | 367 | >500,000 | d6 (>1 ng) | NSI | R5 |
| Du156 | 16 Nov. 1998 | 17 Nov. 1998 | <1 mon | 404 | 22,122 | d6 (>1 ng) | NSI | R5 |
| Du172 | 16 Oct. 1998 | 17 Nov. 1998 | 1 mon | 793 | 1,916 | d6 (<50 pg) | NSI | R5 |
| Du174 | 6 Oct. 1997 | 25 May 1999 | 19.5 mon | 634* | 9,454* | d14 (>1 ng) | NSI | R5 |
| Du179 | 13 Aug. 1997 | 20 May 1999 | 21 mon | 394* | 1,359* | d7 (<50 pg) | SI | R5x4 |
| Du204 | 20 May 1998 | 20 May 1999 | 1 year | 633* | 8,734* | d7 (<50 pg) | NSI | R5 |
| Du258 | 3 Jun. 1998 | 22 Jun. 1999 | 1 year | 433* | 9,114* | — | No isolate | — |
| Du281 | 24 Jul. 1998 | 17 Nov. 1998 | 4 mon | 594 | 24,689 | d6 (1 ng) | NSI | R5 |
| Du285 | 2 Oct. 1998 | — | — | 560* | 161* | — | No isolate | — |
| Du368 | 8 Apr. 1998 | 24 Nov. 1998 | 7.5 mon | 670 | 13,993 | d6 (300 pg) | NSI | R5 |
| Du422 | 2 Oct. 1998 | 28 Jan. 1999 | 4 mon | 397 | 17,118* | d6 (600 pg) | NSI | R5 |
| Du457 | 17 Aug. 1998 | 17 Nov. 1998 | 3 mon | 665 | 6,658 | — | No isolate | — |
| Du467 | 26 Aug. 1998 | — | — | 671 | 19,268 | — | No isolate | — |

*date from November 1998

Genotypic Characterization

To select the vaccine isolate or isolates, a survey covering portions of the three major HIV genes gag (313 contiguous codons, 939 bases), pol (278 contiguous codons, 834 bases) and env (229 codons in two noncontigous segments, 687 bases) was done (FIG. 1). The map of FIG. 1 shows the 5'long terminal repeat, the structural and functional genes (gag, pol and env) as well as the regulatory and accessory proteins (vif tat, rev, nef, vpr and vpu). The gag open reading frame illustrates the regions encoding p17 matrix protein and the p24 core protein and the p7 and p6 nuclear capsid proteins. The pol open reading frame illustrates the protease (PR) p15, reverse transcriptase (RT) p66 and the Rnase H integrase p51. The env open reading frame indicates the region coding for gp120 and the region coding for gp41.

Of a total of 31 isolates, 14 were from the Durban cohort (DU), 15 were from Johannesburg (GG and RB) and 2 from Cape Town (CT). Of these 30 were sequenced in the gag region, 26 in the pol region and 27 in the env region. The isolates that were sequenced are shown in Table 2.

TABLE 2

LIST OF ISOLATES AND THE REGIONS GENES SEQUENCED

| Isolate | Gag sequence | Pol sequence | Env sequence |
|---|---|---|---|
| CTSC1 | ✓ | ✓ | — |
| CTSC2 | ✓ | ✓ | — |
| DU115 | ✓ | ✓ | ✓ |
| DU123 | ✓ | — | ✓ |
| DU151 | — | ✓ | ✓ |
| DU156 | ✓ | ✓ | ✓ |
| DU172 | ✓ | ✓ | ✓ |
| DU174 | ✓ | ✓ | ✓ |
| DU179 | ✓ | ✓ | ✓ |
| DU204 | ✓ | ✓ | ✓ |
| DU258 | ✓ | ✓ | ✓ |
| DU281 | ✓ | — | ✓ |
| DU368 | ✓ | ✓ | ✓ |
| DU422 | ✓ | ✓ | ✓ |
| DU457 | ✓ | ✓ | ✓ |
| DU467 | ✓ | — | ✓ |
| GG1 | ✓ | — | — |
| GG10 | ✓ | ✓ | ✓ |
| GG3 | ✓ | ✓ | ✓ |

TABLE 2-continued

LIST OF ISOLATES AND THE REGIONS GENES SEQUENCED

| Isolate | Gag sequence | Pol sequence | Env sequence |
|---|---|---|---|
| GG4 | ✓ | ✓ | ✓ |
| GG5 | ✓ | ✓ | ✓ |
| GG6 | ✓ | ✓ | ✓ |
| RB12 | ✓ | — | ✓ |
| RI313 | ✓ | ✓ | ✓ |
| RB14 | ✓ | ✓ | ✓ |
| RB15 | ✓ | ✓ | ✓ |
| RB18 | ✓ | ✓ | ✓ |
| RB21 | ✓ | ✓ | ✓ |
| RB22 | ✓ | ✓ | ✓ |
| RB27 | ✓ | ✓ | ✓ |
| RB28 | ✓ | ✓ | ✓ |

Figure 2:
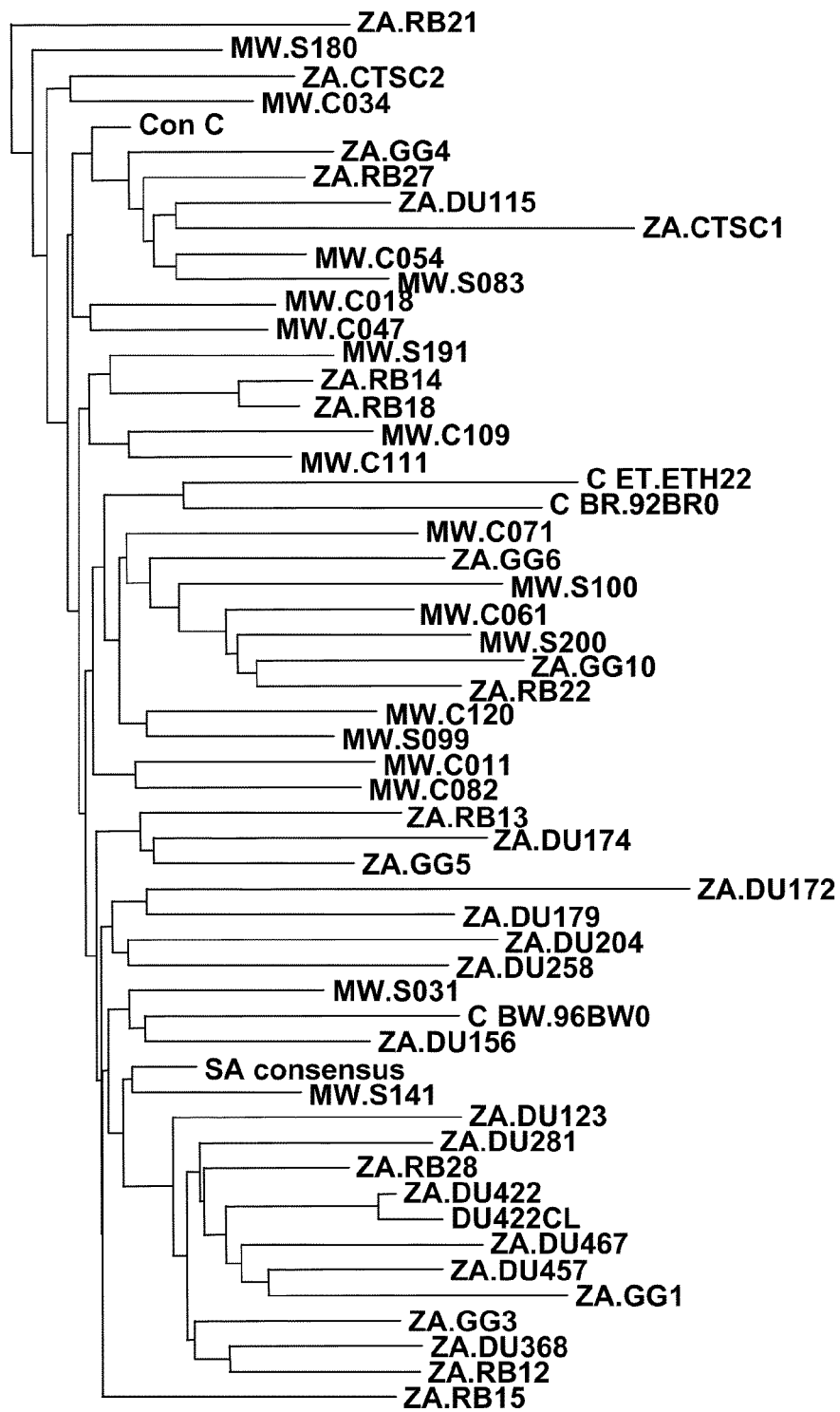
FIG. 2 shows a phylogenetic tree of nucleic acid sequences of various HIV-1 subtype C isolates based on the (partial) sequences of the gag gene of the various isolates and includes a number of consensus sequences as well as the South African consensus sequence of the present invention and a selected isolate, Du422, of the present invention.
Figure 3:
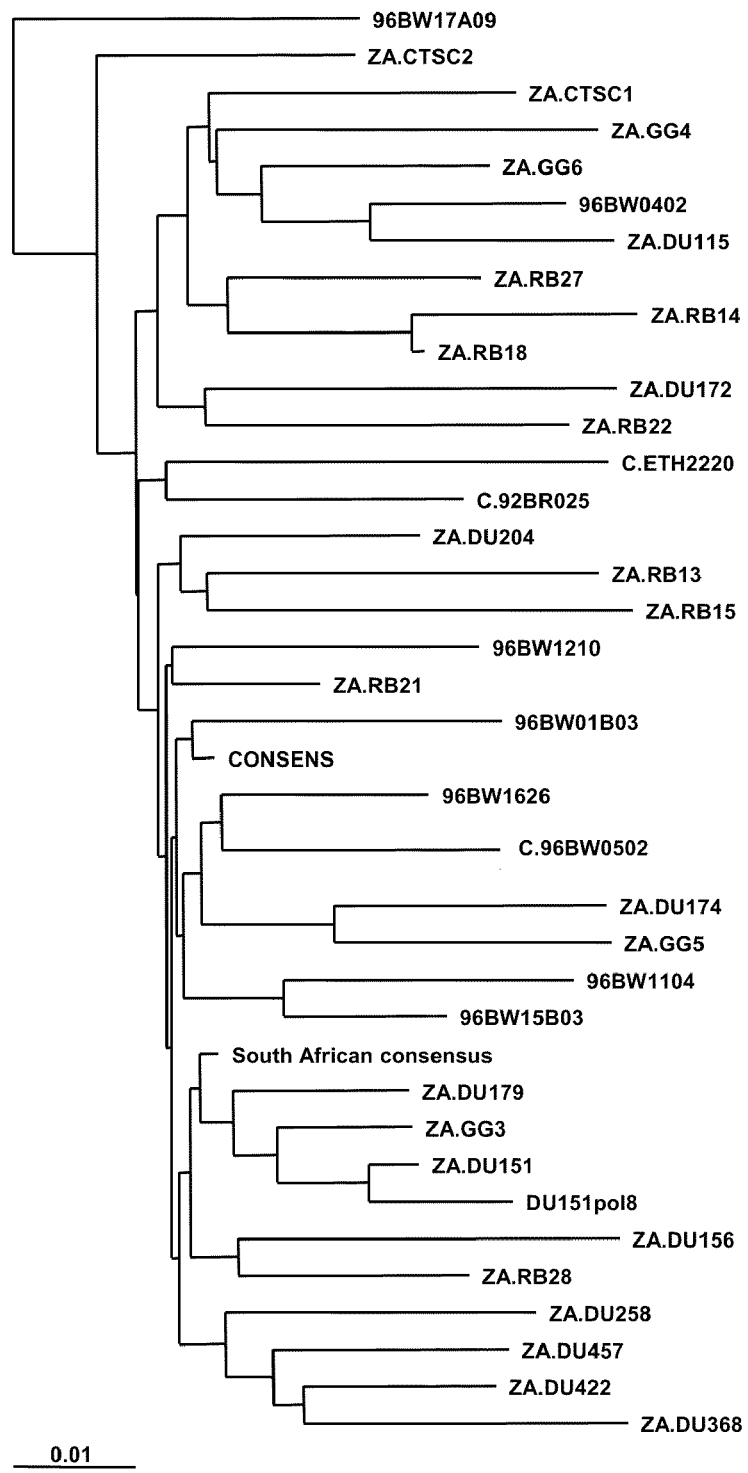
FIG. 3 shows a phylogenetic tree of nucleic acid sequences of various HIV-1 subtype C isolates based on the (partial) sequences of the pol gene of the various isolates and includes a number of consensus sequences as well as the South African consensus sequence of the present invention and a selected isolate, Du151, of the present invention.

The nucleic acid sequences from the Durban (DU) Johannesburg (GG, RB) and Cape Town (CT) cohorts were phylogenetically compared to all available published subtype C sequences (obtained from the Los Alamos HIV Sequence Database) including sequences from the other southern African countries and the overall subtype C consensus from the Los Alamos HIV sequence database. This comparison was done to ensure that the selected vaccine isolates were not phylogenetic outliers when compared to the Southern African sequences and the results of the comparison are shown in FIG. 2, FIG. 3 and FIG. 4. FIGS. 2 to 4 illustrate that the sequences from Southern Africa are divergent and that the Indian sequences form a separate distinct cluster from these African sequences. The South African sequences are not unique and, in general, are as related to each other as they are to other sequences from Southern Africa. Overall this suggests Indian sequences are unique from Southern African subtype C sequences and that we do not have a clonal epidemic in South Africa, but rather South African viruses reflect the diversity of subtype C viruses in the Southern African region.

Determination of a Consensus Sequence

Amino acid sequences were derived from the sequences shown in Table 2 and were used to determine a South African consensus sequence. The most frequently appearing amino acid at each position was selected as the consensus amino acid at that position. In this way, the consensus sequence was determined along the linear length of each of the sequenced gene fragments (gag, pol and env gene fragments). The alignments were done using the Genetics Computer Group (GCG) programs (Pileup and Pretty), which generates a consensus sequence in this manner. These resulted in the consensus sequence for each gene region. The alignments of the amino acid sequences and the resulting consensus sequences are shown in FIGS. 5, 6 and 7.

The phylogenetic tree of amino acids showing a comparison of the South African sequences is set out in FIGS. 8, 9 and 10. The ES2 gag S, which is the sequence of the cloned Du422 gag gene, Du151 pol (clone number) 8, which is the sequence of the cloned Du151 pol gene, and Du151 env (clone number) 25, which is the sequence of the cloned Du151 env gene, are vaccine clones. It can be seen from FIGS. 8, 9 and 10 that they are the same as the original isolates. These phylogenetic trees compare the relationship between the HIV proteins. South African isolates were compared with subtype A, B, C and D consensus sequences as well as with the South African consensus (Sagagcon) derived from the South African sequences, a Malawian consensus (Malgagcon) derived from Malawian sequences and overall consensuses (Cgagcon, Cpolcon and Cenvcon) derived from all subtype C sequences on the Los Alamos database.

The final choice of which isolate or isolates to use was based on the similarity of the sequence of the gag, env and pol genes of a particular isolate to the South African consensus sequence which had been derived as set out above as well as the availability of an R5 isolate which had good replication kinetics as shown in Table 1.

Selection of Vaccine Isolates

Based on the considerations and methodology set out above, three strains were selected from the acute infection cohort as the vaccine strains. The first strain is Du 422 for the gag gene, the second strain is Du 151 for the pol and env genes and the third strain is Du 179 which is a possible alternative for the env gene. These three strains were selected for the following reasons.

1. At the time the samples were obtained, Du 151 had been infected for 6 weeks and had a CD4 count of 367 cells per µl of blood and a viral load above 500,000 copies per ml of plasma. Given the high viral load, and the recorded time from infection, it is probable that the individual was still in the initial stages of viraemia prior to control of HIV replication by the immune system.
2. At the time the samples were obtained, Du422 had been infected for 4 months with a CD4 count of 397 cells per µl of blood and a viral load of 17,118 copies per ml of plasma. In contrast to Du151, this individual had already brought viral replication under control to a certain extent.
3. At the time the samples were obtained, Du179 had been infected for 21 months with a CD4 count of 394 cells per µl of blood and a viral load of 1,359 copies per ml of plasma.

Based on the analysis of the phylogenetic tree shown in FIG. 8 showing the relationship between full length gp120 sequence and other isolates, and the amino acid pairwise comparison shown in FIG. 11, the Du422 gag sequence was shown to be most similar to the South African consensus sequence shown in FIGS. 2 and 5. It shared 98% amino acid sequence identity with the consensus sequence. In addition, the average pairwise distance, which is the percentage difference between the DNA sequences, between the DU422 gag sequence and the other sequences from the seroconverters was the highest of any sequence derived from this cohort, at 93.5%, and nearly as high as the average distance of the isolates to the SA consensus sequence (94.2%). The Du422 gag gene was cloned and the specific clone gave values very similar to the original isolate: having a pairwise identity value with the SA consensus of (98%) and nearly as high an average identity value with the other isolates as the DU422 isolate (93.3%). Thus, both the original DU422 isolate sequence and the generated clone had the highest pairwise percentage similarity to other isolates with the minimal values all being above 90%.

The pol sequences showed the highest values for the pairwise comparisons. Based on the analysis of the phylogenetic tree shown in FIG. 9 and the pairwise identity score with the SA consensus (98.9%) shown in FIG. 12, we chose the DU151 isolate as the source of the pol gene. Other contributing factors in this decision were that this is the same isolate that was chosen for the source of the any gene and that this was an isolate with excellent growth properties in vitro. The actual pol gene clone from the DU151 isolate was somewhat more divergent from the SA consensus sequence (97.8%), and had a smaller average identity score when compared to the other isolates (95.1%). However, we judged the small increase in distance from the consensus not to be significant in this otherwise well conserved HIV-1 gene and therefore chose the DU151 pol gene for further development. Only one of the recent seroconverter sequences was less than 93% identical with the DU151 pol gene segment.

The env gene showed the greatest sequence diversity. Based on the analysis of the phylogenetic tree shown in FIG. 10, we chose the DU151 env gene. The DU151 any gene segment shows an average pairwise comparison score with the other isolates of 87.2%, with the clone being slightly higher (87.9%). The DU151 isolate gene segment has a pairwise identity score of 92.6% with the SA consensus while the DUI 51 clone is at 91.3%. Finally, all pairwise identity scores are above 83% with either the DU151 isolate sequence or the clone when compared to the other recent seroconverters, as shown in FIG. 13. These pairwise scores make the DU151 sequence similar to the best scores in this sequence pool and combine these levels of similarity with an R5 virus with good cell culture replication kinetics.

The clones representing the full length gene for each of the above viral genes were generated by PCR. Viral DNA present in cells infected with the individual isolates were used for the pol and env clones, and DNA derived directly from plasma by RT-PCR was used for the gag clone. Total DNA was extracted from the infected cell pellets using the QIAGFN DNeasy Tissue Kit. This DNA was used in PCR reactions using the following primers (HXBR numbering, Los Alamos database) in a nested PCR amplification strategy:

gag: outer, 623-640, and 2391-2408; inner, 789-810 and 2330-2350;

pol: outer, 2050-2073, and 5119-5148, inner, 2085-2108, and 5068-5094;

env: outer, 6195-6218, and 8807-8830; inner, 6225-6245, and 8758-8795.

The PCR products were blunt-end cloned into pT7Blue using the Novagen pT7Blue Blunt Kit. The inserts were characterized by doing colony PCR to identify clones with gene inserts. The identity of the insert was confirmed by sequencing the insert on both strands and comparing this sequence to the original sequence.

Modification of Clones

Several modifications were introduced to the cloned genes, as shown in FIGS. 23 to 36. In order to increase levels of expression of proteins, the DNA sequence was resynthesized and the following modifications were made:

the codon usage was changed to reflect human codon usage for increased expression; and the inhibitory and rev responsive elements were also removed.

The modifications to the gag gene sequence of Du422 are shown in SEQ ID NOS: 7 and 8 (FIGS. 23 and 24).

Also for the DNA, modified vaccinia ankara (MVA) and BCG vaccines, the pol gene was truncated so that only the protease, reverse transcriptase and RNAse H regions of the pol gene will be expressed. In addition, the active site amino acid motive YMDD has been mutated to YMAA so that the expressed reverse transcriptase will be catalytically inactive. The modifications to the pol gene of Du151 are shown in SEQ ID NOS: 9 and 10 (FIGS. 25 and 26).

Synthetic Genes

The complete gag and env genes were resynthesized to optimise the codons for expression in human cells, also shown in SEQ ID NOS: 9, 10, and nucleotides 7 to 2552 of SEQ ID NO: 11 and amino acids 3 to 852 of SEQ ID NO: 12 (FIGS. 25 to 28). During this process the inhibitory sequences (INS) and rev responsive elements (RRE) are removed which has reported to result in increased expression. The gag gene myristylation signal was mutated as described above and as shown in SEQ ID NOS: 7 and 8 (FIGS. 23 and 24).

The following material has been deposited with the European Collection of Cell Cultures, Centre for Applied Microbiology and Research, Salisbury, Wiltshire SP4 OJG, United Kingdom (ECACC).

| Deposits | | |
|---|---|---|
| Material | ECACC Deposit No. | Deposit Date |
| HIV-1 Viral isolate Du151 | Accession Number 00072724 | 27 Jul. 2000 |
| HIV-1 Viral isolate Du179 | Accession Number 00072725 | 27 Jul. 2000 |
| HIV-1 Viral isolate Du422 | Provisional Accession Number 00072726 | 27 Jul. 2000 |
| | Provisional Accession Number 01032114 | 22 Mar. 2001 |

The deposit was made under the provisions of the Budapest Treaty on the International Recognition of the Deposit of Microorganisms for the Purpose of Patent Procedure and regulations thereunder (Budapest Treaty).

REFERENCES

UNAIDS, AIDS epidemic update, December 1999. www.unaids.org/hivaidsinfo/documents.html Binley J M, Sanders R W, Clas B, Schuelke N, Master A, Guo Y, Kajumo F, Anselma D J, Madden P J, Olson W C, Moore J P., *J. Virol.* 2000 January; 74(2):627-43

Bjorndal, A., Sonnerborg, A., Tscheming, C., Albert, J. & Fenyo, E. M. (1999). Phenotypic characteristics of human immunodeficiency virus type 1 subtype C isolates of Ethiopian.

Connor, R., Sheridan, K., Ceraldini, D., Choe, S. & Landau, N. (1997). Changes in co-receptor use correlates with disease progression in HIV-1-infected individuals. *J Exp Med* 185, 621-628.

Durali D, Morvan J, Letourneur F, Schmitt D, Guegan N, Dalod M, Saragosti S, Sicard D, Levy J P & Gomard E (1998). Cross-reactions between the cytotoxic T-lymphocyte responses of human immunodeficiency virus-infected African and European patients. *J Virol.* 72:3547-53.

Ferrari G, Humphrey W, McElrath M J, Excler J L, Duliege A M, Clements M L, Corey L C, Bolognesi D P & Weinhold K J (1997). Glade B-based HIV-1 vaccines elicit crosscade cytotoxic T lymphocyte reactivities in uninfected volunteers. *Proc Natl Acad Sci USA* 18; 94(4):1396-401.

HIV Molecular Immunology Database 1998: Korber B, Brander C, Koup R, Walker B, Haynes B, & Moore J, Eds. Theoretical Biology and Biophysics Group, Los Alamos National Laboratory, Los Alamos, N.M.

Kostrikis, L. G., Cao, Y., Ngai, H., Moore, J. P. & Ho, D. D (1996). Quantitative analysis of serum neutralization of human immunodeficiency virus type 1 from subtypes A, B, C, D, E, F, and I: lack of direct correlation between neutralization serotypes and genetic subtypes and evidence for prevalent serum-dependent infectivity enhancement. *J. Virol.* 70, 445-458.

Koup R A, Safrit J T, Cao Y, Andrews C A, McLeod G, Borkowsky W, Farthing C, Ho D D (1994). Temporal association of cellular immune responses with the initial control of viremia in primary human immunodeficiency virus type 1 syndrome. *J Virol.* 68(7):4650-5.

Moore J P, Cao Y, Leu J, Qin L, Korber B & Ho D D (1996). Inter- and intraclade neutralization of human immunodeficiency virus type 1: genetic clades do not correspond to neutralization serotypes but partially correspond to gp120 antigenic serotypes. *J. Virol.* 70, 427-444.

Ogg G S, Kostense S, Klein M R, Jurriaans S, Hamann D, McMichael A J & Miedema F (1999). Longitudinal phenotypic analysis of human immunodeficiency virus type 1-specific cytotoxic T lymphocytes: correlation with disease progression. *J Virol.* 73(11):9153-60.

Peeters, M., Vincent, R., Perret, J.-L., Lasky, M., Patrel, D., Liegeois, F., Courgnaud, V., Seng, R., Mallon, T., Molinier, S. & Delaporte, E. (1999). Evidence for differences in MT2 cell tropism according to genetic subtypes of HIV-1: syncitium-inducing variants seem rare among subtype C HIV-1 viruses. *J. Acquir Imm Def Synd* 20, 115-121.

Richman, D. & Bozzette, S. (1994). The impact of the syncytium-inducing phenotype of human immunodeficiency virus on disease progression. *J Inf Dis* 169, 968-974.

Robertson D L, Anderson J P, Bradac J A, Carr J K, Foley B, Funkhouser R K, Gao R, Hahn B H, Kalish M L, Kuiken C, Leam G H Leitner T, McCutchan F, Osmanov S, Peeters M, Pieniazek D, Salminen M, Sharp P M, Wolinsky S, Korber B (2000). HIV nomenclature proposal. *Science* 7; 288 (5463):55-6.

Rowland-Jones S L, Dong T, Fowke K R, Kimani J, Krausa P, Newell H, Blanchard T, Ariyoshi K, Dyugi J, Ngugi E, Bwayo J, MacDonald K S, McMichael A J & Plummer F A (1998). Cytotoxic T-cell responses to multiple conserved epitopes in HIV-resistant prostitutes in Nairobi. *J. Clin. Invest.* 102 (9); 1758-1765.

Scarlatti, G., Tresoldi, E., Bjomdal, A., Fredriksson, R., Colognesi, C., Deng, H., Malnati, M., Plebani, A., Siccardi, A., Littman, D., Fenyo, E. & Lusso, P. (1997). In vivo evolution of HIV-1 co-receptor usage and sensitivity to chemokine-mediated suppression. *Nat Med* 3, 1259-1265.

Schmitz J E, Kuroda M J, Santra S, Sasseville V G, Simon M A, Litton M A, Racz P, Tenner-Racz K, Dalesandro M, Scallon B J, Ghrayeb J, Forman M A, Montefiori D C, Rieber E P, Letvin N L, Reimann K A (1999). Control of viremia in simian immunodeficiency virus infection by CD8+ lymphocytes. *Science* 5; 283(5403):857-60.

Summary Report National HIV sero-prevalence survey of women attending public antenatal clinics in South Africa, 1999 (2000). Department of Health, Directorate: Health Systems Research & Epidemiology, April 2000.

Tscheming, C., Alaeus, A., Fredriksson, R., Bjorndal, A., Deng, H., Littman, D., Fenyo, E. M. & Alberts, J. (1998). Differences in chemokine co-receptor usage between genetic subtypes of HIV-1. *Virology* 241, 181-188.

Wyatt R and Sodroski J (1998). The HIV-1 envelope glycoproteins: Fusogens, antigens and immunogens. *Science,* 280 (5371):1884-8.

Wyatt R, Kwong, Desjardins E, Sweet R W, Robinson J, Hendrickson W A & Sodroski J G (1998). The antigenic structure of the HIV gpl 20 envelope glycoprotein. *Nature,* 393(6686):705-11.

That which is claimed is:

1. An isolated nucleic acid molecule comprising a sequence that encodes an HIV Gag polypeptide as set forth in SEQ ID NO: 8, or a sequence at least 98% genetically related to the full-length sequence of SEQ ID NO: 8.

2. The isolated nucleic acid molecule of claim 1 wherein the HIV gag polypeptide is as set forth in SEQ ID NO: 2.

3. The isolated nucleic acid molecule of claim 1 comprising:
   (i) the sequence as set forth in SEQ ID NO: 1 or a sequence at least 98% genetically related to the full-length sequence of SEQ ID NO:1;
   (ii) the sequence as set forth in SEQ ID NO: 1 modified to remove a myristylation site and to reflect human codon usage;
   (iii) the sequence as set forth in SEQ ID NO: 7 or a sequence at least 98% genetically related to the full-length sequence of SEQ ID NO: 7;
   (iv) a sequence which is complementary to (i)-(iii); or (v) an RNA sequence encoded by (i)-(iv).

4. An isolated polypeptide comprising the Gag sequence as set forth in SEQ ID NO: 2 or as set forth in SEQ ID NO: 8, or a sequence at least 98% genetically related to the full-length sequence of SEQ ID NO: 2 or at least 98% genetically related to the full-length sequence of SEQ ID NO: 8.

5. A composition comprising a nucleic acid molecule comprising a sequence that encodes an HIV Gag polypeptide as set forth in SEQ ID NO: 2 or as set forth in SEQ ID NO: 8, or a sequence at least 98% genetically related to the full-length sequence of SEQ ID NO: 2 or at least 98% genetically related to the full-length sequence of SEQ ID NO: 8, in a pharmaceutical carrier.

6. The composition of claim 5, wherein the nucleic acid molecule comprises:
   the sequence as set forth in SEQ ID NO: 1 or a sequence at least 98% genetically related to the full-length sequence of SEQ ID NO: 1;
   (ii) the sequence as set forth in SEQ ID NO: 1 modified to remove a myristylation site and to reflect human codon usage;
   (iii) the sequence as set forth in SEQ ID NO: 7 or a sequence at least 98% genetically related to the full-length sequence of SEQ ID NO: 7;
   (iv) a sequence which is complementary to (i)-(iii); or
   (v) an RNA sequence encoded by (i)-(iv).

* * * * *